US012617856B2

(12) United States Patent (10) Patent No.: US 12,617,856 B2
Vasiljeva et al. (45) Date of Patent: May 5, 2026

(54) PROTEASE-CLEAVABLE SUBSTRATES AND METHODS OF USE THEREOF

(71) Applicant: CytomX Therapeutics, Inc., South San Francisco, CA (US)

(72) Inventors: Olga Vasiljeva, Highlands Ranch, CO (US); Michael B. Winter, San Francisco, CA (US)

(73) Assignee: CYTOMX THERAPEUTICS, INC., South San Francisco, CA (US)

( * ) Notice: Subject to any disclaimer, the term of this patent is extended or adjusted under 35 U.S.C. 154(b) by 0 days.

(21) Appl. No.: 19/081,340

(22) Filed: Mar. 17, 2025

(65) Prior Publication Data

US 2025/0215095 A1 Jul. 3, 2025

Related U.S. Application Data

(63) Continuation of application No. 19/100,493, filed as application No. PCT/US2023/071310 on Jul. 31, 2023.

(60) Provisional application No. 63/370,026, filed on Aug. 1, 2022.

(51) Int. Cl.
| | |
|---|---|
| *C07K 16/28* | (2006.01) |
| *A61K 38/00* | (2006.01) |
| *A61K 39/00* | (2006.01) |
| *A61P 35/00* | (2006.01) |
| *C12N 9/64* | (2006.01) |
| *C12N 15/16* | (2006.01) |
| *C12N 15/62* | (2006.01) |

(52) U.S. Cl.
CPC .......... *C07K 16/2863* (2013.01); *A61P 35/00* (2018.01); *C12N 15/62* (2013.01); *A61K 38/00* (2013.01); *A61K 2039/505* (2013.01); *C07K 2317/24* (2013.01); *C07K 2317/92* (2013.01); *C07K 2319/50* (2013.01); *C07K 2319/70* (2013.01); *C12Y 304/24024* (2013.01); *C12Y 304/24035* (2013.01); *C12Y 304/2408* (2013.01)

(58) Field of Classification Search
CPC ............ C07K 16/2863; C07K 2317/24; C07K 2317/92; C07K 2319/50; C07K 2319/70; A61P 35/00; A61K 2039/505; A61K 38/00; C12Y 304/24035; C12Y 304/24024; C12Y 304/2408; C12N 15/62; C12N 9/6491
See application file for complete search history.

(56) References Cited

U.S. PATENT DOCUMENTS

2003/0194704 A1* 10/2003 Penn .................... C12Q 1/6876
536/24.3

FOREIGN PATENT DOCUMENTS

| | | |
|---|---|---|
| WO | 2015/048329 A2 | 4/2015 |
| WO | 2015/116933 A2 | 8/2015 |
| WO | 2016/118629 A1 | 7/2016 |
| WO | 2020/118109 A2 | 6/2020 |
| WO | 2024/030843 A1 | 2/2024 |
| WO | 2024/030845 A1 | 2/2024 |
| WO | 2024/030847 A1 | 2/2024 |
| WO | 2024030858 A1 | 2/2024 |

OTHER PUBLICATIONS

Geiger, Martina, et al. "Protease-activation using anti-idiotypic masks enables tumor specificity of a folate receptor 1-T cell bispecific antibody." Nature communications 11.1 (2020): 3196. (Year: 2020).*
UniProt Database Accession No. A0A1H3CH17; "SubName: Full= ABC-2 type transport system ATP-binding protein {ECO:0000313|EMBL:SDX53310.1}"; XP93097912; Retrieved on Nov. 22, 2017.
UniProt Database Accession No. A0A6M1U8N7; "SubName: Full= Polysaccharide pyruvyl transferase family protein {ECO:0000313|EMBL:NGQ92975.1}", XP93096894; Retrieved on Oct. 7, 2020.
Darragh et al., "MT-SP1 proteolysis and regulation of cell-microenvironment interactions", Front. Biosci. (2008) 13:528-539.
Levesque et al., "Characterization of hematopoietic progenitor mobilization in protease-deficient mice", Blood, (2004) 104(1):65-72.
Lucchi et al., "The Masking Game: Design of Activatable Antibodies and Mimetics for Selective Therapeutics and Cell Control", ACS Central Science (2021) 7(5):724-738.
International Search Report and Written Opinion for PCT/US2023/071310 dated Nov. 14, 2023 (15 pages).
Notice of Allowance for co-pending U.S. Appl. No. 19/081,458 dated Oct. 14, 2025. (9 pages).
M. Geiger, et al. "Protease-activation using anti-idiotypic masks enables tumor specificity of a folate receptor 1-T cell bispecific antibody" Nature communications 11.1 (2020): 3196. (38 pp).
Non-Final Office Action for co-pending U.S. Appl. No. 19/080,251 dated Aug. 14, 2025. (9 pages).
Non-Final Office Action for co-pending U.S. Appl. No. 19/081,458 dated Jun. 30, 2025. (14 pages).
M. Ozols, et al. "Predicting and validating protein degradation in proteomes using deep learning." bioRxiv, Nov. 2020; (38 pages).
UniProt entry A0A1K1MYK5_9BURK; "Glutathione import ATP-binding protein GsiA—*Burkholderia* sp. NFACC33-1"; UniProtKB; URL: https://www.uniprot.org/uniprotkb/A0A1K1MYK5/entry; 2017; (7 pages).

(Continued)

*Primary Examiner* — Mark Halvorson
*Assistant Examiner* — Lea S O'Brien
(74) *Attorney, Agent, or Firm* — ROTHWELL, FIGG, ERNST & MANBECK, P.C.

(57) ABSTRACT

Isolated polypeptides that include a cleavable moiety that is a substrate for at least one protease (e.g., MT-SP1 and/or an MMP) and isolated polypeptides that include a substrate that has a first cleavable moiety cleavable by a first protease and a second cleavable moiety cleavable by a second protease are disclosed. Activatable molecules including the isolated polypeptides are disclosed. Methods of making and using the isolated polypeptides and activatable molecules including the isolated polypeptides in a variety of therapeutic, diagnostic, and prophylactic applications are disclosed.

30 Claims, 11 Drawing Sheets

Specification includes a Sequence Listing.

(56) References Cited

OTHER PUBLICATIONS

UniProt entry A0A2R4MJ55_9HYPH; "DUF4345 domain-containing protein—Maritalea myrionectae"; UniProtKB; URL: https://www.uniprot.org/uniprotkb/A0A2R4MJ55/entry; 2018; (5 pages).
UniProt entry A0A2R8BVN5_9RHOB; "galB—4-oxalmesaconate hydratase—Palleronia abyssalis"; UniProtKB; URL: https://www.uniprot.org/uniprotkb/A0A2R8BVN5/entry; 2018; (4 pages).
UniProt entry A0A8T1PYV5_CARIL; "F-actin-capping protein subunit alpha—*Carya illinoinensis* (Pecan)"; UniProtKB; URL: https://www.uniprot.org/uniprotkb/A0A8T1PYV5/entry; 2022; (5 pages).
UniProt entry A0A957YGH2_9CHLR; "Response regulator—Anaerolineae bacterium"; URL: https://www.uniprot.org/uniprotkb/A0A957YGH2/entry#sequences; 2023; (5 pages).
GenBank Accession MCB0211682.1; "MAG: response regulator [Anaerolineae bacterium]"—Protein—NCBI; URL: https://www.ncbi.nlm.nih.gov/protein/MCB0211682.1; 2021; (2 pages).
Uniprot Database Accession No. A0A074RII3; "SubName: Full=Putative aromatic di-alanine and TPR containing protein {ECO:0000313|EMBL:KEP46916.1}"; XP93095538; Retrieved on Oct. 1, 2014.
Uniprot Database Accession No. A0A137QY42; "SubName: Full=ATP-dependent bile acid permease {ECO:0000313|EMBL:KXN92134.1}"; XP93095548; Retrieved on May 11, 2016.
Uniprot Database Accession No. A0A197K6Z3; "SubName: Full=Uncharacterized protein {ECO:0000313|EMBL:OAQ32481.1}"; XP93095423; Retrieved on Oct. 5, 2016.
Uniprot Database Accession No. A0A836AHN9; "ecName: Full=thioredoxin-dependent peroxiredoxin {ECO:0000256|ARBA:ARBA00013017}; EC=1.11.1.24 {ECO:0000256|ARBA:ARBA00013017}"; XP93095433; Retrieved on Sep. 29, 2021.
Elter et al., "Protease-Activation of Fe-Masked Therapeutic Antibodies to Alleviate Off-Tumor Cytotoxicity", Front. Immunol. (2021) vol. 12; Article 715719.
International Search Report and Written Opinion for PCT/US2023/071326 mailed Nov. 13, 2023 (14 pages).
Geneseq Accession No. BFF77299 sequence; "Matrix metalloprotease-cleavable substrate peptide sequence, SEQ ID 14"., XP93096800; Retrieved on Jun. 14, 2018.
UniProt Database Accession No. A0A409YG42; "RecName: Full=Wax synthase domain-containing protein {ECO:0000259|Pfam:PF13813}", XP93094943; Retrieved on May 8, 2019.
UniProt Database Accession No. A0A3A8ZXS7; "SubName: Full=DUF354 domain-containing protein {ECO:0000313|EMBL:RKI84039.1}"; XP93094568; Retrieved on Dec. 5, 2018.
UniProt Database Accession No. D6PNE5; "SubName: Full=AT1G14580-like protein {ECO:0000313|EMBL:ADG37877.1}; Flags: Fragment;"; XP93094834; Retrieved on Jul. 13, 2012.
UniProt Accession No. A0A1N7KFJO sequence; "SubName: Full=Uncharacterized protein {ECO:0000313|EMBL:SIS60363.1}; Flags: Fragment"; XP055774600; Retrieved on Mar. 15, 2017.
UniProt Accession No. A0A1F4XHY9 sequence; "SubName: Full=Cytidine deaminase {ECO:0000313|EMBL:OGC81244.1}"; 11; XP93096679; Retrieved on Feb. 15, 2017.

UniProt Accession No. A0A2E8KWV9 sequence; "SubName: Full=Alpha/beta hydrolase {ECO:0000313|EMBL:MBQ83167.1}; Flags: Fragment", XP93096813; Retrieved on Jan. 31, 2018.
UniProt Accession No. A0A3P6QZ33 sequence; "SubName: Full=Uncharacterized protein {ECO:0000313|EMBL:VDK48083.1}; Flags: Fragment", XP93096714; Retrieved on Feb. 13, 2019.
UniProt Accession No. A0A8E2VWQ4 sequence; "SubName: Full=Uncharacterized protein {ECO:0000313|EMBL:PVY67208.1}"; XP93096425; Retrieved on Jan. 19, 2022.
UniProt Accession No. A0A067BKA2 sequence; "SubName: Full=Uncharacterized protein {ECO:0000313|EMBL:KDO17145.1}; Flags: Fragment"; XP93096699; Retrieved on Sep. 3, 2014.
UniProt Accession No. A0A554LG77 sequence; "SubName: Full=Uncharacterized protein {ECO:0000313|EMBL:TSC91857.1}"; XP93096706; Retrieved on Oct. 16, 2019.
UniProt Database Accession No. A0A1Z9LPE2; "SubName: Full=Ribosomal-protein-alanine acetyltransferase {ECO:0000313|EMBL:OUW57190.1}"; XP93095919; Retrieved on Nov. 22, 2017.
UniProt Database Accession No. A0A2D9SJ69; "SubName: Full=Copper resistance protein CopB {ECO:0000313|EMBL:MAQ08488.1}"; XP93095978; Retrieved on Apr. 25, 2018.
UniProt Database Accession No. A0A4V2F418; "RecName: Full=DUF2730 family protein {ECO:0008006|Google: ProtNLM}"; XP93095984; Retrieved on Jul. 31, 2019.
UniProt Database Accession No. A0A4Y8NRA3; "SubName: Full=Ribosomal-protein-alanine acetyltransferase {ECO:0000313|EMBL:TFE54718.1}; Flags: Fragment"; XP93095972; Retrieved on Sep. 18, 2019.
UniProt Database Accession No. A0A6A6EE67; "RecName: Full=Heterokaryon incompatibility domain-containing protein {ECO:0008006|Google: ProtNLM}; Flags: Fragment"; XP93095981; Retrieved on Jun. 17, 2020.
UniProt Database Accession No. A0A518GXK2; RecName: Full=Phosphoribosylglycinamide formyltransferase {ECO:0000256|HAMAP-Rule:MF_01930}; EC=2.1.2.2 {ECO:0000256|HAMAP-Rule: MF_01930}; AltName: Full=5'-phosphoribosylglycinamide transformylase {ECO:0000256|HAMAP-Rule:MF_01930}; AltName: Full=GAR transformylase {ECO:0000256|HAMAP-Rule:MF_01930}; XP93095967; Retrieved on Oct. 16, 2019.
UniProt Database Accession No. A0A838VSQ7; "RecName: Full=histidine kinase {ECO:0000256|ARBA:ARBA00012438}; EC=2.7.13.3 {ECO:0000256|ARBA:ARBA00012438}"; XP93095987; Retrieved on Sep. 29, 2021.
Kukreja et al., "The high throughput multiplexed peptide-centric profiling illustrates both the substrate cleavage redundancy and specificity in the MMP family", Chem. Biol. (2015) 22(8):1122-1133.
UniProt Database Accession No. A0A7S2GUI1; "SubName: Full=Uncharacterized protein {ECO:0000313|EMBL:CAD9470403.1}", XP93094976; Retrieved on Jun. 2, 2021.
UniProt Database Accession No. Q94NY5; "RecName: Full=NADH-ubiquinone oxidoreductase chain 1 {ECO:0000256|ARBA:ARBA00021009, ECO:0000256|RuleBase:RU000473}; EC=7.1.1.2 {ECO:0000256|RuleBase:RU000473}; Flags: Fragment"; XP93096766; Retrieved on Dec. 1, 2001.
International Search Report and Written Opinion for PCT/US2023/071310 mailed Nov. 14, 2023 (15 pages).

* cited by examiner

*In vitro* Masking Efficiency of anti-EGFR Activatable Antibodies with Exemplary Substrates

In vitro Masking Efficiency of anti-EGFR Activatable Antibodies with Exemplary Substrates

Regression of Established H292 Tumors in nu/nu Mice Dosed at 7.5 mg/kg

Regression of Established H292 Tumors in nu/nu Mice Dosed at 7.5 mg/kg

Regression of Established H292 Tumors in nu/nu Mice Dosed at 7.5 mg/kg

Regression of Established SUM149 Tumors in nu/nu Mice dosed at 5 mg/kg

In vivo Intratumoral Activation of C225
Activatable Antibodies in H292 Tumors at Day 8

In vivo Intratumoral Activation of C225 Activatable Antibodies in H292 Tumors at Day 7

In situ Stability of anti-EGFR Activatable Antibodies in Human Bone Marrow Aspirates

In situ Stability of anti-EGFR Activatable Antibodies in Human Bone Marrow Aspirates

In situ Stability of anti-EGFR Activatable Antibodies in Human Bone Marrow Aspirates

PROTEASE-CLEAVABLE SUBSTRATES AND METHODS OF USE THEREOF

CROSS-REFERENCE TO RELATED APPLICATIONS

This application is a continuation of U.S. application Ser. No. 19/100,493, filed Jan. 31, 2025, which is a 35 U.S.C. 371 National Phase Entry Application of PCT/US2023/071310, filed Jul. 31, 2023, which claims the priority benefit of U.S. Provisional Application No. 63/370,026 filed Aug. 1, 2022, the contents of which are incorporated herein in their entireties by reference thereto.

SEQUENCE LISTING

The instant application contains a Sequence Listing which has been submitted electronically in XML format and is hereby incorporated by reference in its entirety. Said XML copy, created on Jul. 27, 2023 is named CYTX-095-PCT-_SL.xml and is 562,378 bytes in size.

TECHNICAL FIELD

The present disclosure generally relates to polypeptides that include a substrate comprising one or more cleavable moieties, each of which is cleavable by a protease, and to methods of making and using the polypeptides and activatable molecules in a variety of therapeutic, diagnostic, and prophylactic applications.

BACKGROUND

Proteases are enzymes that catalyze the hydrolysis of peptide bonds between amino acid residues. Some proteases are known to break specific peptide bonds based on the presence of a particular amino acid sequence within a protein. Proteases occur naturally in all organisms and are involved in a variety of physiological reactions from simple degradation to highly regulated pathways. Some proteases break specific peptide bonds based on the presence of a particular amino acid sequence within a protein while some amino acid sequences are resistant to cleavage by particular proteases.

Accordingly, there exists a need to identify new substrates for proteases and to use these substrates in a variety of therapeutic, diagnostic and prophylactic applications.

SUMMARY OF THE INVENTION

In one aspect, the present disclosure provides an isolated polypeptide comprising a substrate, wherein the substrate comprises a first cleavable moiety (CM1) cleavable by at least a first protease and a second cleavable moiety (CM2) cleavable by at least a second protease, and wherein the CM1 comprises the amino acid sequence of PXGL, wherein X is W, Y, F, R, K, Q, A, or M.

In one aspect, the present disclosure provides an isolated polypeptide comprising a substrate, wherein the substrate comprises a first cleavable moiety (CM1) cleavable by at least a first protease and a second cleavable moiety (CM2) cleavable by at least a second protease, and wherein the CM1 comprises the amino acid sequence of PXGL, wherein X is W, Y, F, R, K, Q, or M.

In some embodiments, the CM2 comprises the amino acid sequence of RS. In some embodiments, the CM1 comprises the amino acid sequence of PWGL (SEQ ID NO: 2). In some embodiments, the substrate comprises the amino acid sequence of RSPWGLN (SEQ ID NO: 10), RSPWGL (SEQ ID NO: 90), PWGLRS (SEQ ID NO: 48), PWGLSGKS (SEQ ID NO: 150), or PWGLRSN (SEQ ID NO: 9). In some embodiments, the CM2 comprises the amino acid sequence of GRS. In some embodiments, the CM2 comprises the amino acid sequence of SGRS (SEQ ID NO: 31), SGRSNI (SEQ ID NO: 32), or LSGRSNI (SEQ ID NO: 26). In some embodiments, the CM1 comprises the amino acid sequence of PWGL (SEQ ID NO: 2). In some embodiments, the substrate comprises the amino acid sequence of GPWGLS-GRSNI (SEQ ID NO: 11), PWGLSGRS (SEQ ID NO: 12), GRSPWGLL (SEQ ID NO: 13), APMGLKHLSGRSNI (SEQ ID NO: 14), or GPYGLSGRSNI (SEQ ID NO: 15). In some embodiments, the CM2 comprises the amino acid sequence of PRS. In some embodiments, the CM2 comprises the amino acid sequence of APRS (SEQ ID NO: 34). In some embodiments, the CM1 comprises the amino acid sequence of PWGL (SEQ ID NO: 2). In some embodiments, the substrate comprises an amino acid sequence of APR-SPWGL (SEQ ID NO: 16), PWGLPRS (SEQ ID NO: 17), PRSPWGL (SEQ ID NO: 313) or PRSPWGLL (SEQ ID NO: 18). In some embodiments, the CM2 comprises the amino acid sequence of SRS. In some embodiments, the CM2 comprises the amino acid sequence of HQSRS (SEQ ID NO: 28). In some embodiments, the substrate comprises the amino acid sequence of PWGLSRS (SEQ ID NO: 19), PFGLSRS (SEQ ID NO: 20), APMGLKHDHQSRS (SEQ ID NO: 21) or DHQSRSAPMGLKH (SEQ ID NO: 22). In some embodiments, the substrate comprises the amino acid sequence of KPRGL (SEQ ID NO: 664). In some embodiments, the substrate comprises the amino acid sequence of KPRGLN (SEQ ID NO: 23) or KPRGLF (SEQ ID NO: 24). In some embodiments, the substrate comprises the amino acid sequence of PYGLSGRS (SEQ ID NO: 151). In some embodiments, the substrate comprises the amino acid sequence of PFGLSGRS (SEQ ID NO: 152). In some embodiments, the substrate comprises the amino acid sequence of PRGLSGRS (SEQ ID NO: 153). In some embodiments, the substrate comprises the amino acid sequence of PAGLSGRS (SEQ ID NO: 687). In some embodiments, the substrate comprises the amino acid sequence of LSGRSPWGL (SEQ ID NO: 177). In some embodiments, the substrate comprises the amino acid sequence of LSGKSPWGL (SEQ ID NO: 178). In some embodiments, the substrate comprises the amino acid sequence of PWGLAGRS (SEQ ID NO: 690). In some embodiments, the substrate comprises the amino acid sequence of PWGLSARS (SEQ ID NO: 691). In some embodiments, the substrate comprises the amino acid sequence of PWGLSARS (SEQ ID NO: 163). In some embodiments, the substrate comprises the amino acid sequence of PWGLSGAS (SEQ ID NO: 692). In some embodiments, the substrate comprises the amino acid sequence of PWGLSGRA (SEQ ID NO: 693). In some embodiments, the substrate comprises the amino acid sequence of LSGRSPAGL (SEQ ID NO: 694). In some embodiments, the substrate comprises the amino acid sequence of LSGRSPWGLS (SEQ ID NO: 695).

According to some embodiments of the present disclosures, the isolated polypeptide is a molecule in which cleavage of the CM by a protease results in a part or component of the molecule being separated from the remainder of the molecule. In some aspects of the present disclosure, cleavage of the CM by a protease activates the molecule. In some aspects, the isolated polypeptide is a molecule in which multiple proteases cleave the CM. In some aspects, the isolated polypeptide is a molecule in which MMP2 cleaves the CM. In some aspects, the isolated polypeptide is a molecule in which MMP9 cleaves the CM. In some aspects, the isolated polypeptide is a molecule in which MMP14 cleaves the CM. In some aspects, the isolated polypeptide is a molecule in which MT-SP1 cleaves the CM. In some aspects, the isolated polypeptide is a molecule in which uPA cleaves the CM. In some aspects, the isolated polypeptide is a molecule in which two, three, four, or all of MMP2, MMP9, MMP14, MT-SP1, and uPA cleave the CM. In some aspects, the isolated polypeptide is a molecule in which the % cleavability of the CM is at least 50%, at least 60%, at least 70%, at least 80%, at least 90%, or at least 95%, or 100%, e.g., at least 50%, at least 60%, at least 70%, at least 80%, at least 90%, or at least 95%, or 100% cleavable by any one of MMP2, MMP9, MMP14, MT-SP1, and uPA, or any two of MMP2, MMP9, MMP14, MT-SP1, and uPA, or any three of MMP2, MMP9, MMP14, MT-SP1, and uPA, or any four of MMP2, MMP9, MMP14, MT-SP1, and uPA, or each of MMP2, MMP9, MMP14, MT-SP1. In some aspects, the isolated polypeptide is a molecule in which the % cleavability of the CM is improved by 1.5×, 2×, 2.5×, 3×, 4×, 5×, 7×, 8×, or 10× or more over the % cleavability of SEQ ID NO: 78 (see, e.g., Example 2). According to some embodiments of the present disclosures, the isolated polypeptide is a molecule that has high in vivo stability such that it is not cleaved in plasma as demonstrated by less than 50%, less than 40%, less than 30%, or less than 25% in vivo activation following 7 days of administration in vivo (see, e.g., Example 3). According to embodiments of the present disclosures, the isolated polypeptide is a molecule comprising a CM that has a $k_{cat}/K_M$ ($M^{-1}$ $s^{-1}$) of greater than $1 \times 10^2$ $M^{-1}$ $s^{-1}$. According to some embodiments of the present disclosures, the isolated polypeptide is a molecule comprising a CM that has a $k_{cat}/K_M$ ($M^{-1}$ $s^{-1}$) of greater than $1 \times 10^3$ $M^{-1}$ $s^{-1}$. According to some embodiments of the present disclosures, the isolated polypeptide is a molecule comprising a CM that has a $k_{cat}/K_M$ ($M^{-1}$ $s^{-1}$) of greater than $1 \times 10^4$ $M^{-1}$ $s^{-1}$. According to some embodiments of the present disclosures, the isolated polypeptide is a molecule comprising a CM that has a $k_{cat}/K_M$ ($M^{-1}$ $s^{-1}$) of greater than $1 \times 10^5$ $M^{-1}$ $s^{-1}$.

In certain aspects, the present disclosure may include substitution of any alanine (A) in the disclosed CM sequences with a valine (V).

In some embodiments, the N-terminal to C-terminal arrangement of the substrate is CM1-CM2. In some embodiments, the N-terminal to C-terminal arrangement of the substrate is CM2-CM1. In some embodiments, the CM1 and CM2 are indirectly coupled via a linking peptide. In some embodiments, the CM1 and CM2 are directly coupled to each other. In some embodiments, at least a portion of the CM1 overlaps with at least a portion of the CM2. In some embodiments, the substrate comprises one or more CMs in addition to the CM1 and the CM2. In some embodiments, the substrate comprises CM1 cleavable by a first protease, CM2 cleavable by a second protease, and CM3 cleavable by a third protease. In some embodiments, the substrate comprises CM1 cleavable by a first protease, CM2 cleavable by a second protease, CM3 cleavable by a third protease, and CM4 cleavable by a fourth protease.

In some embodiments, the isolated polypeptide is an activatable molecule and further comprises an "active moiety" (AM) that specifically binds a target. In some embodiments, the AM is an antibody or antigen binding fragment thereof. In some embodiments, the antibody is a full-length antibody. single-chain variable fragment (scFv), diabody (a noncovalent dimer of scFv), single chain antibody (scab), a VHH, a domain antibody (dAb) or single domain antibody (nanobody, e.g., single domain heavy chain antibody, single domain light chain antibody). In some embodiments, the antibody is a monoclonal antibody, single chain antibody, Fab fragment, F(ab')₂ fragment, single-chain variable fragment (scFv), diabody (a noncovalent dimer of scFv), single chain antibody (scab), a VHH, a domain antibody (dAb) or single domain antibody (nanobody, e.g., single domain heavy chain antibody, single domain light chain antibody). According to some embodiments of the present disclosures, the isolated polypeptide is an activatable molecule that has high in vivo stability such that it is not cleaved in plasma as demonstrated by less than 50%, less than 40%, less than 30%, or less than 25% in vivo activation following 7 days of administration in vivo (e.g., as exemplified in Example 3). According to some embodiments of the present disclosures, the isolated polypeptide is an activatable molecule that has masking efficiency of 18×, 26×, 30×, 33×, 50×, 60×, 70×, 77×, 95×, 100×, 112×, 123×, 135×, 139×, 150×, 200×, 234×, 300×, or higher (e.g., as exemplified in Example 4). According to some embodiments of the present disclosures, the activatable molecule is activated by one, two, three, four, or all of MMP2, MMP9, MMP14, MT-SP1, and uPA. According to some embodiments of the present disclosures, the activatable molecule is activated to an extent of having a cleavability percentage of at least 40%, at least 50%, at least 60%, at least 70%, at least 80%, at least 90%, or at least 95%, or 100%, e.g., at least 50%, at least 60%, at least 70%, at least 80%, at least 90%, or at least 95%, or 100% cleavable by any one of MMP2, MMP9, MMP14 and MT-SP1, or any two of MMP2, MMP9, MMP14, MT-SP1, and uPA, or any three of MMP2, MMP9, MMP14, MT-SP1, and uPA, or any four of MMP2, MMP9, MMP14, MT-SP1, and uPA, or each of MMP2, MMP9, MMP14, MT-SP1. In some embodiments, the AM is a therapeutic macromolecule. In some embodiments, the AM is a cytokine. In some embodiments, the AM is a chimeric antigen receptor. In some aspects, the AM is a drug or agent, e.g., a therapeutic, an imaging, or diagnostic agent.

In some embodiments, the AM is coupled to the CM1. In some embodiments, the AM is directly coupled to the CM1. In some embodiments, the AM is coupled to the CM1 indirectly via a linking peptide. In some embodiments, the AM is coupled to the CM2. In some embodiments, the AM is directly coupled to the CM2. In some embodiments, the AM is indirectly coupled to the CM2 via a linking peptide. In some embodiments, the AM is coupled to the CM3. In some embodiments, the AM is directly coupled to the CM3. In some embodiments, the AM is indirectly coupled to the CM3 via a linking peptide. In some embodiments, the AM is indirectly coupled to the CM1 via one or more components of the activatable protein. In some embodiments, the AM is indirectly coupled to the CM2 via one or more components of the activatable protein. In some embodiments, the AM is indirectly coupled to the CM3 via one or more components of the activatable protein.

In some embodiments, the isolated polypeptide further comprises a masking moiety (MM). In some embodiments, the MM has a dissociation constant for binding to the AM that is greater than the dissociation constant of the AM for binding to the target. In some embodiments, the MM does not interfere or compete with the AM for binding to the target in in the activated molecule (i.e., following cleavage of the CM by a protease). In some embodiments, the MM is 2 to 40 amino acids in length. In some embodiments, the MM does not bind the AM, but still interferes with AM's binding to its binding partner through non-specific interactions. In some embodiments, the MM is a steric mask. In some embodiments, the MM is a protein. In some embodiments, the MM is coupled to the substrate such that the isolated polypeptide comprises a structural arrangement from N-terminus to C-terminus as follows: MM-CM1-CM2-AM, MM-CM2-CM1-AM, AM-CM1-CM2-MM, AM-CM2-CM1-MM, MM-CM2-CM1-CM3-AM, MM-CM1-CM2-CM3-AM, MM-CM1-CM3-CM2-AM, MM-CM3-CM1-CM2-AM, or MM-CM3-CM2-CM1-AM. In some embodiments, the MM is directly coupled to the CM1. In some embodiments, the MM is directly coupled to the CM2. In some embodiments, the MM is directly coupled to the CM3.

In some embodiments, the MM is indirectly coupled to the CM1. In some embodiments, the MM is indirectly coupled to the CM2. In some embodiments, the MM is indirectly coupled to the CM1 via a linking peptide. In some embodiments, the MM is indirectly coupled to the CM2 via a linking peptide. In some embodiments, the MM is indirectly coupled to the CM3 via a linking peptide. In some embodiments, the isolated polypeptide comprises a linking peptide (LP) and wherein the isolated polypeptide has a structural arrangement from N-terminus to C-terminus as follows: MM-LP-CM1-CM2-AM, MM-CM1-CM2-LP-AM, MM-LP-CM2-CM1-AM, MM-CM2-CM1-LP-AM, MM-LP-CM2-CM1-CM3-AM, MM-LP-CM1-CM2-CM3-AM, MM-LP-CM1-CM3-CM2-AM, MM-LP-CM3-CM1-CM2-AM, MM-LP-CM3-CM2-CM1-AM, MM-CM2-CM1-CM3-LP-AM, MM-CM1-CM2-CM3-LP-AM, MM-CM1-CM3-CM2-LP-AM, MM-CM3-CM1-CM2-LP-AM, or MM-CM3-CM2-CM1-LP-AM. In some embodiments, the isolated polypeptide comprises a first linking peptide (LP1) and a second linking peptide (LP2), and wherein the isolated polypeptide has a structural arrangement from N-terminus to C-terminus as follows: MM-LP1-CM1-CM2-LP2-AM, MM-LP1-CM2-CM1-LP2-AM, AM-LP1-CM1-CM2-LP2-MM, or AM-LP1-CM2-CM1-LP2-MM, MM-LP1-CM2-CM1-CM3-LP2-AM, MM-LP1-CM1-CM2-CM3-LP2-AM, MM-LP1-CM1-CM3-CM2-LP2-AM, MM-LP1-CM3-CM1-CM2-LP2-AM, MM-LP1-CM3-CM2-CM1-LP2-AM, MM-LP2-CM2-CM1-CM3-LP1-AM, MM-LP2-CM1-CM2-CM3-LP1-AM, MM-LP2-CM1-CM3-CM2-LP1-AM, MM-LP2-CM3-CM1-CM2-LP1-AM, or MM-LP2-CM3-CM2-CM1-LP1-AM. In some embodiments, the LP1 and LP2 are not identical to each other. In some embodiments, the LP1 and LP2 are identical to each other. In some embodiments, each of the LP1 and LP2 is a peptide of 1 to 20 amino acids in length.

In some embodiments, the isolated polypeptide comprises an additional linking peptide (LP3) and wherein the isolated polypeptide has a structural arrangement from N-terminus to C-terminus as follows: MM-LP-CM1-LP3-CM2-AM, MM-CM1-LP3-CM2-LP-AM, MM-LP-CM2-LP3-CM1-AM, MM-CM2-LP3-CM1-LP-AM, MM-LP-CM2-LP3-CM1-CM3-AM, MM-LP-CM1-LP3-CM2-CM3-AM, MM-LP-CM1-LP3-CM3-CM2-AM, MM-LP-CM3-LP3-CM1-CM2-AM, MM-LP-CM3-LP3-CM2-CM1-AM, MM-CM2-LP3-CM1-CM3-LP-AM, MM-CM1-LP3-CM2-CM3-LP-AM, MM-CM1-LP3-CM3-CM2-LP-AM, MM-CM3-LP3-CM1-CM2-LP-AM, MM-CM3-LP3-CM2-CM1-LP-AM, MM-LP-CM2-CM1-LP3-CM3-AM, MM-LP-CM1-CM2-LP3-CM3-AM, MM-LP-CM1-CM3-LP3-CM2-AM, MM-LP-CM3-CM2-LP3-CM1-AM, MM-CM2-CM1-LP3-CM3-LP-AM, MM-CM1-CM2-LP3-CM3-LP-AM, MM-CM1-CM3-LP3-CM2-LP-AM, MM-CM3-CM1-LP3-

CM2-LP-AM, MM-CM3-CM2-LP3-CM1-LP-AM, MM-LP1-CM1-LP3-CM2-LP2-AM, MM-LP1-CM2-LP3-CM1-LP2-AM, AM-LP1-CM1-LP3-CM2-LP2-MM, or AM-LP1-CM2-LP3-CM1-LP2-MM, MM-LP1-CM2-LP3-CM1-CM3-LP2-AM, MM-LP1-CM1-LP3-CM2-CM3-LP2-AM, MM-LP1-CM1-LP3-CM3-CM2-LP2-AM, MM-LP1-CM3-LP3-CM1-CM2-LP2-AM, MM-LP1-CM3-LP3-CM2-CM1-LP2-AM, MM-LP2-CM2-LP3-CM1-CM3-LP1-AM, MM-LP2-CM1-LP3-CM2-CM3-LP1-AM, MM-LP2-CM1-LP3-CM3-CM2-LP1-AM, MM-LP2-CM3-LP3-CM1-CM2-LP1-AM, or MM-LP2-CM3-LP3-CM2-CM1-LP1-AM. In some embodiments, the LP1, LP2 and LP3 are not identical to each other. In some embodiments, the LP1, LP2 and LP3 are identical to each other. In some embodiments, each of the LP1, LP2 and LP3 is a peptide of 1 to 20 amino acids in length.

In some embodiments, the isolated polypeptide comprises an additional linking peptide (LP4) and wherein the isolated polypeptide has a structural arrangement from N-terminus to C-terminus as follows: MM-LP-CM2-LP3-CM1-LP4-CM3-AM, MM-LP-CM1-LP3-CM2-LP4-CM3-AM, MM-LP-CM1-LP3-CM3-LP4-CM2-AM, MM-LP-CM3-LP3-CM1-LP4-CM2-AM, MM-LP-CM3-LP3-CM2-LP4-CM1-AM, MM-CM2-LP3-CM1-LP4-CM3-LP-AM, MM-CM1-LP3-CM2-LP4-CM3-LP-AM, MM-CM1-LP3-CM3-LP4-CM2-LP-AM, MM-CM3-LP3-CM1-LP4-CM2-LP-AM, MM-CM3-LP3-CM2-LP4-CM1-LP-AM, MM-LP-CM2-LP4-CM1-LP3-CM3-AM, MM-LP-CM1-LP4-CM2-LP3-CM3-AM, MM-LP-CM1-LP4-CM3-LP3-CM2-AM, MM-LP-CM3-LP4-CM1-LP3-CM2-AM, MM-LP-CM3-LP4-CM2-LP3-CM1-AM, MM-CM2-LP4-CM1-LP3-CM3-LP-AM, MM-CM1-LP4-CM2-LP3-CM3-LP-AM, MM-CM1-LP4-CM3-LP3-CM2-LP-AM, MM-CM3-LP4-CM1-LP3-CM2-LP-AM, MM-CM3-LP4-CM2-LP3-CM1-LP-AM, MM-LP1-CM2-LP3-CM1-LP4-CM3-LP2-AM, MM-LP1-CM1-LP3-CM2-LP4-CM3-LP2-AM, MM-LP1-CM1-LP3-CM3-LP4-CM2-LP2-AM, MM-LP1-CM3-LP3-CM1-LP4-CM2-LP2-AM, MM-LP1-CM3-LP3-CM2-LP4-CM1-LP2-AM, MM-LP2-CM2-LP3-CM1-LP4-CM3-LP1-AM, MM-LP2-CM1-LP3-CM2-LP4-CM3-LP1-AM, MM-LP2-CM1-LP3-CM3-LP4-CM2-LP1-AM, MM-LP2-CM3-LP3-CM1-LP4-CM2-LP1-AM, or MM-LP2-CM3-LP3-CM2-LP4-CM1-LP1-AM. In some embodiments, the LP1, LP2, LP3 and LP4 are not identical to each other. In some embodiments, the LP1, LP2, LP3 and LP4 are identical to each other. In some embodiments, each of the LP1, LP2, LP3 and LP4 is a peptide of 1 to 20 amino acids in length.

In some embodiments, the first protease or proteases are represented by a matrix metalloproteinase (MMP). In some embodiments, the MMP is MMP2, MMP9, or MMP14. In some embodiments, the $k_{cat}/K_M$ of the substrate by MMP14 cleavage is at least $1 \times 10^3$ $M^{-1}$ $s^{-1}$. In some embodiments, the $k_{cat}/K_M$ of the substrate by MMP9 cleavage is at least $1 \times 10^3$ $M^{-1}$ $s^{-1}$. In some embodiments, the $k_{cat}/K_M$ of the substrate by MMP9 cleavage is at least $1 \times 10^4$ $M^{-1}$ $s^{-1}$. In some embodiments, the $k_{cat}/K_M$ of the substrate by MMP2 cleavage is at least $1 \times 10^3$ $M^{-1}$ $s^{-1}$. In some embodiments, the $k_{cat}/K_M$ of the substrate by MMP2 cleavage is at least $1 \times 10^4$ $M^{-1}$ $s^{-1}$. In some embodiments, the second protease is a serine protease. In some embodiments, the serine protease is membrane type serine protease 1 (MT-SP1). In some embodiments, the $k_{cat}/K_M$ of the substrate by MT-SP1 cleavage is at least $1 \times 10^3$ $M^{-1}$ $s^{-1}$. In some embodiments, the $k_{cat}/K_M$ of the substrate by MT-SP1 cleavage is at least $1 \times 10^4$ $M^{-1}$ $s^{-1}$. In some embodiments, the serine protease is urokinase-type plasminogen activator (uPA). In some embodiments, the $k_{cat}/K_M$ of the substrate by uPA cleavage is at least $1 \times 10^3$ M$^{-1}$ s$^{-1}$.

In some embodiments, the isolated polypeptide is resistant to cleavage in situ in human bone marrow.

In some embodiments, the isolated polypeptide is resistant to cleavage in vivo in human bone marrow.

In another aspect, the present disclosure provides an isolated polypeptide comprising a cleavable moiety (CM) comprising an amino acid sequence with one-amino acid or two-amino acid mutation(s) of any one of SEQ ID NOs: 9-24, 37-73, 83-353, 382-385, and 560-695. In another aspect, the present disclosure provides an isolated polypeptide comprising a cleavable moiety (CM) comprising an amino acid sequence with one-amino acid or two-amino acid mutation(s) of any one of SEQ ID NOs: 9-24, 37-73, 83-353, 382-385, and 560-683, wherein the CM is a substrate for a protease. For example, the mutations may include substitution between any one of lysine, arginine, and histidine residues. In certain aspects, the present disclosure may include substitution of any arginine in the disclosed sequences with a lysine. In other aspects, the present disclosure also includes substitution of any arginine in the disclosed sequences with an amino acid that is not lysine. In certain aspects, the present disclosure may include substitution of any alanine in the disclosed sequences with a valine. For example, the mutations may include substitution between any one of alanine, valine, leucine, isoleucine, proline, phenylalanine, methionine, and tryptophan residues. For example, the mutations may include substitution between any one of glycine, asparagine, glutamine, cysteine, serine, threonine, and tyrosine residues. For example, the mutations may include substitution between any one of arginine, asparagine, aspartate, glutamine, glutamate, histidine, lysine, serine, and threonine residues. For example, the mutations may include substitution between any one of alanine, cysteine, isoleucine, leucine, methionine, phenylalanine, proline, tryptophan, tyrosine and valine residues. For example, the mutations may include substitution between any one of serine and threonine residues. For example, the mutations may include substitution between any one of asparagine and glutamine residues. For example, the mutations may include substitution between any one of alanine, valine, leucine and isoleucine residues. For example, the mutations may include substitution between any one of phenylalanine, tryptophan, and tyrosine residues.

In another aspect, the present disclosure provides an isolated polypeptide comprising a substrate, wherein the substrate comprises: APRG (SEQ ID NO: 382), or a first cleavable moiety (CM1) cleavable by a first protease and a second cleavable moiety (CM2) cleavable by a second protease, and wherein the substrate comprises an APR core and the substrate comprises the amino acid sequence of APRSL (SEQ ID NO: 669), APRSY (SEQ ID NO: 39), APRSM (SEQ ID NO: 383), APRGL (SEQ ID NO: 672), APRGY (SEQ ID NO: 384), or APRGM. (SEQ ID NO: 385).

In some embodiments, the substrate comprises the amino acid sequence of APRSL (SEQ ID NO: 669), APRSY (SEQ ID NO: 39), or APRSM (SEQ ID NO: 383). In some embodiments, the substrate comprises the amino acid sequence of APRGL (SEQ ID NO: 672), APRGY (SEQ ID NO: 384), or APRGM (SEQ ID NO: 385). In some embodiments, the substrate comprises the amino acid sequence of APRSLL (SEQ ID NO: 37), APRGLL (SEQ ID NO: 38), APRSY (SEQ ID NO: 39), or VAPRSMR (SEQ ID NO: 40).

In some embodiments, the isolated polypeptide is an activatable molecule and further comprises an active moiety (AM) that specifically binds to a target. In some embodiments, the AM is an antibody or antigen binding fragment thereof. In some embodiments, the antigen binding fragment thereof is selected from the group consisting of a Fab fragment, a F(ab') 2 fragment, a scFv, a scAb, a dAb, a single domain heavy chain antibody, and a single domain light chain antibody. In some embodiments, the AM is a therapeutic macromolecule. In some embodiments, the AM is a cytokine or a chimeric antigen receptor. In some aspects, the AM is a drug or agent, e.g., a therapeutic, imaging or diagnostic agent.

In some embodiments, the AM is coupled to the substrate. In some embodiments, the AM is directly coupled to the substrate. In some embodiments, the AM is indirectly coupled to the substrate via a linking peptide. In some embodiments, the AM is coupled to an N-terminus of the substrate. In some embodiments, the AM is coupled to a C-terminus of the substrate. In some embodiments, the AM is indirectly coupled to the CM1 via one or more components of the activatable protein. In some embodiments, the AM is indirectly coupled to the CM2 via one or more components of the activatable protein.

In some embodiments, the isolated polypeptide further comprises a masking moiety (MM). In some embodiments, the MM has a dissociation constant for binding to the AM that is greater than the dissociation constant of the AM for binding to the target. In some embodiments, the MM does not interfere or compete with the AM for binding to the target in in the activated molecule (i.e., following cleavage of the CM by a protease). In some embodiments, the MM is 2 to 40 amino acids in length. In some embodiments, the MM is 2 to 40 amino acids in length. In some embodiments, the MM does not bind the AM, but still interferes with AM's binding to its binding partner through non-specific interactions. In some embodiments, the MM is a steric mask. In some embodiments, the MM is a protein. In some embodiments, the MM is coupled to the substrate such that the isolated polypeptide comprises a structural arrangement from N-terminus to C-terminus as follows: MM-substrate-AM or AM-substrate-MM. In some embodiments, the MM is directly coupled to the substrate.

In some embodiments, the MM is indirectly coupled to the substrate. In some embodiments, the MM is indirectly coupled to the substrate via a linking peptide. In some embodiments, the isolated polypeptide comprises a first linking peptide (LP1) and a second linking peptide (LP2), and wherein the isolated polypeptide has a structural arrangement from N-terminus to C-terminus as follows: MM-LP1-substrate-LP2-AM, or AM-LP1-substrate-LP2-MM. In some embodiments, the LP1 and LP2 are not identical to each other. In some embodiments, the LP1 and LP2 are identical to each other. In some embodiments, each of the LP1 and LP2 is a peptide of 1 to 20 amino acids in length.

In some embodiments, the first protease is a serine protease. In some embodiments, the serine protease is membrane type serine protease 1 (MT-SP1). In some embodiments, the $k_{cat}/K_M$ of the substrate by MT-SP1 cleavage is at least $1 \times 10^3$ M$^{-1}$ s$^{-1}$. In some embodiments, the $k_{cat}/K_M$ of the substrate by MT-SP1 cleavage is at least $1 \times 10^4$ M$^{-1}$ s$^{-1}$. In some embodiments, the second protease is a matrix metalloproteinase (MMP). In some embodiments, the MMP is MMP2, MMP9, or MMP14. In some embodiments, the $k_{cat}/K_M$ of the substrate by MMP14 cleavage is at least $1 \times 10^3$ M$^{-1}$ s$^{-1}$. In some embodiments, the $k_{cat}/K_M$ of the substrate by MMP9 cleavage is at least $1 \times 10^3$ $M^{-1}$ $s^{-1}$. In some embodiments, the $k_{cat}/K_M$ of the substrate by MMP9 cleavage is at least $1 \times 10^4$ $M^{-1}$ $s^{-1}$. In some embodiments, the $k_{cat}/K_M$ of the substrate by MMP2 cleavage is at least $1 \times 10^3$ $M^{-1}$ $s^{-1}$. In some embodiments, the $k_{cat}/K_M$ of the substrate by MMP2 cleavage is at least $1 \times 10^4$ $M^{-1}$ $s^{-1}$. In some embodiments, the serine protease is urokinase-type plasminogen activator (uPA). In some embodiments, the $k_{cat}/K_M$ of the substrate by uPA cleavage is at least $1 \times 10^3$ $M^{-1}$ $s^{-1}$. In some embodiments, the $k_{cat}/K_M$ of the substrate by uPA cleavage is at least $1 \times 10^4$ $M^{-1}$ $s^{-1}$.

In some embodiments, the isolated polypeptide is resistant to cleavage in situ in human bone marrow.

In some embodiments, the CM is resistant to cleavage in vivo in human bone marrow tissue, e.g., bone marrow aspirate.

In another aspect, the present disclosure provides an isolated polypeptide comprising a substrate cleavable by an MMP and a serine protease (e.g., MT-SP1), wherein the substrate comprises an amino acid sequence selected from SEQ ID NOs: 9-24, 37-73, 83-353, 383-385, and 560-695. In another aspect, the present disclosure provides an isolated polypeptide comprising a substrate cleavable by an MMP and a serine protease (e.g., MT-SP1), wherein the substrate comprises an amino acid sequence selected from SEQ ID NOs: 9-24, 37-73, 83-353, 383-385, and 560-683.

In another aspect, the present disclosure provides an isolated polypeptide comprising a substrate, wherein the substrate comprises a first cleavable moiety (CM1) cleavable by a first protease and a second cleavable moiety (CM2) cleavable by a second protease, and wherein the substrate comprises an amino acid sequence with one-amino acid or two-amino acid mutation(s) of any one of SEQ ID NOs: 9-24, 37-73, 83-353, 383-385, and 560-695. In another aspect, the present disclosure provides an isolated polypeptide comprising a substrate, wherein the substrate comprises a first cleavable moiety (CM1) cleavable by a first protease and a second cleavable moiety (CM2) cleavable by a second protease, and wherein the substrate comprises an amino acid sequence with one-amino acid or two-amino acid mutation(s) of any one of SEQ ID NOs: 9-24, 37-73, 83-353, 383-385, and 560-683.

In another aspect, the present disclosure provides an isolated polypeptide comprising a cleavable moiety (CM) comprising an amino acid sequence with one-amino acid or two-amino acid mutation(s) of any one of SEQ ID NO: 382, wherein the CM is a substrate for a protease.

In general, in each embodiment herein, unless otherwise stated, a polypeptide may comprise one or more optional linkers between each of the elements listed, and such linkers may be 1 to 30, 6 to 29, 7 to 28, 8 to 27, 9 to 26, 10 to 25, 1, 2, 3, 4, 5, 6, 7, 8, 9, 10, 11, 12, 13, 14, 15, 16, 17, 18, 19, 20, 21, 22, 23, 24, 25, 26, or 27 amino acids in length.

In another aspect, the present disclosure provides a polypeptide complex comprising one or more of the isolated polypeptides herein bound to a second isolated polypeptide. In some aspects, the complex comprises one or more of the isolated polypeptides of the present disclosure bound to a second isolated polypeptide, e.g., via protein-protein affinity interactions, hydrophobic interactions, disulfide linkage(s), cross-link(s), covalent bond(s), chemical linkage(s), or any other type of binding between two polypeptides.

In another aspect, the present disclosure provides a conjugated polypeptide comprising the isolated polypeptide or the AM herein conjugated to an agent. In some embodiments, the agent is conjugated to the isolated polypeptide or the AM via a linker. In some embodiments, the linker is a cleavable linker. In some embodiments, the linker is a non-cleavable linker. In some embodiments, the conjugating linker comprises an amino acid sequence selected from SEQ ID NOs: 9-24, 37-73, 83-353, 382-385, and 560-695. In some embodiments, the conjugating linker comprises an amino acid sequence selected from SEQ ID NOs: 9-24, 37-73, 83-353, 382-385, and 560-683. In some embodiments, the agent is a toxin, a microtubule inhibitor, a nucleic acid damaging agent, a dolastatin, an auristatin, a maytansinoid, a duocarmycin, a calicheamicin, or a combination thereof.

In another aspect, the present disclosure provides a composition comprising the isolated polypeptide, the polypeptide complex, or the conjugated activatable molecule herein, and a carrier. In some embodiments, the carrier is a pharmaceutically acceptable carrier. In some embodiments, the composition comprises an additional agent. In some embodiments, the additional agent is a therapeutic, imaging, or diagnostic agent.

In each of the foregoing embodiments, and unless otherwise stated, the polypeptide may comprise, e.g., one or more optional linkers between each of the elements listed. In some embodiments, a linker is a peptide having a length of 5 to 30, 6 to 29, 7 to 28, 8 to 27, 9 to 26, 10 to 25, 11, 12, 13, 14, 15, 16, 17, 18, 19, 20, 21, 22, 23, or 24 amino acids. In the disclosed structural arrangements in the foregoing paragraphs and throughout this disclosure, one or more linkers may optionally be present between the elements. Further, this disclosure also contemplates and includes activatable proteins in which any one or more of the disclosed elements optionally directly abut each other such that there are no linkers or other amino acid sequences between the elements.

In another aspect, the present disclosure provides an isolated nucleic acid molecule encoding the isolated polypeptide herein.

In another aspect, the present disclosure provides a vector comprising the isolated nucleic acid molecule herein.

In another aspect, the present disclosure provides a cell comprising the isolated nucleic acid molecule or the vector herein.

In another aspect, the present disclosure provides a method of manufacturing an activatable molecule that contains a substrate, the method comprising expressing and recovering a polypeptide comprising the isolated polypeptide herein.

In another aspect, the present disclosure provides a method of treating, alleviating a symptom of, or delaying the progression of a disease or disorder in a subject, comprising administering a therapeutically effective amount of the isolated polypeptide, the polypeptide complex, the conjugated activatable molecule, or the composition herein to the subject. In some embodiments, the disease is a cancer, an infection, a cardiovascular disorder, a neurodegenerative disorder, an inflammatory disorder, or an autoimmune disorder.

In another aspect, the present disclosure provides a method of detecting or diagnosing a disease or health condition of a subject, comprising: contacting the isolated polypeptide, the polypeptide complex, the conjugated activatable molecule, or the composition herein with a sample from the subject; and measuring a level of cleavage of the isolated polypeptide, thereby detecting or diagnosing the disease or health condition of the subject. In some embodiments, the disease is a cancer, an infection, a cardiovascular disorder, a neurodegenerative disorder, an inflammatory disorder, or an autoimmune disorder.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which.

DETAILED DESCRIPTION OF THE INVENTION

Figure 1A:
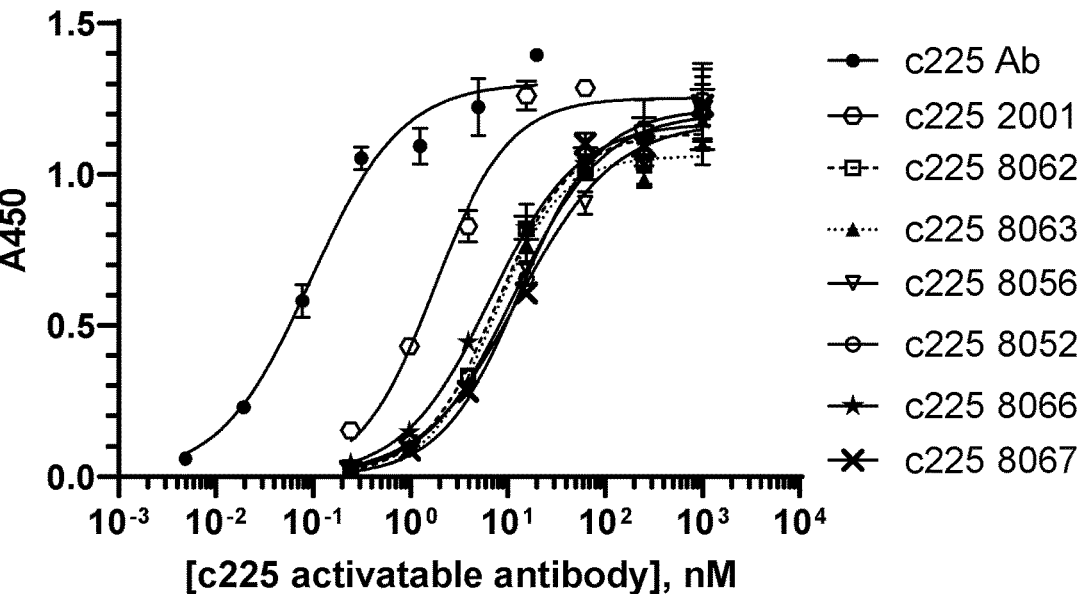
FIGS. 1A and 1B show the in vitro masking efficiency of exemplary anti-EGFR activatable antibodies of the present disclosure. These exemplary results showed that the substrates affected the masking efficiency of the prodomain of the activatable antibody.

Proteases play a critical role in the homeostasis of healthy tissues but are known to be dysregulated within diseases, including cancer and autoimmune disorders (Vasiljeva et al. "The multifaceted roles of tumor-associated proteases and harnessing their activity for prodrug activation," Biol. Chem. 2019 Apr. 22). This dysregulation of protease activity provides new opportunities for the development of protease-activatable therapeutic molecules, which are preferentially activated in the local tissue microenvironment. These therapeutics have demonstrated a greater therapeutic window and safety profile with less on-target toxicities occurring in healthy tissues. Hence, there is a need for identification of substrates that act as cleavage recognition sites for proteases that are found to be dysregulated in disease tissues. These substrates or cleavable moieties (CMs) may have multiple cleavage sites for leveraging the activities of multiple disease-associated proteases.

Understanding the substrate cleavage profile and using these substrates as tools for activation in a specific disease or cancer type will enable the development of new therapeutic protease-activatable molecules. Fine tuning the therapeutic-activatable molecules by using protease substrates with unique cleavage profiles will allow for treatment options for a broader spectrum of patients while offering an improved therapeutic index. For example, "omics" studies have demonstrated the distribution of numerous matrix metalloproteases (MMPs) across numerous cancer types and differences in the expression of the MMPs compared to normal tissues (Gobin et al. "A pan-cancer perspective of matrix metalloproteases (MMP) gene expression profile and their diagnostic/prognostic potential," BMC Cancer. 2019 Jun. 14; 19 (1): 581), highlighting the need for appropriate cleavable moiety selection. Indeed, the first protease-activatable antibodies were designed using MMP substrates (Bleuez et al., "Exploiting protease activation for therapy," Drug Discovery Today, 2022 June; 27 (6): 1743-1754). In addition, membrane type serine protease 1 (MT-SP1) shows great potential for protease-activatable antibody development (Howng, B. et al. "Novel Ex Vivo Zymography Approach for Assessment of Protease Activity in Tissues with Activatable Antibodies," Pharmaceutics 2021, 13 (9), 1390).

The present disclosure provides polypeptides comprising a substrate that comprise one or a plurality of cleavage moieties (CMs), each of which is cleavable by a protease. In some examples, the substrate may comprise a first CM (CM1) cleavable by a MMP and a second CM (CM2) cleavable by a serine protease (e.g., MT-SP1). In some aspects, the substrates herein are cleaved in a diseased tissue (e.g., tumor tissue) but less in a healthy tissue. These substrates are useful in a variety of therapeutic, diagnostic and prophylactic applications. In some embodiments, the substrate-containing polypeptides are activatable molecules and further comprise an active moiety (AM) that specifically binds a target. For example, the AM may be a therapeutic protein, a therapeutic agent, an imaging agent, a diagnostic agent, an antibody or antigen-binding fragment, a cytokine, chimeric antigen receptor or other molecules used in therapeutic and diagnostic applications.

Also provided herein are related compositions, kits, nucleic acids, vectors, and recombinant cells, as well as related methods, including methods of using and methods of producing any of the substrate-containing polypeptides described herein.

Definitions

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The terms "a" and "an" refer to one or more (i.e., at least one) of the grammatical object of the article. By way of example, "a cell" encompasses one or more cells.

As used herein, the terms "about" and "approximately," when used to modify an amount specified in a numeric value or range, indicate that the numeric value as well as reasonable deviations from the value known to the skilled person in the art. For example ±20%, ±10%, or ±5%, are within the intended meaning of the recited value where appropriate.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 to 2.0" should be interpreted to include not only the explicitly recited values of about 0.01 to about 2.0, but also include individual values and sub-ranges within the indicated range. Thus, included in this numerical range are individual values such as 0.5, 0.7, and 1.5, and sub-ranges such as from 0.5 to 1.7, 0.7 to 1.5, and from 1.0 to 1.5, etc. Furthermore, such an interpretation should apply regardless of the breadth of the range or the characteristics being described. Additionally, it is noted that all percentages are in weight, unless specified otherwise.

In understanding the scope of the present disclosure, the terms "including" or "comprising" and their derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of," as used herein, is intended to specify the presence of the stated features, elements, components, groups, integers, and/or steps as well as those that do not materially affect the basic and novel characteristic(s) of features, elements, components, groups, integers, and/or steps. It is understood that reference to any one of these transition terms (i.e. "comprising," "consisting," or "consisting essentially") provides direct support for replacement to any of the other transition term not specifically used. For example, amending a term from "comprising" to "consisting essentially of" or "consisting of" would find direct support due to this definition for any elements disclosed throughout this disclosure. Based on this definition, any element disclosed herein or incorporated by reference may be included in or excluded from the claimed invention.

As used herein, a plurality of compounds, elements, or steps may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

The term "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a more concrete fashion.

Furthermore, certain molecules, constructs, compositions, elements, moieties, excipients, disorders, conditions, properties, steps, or the like may be discussed in the context of one specific embodiment or aspect or in a separate paragraph or section of this disclosure. It is understood that this is merely for convenience and brevity, and any such disclosure is equally applicable to and intended to be combined with any other embodiments or aspects found anywhere in the present disclosure and claims, which all form the application and claimed invention at the filing date. For example, a list of constructs, molecules, method steps, kits, or compositions described with respect to a construct, molecule, isolated polypeptide, activatable molecule, composition, or method is intended to and does find direct support for embodiments related to constructs, molecules, isolated polypeptides, activatable molecules, compositions, formulations, and methods described in any other part of this disclosure, even if those method steps, active agents, kits, or compositions are not re-listed in the context or section of that embodiment or aspect.

The term "isolated polynucleotide" as used herein shall mean a polynucleotide of genomic, cDNA, RNA, mRNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, and/or (3) does not occur in nature as part of a larger sequence. In some embodiments, polynucleotides include the nucleic acid molecules encoding heavy chain immunoglobulin molecules, and nucleic acid molecules encoding light chain immunoglobulin molecules.

The term "isolated polypeptide" as used herein refers a polypeptide that is present in a form other than that found in nature. An "isolated polypeptide" as used herein may be encoded by cDNA, recombinant RNA, recombinant DNA, messenger RNA, or a polynucleotide of synthetic origin or some combination thereof. By virtue of its origin, or source of derivation, the "isolated polypeptide" (1) is not in a naturally occurring organism (e.g., is not an endogenous polypeptide of a naturally occurring organism) and (2) is present in a form not found in nature. In some aspects, the "isolated polypeptide" is expressed by a cell from a different species. In some aspects, the "isolated polypeptide" is a therapeutic protein or a diagnostic protein and not a naturally occurring protein. For example, as used herein, the "isolated polypeptide" is not a plant protein or a protein naturally occurring in bacteria or other natural organisms. The term isolated polypeptide includes and provides support for activatable molecules including activatable macromolecules, activatable polypeptides, activatable antibodies, activatable cytokines, and the like. The term isolated polypeptide includes and provides support for activatable molecules in which cleavage of the CM activates the molecule.

The term "polypeptide" is used herein as a generic term to refer to a native protein, fragments, or analogs of a polypeptide sequence. Hence, proteins, protein fragments, and analogs are species of the polypeptide genus. In some embodiments, polypeptides in accordance with the disclosure comprise the heavy chain immunoglobulin, and the light chain immunoglobulin molecules, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

As discussed herein, minor variations in the amino acid sequences of polypeptides are contemplated as being encompassed by the present disclosure, providing that the variations in the amino acid sequence maintain at least 75%, in some embodiments, at least 80%, at least 90%, at least 95%, and in some embodiments, at least 99% identity to the amino acid sequence that is not varied. In particular, conservative amino acid substitutions are contemplated. Conservative substitutions include those that take place within a family of amino acids that are related in their side chains. Genetically encoded amino acids are generally divided into families: (1) acidic amino acids are aspartate, glutamate; (2) basic amino acids are lysine, arginine, histidine; (3) nonpolar amino acids are alanine, valine, leucine, isoleucine, proline, phenylalanine, methionine, tryptophan; and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Suitable amino- and carboxyl-termini of fragments or analogs occur near boundaries of functional domains. Structural and functional domains can be identified by comparison of the nucleotide and/or amino acid sequence data to public or proprietary sequence databases. In some embodiments, computerized comparison methods are used to identify sequence motifs or predicted protein conformation domains that occur in other proteins of known structure and/or function. Methods to identify protein sequences that fold into a known three-dimensional structure are known, e.g., as described in Bowie et al. Science 253:164 (1991). Thus, the foregoing examples demonstrate that those of skill in the art can recognize sequence motifs and structural conformations that may be used to define structural and functional domains in accordance with the disclosure.

Suitable amino acid substitutions include those that: (1) alter susceptibility to proteolysis, (2) reduce susceptibility to oxidation, (3) alter binding affinity for forming protein complexes, (4) alter binding affinities, and (5) confer or modify other physicochemical or functional properties of such analogs. Analogs can include various muteins of a sequence other than the naturally-occurring peptide sequence. For example, single or multiple amino acid substitutions (for example, conservative amino acid substitutions) may be made in the naturally-occurring sequence (for example, in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "sample" is intended to include tissues, cells and biological fluids isolated from a subject, as well as tissues, cells and fluids present within a subject. Included within the usage of the term "sample," therefore, is blood and a fraction or component of blood including blood serum, blood plasma, or lymph.

The term "therapeutic macromolecule" refers to any protein or nucleic acid that may be administered to a subject and have a therapeutic effect. In some embodiments, the therapeutic macromolecule may be a therapeutic polynucleotide or therapeutic polypeptide, i.e., a polynucleotide or polynucleotide that may be used in therapy.

As generally provided herein, an activatable molecule may comprise MM-substrate construct(s), also referred to herein as a prodomain. Accordingly, as used herein, the term "prodomain" refers to a polypeptide domain comprising a masking moiety (MM) and a cleavable substrate. The substrate may comprise one, two, three, or more CMs. In some embodiments, the MM and the substrate are separated by a linker, referred to herein as LP1. In some embodiments, the prodomain comprises a linker (referred to herein as LP2) that links the substrate of the prodomain to the active moiety (AM) in an activatable molecule. In some embodiments, the prodomain comprises a linker between the MM and the substrate and a linker between the substrate and the AM. In some embodiments, the MM and the substrate are not separated by a linker. In certain embodiments, a prodomain comprises one of the following formulas (where the formulas below represent amino acid sequences in either N- to C-terminal direction or C- to N-terminal direction): MM-LP1-substrate, MM-substrate-LP2, MM-LP1-substrate-LP2, or MM-substrate. As used herein and unless otherwise stated, each dash (-) between the components of the activatable molecule represents either a direct linkage or indirect linkage via one or more linking peptides.

Proteases are involved in the control of numerous physiological processes, and their dysregulation has been identified in a number of pathologies, such as, for example, oncological, cardiovascular, autoimmune, and neurodegenerative diseases. See, e.g., O. Vasiljeva, et al., "Monitoring protease activity in biological tissues using antibody prodrugs as sensing probes," *Scientific Reports,* 10, 5894 (2020); O. Erster, et al., "Site-specific targeting of antibody activity in vivo mediated by disease-associated proteases," *J. Control Release,* 161 (3): 804-812 (2012); L. Desnoyers, et al., "Tumor-specific activation of an EGFR-targeting probody enhances therapeutic index," *Science Translational Medicine,* 5 (207): 207ra144 (2013); and B. Turk "Targeting proteases: successes, failures and future prospects" Nature Reviews Drug Discovery, 5 (2006). Protease-activated antibodies have been described in the literature that are activated by native proteases which are more prevalently active in, for example, tumor tissue, and the like, when compared to normal tissue. Id. These prodrugs have incorporated within their structure, a protease substrate that releases active drug following exposure to the appropriate protease and its subsequent cleavage. What appears evident, however, is that the profile of dysregulated protease activity in diseased tissue may differ from one type of disease tissue/disorder to another. Thus, it is desirable to have a collection of substrates that target a variety of different protease activity profiles.

In some aspects, the present disclosure provides a substrate that comprises a cleavable moiety comprising a core amino acid sequence of APR.

In some aspects, the present disclosure provides a substrate that comprises a first cleavable moiety (CM1) cleavable by a first protease and a second cleavable moiety (CM2) cleavable by a second protease. In some embodiments, the first protease is an MMP (e.g., MMP2, MMP9, or MMP14). In some embodiments, the second protease is a serine protease (e.g., a membrane type serine protease 1 (MT-SP1) or uPA). In some embodiments, the first protease is a serine protease (e.g., MT-SP1 or uPA) and the second protease is an MMP (e.g., MMP2, MMP9, or MMP14). In some embodiments, the CM1 is cleavable by a first set of proteases and the CM2 is cleavable by a second set of proteases. In some examples, the first and the second sets of proteases may overlap, i.e., one or more proteases in the first set are also in the second set. In some alternative examples, the first and second sets of proteases do not overlap, i.e., the first set does not include any protease in the second set.

In certain aspects, the substrates are selectively cleavable by certain proteases (e.g., MMP and/or MT-SP1), but have reduced or no cleavability by another protease. For example, the substrates may be resistant or substantially resistant to cleavage in bone marrow tissue, e.g., bone marrow aspirate. In some aspects, resistance of substrates to protease cleavage in healthy tissue may reduce systemic toxicities by limiting binding of the activatable molecule to targets that also may be present in healthy tissues. Therefore, substrates with bone marrow tissue resistance have the potential to demonstrate a greater therapeutic window and safety profile with less on-target toxicities occurring in healthy tissues.

In a specific aspect, the present disclosure provides poly-peptides (e.g., isolated polypeptides) comprising a substrate comprising one or a plurality of cleavable moieties (CMs). A CM is a polypeptide that comprises a substrate for a sequence-specific protease. In some aspects, the present disclosure provides polypeptides and polypeptide complexes comprising a substrate and an active moiety.

In some embodiments, the CM1 in the substrate comprises the amino acid sequence of SEQ ID NO: 1. In some embodiments, the CM1 in the substrate comprises the amino acid sequence of SEQ ID NO: 2. In some embodiments, the CM1 in the substrate comprises the amino acid sequence of SEQ ID NO: 3. In some embodiments, the CM1 in the substrate comprises the amino acid sequence of SEQ ID NO: 4. In some embodiments, the CM1 in the substrate comprises the amino acid sequence of SEQ ID NO: 5. In some embodiments, the CM1 in the substrate comprises the amino acid sequence of SEQ ID NO: 6. In some embodiments, the CM1 in the substrate comprises the amino acid sequence of SEQ ID NO: 7. In some embodiments, the CM1 in the substrate comprises the amino acid sequence of SEQ ID NO: 8. In some embodiments, the CM1 in the substrates comprises the amino acid sequence of SEQ ID NO: 664.

In some embodiments, the CM1 in the substrate consists of the amino acid sequence of SEQ ID NO: 1. In some embodiments, the CM1 in the substrate consists of the amino acid sequence of SEQ ID NO: 2. In some embodiments, the CM1 in the substrate consists of the amino acid sequence of SEQ ID NO: 3. In some embodiments, the CM1 in the substrate consists of the amino acid sequence of SEQ ID NO: 4. In some embodiments, the CM1 in the substrate consists of the amino acid sequence of SEQ ID NO: 5. In some embodiments, the CM1 in the substrate consists of the amino acid sequence of SEQ ID NO: 6. In some embodiments, the CM1 in the substrate consists of the amino acid sequence of SEQ ID NO: 7. In some embodiments, the CM1 in the substrate consists of the amino acid sequence of SEQ ID NO: 8. In some embodiments, the CM1 in the substrates consists of the amino acid sequence of SEQ ID NO: 664.

In some embodiments, the CM2 in the substrate comprises the amino acid sequence of SEQ ID NO: 25. In some embodiments, the CM2 in the substrate comprises the amino acid sequence of SEQ ID NO: 26. In some embodiments, the CM2 in the substrate comprises the amino acid sequence of SEQ ID NO: 27. In some embodiments, the CM2 in the substrate comprises the amino acid sequence of SEQ ID NO: 28. In some embodiments, the CM2 in the substrate comprises the amino acid sequence of SEQ ID NO: 29. In some embodiments, the CM2 in the substrate comprises the amino acid sequence of SEQ ID NO: 30. In some embodiments, the CM2 in the substrate comprises the amino acid sequence of SEQ ID NO: 31. In some embodiments, the CM2 in the substrate comprises the amino acid sequence of SEQ ID NO: 32. In some embodiments, the CM2 in the substrate comprises the amino acid sequence of SEQ ID NO: 33. In some embodiments, the CM2 in the substrate comprises the amino acid sequence of SEQ ID NO: 34. In some embodiments, the CM2 in the substrate comprises the amino acid sequence of SEQ ID NO: 35. In some embodiments, the CM2 in the substrate comprises the amino acid sequence of SEQ ID NO: 36.

In some embodiments, the CM2 in the substrate consists of the amino acid sequence of SEQ ID NO: 25. In some embodiments, the CM2 in the substrate consists of the amino acid sequence of SEQ ID NO: 26. In some embodiments, the CM2 in the substrate consists of the amino acid sequence of SEQ ID NO: 27. In some embodiments, the CM2 in the substrate consists of the amino acid sequence of SEQ ID NO: 28. In some embodiments, the CM2 in the substrate consists of the amino acid sequence of SEQ ID NO: 29. In some embodiments, the CM2 in the substrate consists of the amino acid sequence of SEQ ID NO: 30. In some embodiments, the CM2 in the substrate consists of the amino acid sequence of SEQ ID NO: 31. In some embodiments, the CM2 in the substrate consists of the amino acid sequence of SEQ ID NO: 32. In some embodiments, the CM2 in the substrate consists of the amino acid sequence of SEQ ID NO: 33. In some embodiments, the CM2 in the substrate consists of the amino acid sequence of SEQ ID NO: 34. In some embodiments, the CM2 in the substrate consists of the amino acid sequence of SEQ ID NO: 35. In some embodiments, the CM2 in the substrate consists of the amino acid sequence of SEQ ID NO: 36.

The substrate may comprise an amino acid sequence selected from SEQ ID NOs: 9-24, 37-73, 83-353, 382-385, and 560-695 The substrate may comprise an amino acid sequence selected from SEQ ID NOs: 9-24, 37-73, 83-353, 382-385, and 560-683. In some embodiments, the substrate comprises the amino acid sequence of SEQ ID NO: 9. In some embodiments, the substrate comprises the amino acid sequence of SEQ ID NO: 10. In some embodiments, the substrate comprises the amino acid sequence of SEQ ID NO: 11. In some embodiments, the substrate comprises the amino acid sequence of SEQ ID NO: 12. In some embodiments, the substrate comprises the amino acid sequence of SEQ ID NO: 13. In some embodiments, the substrate comprises the amino acid sequence of SEQ ID NO: 14. In some embodiments, the substrate comprises the amino acid sequence of SEQ ID NO: 15. In some embodiments, the substrate comprises the amino acid sequence of SEQ ID NO: 16. In some embodiments, the substrate comprises the amino acid sequence of SEQ ID NO: 17. In some embodiments, the substrate comprises the amino acid sequence of SEQ ID NO: 18. In some embodiments, the substrate comprises the amino acid sequence of SEQ ID NO: 19. In some embodiments, the substrate comprises the amino acid sequence of SEQ ID NO: 20. In some embodiments, the substrate comprises the amino acid sequence of SEQ ID NO: 21. In some embodiments, the substrate comprises the amino acid sequence of SEQ ID NO: 22. In some embodiments, the substrate comprises the amino acid sequence of SEQ ID NO: 23. In some embodiments, the substrate comprises the amino acid sequence of SEQ ID NO: 24. In some embodiments, the substrate comprises the amino acid sequence of SEQ ID NO: 37. In some embodiments, the substrate comprises the amino acid sequence of SEQ ID NO: 38. In some embodiments, the substrate comprises the amino acid sequence of SEQ ID NO: 39. In some embodiments, the substrate comprises the amino acid sequence of SEQ ID NO: 40. In some embodiments, the substrate comprises the amino acid sequence of SEQ ID NO: 41. In some embodiments, the substrate comprises the amino acid sequence of SEQ ID NO: 42. In some embodiments, the substrate comprises the amino acid sequence of SEQ ID NO: 43. In some embodiments, the substrate comprises the amino acid sequence of SEQ ID NO: 44. In some embodiments, the substrate comprises the amino acid sequence of SEQ ID NO: 45. In some embodiments, the substrate comprises the amino acid sequence of SEQ ID NO: 46. In some embodiments, the substrate comprises the amino acid sequence of SEQ ID NO: 47. In some embodiments, the substrate comprises the amino acid sequence of SEQ ID NO: 48. In some embodiments, the substrate comprises the amino acid sequence of SEQ ID NO: 49. In some embodiments, the substrate comprises the amino acid sequence of SEQ ID NO: 50. In some embodiments, the substrate comprises the amino acid sequence of SEQ ID NO: 51. In some embodiments, the substrate comprises the amino acid sequence of SEQ ID NO: 52. In some embodiments, the substrate comprises the amino acid sequence of SEQ ID NO: 53. In some embodiments, the substrate comprises the amino acid sequence of SEQ ID NO: 54. In some embodiments, the substrate comprises the amino acid sequence of SEQ ID NO: 55. In some embodiments, the substrate comprises the amino acid sequence of SEQ ID NO: 56. In some embodiments, the substrate comprises the amino acid sequence of SEQ ID NO: 57. In some embodiments, the substrate comprises the amino acid sequence of SEQ ID NO: 58. In some embodiments, the substrate comprises the amino acid sequence of SEQ ID NO: 59. In some embodiments, the substrate comprises the amino acid sequence of SEQ ID NO: 60. In some embodiments, the substrate comprises the amino acid sequence of SEQ ID NO: 61. In some embodiments, the substrate comprises the amino acid sequence of SEQ ID NO: 62. In some embodiments, the substrate comprises the amino acid sequence of SEQ ID NO: 63. In some embodiments, the substrate comprises the amino acid sequence of SEQ ID NO: 64. In some embodiments, the substrate comprises the amino acid sequence of SEQ ID NO: 65. In some embodiments, the substrate comprises the amino acid sequence of SEQ ID NO: 66. In some embodiments, the substrate comprises the amino acid sequence of SEQ ID NO: 67. In some embodiments, the substrate comprises the amino acid sequence of SEQ ID NO: 68. In some embodiments, the substrate comprises the amino acid sequence of SEQ ID NO: 69. In some embodiments, the substrate comprises the amino acid sequence of SEQ ID NO: 70. In some embodiments, the substrate comprises the amino acid sequence of SEQ ID NO: 71. In some embodiments, the substrate comprises the amino acid sequence of SEQ ID NO: 72. In some embodiments, the substrate comprises the amino acid sequence of SEQ ID NO: 73. In some embodiments, the substrate comprises the amino acid sequence of SEQ ID NO: 82. In some embodiments, the substrate comprises the amino acid sequence of SEQ ID NO: 83. In some embodiments, the substrate comprises the amino acid sequence of SEQ ID NO: 84. In some embodiments, the substrate comprises the amino acid sequence of SEQ ID NO: 85. In some embodiments, the substrate comprises the amino acid sequence of SEQ ID NO: 86. In some embodiments, the substrate comprises the amino acid sequence of SEQ ID NO: 87. In some embodiments, the substrate comprises the amino acid sequence of SEQ ID NO: 88. In some embodiments, the substrate comprises the amino acid sequence of SEQ ID NO: 89. In some embodiments, the substrate comprises the amino acid sequence of SEQ ID NO: 90. In some embodiments, the substrate comprises the amino acid sequence of SEQ ID NO: 91. In some embodiments, the substrate comprises the amino acid sequence of SEQ ID NO: 92. In some embodiments, the substrate comprises the amino acid sequence of SEQ ID NO: 93. In some embodiments, the substrate comprises the amino acid sequence of SEQ ID NO: 94. In some embodiments, the substrate comprises the amino acid sequence of SEQ ID NO: 95. In some embodiments, the substrate comprises the amino acid sequence of SEQ ID NO: 96. In some embodiments, the substrate comprises the amino acid sequence of SEQ ID NO: 97. In some embodiments, the substrate comprises the amino acid sequence of SEQ ID NO: 98. In some embodiments, the substrate comprises the amino acid sequence of SEQ ID NO: 99. In some embodiments, the substrate comprises the amino acid sequence of SEQ ID NO: 100. In some embodiments, the substrate comprises the amino acid sequence of SEQ ID NO: 101. In some embodiments, the substrate comprises the amino acid sequence of SEQ ID NO: 102. In some embodiments, the substrate comprises the amino acid sequence of SEQ ID NO: 103. In some embodiments, the substrate comprises the amino acid sequence of SEQ ID NO: 104. In some embodiments, the substrate comprises the amino acid sequence of SEQ ID NO: 105. In some embodiments, the substrate comprises the amino acid sequence of SEQ ID NO: 106. In some embodiments, the substrate comprises the amino acid sequence of SEQ ID NO: 107. In some embodiments, the substrate comprises the amino acid sequence of SEQ ID NO: 108. In some embodiments, the substrate comprises the amino acid sequence of SEQ ID NO: 109. In some embodiments, the substrate comprises the amino acid sequence of SEQ ID NO: 110. In some embodiments, the substrate comprises the amino acid sequence of SEQ ID NO: 111. In some embodiments, the substrate comprises the amino acid sequence of SEQ ID NO: 112. In some embodiments, the substrate comprises the amino acid sequence of SEQ ID NO: 113. In some embodiments, the substrate comprises the amino acid sequence of SEQ ID NO: 114. In some embodiments, the substrate comprises the amino acid sequence of SEQ ID NO: 115. In some embodiments, the substrate comprises the amino acid sequence of SEQ ID NO: 116. In some embodiments, the substrate comprises the amino acid sequence of SEQ ID NO: 117. In some embodiments, the substrate comprises the amino acid sequence of SEQ ID NO: 118. In some embodiments, the substrate comprises the amino acid sequence of SEQ ID NO: 119. In some embodiments, the substrate comprises the amino acid sequence of SEQ ID NO: 120. In some embodiments, the substrate comprises the amino acid sequence of SEQ ID NO: 121. In some embodiments, the substrate comprises the amino acid sequence of SEQ ID NO: 122. In some embodiments, the substrate comprises the amino acid sequence of SEQ ID NO: 123. In some embodiments, the substrate comprises the amino acid sequence of SEQ ID NO: 124. In some embodiments, the substrate comprises the amino acid sequence of SEQ ID NO: 125. In some embodiments, the substrate comprises the amino acid sequence of SEQ ID NO: 126. In some embodiments, the substrate comprises the amino acid sequence of SEQ ID NO: 127. In some embodiments, the substrate comprises the amino acid sequence of SEQ ID NO: 128. In some embodiments, the substrate comprises the amino acid sequence of SEQ ID NO: 129. In some embodiments, the substrate comprises the amino acid sequence of SEQ ID NO: 130. In some embodiments, the substrate comprises the amino acid sequence of SEQ ID NO: 131. In some embodiments, the substrate comprises the amino acid sequence of SEQ ID NO: 132. In some embodiments, the substrate comprises the amino acid sequence of SEQ ID NO: 133. In some embodiments, the substrate comprises the amino acid sequence of SEQ ID NO: 134. In some embodiments, the substrate comprises the amino acid sequence of SEQ ID NO: 135. In some embodiments, the substrate comprises the amino acid sequence of SEQ ID NO: 136. In some embodiments, the substrate comprises the amino acid sequence of SEQ ID NO: 137. In some embodiments, the substrate comprises the amino acid sequence of SEQ ID NO: 138. In some embodiments, the substrate comprises the amino acid sequence of SEQ ID NO: 139. In some embodiments, the substrate comprises the amino acid sequence of SEQ ID NO: 140. In some embodiments, the substrate comprises the amino acid sequence of SEQ ID NO: 141. In some embodiments, the substrate comprises the amino acid sequence of SEQ ID NO: 142. In some embodiments, the substrate comprises the amino acid sequence of SEQ ID NO: 143. In some embodiments, the substrate comprises the amino acid sequence of SEQ ID NO: 144. In some embodiments, the substrate comprises the amino acid sequence of SEQ ID NO: 145. In some embodiments, the substrate comprises the amino acid sequence of SEQ ID NO: 146. In some embodiments, the substrate comprises the amino acid sequence of SEQ ID NO: 147. In some embodiments, the substrate comprises the amino acid sequence of SEQ ID NO: 148. In some embodiments, the substrate comprises the amino acid sequence of SEQ ID NO: 149. In some embodiments, the substrate comprises the amino acid sequence of SEQ ID NO: 150. In some embodiments, the substrate comprises the amino acid sequence of SEQ ID NO: 151. In some embodiments, the substrate comprises the amino acid sequence of SEQ ID NO: 152. In some embodiments, the substrate comprises the amino acid sequence of SEQ ID NO: 153. In some embodiments, the substrate comprises the amino acid sequence of SEQ ID NO: 154. In some embodiments, the substrate comprises the amino acid sequence of SEQ ID NO: 155. In some embodiments, the substrate comprises the amino acid sequence of SEQ ID NO: 156. In some embodiments, the substrate comprises the amino acid sequence of SEQ ID NO: 157. In some embodiments, the substrate comprises the amino acid sequence of SEQ ID NO: 158. In some embodiments, the substrate comprises the amino acid sequence of SEQ ID NO: 159. In some embodiments, the substrate comprises the amino acid sequence of SEQ ID NO: 160. In some embodiments, the substrate comprises the amino acid sequence of SEQ ID NO: 161. In some embodiments, the substrate comprises the amino acid sequence of SEQ ID NO: 162. In some embodiments, the substrate comprises the amino acid sequence of SEQ ID NO: 163. In some embodiments, the substrate comprises the amino acid sequence of SEQ ID NO: 164. In some embodiments, the substrate comprises the amino acid sequence of SEQ ID NO: 165. In some embodiments, the substrate comprises the amino acid sequence of SEQ ID NO: 166. In some embodiments, the substrate comprises the amino acid sequence of SEQ ID NO: 167. In some embodiments, the substrate comprises the amino acid sequence of SEQ ID NO: 168. In some embodiments, the substrate comprises the amino acid sequence of SEQ ID NO: 169. In some embodiments, the substrate comprises the amino acid sequence of SEQ ID NO: 170. In some embodiments, the substrate comprises the amino acid sequence of SEQ ID NO: 171. In some embodiments, the substrate comprises the amino acid sequence of SEQ ID NO: 172. In some embodiments, the substrate comprises the amino acid sequence of SEQ ID NO: 173. In some embodiments, the substrate comprises the amino acid sequence of SEQ ID NO: 174. In some embodiments, the substrate comprises the amino acid sequence of SEQ ID NO: 175. In some embodiments, the substrate comprises the amino acid sequence of SEQ ID NO: 176. In some embodiments, the substrate comprises the amino acid sequence of SEQ ID NO: 177. In some embodiments, the substrate comprises the amino acid sequence of SEQ ID NO: 178. In some embodiments, the substrate comprises the amino acid sequence of SEQ ID NO: 179. In some embodiments, the substrate comprises the amino acid sequence of SEQ ID NO: 180. In some embodiments, the substrate comprises the amino acid sequence of SEQ ID NO: 181. In some embodiments, the substrate comprises the amino acid sequence of SEQ ID NO: 182. In some embodiments, the substrate comprises the amino acid sequence of SEQ ID NO: 183. In some embodiments, the substrate comprises the amino acid sequence of SEQ ID NO: 184. In some embodiments, the substrate comprises the amino acid sequence of SEQ ID NO: 185. In some embodiments, the substrate comprises the amino acid sequence of SEQ ID NO: 186. In some embodiments, the substrate comprises the amino acid sequence of SEQ ID NO: 187. In some embodiments, the substrate comprises the amino acid sequence of SEQ ID NO: 188. In some embodiments, the substrate comprises the amino acid sequence of SEQ ID NO: 189. In some embodiments, the substrate comprises the amino acid sequence of SEQ ID NO: 190. In some embodiments, the substrate comprises the amino acid sequence of SEQ ID NO: 191. In some embodiments, the substrate comprises the amino acid sequence of SEQ ID NO: 192. In some embodiments, the substrate comprises the amino acid sequence of SEQ ID NO: 193. In some embodiments, the substrate comprises the amino acid sequence of SEQ ID NO: 194. In some embodiments, the substrate comprises the amino acid sequence of SEQ ID NO: 195. In some embodiments, the substrate comprises the amino acid sequence of SEQ ID NO: 196. In some embodiments, the substrate comprises the amino acid sequence of SEQ ID NO: 197. In some embodiments, the substrate comprises the amino acid sequence of SEQ ID NO: 198. In some embodiments, the substrate comprises the amino acid sequence of SEQ ID NO: 199. In some embodiments, the substrate comprises the amino acid sequence of SEQ ID NO: 200. In some embodiments, the substrate comprises the amino acid sequence of SEQ ID NO: 201. In some embodiments, the substrate comprises the amino acid sequence of SEQ ID NO: 202. In some embodiments, the substrate comprises the amino acid sequence of SEQ ID NO: 203. In some embodiments, the substrate comprises the amino acid sequence of SEQ ID NO: 204. In some embodiments, the substrate comprises the amino acid sequence of SEQ ID NO: 205. In some embodiments, the substrate comprises the amino acid sequence of SEQ ID NO: 206. In some embodiments, the substrate comprises the amino acid sequence of SEQ ID NO: 207. In some embodiments, the substrate comprises the amino acid sequence of SEQ ID NO: 208. In some embodiments, the substrate comprises the amino acid sequence of SEQ ID NO: 209. In some embodiments, the substrate comprises the amino acid sequence of SEQ ID NO: 210. In some embodiments, the substrate comprises the amino acid sequence of SEQ ID NO: 211. In some embodiments, the substrate comprises the amino acid sequence of SEQ ID NO: 212. In some embodiments, the substrate comprises the amino acid sequence of SEQ ID NO: 213. In some embodiments, the substrate comprises the amino acid sequence of SEQ ID NO: 214. In some embodiments, the substrate comprises the amino acid sequence of SEQ ID NO: 215. In some embodiments, the substrate comprises the amino acid sequence of SEQ ID NO: 216. In some embodiments, the substrate comprises the amino acid sequence of SEQ ID NO: 217. In some embodiments, the substrate comprises the amino acid sequence of SEQ ID NO: 218. In some embodiments, the substrate comprises the amino acid sequence of SEQ ID NO: 219. In some embodiments, the substrate comprises the amino acid sequence of SEQ ID NO: 220. In some embodiments, the substrate comprises the amino acid sequence of SEQ ID NO: 221. In some embodiments, the substrate comprises the amino acid sequence of SEQ ID NO: 222. In some embodiments, the substrate comprises the amino acid sequence of SEQ ID NO: 223. In some embodiments, the substrate comprises the amino acid sequence of SEQ ID NO: 224. In some embodiments, the substrate comprises the amino acid sequence of SEQ ID NO: 225. In some embodiments, the substrate comprises the amino acid sequence of SEQ ID NO: 226. In some embodiments, the substrate comprises the amino acid sequence of SEQ ID NO: 227. In some embodiments, the substrate comprises the amino acid sequence of SEQ ID NO: 228. In some embodiments, the substrate comprises the amino acid sequence of SEQ ID NO: 229. In some embodiments, the substrate comprises the amino acid sequence of SEQ ID NO: 230. In some embodiments, the substrate comprises the amino acid sequence of SEQ ID NO: 231. In some embodiments, the substrate comprises the amino acid sequence of SEQ ID NO: 232. In some embodiments, the substrate comprises the amino acid sequence of SEQ ID NO: 233. In some embodiments, the substrate comprises the amino acid sequence of SEQ ID NO: 234. In some embodiments, the substrate comprises the amino acid sequence of SEQ ID NO: 235. In some embodiments, the substrate comprises the amino acid sequence of SEQ ID NO: 236. In some embodiments, the substrate comprises the amino acid sequence of SEQ ID NO: 237. In some embodiments, the substrate comprises the amino acid sequence of SEQ ID NO: 238. In some embodiments, the substrate comprises the amino acid sequence of SEQ ID NO: 239. In some embodiments, the substrate comprises the amino acid sequence of SEQ ID NO: 240. In some embodiments, the substrate comprises the amino acid sequence of SEQ ID NO: 241. In some embodiments, the substrate comprises the amino acid sequence of SEQ ID NO: 242. In some embodiments, the substrate comprises the amino acid sequence of SEQ ID NO: 243. In some embodiments, the substrate comprises the amino acid sequence of SEQ ID NO: 244. In some embodiments, the substrate comprises the amino acid sequence of SEQ ID NO: 245. In some embodiments, the substrate comprises the amino acid sequence of SEQ ID NO: 246. In some embodiments, the substrate comprises the amino acid sequence of SEQ ID NO: 247. In some embodiments, the substrate comprises the amino acid sequence of SEQ ID NO: 248. In some embodiments, the substrate comprises the amino acid sequence of SEQ ID NO: 249. In some embodiments, the substrate comprises the amino acid sequence of SEQ ID NO: 250. In some embodiments, the substrate comprises the amino acid sequence of SEQ ID NO: 251. In some embodiments, the substrate comprises the amino acid sequence of SEQ ID NO: 252. In some embodiments, the substrate comprises the amino acid sequence of SEQ ID NO: 253. In some embodiments, the substrate comprises the amino acid sequence of SEQ ID NO: 254. In some embodiments, the substrate comprises the amino acid sequence of SEQ ID NO: 255. In some embodiments, the substrate comprises the amino acid sequence of SEQ ID NO: 256. In some embodiments, the substrate comprises the amino acid sequence of SEQ ID NO: 257. In some embodiments, the substrate comprises the amino acid sequence of SEQ ID NO: 258. In some embodiments, the substrate comprises the amino acid sequence of SEQ ID NO: 259. In some embodiments, the substrate comprises the amino acid sequence of SEQ ID NO: 260. In some embodiments, the substrate comprises the amino acid sequence of SEQ ID NO: 261. In some embodiments, the substrate comprises the amino acid sequence of SEQ ID NO: 262. In some embodiments, the substrate comprises the amino acid sequence of SEQ ID NO: 263. In some embodiments, the substrate comprises the amino acid sequence of SEQ ID NO: 264. In some embodiments, the substrate comprises the amino acid sequence of SEQ ID NO: 265. In some embodiments, the substrate comprises the amino acid sequence of SEQ ID NO: 266. In some embodiments, the substrate comprises the amino acid sequence of SEQ ID NO: 267. In some embodiments, the substrate comprises the amino acid sequence of SEQ ID NO: 268. In some embodiments, the substrate comprises the amino acid sequence of SEQ ID NO: 269. In some embodiments, the substrate comprises the amino acid sequence of SEQ ID NO: 270. In some embodiments, the substrate comprises the amino acid sequence of SEQ ID NO: 271. In some embodiments, the substrate comprises the amino acid sequence of SEQ ID NO: 272. In some embodiments, the substrate comprises the amino acid sequence of SEQ ID NO: 273. In some embodiments, the substrate comprises the amino acid sequence of SEQ ID NO: 274. In some embodiments, the substrate comprises the amino acid sequence of SEQ ID NO: 275. In some embodiments, the substrate comprises the amino acid sequence of SEQ ID NO: 276. In some embodiments, the substrate comprises the amino acid sequence of SEQ ID NO: 277. In some embodiments, the substrate comprises the amino acid sequence of SEQ ID NO: 278. In some embodiments, the substrate comprises the amino acid sequence of SEQ ID NO: 279. In some embodiments, the substrate comprises the amino acid sequence of SEQ ID NO: 280. In some embodiments, the substrate comprises the amino acid sequence of SEQ ID NO: 281. In some embodiments, the substrate comprises the amino acid sequence of SEQ ID NO: 282. In some embodiments, the substrate comprises the amino acid sequence of SEQ ID NO: 283. In some embodiments, the substrate comprises the amino acid sequence of SEQ ID NO: 284. In some embodiments, the substrate comprises the amino acid sequence of SEQ ID NO: 285. In some embodiments, the substrate comprises the amino acid sequence of SEQ ID NO: 286. In some embodiments, the substrate comprises the amino acid sequence of SEQ ID NO: 287. In some embodiments, the substrate comprises the amino acid sequence of SEQ ID NO: 288. In some embodiments, the substrate comprises the amino acid sequence of SEQ ID NO: 289. In some embodiments, the substrate comprises the amino acid sequence of SEQ ID NO: 290. In some embodiments, the substrate comprises the amino acid sequence of SEQ ID NO: 291. In some embodiments, the substrate comprises the amino acid sequence of SEQ ID NO: 292. In some embodiments, the substrate comprises the amino acid sequence of SEQ ID NO: 293. In some embodiments, the substrate comprises the amino acid sequence of SEQ ID NO: 294. In some embodiments, the substrate comprises the amino acid sequence of SEQ ID NO: 295. In some embodiments, the substrate comprises the amino acid sequence of SEQ ID NO: 296. In some embodiments, the substrate comprises the amino acid sequence of SEQ ID NO: 297. In some embodiments, the substrate comprises the amino acid sequence of SEQ ID NO: 298. In some embodiments, the substrate comprises the amino acid sequence of SEQ ID NO: 299. In some embodiments, the substrate comprises the amino acid sequence of SEQ ID NO: 300. In some embodiments, the substrate comprises the amino acid sequence of SEQ ID NO: 301. In some embodiments, the substrate comprises the amino acid sequence of SEQ ID NO: 302. In some embodiments, the substrate comprises the amino acid sequence of SEQ ID NO: 303. In some embodiments, the substrate comprises the amino acid sequence of SEQ ID NO: 304. In some embodiments, the substrate comprises the amino acid sequence of SEQ ID NO: 305. In some embodiments, the substrate comprises the amino acid sequence of SEQ ID NO: 306. In some embodiments, the substrate comprises the amino acid sequence of SEQ ID NO: 307. In some embodiments, the substrate comprises the amino acid sequence of SEQ ID NO: 308. In some embodiments, the substrate comprises the amino acid sequence of SEQ ID NO: 309. In some embodiments, the substrate comprises the amino acid sequence of SEQ ID NO: 310. In some embodiments, the substrate comprises the amino acid sequence of SEQ ID NO: 311. In some embodiments, the substrate comprises the amino acid sequence of SEQ ID NO: 312. In some embodiments, the substrate comprises the amino acid sequence of SEQ ID NO: 313. In some embodiments, the substrate comprises the amino acid sequence of SEQ ID NO: 314. In some embodiments, the substrate comprises the amino acid sequence of SEQ ID NO: 315. In some embodiments, the substrate comprises the amino acid sequence of SEQ ID NO: 316. In some embodiments, the substrate comprises the amino acid sequence of SEQ ID NO: 317. In some embodiments, the substrate comprises the amino acid sequence of SEQ ID NO: 318. In some embodiments, the substrate comprises the amino acid sequence of SEQ ID NO: 319. In some embodiments, the substrate comprises the amino acid sequence of SEQ ID NO: 320. In some embodiments, the substrate comprises the amino acid sequence of SEQ ID NO: 321. In some embodiments, the substrate comprises the amino acid sequence of SEQ ID NO: 322. In some embodiments, the substrate comprises the amino acid sequence of SEQ ID NO: 323. In some embodiments, the substrate comprises the amino acid sequence of SEQ ID NO: 324. In some embodiments, the substrate comprises the amino acid sequence of SEQ ID NO: 325. In some embodiments, the substrate comprises the amino acid sequence of SEQ ID NO: 326. In some embodiments, the substrate comprises the amino acid sequence of SEQ ID NO: 327. In some embodiments, the substrate comprises the amino acid sequence of SEQ ID NO: 328. In some embodiments, the substrate comprises the amino acid sequence of SEQ ID NO: 329. In some embodiments, the substrate comprises the amino acid sequence of SEQ ID NO: 330. In some embodiments, the substrate comprises the amino acid sequence of SEQ ID NO: 331. In some embodiments, the substrate comprises the amino acid sequence of SEQ ID NO: 332. In some embodiments, the substrate comprises the amino acid sequence of SEQ ID NO: 333. In some embodiments, the substrate comprises the amino acid sequence of SEQ ID NO: 334. In some embodiments, the substrate comprises the amino acid sequence of SEQ ID NO: 335. In some embodiments, the substrate comprises the amino acid sequence of SEQ ID NO: 336. In some embodiments, the substrate comprises the amino acid sequence of SEQ ID NO: 337. In some embodiments, the substrate comprises the amino acid sequence of SEQ ID NO: 338. In some embodiments, the substrate comprises the amino acid sequence of SEQ ID NO: 339. In some embodiments, the substrate comprises the amino acid sequence of SEQ ID NO: 340. In some embodiments, the substrate comprises the amino acid sequence of SEQ ID NO: 341. In some embodiments, the substrate comprises the amino acid sequence of SEQ ID NO: 342. In some embodiments, the substrate comprises the amino acid sequence of SEQ ID NO: 343. In some embodiments, the substrate comprises the amino acid sequence of SEQ ID NO: 344. In some embodiments, the substrate comprises the amino acid sequence of SEQ ID NO: 345. In some embodiments, the substrate comprises the amino acid sequence of SEQ ID NO: 346. In some embodiments, the substrate comprises the amino acid sequence of SEQ ID NO: 347. In some embodiments, the substrate comprises the amino acid sequence of SEQ ID NO: 348. In some embodiments, the substrate comprises the amino acid sequence of SEQ ID NO: 349. In some embodiments, the substrate comprises the amino acid sequence of SEQ ID NO: 350. In some embodiments, the substrate comprises the amino acid sequence of SEQ ID NO: 351. In some embodiments, the substrate comprises the amino acid sequence of SEQ ID NO: 352. In some embodiments, the substrate comprises the amino acid sequence of SEQ ID NO: 353. In some embodiments, the substrate comprises the amino acid sequence of SEQ ID NO: 382. In some embodiments, the substrate comprises the amino acid sequence of SEQ ID NO: 383. In some embodiments, the substrate comprises the amino acid sequence of SEQ ID NO: 384. In some embodiments, the substrate comprises the amino acid sequence of SEQ ID NO: 385. In some embodiments, the substrate comprises the amino acid sequence of SEQ ID NO: 560. In some embodiments, the substrate comprises the amino acid sequence of SEQ ID NO: 561. In some embodiments, the substrate comprises the amino acid sequence of SEQ ID NO: 562. In some embodiments, the substrate comprises the amino acid sequence of SEQ ID NO: 563. In some embodiments, the substrate comprises the amino acid sequence of SEQ ID NO: 564. In some embodiments, the substrate comprises the amino acid sequence of SEQ ID NO: 565. In some embodiments, the substrate comprises the amino acid sequence of SEQ ID NO: 566. In some embodiments, the substrate comprises the amino acid sequence of SEQ ID NO: 567. In some embodiments, the substrate comprises the amino acid sequence of SEQ ID NO: 568. In some embodiments, the substrate comprises the amino acid sequence of SEQ ID NO: 569. In some embodiments, the substrate comprises the amino acid sequence of SEQ ID NO: 570. In some embodiments, the substrate comprises the amino acid sequence of SEQ ID NO: 571. In some embodiments, the substrate comprises the amino acid sequence of SEQ ID NO: 572. In some embodiments, the substrate comprises the amino acid sequence of SEQ ID NO: 573. In some embodiments, the substrate comprises the amino acid sequence of SEQ ID NO: 574. In some embodiments, the substrate comprises the amino acid sequence of SEQ ID NO: 575. In some embodiments, the substrate comprises the amino acid sequence of SEQ ID NO: 576. In some embodiments, the substrate comprises the amino acid sequence of SEQ ID NO: 577. In some embodiments, the substrate comprises the amino acid sequence of SEQ ID NO: 578. In some embodiments, the substrate comprises the amino acid sequence of SEQ ID NO: 579. In some embodiments, the substrate comprises the amino acid sequence of SEQ ID NO: 580. In some embodiments, the substrate comprises the amino acid sequence of SEQ ID NO: 581. In some embodiments, the substrate comprises the amino acid sequence of SEQ ID NO: 582. In some embodiments, the substrate comprises the amino acid sequence of SEQ ID NO: 583. In some embodiments, the substrate comprises the amino acid sequence of SEQ ID NO: 584. In some embodiments, the substrate comprises the amino acid sequence of SEQ ID NO: 585. In some embodiments, the substrate comprises the amino acid sequence of SEQ ID NO: 586. In some embodiments, the substrate comprises the amino acid sequence of SEQ ID NO: 587. In some embodiments, the substrate comprises the amino acid sequence of SEQ ID NO:

588. In some embodiments, the substrate comprises the amino acid sequence of SEQ ID NO: 589. In some embodiments, the substrate comprises the amino acid sequence of SEQ ID NO: 590. In some embodiments, the substrate comprises the amino acid sequence of SEQ ID NO: 591. In some embodiments, the substrate comprises the amino acid sequence of SEQ ID NO: 592. In some embodiments, the substrate comprises the amino acid sequence of SEQ ID NO: 593. In some embodiments, the substrate comprises the amino acid sequence of SEQ ID NO: 594. In some embodiments, the substrate comprises the amino acid sequence of SEQ ID NO: 595. In some embodiments, the substrate comprises the amino acid sequence of SEQ ID NO: 596. In some embodiments, the substrate comprises the amino acid sequence of SEQ ID NO: 597. In some embodiments, the substrate comprises the amino acid sequence of SEQ ID NO: 598. In some embodiments, the substrate comprises the amino acid sequence of SEQ ID NO: 599. In some embodiments, the substrate comprises the amino acid sequence of SEQ ID NO: 600. In some embodiments, the substrate comprises the amino acid sequence of SEQ ID NO: 601. In some embodiments, the substrate comprises the amino acid sequence of SEQ ID NO: 602. In some embodiments, the substrate comprises the amino acid sequence of SEQ ID NO: 603. In some embodiments, the substrate comprises the amino acid sequence of SEQ ID NO: 604. In some embodiments, the substrate comprises the amino acid sequence of SEQ ID NO: 605. In some embodiments, the substrate comprises the amino acid sequence of SEQ ID NO: 606. In some embodiments, the substrate comprises the amino acid sequence of SEQ ID NO: 607. In some embodiments, the substrate comprises the amino acid sequence of SEQ ID NO: 608. In some embodiments, the substrate comprises the amino acid sequence of SEQ ID NO: 609. In some embodiments, the substrate comprises the amino acid sequence of SEQ ID NO: 610. In some embodiments, the substrate comprises the amino acid sequence of SEQ ID NO: 611. In some embodiments, the substrate comprises the amino acid sequence of SEQ ID NO: 612. In some embodiments, the substrate comprises the amino acid sequence of SEQ ID NO: 613. In some embodiments, the substrate comprises the amino acid sequence of SEQ ID NO: 614. In some embodiments, the substrate comprises the amino acid sequence of SEQ ID NO: 615. In some embodiments, the substrate comprises the amino acid sequence of SEQ ID NO: 616. In some embodiments, the substrate comprises the amino acid sequence of SEQ ID NO: 617. In some embodiments, the substrate comprises the amino acid sequence of SEQ ID NO: 618. In some embodiments, the substrate comprises the amino acid sequence of SEQ ID NO: 619. In some embodiments, the substrate comprises the amino acid sequence of SEQ ID NO: 620. In some embodiments, the substrate comprises the amino acid sequence of SEQ ID NO: 621. In some embodiments, the substrate comprises the amino acid sequence of SEQ ID NO: 622. In some embodiments, the substrate comprises the amino acid sequence of SEQ ID NO: 623. In some embodiments, the substrate comprises the amino acid sequence of SEQ ID NO: 624. In some embodiments, the substrate comprises the amino acid sequence of SEQ ID NO: 625. In some embodiments, the substrate comprises the amino acid sequence of SEQ ID NO: 626. In some embodiments, the substrate comprises the amino acid sequence of SEQ ID NO: 627. In some embodiments, the substrate comprises the amino acid sequence of SEQ ID NO: 628. In some embodiments, the substrate comprises the amino acid sequence of SEQ ID NO: 629. In some embodiments, the substrate comprises the amino acid sequence of SEQ ID NO: 630. In some embodiments, the substrate comprises the amino acid sequence of SEQ ID NO: 631. In some embodiments, the substrate comprises the amino acid sequence of SEQ ID NO: 632. In some embodiments, the substrate comprises the amino acid sequence of SEQ ID NO: 633. In some embodiments, the substrate comprises the amino acid sequence of SEQ ID NO: 634. In some embodiments, the substrate comprises the amino acid sequence of SEQ ID NO: 635. In some embodiments, the substrate comprises the amino acid sequence of SEQ ID NO: 636. In some embodiments, the substrate comprises the amino acid sequence of SEQ ID NO: 637. In some embodiments, the substrate comprises the amino acid sequence of SEQ ID NO: 638. In some embodiments, the substrate comprises the amino acid sequence of SEQ ID NO: 639. In some embodiments, the substrate comprises the amino acid sequence of SEQ ID NO: 640. In some embodiments, the substrate comprises the amino acid sequence of SEQ ID NO: 641. In some embodiments, the substrate comprises the amino acid sequence of SEQ ID NO: 642. In some embodiments, the substrate comprises the amino acid sequence of SEQ ID NO: 643. In some embodiments, the substrate comprises the amino acid sequence of SEQ ID NO: 644. In some embodiments, the substrate comprises the amino acid sequence of SEQ ID NO: 645. In some embodiments, the substrate comprises the amino acid sequence of SEQ ID NO: 646. In some embodiments, the substrate comprises the amino acid sequence of SEQ ID NO: 647. In some embodiments, the substrate comprises the amino acid sequence of SEQ ID NO: 648. In some embodiments, the substrate comprises the amino acid sequence of SEQ ID NO: 649. In some embodiments, the substrate comprises the amino acid sequence of SEQ ID NO: 650. In some embodiments, the substrate comprises the amino acid sequence of SEQ ID NO: 651. In some embodiments, the substrate comprises the amino acid sequence of SEQ ID NO: 652. In some embodiments, the substrate comprises the amino acid sequence of SEQ ID NO: 653. In some embodiments, the substrate comprises the amino acid sequence of SEQ ID NO: 654. In some embodiments, the substrate comprises the amino acid sequence of SEQ ID NO: 655. In some embodiments, the substrate comprises the amino acid sequence of SEQ ID NO: 656. In some embodiments, the substrate comprises the amino acid sequence of SEQ ID NO: 657. In some embodiments, the substrate comprises the amino acid sequence of SEQ ID NO: 658. In some embodiments, the substrate comprises the amino acid sequence of SEQ ID NO: 659. In some embodiments, the substrate comprises the amino acid sequence of SEQ ID NO: 660. In some embodiments, the substrate comprises the amino acid sequence of SEQ ID NO: 661. In some embodiments, the substrate comprises the amino acid sequence of SEQ ID NO: 662. In some embodiments, the substrate comprises the amino acid sequence of SEQ ID NO: 663. In some embodiments, the substrate comprises the amino acid sequence of SEQ ID NO: 664. In some embodiments, the substrate comprises the amino acid sequence of SEQ ID NO: 665. In some embodiments, the substrate comprises the amino acid sequence of SEQ ID NO: 666. In some embodiments, the substrate comprises the amino acid sequence of SEQ ID NO: 667. In some embodiments, the substrate comprises the amino acid sequence of SEQ ID NO: 668. In some embodiments, the substrate comprises the amino acid sequence of SEQ ID NO: 669. In some embodiments, the substrate comprises the amino acid sequence of SEQ ID NO: 670. In some embodiments, the substrate comprises the amino acid sequence of SEQ ID NO: 671. In some embodiments, the substrate comprises the amino acid sequence of SEQ ID NO: 672. In some embodiments, the substrate comprises the amino acid sequence of SEQ ID NO: 673. In some embodiments, the substrate comprises the amino acid sequence of SEQ ID NO: 674. In some embodiments, the substrate comprises the amino acid sequence of SEQ ID NO: 675. In some embodiments, the substrate comprises the amino acid sequence of SEQ ID NO: 676. In some embodiments, the substrate comprises the amino acid sequence of SEQ ID NO: 677. In some embodiments, the substrate comprises the amino acid sequence of SEQ ID NO: 678. In some embodiments, the substrate comprises the amino acid sequence of SEQ ID NO: 679. In some embodiments, the substrate comprises the amino acid sequence of SEQ ID NO: 680. In some embodiments, the substrate comprises the amino acid sequence of SEQ ID NO: 681. In some embodiments, the substrate comprises the amino acid sequence of SEQ ID NO: 682. In some embodiments, the substrate comprises the amino acid sequence of SEQ ID NO: 683. In some embodiments, the substrate comprises the amino acid sequence of SEQ ID NO: 684. In some embodiments, the substrate comprises the amino acid sequence of SEQ ID NO: 685. In some embodiments, the substrate comprises the amino acid sequence of SEQ ID NO: 686. In some embodiments, the substrate comprises the amino acid sequence of SEQ ID NO: 687. In some embodiments, the substrate comprises the amino acid sequence of SEQ ID NO: 688. In some embodiments, the substrate comprises the amino acid sequence of SEQ ID NO: 689. In some embodiments, the substrate comprises the amino acid sequence of SEQ ID NO: 690. In some embodiments, the substrate comprises the amino acid sequence of SEQ ID NO: 691. In some embodiments, the substrate comprises the amino acid sequence of SEQ ID NO: 692. In some embodiments, the substrate comprises the amino acid sequence of SEQ ID NO: 693. In some embodiments, the substrate comprises the amino acid sequence of SEQ ID NO: 694. In some embodiments, the substrate comprises the amino acid sequence of SEQ ID NO: 695.

The substrate may consist of an amino acid sequence selected from SEQ ID NOs: 9-24, 37-73, 83-353, 382-385, and 560-695. The substrate may consist of an amino acid sequence selected from SEQ ID NOs: 9-24, 37-73, 83-353, 382-385, and 560-683. In some embodiments, the substrate consists of the amino acid sequence of SEQ ID NO: 9. In some embodiments, the substrate consists of the amino acid sequence of SEQ ID NO: 10. In some embodiments, the substrate consists of the amino acid sequence of SEQ ID NO: 11. In some embodiments, the substrate consists of the amino acid sequence of SEQ ID NO: 12. In some embodiments, the substrate consists of the amino acid sequence of SEQ ID NO: 13. In some embodiments, the substrate consists of the amino acid sequence of SEQ ID NO: 14. In some embodiments, the substrate consists of the amino acid sequence of SEQ ID NO: 15. In some embodiments, the substrate consists of the amino acid sequence of SEQ ID NO: 16. In some embodiments, the substrate consists of the amino acid sequence of SEQ ID NO: 17. In some embodiments, the substrate consists of the amino acid sequence of SEQ ID NO: 18. In some embodiments, the substrate consists of the amino acid sequence of SEQ ID NO: 19. In some embodiments, the substrate consists of the amino acid sequence of SEQ ID NO: 20. In some embodiments, the substrate consists of the amino acid sequence of SEQ ID NO: 21. In some embodiments, the substrate consists of the amino acid sequence of SEQ ID NO: 22. In some embodiments, the substrate consists of the amino acid sequence of SEQ ID NO: 23. In some embodiments, the substrate consists of the amino acid sequence of SEQ ID NO: 24 . . . . In some embodiments, the substrate consists of the amino acid sequence of SEQ ID NO: 37. In some embodiments, the substrate consists of the amino acid sequence of SEQ ID NO: 38. In some embodiments, the substrate consists of the amino acid sequence of SEQ ID NO: 39. In some embodiments, the substrate consists of the amino acid sequence of SEQ ID NO: 40. In some embodiments, the substrate consists of the amino acid sequence of SEQ ID NO: 41. In some embodiments, the substrate consists of the amino acid sequence of SEQ ID NO: 42. In some embodiments, the substrate consists of the amino acid sequence of SEQ ID NO: 43. In some embodiments, the substrate consists of the amino acid sequence of SEQ ID NO: 44. In some embodiments, the substrate consists of the amino acid sequence of SEQ ID NO: 45. In some embodiments, the substrate consists of the amino acid sequence of SEQ ID NO: 46. In some embodiments, the substrate consists of the amino acid sequence of SEQ ID NO: 47. In some embodiments, the substrate consists of the amino acid sequence of SEQ ID NO: 48. In some embodiments, the substrate consists of the amino acid sequence of SEQ ID NO: 49. In some embodiments, the substrate consists of the amino acid sequence of SEQ ID NO: 50. In some embodiments, the substrate consists of the amino acid sequence of SEQ ID NO: 51. In some embodiments, the substrate consists of the amino acid sequence of SEQ ID NO: 52. In some embodiments, the substrate consists of the amino acid sequence of SEQ ID NO: 53. In some embodiments, the substrate consists of the amino acid sequence of SEQ ID NO: 54. In some embodiments, the substrate consists of the amino acid sequence of SEQ ID NO: 55. In some embodiments, the substrate consists of the amino acid sequence of SEQ ID NO: 56. In some embodiments, the substrate consists of the amino acid sequence of SEQ ID NO: 57. In some embodiments, the substrate consists of the amino acid sequence of SEQ ID NO: 58. In some embodiments, the substrate consists of the amino acid sequence of SEQ ID NO: 59. In some embodiments, the substrate consists of the amino acid sequence of SEQ ID NO: 60. In some embodiments, the substrate consists of the amino acid sequence of SEQ ID NO: 61. In some embodiments, the substrate consists of the amino acid sequence of SEQ ID NO: 62. In some embodiments, the substrate consists of the amino acid sequence of SEQ ID NO: 63. In some embodiments, the substrate consists of the amino acid sequence of SEQ ID NO: 64. In some embodiments, the substrate consists of the amino acid sequence of SEQ ID NO: 65. In some embodiments, the substrate consists of the amino acid sequence of SEQ ID NO: 66. In some embodiments, the substrate consists of the amino acid sequence of SEQ ID NO: 67. In some embodiments, the substrate consists of the amino acid sequence of SEQ ID NO: 68. In some embodiments, the substrate consists of the amino acid sequence of SEQ ID NO: 69. In some embodiments, the substrate consists of the amino acid sequence of SEQ ID NO: 70. In some embodiments, the substrate consists of the amino acid sequence of SEQ ID NO: 71. In some embodiments, the substrate consists of the amino acid sequence of SEQ ID NO: 72. In some embodiments, the substrate consists of the amino acid sequence of SEQ ID NO: 73. In some embodiments, the substrate consists of the amino acid sequence of SEQ ID NO: 83. In some embodiments, the substrate consists of the amino acid sequence of SEQ ID NO: 84. In some embodiments, the substrate consists of the amino acid sequence of SEQ ID NO: 85. In some embodiments, the substrate consists of the amino acid sequence of SEQ ID NO: 86. In some embodiments, the substrate consists of the amino acid sequence of SEQ ID NO: 87. In some embodiments, the substrate consists of the amino acid sequence of SEQ ID NO: 88. In some embodiments, the substrate consists of the amino acid sequence of SEQ ID NO: 89. In some embodiments, the substrate consists of the amino acid sequence of SEQ ID NO: 90. In some embodiments, the substrate consists of the amino acid sequence of SEQ ID NO: 91. In some embodiments, the substrate consists of the amino acid sequence of SEQ ID NO: 92. In some embodiments, the substrate consists of the amino acid sequence of SEQ ID NO: 93. In some embodiments, the substrate consists of the amino acid sequence of SEQ ID NO: 94. In some embodiments, the substrate consists of the amino acid sequence of SEQ ID NO: 95. In some embodiments, the substrate consists of the amino acid sequence of SEQ ID NO: 96. In some embodiments, the substrate consists of the amino acid sequence of SEQ ID NO: 97. In some embodiments, the substrate consists of the amino acid sequence of SEQ ID NO: 98. In some embodiments, the substrate consists of the amino acid sequence of SEQ ID NO: 99. In some embodiments, the substrate consists of the amino acid sequence of SEQ ID NO: 100. In some embodiments, the substrate consists of the amino acid sequence of SEQ ID NO: 101. In some embodiments, the substrate consists of the amino acid sequence of SEQ ID NO: 102. In some embodiments, the substrate consists of the amino acid sequence of SEQ ID NO: 103. In some embodiments, the substrate consists of the amino acid sequence of SEQ ID NO: 104. In some embodiments, the substrate consists of the amino acid sequence of SEQ ID NO: 105. In some embodiments, the substrate consists of the amino acid sequence of SEQ ID NO: 106. In some embodiments, the substrate consists of the amino acid sequence of SEQ ID NO: 107. In some embodiments, the substrate consists of the amino acid sequence of SEQ ID NO: 108. In some embodiments, the substrate consists of the amino acid sequence of SEQ ID NO: 109. In some embodiments, the substrate consists of the amino acid sequence of SEQ ID NO: 110. In some embodiments, the substrate consists of the amino acid sequence of SEQ ID NO: 111. In some embodiments, the substrate consists of the amino acid sequence of SEQ ID NO: 112. In some embodiments, the substrate consists of the amino acid sequence of SEQ ID NO: 113. In some embodiments, the substrate consists of the amino acid sequence of SEQ ID NO: 114. In some embodiments, the substrate consists of the amino acid sequence of SEQ ID NO: 115. In some embodiments, the substrate consists of the amino acid sequence of SEQ ID NO: 116. In some embodiments, the substrate consists of the amino acid sequence of SEQ ID NO: 117. In some embodiments, the substrate consists of the amino acid sequence of SEQ ID NO: 118. In some embodiments, the substrate consists of the amino acid sequence of SEQ ID NO: 119. In some embodiments, the substrate consists of the amino acid sequence of SEQ ID NO: 120. In some embodiments, the substrate consists of the amino acid sequence of SEQ ID NO: 121. In some embodiments, the substrate consists of the amino acid sequence of SEQ ID NO: 122. In some embodiments, the substrate consists of the amino acid sequence of SEQ ID NO: 123. In some embodiments, the substrate consists of the amino acid sequence of SEQ ID NO: 124. In some embodiments, the substrate consists of the amino acid sequence of SEQ ID NO: 125. In some embodiments, the substrate consists of the amino acid sequence of SEQ ID NO: 126. In some embodiments, the substrate consists of the amino acid sequence of SEQ ID NO: 127. In some embodiments, the substrate consists of the amino acid sequence of SEQ ID NO: 128. In some embodiments, the substrate consists of the amino acid sequence of SEQ ID NO: 129. In some embodiments, the substrate consists of the amino acid sequence of SEQ ID NO: 130. In some embodiments, the substrate consists of the amino acid sequence of SEQ ID NO: 131. In some embodiments, the substrate consists of the amino acid sequence of SEQ ID NO: 132. In some embodiments, the substrate consists of the amino acid sequence of SEQ ID NO: 133. In some embodiments, the substrate consists of the amino acid sequence of SEQ ID NO: 134. In some embodiments, the substrate consists of the amino acid sequence of SEQ ID NO: 135. In some embodiments, the substrate consists of the amino acid sequence of SEQ ID NO: 136. In some embodiments, the substrate consists of the amino acid sequence of SEQ ID NO: 137. In some embodiments, the substrate consists of the amino acid sequence of SEQ ID NO: 138. In some embodiments, the substrate consists of the amino acid sequence of SEQ ID NO: 139. In some embodiments, the substrate consists of the amino acid sequence of SEQ ID NO: 140. In some embodiments, the substrate consists of the amino acid sequence of SEQ ID NO: 141. In some embodiments, the substrate consists of the amino acid sequence of SEQ ID NO: 142. In some embodiments, the substrate consists of the amino acid sequence of SEQ ID NO: 143. In some embodiments, the substrate consists of the amino acid sequence of SEQ ID NO: 144. In some embodiments, the substrate consists of the amino acid sequence of SEQ ID NO: 145. In some embodiments, the substrate consists of the amino acid sequence of SEQ ID NO: 146. In some embodiments, the substrate consists of the amino acid sequence of SEQ ID NO: 147. In some embodiments, the substrate consists of the amino acid sequence of SEQ ID NO: 148. In some embodiments, the substrate consists of the amino acid sequence of SEQ ID NO: 149. In some embodiments, the substrate consists of the amino acid sequence of SEQ ID NO: 150. In some embodiments, the substrate consists of the amino acid sequence of SEQ ID NO: 151. In some embodiments, the substrate consists of the amino acid sequence of SEQ ID NO: 152. In some embodiments, the substrate consists of the amino acid sequence of SEQ ID NO: 153. In some embodiments, the substrate consists of the amino acid sequence of SEQ ID NO: 154. In some embodiments, the substrate consists of the amino acid sequence of SEQ ID NO: 155. In some embodiments, the substrate consists of the amino acid sequence of SEQ ID NO: 156. In some embodiments, the substrate consists of the amino acid sequence of SEQ ID NO: 157. In some embodiments, the substrate consists of the amino acid sequence of SEQ ID NO: 158. In some embodiments, the substrate consists of the amino acid sequence of SEQ ID NO: 159. In some embodiments, the substrate consists of the amino acid sequence of SEQ ID NO: 160. In some embodiments, the substrate consists of the amino acid sequence of SEQ ID NO: 161. In some embodiments, the substrate consists of the amino acid sequence of SEQ ID NO: 162. In some embodiments, the substrate consists of the amino acid sequence of SEQ ID NO: 163. In some embodiments, the substrate consists of the amino acid sequence of SEQ ID NO: 164. In some embodiments, the substrate consists of the amino acid sequence of SEQ ID NO: 165. In some embodiments, the substrate consists of the amino acid sequence of SEQ ID NO: 166. In some embodiments, the substrate consists of the amino acid sequence of SEQ ID NO: 167. In some embodiments, the substrate consists of the amino acid sequence of SEQ ID NO: 168. In some embodiments, the substrate consists of the amino acid sequence of SEQ ID NO: 169. In some embodiments, the substrate consists of the amino acid sequence of SEQ ID NO: 170. In some embodiments, the substrate consists of the amino acid sequence of SEQ ID NO: 171. In some embodiments, the substrate consists of the amino acid sequence of SEQ ID NO: 172. In some embodiments, the substrate consists of the amino acid sequence of SEQ ID NO: 173. In some embodiments, the substrate consists of the amino acid sequence of SEQ ID NO: 174. In some embodiments, the substrate consists of the amino acid sequence of SEQ ID NO: 175. In some embodiments, the substrate consists of the amino acid sequence of SEQ ID NO: 176. In some embodiments, the substrate consists of the amino acid sequence of SEQ ID NO: 177. In some embodiments, the substrate consists of the amino acid sequence of SEQ ID NO: 178. In some embodiments, the substrate consists of the amino acid sequence of SEQ ID NO: 179. In some embodiments, the substrate consists of the amino acid sequence of SEQ ID NO: 180. In some embodiments, the substrate consists of the amino acid sequence of SEQ ID NO: 181. In some embodiments, the substrate consists of the amino acid sequence of SEQ ID NO: 182. In some embodiments, the substrate consists of the amino acid sequence of SEQ ID NO: 183. In some embodiments, the substrate consists of the amino acid sequence of SEQ ID NO: 184. In some embodiments, the substrate consists of the amino acid sequence of SEQ ID NO: 185. In some embodiments, the substrate consists of the amino acid sequence of SEQ ID NO: 186. In some embodiments, the substrate consists of the amino acid sequence of SEQ ID NO: 187. In some embodiments, the substrate consists of the amino acid sequence of SEQ ID NO: 188. In some embodiments, the substrate consists of the amino acid sequence of SEQ ID NO: 189. In some embodiments, the substrate consists of the amino acid sequence of SEQ ID NO: 190. In some embodiments, the substrate consists of the amino acid sequence of SEQ ID NO: 191. In some embodiments, the substrate consists of the amino acid sequence of SEQ ID NO: 192. In some embodiments, the substrate consists of the amino acid sequence of SEQ ID NO: 193. In some embodiments, the substrate consists of the amino acid sequence of SEQ ID NO: 194. In some embodiments, the substrate consists of the amino acid sequence of SEQ ID NO: 195. In some embodiments, the substrate consists of the amino acid sequence of SEQ ID NO: 196. In some embodiments, the substrate consists of the amino acid sequence of SEQ ID NO: 197. In some embodiments, the substrate consists of the amino acid sequence of SEQ ID NO: 198. In some embodiments, the substrate consists of the amino acid sequence of SEQ ID NO: 199. In some embodiments, the substrate consists of the amino acid sequence of SEQ ID NO: 200. In some embodiments, the substrate consists of the amino acid sequence of SEQ ID NO: 201. In some embodiments, the substrate consists of the amino acid sequence of SEQ ID NO: 202. In some embodiments, the substrate consists of the amino acid sequence of SEQ ID NO: 203. In some embodiments, the substrate consists of the amino acid sequence of SEQ ID NO: 204. In some embodiments, the substrate consists of the amino acid sequence of SEQ ID NO: 205. In some embodiments, the substrate consists of the amino acid sequence of SEQ ID NO: 206. In some embodiments, the substrate consists of the amino acid sequence of SEQ ID NO: 207. In some embodiments, the substrate consists of the amino acid sequence of SEQ ID NO: 208. In some embodiments, the substrate consists of the amino acid sequence of SEQ ID NO: 209. In some embodiments, the substrate consists of the amino acid sequence of SEQ ID NO: 210. In some embodiments, the substrate consists of the amino acid sequence of SEQ ID NO: 211. In some embodiments, the substrate consists of the amino acid sequence of SEQ ID NO: 212. In some embodiments, the substrate consists of the amino acid sequence of SEQ ID NO: 213. In some embodiments, the substrate consists of the amino acid sequence of SEQ ID NO: 214. In some embodiments, the substrate consists of the amino acid sequence of SEQ ID NO: 215. In some embodiments, the substrate consists of the amino acid sequence of SEQ ID NO: 216. In some embodiments, the substrate consists of the amino acid sequence of SEQ ID NO: 217. In some embodiments, the substrate consists of the amino acid sequence of SEQ ID NO: 218. In some embodiments, the substrate consists of the amino acid sequence of SEQ ID NO: 219. In some embodiments, the substrate consists of the amino acid sequence of SEQ ID NO: 220. In some embodiments, the substrate consists of the amino acid sequence of SEQ ID NO: 221. In some embodiments, the substrate consists of the amino acid sequence of SEQ ID NO: 222. In some embodiments, the substrate consists of the amino acid sequence of SEQ ID NO: 223. In some embodiments, the substrate consists of the amino acid sequence of SEQ ID NO: 224. In some embodiments, the substrate consists of the amino acid sequence of SEQ ID NO: 225. In some embodiments, the substrate consists of the amino acid sequence of SEQ ID NO: 226. In some embodiments, the substrate consists of the amino acid sequence of SEQ ID NO: 227. In some embodiments, the substrate consists of the amino acid sequence of SEQ ID NO: 228. In some embodiments, the substrate consists of the amino acid sequence of SEQ ID NO: 229. In some embodiments, the substrate consists of the amino acid sequence of SEQ ID NO: 230. In some embodiments, the substrate consists of the amino acid sequence of SEQ ID NO: 231. In some embodiments, the substrate consists of the amino acid sequence of SEQ ID NO: 232. In some embodiments, the substrate consists of the amino acid sequence of SEQ ID NO: 233. In some embodiments, the substrate consists of the amino acid sequence of SEQ ID NO: 234. In some embodiments, the substrate consists of the amino acid sequence of SEQ ID NO: 235. In some embodiments, the substrate consists of the amino acid sequence of SEQ ID NO: 236. In some embodiments, the substrate consists of the amino acid sequence of SEQ ID NO: 237. In some embodiments, the substrate consists of the amino acid sequence of SEQ ID NO: 238. In some embodiments, the substrate consists of the amino acid sequence of SEQ ID NO: 239. In some embodiments, the substrate consists of the amino acid sequence of SEQ ID NO: 240. In some embodiments, the substrate consists of the amino acid sequence of SEQ ID NO: 241. In some embodiments, the substrate consists of the amino acid sequence of SEQ ID NO: 242. In some embodiments, the substrate consists of the amino acid sequence of SEQ ID NO: 243. In some embodiments, the substrate consists of the amino acid sequence of SEQ ID NO: 244. In some embodiments, the substrate consists of the amino acid sequence of SEQ ID NO: 245. In some embodiments, the substrate consists of the amino acid sequence of SEQ ID NO: 246. In some embodiments, the substrate consists of the amino acid sequence of SEQ ID NO: 247. In some embodiments, the substrate consists of the amino acid sequence of SEQ ID NO: 248. In some embodiments, the substrate consists of the amino acid sequence of SEQ ID NO: 249. In some embodiments, the substrate consists of the amino acid sequence of SEQ ID NO: 250. In some embodiments, the substrate consists of the amino acid sequence of SEQ ID NO: 251. In some embodiments, the substrate consists of the amino acid sequence of SEQ ID NO: 252. In some embodiments, the substrate consists of the amino acid sequence of SEQ ID NO: 253. In some embodiments, the substrate consists of the amino acid sequence of SEQ ID NO: 254. In some embodiments, the substrate consists of the amino acid sequence of SEQ ID NO: 255. In some embodiments, the substrate consists of the amino acid sequence of SEQ ID NO: 256. In some embodiments, the substrate consists of the amino acid sequence of SEQ ID NO: 257. In some embodiments, the substrate consists of the amino acid sequence of SEQ ID NO: 258. In some embodiments, the substrate consists of the amino acid sequence of SEQ ID NO: 259. In some embodiments, the substrate consists of the amino acid sequence of SEQ ID NO: 260. In some embodiments, the substrate consists of the amino acid sequence of SEQ ID NO: 261. In some embodiments, the substrate consists of the amino acid sequence of SEQ ID NO: 262. In some embodiments, the substrate consists of the amino acid sequence of SEQ ID NO: 263. In some embodiments, the substrate consists of the amino acid sequence of SEQ ID NO: 264. In some embodiments, the substrate consists of the amino acid sequence of SEQ ID NO: 265. In some embodiments, the substrate consists of the amino acid sequence of SEQ ID NO: 266. In some embodiments, the substrate consists of the amino acid sequence of SEQ ID NO: 267. In some embodiments, the substrate consists of the amino acid sequence of SEQ ID NO: 268. In some embodiments, the substrate consists of the amino acid sequence of SEQ ID NO: 269. In some embodiments, the substrate consists of the amino acid sequence of SEQ ID NO: 270. In some embodiments, the substrate consists of the amino acid sequence of SEQ ID NO: 271. In some embodiments, the substrate consists of the amino acid sequence of SEQ ID NO: 272. In some embodiments, the substrate consists of the amino acid sequence of SEQ ID NO: 273. In some embodiments, the substrate consists of the amino acid sequence of SEQ ID NO: 274. In some embodiments, the substrate consists of the amino acid sequence of SEQ ID NO: 275. In some embodiments, the substrate consists of the amino acid sequence of SEQ ID NO: 276. In some embodiments, the substrate consists of the amino acid sequence of SEQ ID NO: 277. In some embodiments, the substrate consists of the amino acid sequence of SEQ ID NO: 278. In some embodiments, the substrate consists of the amino acid sequence of SEQ ID NO: 279. In some embodiments, the substrate consists of the amino acid sequence of SEQ ID NO: 280. In some embodiments, the substrate consists of the amino acid sequence of SEQ ID NO: 281. In some embodiments, the substrate consists of the amino acid sequence of SEQ ID NO: 282. In some embodiments, the substrate consists of the amino acid sequence of SEQ ID NO: 283. In some embodiments, the substrate consists of the amino acid sequence of SEQ ID NO: 284. In some embodiments, the substrate consists of the amino acid sequence of SEQ ID NO: 285. In some embodiments, the substrate consists of the amino acid sequence of SEQ ID NO: 286. In some embodiments, the substrate consists of the amino acid sequence of SEQ ID NO: 287. In some embodiments, the substrate consists of the amino acid sequence of SEQ ID NO: 288. In some embodiments, the substrate consists of the amino acid sequence of SEQ ID NO: 289. In some embodiments, the substrate consists of the amino acid sequence of SEQ ID NO: 290. In some embodiments, the substrate consists of the amino acid sequence of SEQ ID NO: 291. In some embodiments, the substrate consists of the amino acid sequence of SEQ ID NO: 292. In some embodiments, the substrate consists of the amino acid sequence of SEQ ID NO: 293. In some embodiments, the substrate consists of the amino acid sequence of SEQ ID NO: 294. In some embodiments, the substrate consists of the amino acid sequence of SEQ ID NO: 295. In some embodiments, the substrate consists of the amino acid sequence of SEQ ID NO: 296. In some embodiments, the substrate consists of the amino acid sequence of SEQ ID NO: 297. In some embodiments, the substrate consists of the amino acid sequence of SEQ ID NO: 298. In some embodiments, the substrate consists of the amino acid sequence of SEQ ID NO: 299. In some embodiments, the substrate consists of the amino acid sequence of SEQ ID NO: 300. In some embodiments, the substrate consists of the amino acid sequence of SEQ ID NO: 301. In some embodiments, the substrate consists of the amino acid sequence of SEQ ID NO: 302. In some embodiments, the substrate consists of the amino acid sequence of SEQ ID NO: 303. In some embodiments, the substrate consists of the amino acid sequence of SEQ ID NO: 304. In some embodiments, the substrate consists of the amino acid sequence of SEQ ID NO: 305. In some embodiments, the substrate consists of the amino acid sequence of SEQ ID NO: 306. In some embodiments, the substrate consists of the amino acid sequence of SEQ ID NO: 307. In some embodiments, the substrate consists of the amino acid sequence of SEQ ID NO: 308. In some embodiments, the substrate consists of the amino acid sequence of SEQ ID NO: 309. In some embodiments, the substrate consists of the amino acid sequence of SEQ ID NO: 310. In some embodiments, the substrate consists of the amino acid sequence of SEQ ID NO: 311. In some embodiments, the substrate consists of the amino acid sequence of SEQ ID NO: 312. In some embodiments, the substrate consists of the amino acid sequence of SEQ ID NO: 313. In some embodiments, the substrate consists of the amino acid sequence of SEQ ID NO: 314. In some embodiments, the substrate consists of the amino acid sequence of SEQ ID NO: 315. In some embodiments, the substrate consists of the amino acid sequence of SEQ ID NO: 316. In some embodiments, the substrate consists of the amino acid sequence of SEQ ID NO: 317. In some embodiments, the substrate consists of the amino acid sequence of SEQ ID NO: 318. In some embodiments, the substrate consists of the amino acid sequence of SEQ ID NO: 319. In some embodiments, the substrate consists of the amino acid sequence of SEQ ID NO: 320. In some embodiments, the substrate consists of the amino acid sequence of SEQ ID NO: 321. In some embodiments, the substrate consists of the amino acid sequence of SEQ ID NO: 322. In some embodiments, the substrate consists of the amino acid sequence of SEQ ID NO: 323. In some embodiments, the substrate consists of the amino acid sequence of SEQ ID NO: 324. In some embodiments, the substrate consists of the amino acid sequence of SEQ ID NO: 325. In some embodiments, the substrate consists of the amino acid sequence of SEQ ID NO: 326. In some embodiments, the substrate consists of the amino acid sequence of SEQ ID NO: 327. In some embodiments, the substrate consists of the amino acid sequence of SEQ ID NO: 328. In some embodiments, the substrate consists of the amino acid sequence of SEQ ID NO: 329. In some embodiments, the substrate consists of the amino acid sequence of SEQ ID NO: 330. In some embodiments, the substrate consists of the amino acid sequence of SEQ ID NO: 331. In some embodiments, the substrate consists of the amino acid sequence of SEQ ID NO: 332. In some embodiments, the substrate consists of the amino acid sequence of SEQ ID NO: 333. In some embodiments, the substrate consists of the amino acid sequence of SEQ ID NO: 334. In some embodiments, the substrate consists of the amino acid sequence of SEQ ID NO: 335. In some embodiments, the substrate consists of the amino acid sequence of SEQ ID NO: 336. In some embodiments, the substrate consists of the amino acid sequence of SEQ ID NO: 337. In some embodiments, the substrate consists of the amino acid sequence of SEQ ID NO: 338. In some embodiments, the substrate consists of the amino acid sequence of SEQ ID NO: 339. In some embodiments, the substrate consists of the amino acid sequence of SEQ ID NO: 340. In some embodiments, the substrate consists of the amino acid sequence of SEQ ID NO: 341. In some embodiments, the substrate consists of the amino acid sequence of SEQ ID NO: 342. In some embodiments, the substrate consists of the amino acid sequence of SEQ ID NO: 343. In some embodiments, the substrate consists of the amino acid sequence of SEQ ID NO: 344. In some embodiments, the substrate consists of the amino acid sequence of SEQ ID NO: 345. In some embodiments, the substrate consists of the amino acid sequence of SEQ ID NO: 346. In some embodiments, the substrate consists of the amino acid sequence of SEQ ID NO: 347. In some embodiments, the substrate consists of the amino acid sequence of SEQ ID NO: 348. In some embodiments, the substrate consists of the amino acid sequence of SEQ ID NO: 349. In some embodiments, the substrate consists of the amino acid sequence of SEQ ID NO: 350. In some embodiments, the substrate consists of the amino acid sequence of SEQ ID NO: 351. In some embodiments, the substrate consists of the amino acid sequence of SEQ ID NO: 352. In some embodiments, the substrate consists of the amino acid sequence of SEQ ID NO: 353. In some embodiments, the substrate consists of the amino acid sequence of SEQ ID NO: 382. In some embodiments, the substrate consists of the amino acid sequence of SEQ ID NO: 383. In some embodiments, the substrate consists of the amino acid sequence of SEQ ID NO: 384. In some embodiments, the substrate consists of the amino acid sequence of SEQ ID NO: 385. In some embodiments, the substrate consists of the amino acid sequence of SEQ ID NO: 560. In some embodiments, the substrate consists of the amino acid sequence of SEQ ID NO: 561. In some embodiments, the substrate consists of the amino acid sequence of SEQ ID NO: 562. In some embodiments, the substrate consists of the amino acid sequence of SEQ ID NO: 563. In some embodiments, the substrate consists of the amino acid sequence of SEQ ID NO: 564. In some embodiments, the substrate consists of the amino acid sequence of SEQ ID NO: 565. In some embodiments, the substrate consists of the amino acid sequence of SEQ ID NO: 566. In some embodiments, the substrate consists of the amino acid sequence of SEQ ID NO: 567. In some embodiments, the substrate consists of the amino acid sequence of SEQ ID NO: 568. In some embodiments, the substrate consists of the amino acid sequence of SEQ ID NO: 569. In some embodiments, the substrate consists of the amino acid sequence of SEQ ID NO: 570. In some embodiments, the substrate consists of the amino acid sequence of SEQ ID NO: 571. In some embodiments, the substrate consists of the amino acid sequence of SEQ ID NO: 572. In some embodiments, the substrate consists of the amino acid sequence of SEQ ID NO: 573. In some embodiments, the substrate consists of the amino acid sequence of SEQ ID NO: 574. In some embodiments, the substrate consists of the amino acid sequence of SEQ ID NO: 575. In some embodiments, the substrate consists of the amino acid sequence of SEQ ID NO: 576. In some embodiments, the substrate consists of the amino acid sequence of SEQ ID NO: 577. In some embodiments, the substrate consists of the amino acid sequence of SEQ ID NO: 578. In some embodiments, the substrate consists of the amino acid sequence of SEQ ID NO: 579. In some embodiments, the substrate consists of the amino acid sequence of SEQ ID NO: 580. In some embodiments, the substrate consists of the amino acid sequence of SEQ ID NO: 581. In some embodiments, the substrate consists of the amino acid sequence of SEQ ID NO: 582. In some embodiments, the substrate consists of the amino acid sequence of SEQ ID NO: 583. In some embodiments, the substrate consists of the amino acid sequence of SEQ ID NO: 584. In some embodiments, the substrate consists of the amino acid sequence of SEQ ID NO: 585. In some embodiments, the substrate consists of the amino acid sequence of SEQ ID NO: 586. In some embodiments, the substrate consists of the amino acid sequence of SEQ ID NO: 587. In some embodiments, the substrate consists of the amino acid sequence of SEQ ID NO: 588. In some embodiments, the substrate consists of the amino acid sequence of SEQ ID NO: 589. In some embodiments, the substrate consists of the amino acid sequence of SEQ ID NO: 590. In some embodiments, the substrate consists of the amino acid sequence of SEQ ID NO: 591. In some embodiments, the substrate consists of the amino acid sequence of SEQ ID NO: 592. In some embodiments, the substrate consists of the amino acid sequence of SEQ ID NO: 593. In some embodiments, the substrate consists of the amino acid sequence of SEQ ID NO: 594. In some embodiments, the substrate consists of the amino acid sequence of SEQ ID NO: 595. In some embodiments, the substrate consists of the amino acid sequence of SEQ ID NO: 596. In some embodiments, the substrate consists of the amino acid sequence of SEQ ID NO: 597. In some embodiments, the substrate consists of the amino acid sequence of SEQ ID NO: 598. In some embodiments, the substrate consists of the amino acid sequence of SEQ ID NO: 599. In some embodiments, the substrate consists of the amino acid sequence of SEQ ID NO: 600. In some embodiments, the substrate consists of the amino acid sequence of SEQ ID NO: 601. In some embodiments, the substrate consists of the amino acid sequence of SEQ ID NO: 602. In some embodiments, the substrate consists of the amino acid sequence of SEQ ID NO: 603. In some embodiments, the substrate consists of the amino acid sequence of SEQ ID NO: 604. In some embodiments, the substrate consists of the amino acid sequence of SEQ ID NO: 605. In some embodiments, the substrate consists of the amino acid sequence of SEQ ID NO: 606. In some embodiments, the substrate consists of the amino acid sequence of SEQ ID NO: 607. In some embodiments, the substrate consists of the amino acid sequence of SEQ ID NO: 608. In some embodiments, the substrate consists of the amino acid sequence of SEQ ID NO: 609. In some embodiments, the substrate consists of the amino acid sequence of SEQ ID NO: 610. In some embodiments, the substrate consists of the amino acid sequence of SEQ ID NO: 611. In some embodiments, the substrate consists of the amino acid sequence of SEQ ID NO: 612. In some embodiments, the substrate consists of the amino acid sequence of SEQ ID NO: 613. In some embodiments, the substrate consists of the amino acid sequence of SEQ ID NO: 614. In some embodiments, the substrate consists of the amino acid sequence of SEQ ID NO: 615. In some embodiments, the substrate consists of the amino acid sequence of SEQ ID NO: 616. In some embodiments, the substrate consists of the amino acid sequence of SEQ ID NO: 617. In some embodiments, the substrate consists of the amino acid sequence of SEQ ID NO: 618. In some embodiments, the substrate consists of the amino acid sequence of SEQ ID NO: 619. In some embodiments, the substrate consists of the amino acid sequence of SEQ ID NO: 620. In some embodiments, the substrate consists of the amino acid sequence of SEQ ID NO: 621. In some embodiments, the substrate consists of the amino acid sequence of SEQ ID NO: 622. In some embodiments, the substrate consists of the amino acid sequence of SEQ ID NO: 623. In some embodiments, the substrate consists of the amino acid sequence of SEQ ID NO: 624. In some embodiments, the substrate consists of the amino acid sequence of SEQ ID NO: 625. In some embodiments, the substrate consists of the amino acid sequence of SEQ ID NO: 626. In some embodiments, the substrate consists of the amino acid sequence of SEQ ID NO: 627. In some embodiments, the substrate consists of the amino acid sequence of SEQ ID NO: 628. In some embodiments, the substrate consists of the amino acid sequence of SEQ ID NO: 629. In some embodiments, the substrate consists of the amino acid sequence of SEQ ID NO: 630. In some embodiments, the substrate consists of the amino acid sequence of SEQ ID NO: 631. In some embodiments, the substrate consists of the amino acid sequence of SEQ ID NO: 632. In some embodiments, the substrate consists of the amino acid sequence of SEQ ID NO: 633. In some embodiments, the substrate consists of the amino acid sequence of SEQ ID NO: 634. In some embodiments, the substrate consists of the amino acid sequence of SEQ ID NO: 635. In some embodiments, the substrate consists of the amino acid sequence of SEQ ID NO: 636. In some embodiments, the substrate consists of the amino acid sequence of SEQ ID NO: 637. In some embodiments, the substrate consists of the amino acid sequence of SEQ ID NO: 638. In some embodiments, the substrate consists of the amino acid sequence of SEQ ID NO: 639. In some embodiments, the substrate consists of the amino acid sequence of SEQ ID NO: 640. In some embodiments, the substrate consists of the amino acid sequence of SEQ ID NO: 641. In some embodiments, the substrate consists of the amino acid sequence of SEQ ID NO: 642. In some embodiments, the substrate consists of the amino acid sequence of SEQ ID NO: 643. In some embodiments, the substrate consists of the amino acid sequence of SEQ ID NO: 644. In some embodiments, the substrate consists of the amino acid sequence of SEQ ID NO: 645. In some embodiments, the substrate consists of the amino acid sequence of SEQ ID NO: 646. In some embodiments, the substrate consists of the amino acid sequence of SEQ ID NO: 647. In some embodiments, the substrate consists of the amino acid sequence of SEQ ID NO: 648. In some embodiments, the substrate consists of the amino acid sequence of SEQ ID NO: 649. In some embodiments, the substrate consists of the amino acid sequence of SEQ ID NO: 650. In some embodiments, the substrate consists of the amino acid sequence of SEQ ID NO: 651. In some embodiments, the substrate consists of the amino acid sequence of SEQ ID NO: 652. In some embodiments, the substrate consists of the amino acid sequence of SEQ ID NO: 653. In some embodiments, the substrate consists of the amino acid sequence of SEQ ID NO: 654. In some embodiments, the substrate consists of the amino acid sequence of SEQ ID NO: 655. In some embodiments, the substrate consists of the amino acid sequence of SEQ ID NO: 656. In some embodiments, the substrate consists of the amino acid sequence of SEQ ID NO: 657. In some embodiments, the substrate consists of the amino acid sequence of SEQ ID NO: 658. In some embodiments, the substrate consists of the amino acid sequence of SEQ ID NO: 659. In some embodiments, the substrate consists of the amino acid sequence of SEQ ID NO: 660. In some embodiments, the substrate consists of the amino acid sequence of SEQ ID NO: 661. In some embodiments, the substrate consists of the amino acid sequence of SEQ ID NO: 662. In some embodiments, the substrate consists of the amino acid sequence of SEQ ID NO: 663. In some embodiments, the substrate consists of the amino acid sequence of SEQ ID NO: 664. In some embodiments, the substrate consists of the amino acid sequence of SEQ ID NO: 665. In some embodiments, the substrate consists of the amino acid sequence of SEQ ID NO: 666. In some embodiments, the substrate consists of the amino acid sequence of SEQ ID NO: 667. In some embodiments, the substrate consists of the amino acid sequence of SEQ ID NO: 668. In some embodiments, the substrate consists of the amino acid sequence of SEQ ID NO: 669. In some embodiments, the substrate consists of the amino acid sequence of SEQ ID NO: 670. In some embodiments, the substrate consists of the amino acid sequence of SEQ ID NO: 671. In some embodiments, the substrate consists of the amino acid sequence of SEQ ID NO: 672. In some embodiments, the substrate consists of the amino acid sequence of SEQ ID NO: 673. In some embodiments, the substrate consists of the amino acid sequence of SEQ ID NO: 674. In some embodiments, the substrate consists of the amino acid sequence of SEQ ID NO: 675. In some embodiments, the substrate consists of the amino acid sequence of SEQ ID NO: 676. In some embodiments, the substrate consists of the amino acid sequence of SEQ ID NO: 677. In some embodiments, the substrate consists of the amino acid sequence of SEQ ID NO: 678. In some embodiments, the substrate consists of the amino acid sequence of SEQ ID NO: 679. In some embodiments, the substrate consists of the amino acid sequence of SEQ ID NO: 680. In some embodiments, the substrate consists of the amino acid sequence of SEQ ID NO: 681. In some embodiments, the substrate consists of the amino acid sequence of SEQ ID NO: 682. In some embodiments, the substrate consists of the amino acid sequence of SEQ ID NO: 683. In some embodiments, the substrate consists of the amino acid sequence of SEQ ID NO: 684. In some embodiments, the substrate consists of the amino acid sequence of SEQ ID NO: 685. In some embodiments, the substrate consists of the amino acid sequence of SEQ ID NO: 686. In some embodiments, the substrate consists of the amino acid sequence of SEQ ID NO: 687. In some embodiments, the substrate consists of the amino acid sequence of SEQ ID NO: 688. In some embodiments, the substrate consists of the amino acid sequence of SEQ ID NO: 689. In some embodiments, the substrate consists of the amino acid sequence of SEQ ID NO: 690. In some embodiments, the substrate consists of the amino acid sequence of SEQ ID NO: 691. In some embodiments, the substrate consists of the amino acid sequence of SEQ ID NO: 692. In some embodiments, the substrate consists of the amino acid sequence of SEQ ID NO: 693. In some embodiments, the substrate consists of the amino acid sequence of SEQ ID NO: 694. In some embodiments, the substrate consists of the amino acid sequence of SEQ ID NO: 695.

In some embodiments, the substrate comprises a combination, a C-terminal truncation variant, a C-terminal extension variant, an N-terminal truncation variant, or an N-terminal extension variant of the amino acid sequences of any one of SEQ ID NOs: 9-24, 37-73, 83-353, 382-385, and 560-695. In some embodiments, the substrate comprises a combination, a C-terminal truncation variant, a C-terminal extension variant, an N-terminal truncation variant, or an N-terminal extension variant of the amino acid sequences of any one of SEQ ID NOs: 9-24, 37-73, 83-353, 382-385, and 560-683. Truncation variants of the aforementioned amino acid sequences that are suitable for use in a substrate may be any that retain the recognition site for the corresponding protease. In certain embodiments, the truncation variant comprises a C-terminal deletion and/or an N-terminal deletion of one amino acid residue from an amino acid sequence selected from the group consisting of SEQ ID NOS: 9-24, 37-73, 83-353, 382-385, and 560-695. These include C-terminal and/or N-terminal truncation variants comprising at least 1, 2, 3, 4, 5, or more contiguous amino acids of the above-described amino acid sequences that retain a recognition site for a protease. In certain embodiments, the truncation variant comprises a C-terminal deletion and/or an N-terminal deletion of one amino acid residue from an amino acid sequence selected from the group consisting of SEQ ID NOs: 9-24, 37-73, 83-353, 382-385, and 560-683. Extension variants of the aforementioned amino acid sequences that are suitable for use in a substrate may be any that have one or more (e.g., 1, 2, 3, 4, 5 or more) additional amino acids and retain the recognition site for the corresponding protease. In some examples, the additional amino acids are coupled to the C-terminus of the aforementioned amino acid sequences. In some examples, the additional amino acids are coupled to the N-terminus of the aforementioned amino acid sequences. In some examples, the extension variants may comprise additional amino acids coupled to both the C-terminus and the N-terminus of the aforementioned amino acid sequences. In some instances, the C-terminus or N-terminus extension variants can have a C-terminal glycine or an N-terminal serine amino acid.

In some embodiments, the substrate comprises one, two, three, four, five, six or more amino acids in addition to the amino acid sequence of any one of SEQ ID NOs: 9-24, 37-73, 83-353, 382-385, and 560-695. In some embodiments, the substrate comprises one, two, three, four, five, six or more amino acids in addition to the amino acid sequence of any one of SEQ ID NOs: 9-24, 37-73, 83-353, 382-385, and 560-683. In some examples, the substrate comprises one, two, three, four, five, six or more additional amino acids at the N-terminus of the amino acid sequence of any one of SEQ ID NOs: 9-24, 37-73, 83-353, 382-385, and 560-695. In some examples, the substrate comprises one, two, three, four, five, six or more additional amino acids at the N-terminus of the amino acid sequence of any one of SEQ ID NOs: 9-24, 37-73, 83-353, 382-385, and 560-683. In some examples, the substrate comprises one, two, three, four, five, six or more additional amino acids at the C-terminus of the amino acid sequence of any one of SEQ ID NOs: 9-24, 37-73, 83-353, 382-385, and 560-695. In some examples, the substrate comprises one, two, three, four, five, six or more additional amino acids at the C-terminus of the amino acid sequence of any one of SEQ ID NOs: 9-24, 37-73, 83-353, 382-385, and 560-683. In some examples, the substrate comprises one, two, three, four, five, six or more additional amino acids at the N-terminus, and one, two, three, four, five, six or more additional amino acids at the C-terminus of the amino acid sequence of any one of SEQ ID NOs: 9-24, 37-73, 83-353, 382-385, and 560-695. In some examples, the substrate comprises one, two, three, four, five, six or more additional amino acids at the N-terminus, and one, two, three, four, five, six or more additional amino acids at the C-terminus of the amino acid sequence of any one of SEQ ID NOs: 9-24, 37-73, 83-353, 382-385, and 560-683.

In some embodiments, the substrate comprises a sequence with mutation(s) of one or more amino acid of the amino acid sequence of any one of SEQ ID NOs: 9-24, 37-73, 83-353, 382-385, and 560-695. In some embodiments, the substrate comprises a sequence with mutation(s) of one or more amino acid of the amino acid sequence of any one of SEQ ID NOs: 9-24, 37-73, 83-353, 382-385, and 560-683. For example, the substrate comprises a sequence with one-amino acid, two-amino acid, three-amino acid, four-amino acid, or five-amino acid mutations of the amino acid sequence of any one of SEQ ID NOs: 9-24, 37-73, 83-353, 382-385, and 560-695. For example, the substrate comprises a sequence with one-amino acid, two-amino acid, three-amino acid, four-amino acid, or five-amino acid mutations of the amino acid sequence of any one of SEQ ID NOs: 9-24, 37-73, 83-353, 382-385, and 560-683. In some embodiments, the substrate comprises an amino acid sequence selected from the group consisting of SEQ ID NOs: 9-24, 37-73, 83-353, 382-385, and 560-695 and having one conservative substitution. In some embodiments, the substrate comprises an amino acid sequence selected from the group consisting of SEQ ID NOs: 9-24, 37-73, 83-353, 382-385, and 560-683 and having one conservative substitution.

In some embodiments, the substrate consists of a sequence with mutation(s) of one or more amino acid of the amino acid sequence of any one of SEQ ID NOs: 9-24, 37-73, 83-353, 382-385, and 560-695. In some embodiments, the substrate consists of a sequence with mutation(s) of one or more amino acid of the amino acid sequence of any one of SEQ ID NOs: 9-24, 37-73, 83-353, 382-385, and 560-683. For example, the substrate consists of a sequence with one-amino acid, two-amino acid, three-amino acid, four-amino acid, or five-amino acid mutation(s) of the amino acid sequence of any one of SEQ ID NOs: 9-24, 37-73, 83-353, 382-385, and 560-695. For example, the substrate consists of a sequence with one-amino acid, two-amino acid, three-amino acid, four-amino acid, or five-amino acid mutation(s) of the amino acid sequence of any one of SEQ ID NOs: 9-24, 37-73, 83-353, 382-385, and 560-683.

In some embodiments, the substrate comprises a total of 3 amino acids to 25 amino acids. For example, the substrate may comprise a total of 3 to 25, 3 to 20, 3 to 15, 3 to 10, 3 to 5, 5 to 25, 5 to 20, 5 to 15, 5 to 10, 10 to 25, 10 to 20, 10 to 15, 15 to 25, 15 to 20, or 20 to 25 amino acids. In some embodiments, the substrate consists of a total of 3 amino acids to 25 amino acids. For example, the substrate may consist of a total of 3 to 25, 3 to 20, 3 to 15, 3 to 10, 3 to 5, 5 to 25, 5 to 20, 5 to 15, 5 to 10, 10 to 25, 10 to 20, 10 to 15, 15 to 25, 15 to 20, or 20 to 25 amino acids.

The substrate may be specifically cleaved by one or more protease (e.g., by MT-SP1 and/or MMP) at a desired rate. The rate may be measured as substrate cleavage kinetics ($k_{cat}/K_M$) as disclosed in WO2016118629, which is incorporated by reference in its entirety. In brief, $k_{cat}$ is the turnover number and describes how many substrate molecules are transformed into products per unit time by a protease. The $K_M$ value describes the affinity of the substrate to the active site of the protease. The $k_{cat}/K_M$ ratio provides a measurement of cleavability of the substrate by the protease. In general, the greater the ratio, the higher the rate of cleavability is; conversely, the lower the ratio, the slower the rate of cleavability is. The $k_{cat}/K_M$ values may be determined with the following equation $$\frac{k_{cat}}{K_M} = -\ln(1 - C)/(t * p)$$

where C is product conversion, t is time(s), and p is protease concentration (M), which assumes that the substrate concentration is below the $K_M$ and in excess of the protease concentration.

In some embodiments, the substrate is cleaved by MT-SP1 at a rate that has a $k_{cat}/K_M$ value from $1 \times 10$ to $1 \times 10^6$ $M^{-1}$ $s^{-1}$, e.g., from $1 \times 10$ to $5 \times 10$, from $5 \times 10$ to $1 \times 10^2$, from $1 \times 10^2$ to $5 \times 10^2$, from $5 \times 10^2$ to $1 \times 10^3$, from $1 \times 10^3$ to $5 \times 10^3$, from $5 \times 10^3$ to $1 \times 10^4$, from $1 \times 10^4$ to $5 \times 10^4$, from $5 \times 10^4$ to $1 \times 10^5$, from $1 \times 10^5$ to $5 \times 10^5$, or from $5 \times 10^5$ to $1 \times 10^6$ $M^{-1}$ $s^{-1}$. In some embodiments, the substrate is cleaved by MT-SP1 at a rate that has a $k_{cat}/K_M$ value of at least $1\times10$, at least $5\times10$, at least $1\times10^2$, at least $5\times10^2$, at least $1\times10^3$, $5\times10^3$, at least $1\times10^4$, at least $5\times10^4$, at least $1\times10^5$, at least $5\times10^5$, or at least $1\times10^6$ $M^{-1}$ $s^{-1}$.

In some embodiments, the substrate is cleaved by an MMP at a rate that has a $k_{cat}/K_M$ value from $1\times10$ to $1\times10^6$ $M^{-1}$ $s^{-1}$, e.g., from $1\times10$ to $5\times10$, from $5\times10$ to $1\times10^2$, from $1\times10^2$ to $5\times10^2$, from $5\times10^2$ to $1\times10^3$, from $1\times10^3$ to $5\times10^3$, from $5\times10^3$ to $1\times10^4$, from $1\times10^4$ to $5\times10^4$, from $5\times10^4$ to $1\times10^5$, from $1\times10^5$ to $5\times10^5$, or from $5\times10^5$ to $1\times10^6$ $M^{-1}$ $s^{-1}$. In some embodiments, the substrate is cleaved by an MMP at a rate that has a $k_{cat}/K_M$ value of at least $1\times10$, at least $5\times10$, at least $1\times10^2$, at least $5\times10^2$, at least $1\times10^3$, $5\times10^3$, at least $1\times10^4$, at least $5\times10^4$, at least $1\times10^5$, at least $5\times10^5$, or at least $1\times10^6$ $M^{-1}$ $s^{-1}$.

In some embodiments, the substrate is cleaved by MMP2 at a rate that has a $k_{cat}/K_M$ value from $1\times10$ to $1\times10^6$ $M^{-1}$ $s^{-1}$, e.g., from $1\times10$ to $5\times10$, from $5\times10$ to $1\times10^2$, from $1\times10^2$ to $5\times10^2$, from $5\times10^2$ to $1\times10^3$, from $1\times10^3$ to $5\times10^3$, from $5\times10^3$ to $1\times10^4$, from $1\times10^4$ to $5\times10^4$, from $5\times10^4$ to $1\times10^5$, from $1\times10^5$ to $5\times10^5$, or from $5\times10^5$ to $1\times10^6$ $M^{-1}$ $s^{-1}$. In some embodiments, the substrate is cleaved by MMP2 at a rate that has a $k_{cat}/K_M$ value of at least $1\times10$, at least $5\times10$, at least $1\times10^2$, at least $5\times10^2$, at least $1\times10^3$, $5\times10^3$, at least $1\times10^4$, at least $5\times10^4$, at least $1\times10^5$, at least $5\times10^5$, or at least $1\times10^6$ $M^{-1}$ $s^{-1}$.

In some embodiments, the substrate is cleaved by MMP9 at a rate that has a $k_{cat}/K_M$ value from $1\times10$ to $1\times10^6$ $M^{-1}$ $s^{-1}$, e.g., from $1\times10$ to $5\times10$, from $5\times10$ to $1\times10^2$, from $1\times10^2$ to $5\times10^2$, from $5\times10^2$ to $1\times10^3$, from $1\times10^3$ to $5\times10^3$, from $5\times10^3$ to $1\times10^4$, from $1\times10^4$ to $5\times10^4$, from $5\times10^4$ to $1\times10^5$, from $1\times10^5$ to $5\times10^5$, or from $5\times10^5$ to $1\times10^6$ $M^{-1}$ $s^{-1}$. In some embodiments, the substrate is cleaved by MMP9 at a rate that has a $k_{cat}/K_M$ value of at least $1\times10$, at least $5\times10$, at least $1\times10^2$, at least $5\times10^2$, at least $1\times10^3$, $5\times10^3$, at least $1\times10^4$, at least $5\times10^4$, at least $1\times10^5$, at least $5\times10^5$, or at least $1\times10^6$ $M^{-1}$ $s^{-1}$.

In some embodiments, the substrate is cleaved by MMP14 at a rate that has a $K_{cat}/K_M$ value from $1\times10$ to $1\times10^6$ $M^{-1}$ $s^{-1}$, e.g., from $1\times10$ to $5\times10$, from $5\times10$ to $1\times10^2$, from $1\times10^2$ to $5\times10^2$, from $5\times10^2$ to $1\times10^3$, from $1\times10^3$ to $5\times10^3$, from $5\times10^3$ to $1\times10^4$, from $1\times10^4$ to $5\times10^4$, from $5\times10^4$ to $1\times10^5$, from $1\times10^5$ to $5\times10^5$, or from $5\times10^5$ to $1\times10^6$ $M^{-1}$ $s^{-1}$. In some embodiments, the substrate is cleaved by MMP14 at a rate that has a $k_{cat}/K_M$ value of at least $1\times10$, at least $5\times10$, at least $1\times10^2$, at least $5\times10^2$, at least $1\times10^3$, $5\times10^3$, at least $1\times10^4$, at least $5\times10^4$, at least $1\times10^5$, at least $5\times10^5$, or at least $1\times10^6$ $M^{-1}$ $s^{-1}$.

In some embodiments, the substrate is cleaved by a protease in a bone marrow tissue, e.g., in a bone marrow aspirate, at a rate that has a $k_{cat}/K_M$ value from $1\times10$ to $1\times10^6$ $M^{-1}$ $s^{-1}$, e.g., from $1\times10$ to $5\times10$, from $5\times10$ to $1\times10^2$, from $1\times10^2$ to $5\times10^2$, from $5\times10^2$ to $1\times10^3$, from $1\times10^3$ to $5\times10^3$, from $5\times10^3$ to $1\times10^4$, from $1\times10^4$ to $5\times10^4$, from $5\times10^4$ to $1\times10^5$, from $1\times10^5$ to $5\times10^5$, or from $5\times10^5$ to $1\times10^6$ $M^{-1}$ $s^{-1}$. In some embodiments, the substrate is cleaved by a protease in bone marrow tissue e.g. in a bone marrow aspirate at a rate that has a $k_{cat}/K_M$ value of at least $1\times10$, at least $5\times10$, at least $1\times10^2$, at least $5\times10^2$, at least $1\times10^3$, $5\times10^3$, at least $1\times10^4$, at least $5\times10^4$, at least $1\times10^5$, at least $5\times10^5$, or at least $1\times10^6$ $M^{-1}$ $s^{-1}$.

In some embodiments, the cleavability of the substrates are presented as the percentage of the fraction of cleaved substrates (or polypeptides comprising the substrates), e.g., as determined in a capillary electrophoresis assay described Example 2. In some examples, the cleavability of the substrate by a protease is at least 50%, at least 60%, at least 70%, at least 80%, at least 90%, or at least 95%, or 100%, when 500 nM activatable antibody c225 containing a prodomain with the substrate being tested was incubated with 10 nM of a protease for 1.5 hours or 4 hours at 37° C. In some examples, the cleavability of the substrate by MT-SP1 is at least 50%, at least 60%, at least 70%, at least 80%, at least 90%, or at least 95%, or 100%, when 500 nM activatable antibody c225 containing a prodomain with the substrate being tested was incubated with 10 nM of MT-SP1 for 1.5 hours or 4 hours at 37° C. In some examples, the cleavability of the substrate by an MMP is at least 50%, at least 60%, at least 70%, at least 80%, at least 90%, or at least 95%, or 100% when 500 nM activatable antibody c225 containing a prodomain with the substrate being tested was incubated with 10 nM of MMP for 1.5 hours at 37° C. In some examples, the cleavability of the substrate by MMP2 is at least 50%, at least 60%, at least 70%, at least 80%, at least 90%, or at least 95%, or 100%, when 500 nM activatable antibody c225 containing a prodomain with the substrate being tested was incubated with 10 nM of MMP2 for 1.5 hours at 37° C. In some examples, the cleavability of the substrate by MMP9 is at least 50%, at least 60%, at least 70%, at least 80%, at least 90%, or at least 95%, or 100%, when 500 nM activatable antibody c225 containing a prodomain with the substrate being tested was incubated with 10 nM of MMP9 for 1.5 hours at 37° C. In some examples, the cleavability of the substrate by MMP14 is at least 50%, at least 60%, at least 70%, at least 80%, at least 90%, or at least 95%, or 100%, when 500 nM activatable antibody c225 containing a prodomain with the substrate being tested was incubated with 10 nM of MMP14 for 1.5 hours at 37° C. In some examples, the cleavability of the substrate by a protease in a bone marrow tissue (e.g., a bone marrow aspirate) is at least 50%, at least 60%, at least 70%, at least 80%, at least 90%, or at least 95%, or 100%, when incubated with a bone marrow tissue (e.g., a bone marrow aspirate) for 1.5 hours or 4 hours at 37° C. In some embodiments, for specific cleavage by an enzyme, contact between the enzyme and substrate is made. When a substrate-containing polypeptide (e.g., activatable molecule comprising an AM coupled to a MM and a substrate) is in the presence of target and sufficient protease activity, the substrate can be cleaved. Sufficient protease activity refers to the ability of the protease to access the substrate and effect cleavage.

In some embodiments, a substrate according to the present disclosure and a reference polypeptide can be cleaved by the same protease, but the substrate according to the present disclosure has reduced cleavage or resistance to cleavage (e.g., by a different protease) in certain tissues in situ compared to a reference polypeptide. In some examples, a substrate according to the present disclosure and a reference polypeptide can be cleaved by MT-SP1 and/or MMP, but the substrate according to the present disclosure has reduced cleavage or resistance to cleavage (e.g., by a different protease(s) than MT-SP1 and/or MMP2, MMP9, and MMP14 in the bone marrow in situ compared to a reference polypeptide. For example, the cleavage (e.g., by a different protease than MT-SP1 and/or MMP) in the bone marrow in situ of the substrate may be less than 99%, less than 95%, less than 90%, less than 80%, less than 70%, less than 60%, less than 50%, less than 40%, less than 30%, less than 20%, less than 10%, less than 5%, or less than 1% compared to the cleavage of the reference polypeptide. In some examples, such proteases different than an MMP may be other proteases in the bone marrow or other normal tissues, as well as other proteases involved in inflammation and wound healing. In some examples, the cleavage (e.g., by a different protease than MT-SP1 and/or MMP) in the bone marrow in situ may be measured by increased activity of an activatable molecule comprising the substrate or the reference polypeptide in the bone marrow, e.g., the method described in Example 6. A substrate that is resistant to cleavage by a protease, or a sample or tissue comprising a protease, refers to (i) a substrate in which no peptide bond is hydrolyzed by the protease, or no peptide bond is hydrolyzed when incubated in the sample or tissue comprising the protease, or (ii) a substrate in which a reduced level of peptide bond is hydrolyzed by the protease, or reduced level of peptide bond is hydrolyzed when incubated in the sample or tissue comprising the protease, compared to a reference substrate.

In some embodiments, the substrate is cleavable by more than two proteases. For example, the substrate may be cleaved by a serine protease (e.g., MT-SP1) and an MMP (e.g., MMP2, MMP9, and/or MMP14) and by one or more additional proteases. Examples of the additional protease could be any one or more of the following proteases: a disintegrin and metalloprotease (ADAM), an ADAM-like, or a disintegrin and metalloproteinase with thrombospondin motifs (ADAMTS, such as, for example, ADAM8, ADAM9, ADAM10, ADAM12, ADAM15, ADAM17/TACE, ADAM-DEC1, ADAMTS1, ADAMTS4, ADAMTS5); an aspartate protease (such as, for example, BACE, Renin, and the like); an aspartic cathepsin (such as, for example, Cathepsin D, Cathepsin E, and the like); a caspase (such as, for example, Caspase 1, Caspase 2, Caspase 3, Caspase 4, Caspase 5, Caspase 6, Caspase 7, Caspase 8, Caspase 9, Caspase 10, Caspase 14, and the like); a cysteine cathepsin (such as, for example, Cathepsin B, Cathepsin C, Cathepsin K, Cathepsin L, Cathepsin S, Cathepsin V/L2, Cathepsin X/Z/P); a cysteine proteinase (such as, for example, Cruzipain, Legumain, Otubain-2, and the like); a kallikrein-related peptidase (KLK) (such as, for example, KLK4, KLK5, KLK6, KLK7, KLK8, KLK10, KLK11, KLK13, KLK14, and the like); a metalloproteinase (such as, for example, Meprin, Neprilysin, prostate-specific membrane antigen (PSMA), bone morphogenetic protein 1 (BMP-1), and the like); a matrix metalloproteinase (MMP, such as, for example, MMP1, MMP2, MMP3, MMP7, MMP8, MMP9, MMP10, MMP11, MMP12, MMP13, MMP14, MMP15, MMP16, MMP17, MMP19, MMP20, MMP23, MMP24, MMP26, MMP27, and the like); a serine protease (such as, for example, activated protein C, Cathepsin A, Cathepsin G, Chymase, a coagulation factor protease (such as, for example, FVIIa, FIXa, FXa, FXIa, FXIIa, and the like); elastase, granzyme B, Guanidinobenzoatase, HtrA1, proteinase 3, neutrophil elastase, neutrophil serine protease 4 (NSP4), Lactoferrin, Marapsin, NS3/4A, PACE4, Plasmin, prostate-specific antigen (PSA), tissue plasminogen activator (tPA), Thrombin, Tryptase, urokinase-type plasminogen activator (uPA), a Type II transmembrane Serine Protease (TTSP) (such as, for example, DESC1, DPP-4, FAP, Hepsin, Matriptase-2, MT-SP1/Matriptase, TMPRSS2, TMPRSS3, TMPRSS4, TMPRSS5, TMPRSS6, TMPRSS7, TMPRSS8, TMPRSS9, TMPRSS10, TMPRSS11, and the like), and the like. Specific substrates are described, for example, in WO 2010/081173, WO 2015/048329, WO 2015/116933, and WO 2016/118629, each of which is incorporated herein by reference in its entirety.

In some embodiments, at least a portion of the CM1 in a substrate overlaps with at least a portion of the CM2 in the substrate, such that one or more amino acids in the substrate belongs to both CM1 and CM2. For example, a substrate with the sequence $X_1X_2X_3X_4X_5X_6$ (each X is an amino acid), may comprise overlapping CM1 and CM2, in which CM1 is $X_1X_2X_3X_4$ and CM2 is $X_3X_4X_5X_6$.

In some embodiments, the CM1 and CM2 in a substrate do not overlap in amino acid sequence such that no amino acid in the substrate belongs to both CM1 and CM2. For example, a substrate with the sequence $X_1X_2X_3X_4X_5X_6X_7X_8$ (each X is an amino acid) may comprise non-overlapping CM1 and CM2, in which CM1 is $X_1X_2X_3X_4$ and CM2 is $X_5X_6X_7X_8$. In some embodiments, the non-overlapping CM1 and CM2 are coupled directly. In some embodiments, the non-overlapping CM1 and CM2 are coupled indirectly (e.g., via a linking peptide).

In some embodiments, the CM1 and CM2 in a substrate have a structural arrangement from N-terminus to C-terminus as CM1-CM2. In some embodiments, the CM1 and the CM2 in a substrate have a structural arrangement from N-terminus to C-terminus as CM2-CM1. As used herein, the CM1 and CM2 in the formula CM1-CM2 or CM2-CM1 may be overlapping CM1 and CM2, non-overlapping CM1 and CM2 coupled directly, or non-overlapping CM1 and CM2 coupled indirectly (e.g., via a linking peptide).

Activatable Molecules

In some embodiments, the polypeptide or polypeptide complex comprising a substrate is an activatable molecule. The activatable molecule may comprise an active moiety (AM) that specifically binds a target. The AM may be coupled to the substrate. In some embodiments, the activatable molecule comprises a masking moiety (MM) coupled with the AM via the substrate.

The coupling of two components in a polypeptide or polypeptide complex (e.g., an activatable molecule) may be direct or indirect. When the two components are coupled directly, the amino acid residue at the C-terminus of a component forms a peptide bond with the amino acid residue at the N-terminus of the other component. When the two components are coupled indirectly, there is a stretch of amino acids between the two components. In some examples, the two components of a polypeptide may be indirectly coupled via one or more other components in the polypeptide, i.e., the one or more other components are between the two coupled components. For indirectly coupling or linking via another component, the one or more other components may be a linker, AM(s), CM(s), MM(s), or any combination thereof.

As used herein, the term "activatable molecule" refers to a molecule that comprises at least one set of MM, substrate, and AM and which exhibits attenuated binding to a target as compared to the binding of a counterpart "activated" molecule comprising the same AM to the same target. The terms "activated molecule," and "cleaved activatable molecule," are used interchangeably herein to refer to the AM-containing cleavage product that is generated after exposure of the activatable molecule to a substrate-specific protease (i.e., after cleavage of the substrate by at least one protease). In some embodiments, a cleaved activatable molecule may lack a MM due to cleavage of the substrate (e.g., by a protease), resulting in release of the MM.

An AM may be any polypeptide that specifically binds a target. In some examples, the AM may be a therapeutic macromolecule. In some examples, the AM may be an antibody or an antigen-binding fragment. In some examples, the AM may be an anti-neoplastic macromolecule. In some examples, the AM may be a cytokine. In some examples, the AM may be a chimeric antigen receptor.

In some examples, the AM may be a diagnostic macromolecule. For example, the diagnostic macromolecule may be a diagnostic polypeptide having 3 to 30, 5 to 25, 7 to 20, or 9 to 15 amino acids in length. Such diagnostic polypeptide may be used, in non-limiting aspects, e.g., for testing cleavage in tissues, and/or assessment of the tissue microenvironment.

As used herein, the terms "specific binding" and "specifically binds" refer to the non-covalent interactions of the type that occur between an AM and its target, e.g., an immunoglobulin molecule and an antigen or a cytokine and its receptor, for which the AM is specific. The strength or affinity of binding interactions can be expressed in terms of the dissociation constant ($K_d$) of the interaction, wherein a smaller $K_d$ represents a greater affinity. Unless indicated otherwise, as used herein, "affinity" refers to intrinsic binding affinity, which reflects a 1:1 interaction between members of an AM and its target. Affinity can be measured by common methods known in the art, including those described herein. Affinity can be determined, for example, using surface plasmon resonance (SPR) technology (e.g., BIACORE®) or biolayer interferometry (e.g., FORTEBIO®). Additional methods for determining the affinity for an AM and its target are known in the art. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). As used herein, a statement that an AM "specifically binds" to its target refers to an AM that binds its target with a dissociation constant ($K_d$) of less than 100 µM (e.g., less than 5 µM or 10 µM). In some examples, the AM specifically binds its target with a $K_d$ of about 0.01 nM to about 500 nM. In some examples, an AM is said to specifically bind the target, when the equilibrium binding constant ($K_d$) is ≤1 µM, in some embodiments≤100 nM, in some embodiments≤10 nM, and in some embodiments≤100 pM to about 1 pM, as measured by assays such as radioligand binding assays or similar assays known to those skilled in the art.

In general, an activatable molecule may be designed by selecting an AM of interest and constructing the remainder of the activatable molecule so that, when conformationally constrained, the MM provides for masking of the AM or reduction of binding of the AM to its target. Structural design criteria can be to be taken into account to provide for this functional feature.

Activatable molecules may be provided in a variety of structural configurations. Exemplary formulas for activatable molecules are provided below. It is contemplated that the N- to C-terminal order of the AM, MM and substrate may be reversed within an activatable molecule. For example, activatable molecules can be represented by the following formulas (in order from an amino (N) terminal region to carboxyl (C) terminal region):

MM-Substrate-AM,
    AM-Substrate-MM
    MM-CM1-CM2-AM,
    MM-CM2-CM1-AM,
    AM-CM1-CM2-MM, or
    AM-CM2-CM1-MM In some aspects, a CM3 or a CM3 and a CM4 may also be provided between the AM and MM.

As used herein and unless otherwise stated, each dash (-) between the components of the activatable molecule represents either a direct linkage or indirect linkage via one or more linkers, or overlapping between the components. It should be noted that although MM and substrate are indicated as distinct components in the formulas above, in all exemplary embodiments (including formulae) disclosed herein it is contemplated that the amino acid sequences of the MM and the substrate may overlap, e.g., such that the substrate is completely or partially contained within the MM. In addition, the formulas above provide for additional amino acid sequences that may be positioned N-terminal or C-terminal to the activatable molecules components. Examples include targeting moieties (e.g., a ligand for a receptor of a cell present in a target tissue) and half-life extending moieties.

In some embodiments, MM, substrate, and/or AM are coupled indirectly via one or more linkers (e.g., a linking peptide (LP)). For example, an activatable molecule may comprise one of the following formulas (in order from an amino (N) terminal region to carboxyl (C) terminal region):

MM-LP-Substrate-AM
    MM-Substrate-LP-AM
    MM-LP1-Substrate-LP2-AM
    MM-LP2-Substrate-LP1-AM
    AM-LP-Substrate-MM
    AM-Substrate-LP-MM
    AM-LP2-Substrate-LP1-MM
    AM-LP1-Substrate-LP2-MMMM-LP-CM1-CM2-AM
    MM-LP-CM2-CM1-AM
    MM-CM1-CM2-LP-AM
    MM-CM2-CM1-LP-AM
    MM-LP1-CM1-CM2-LP2-AM
    MM-LP1-CM2-CM1-LP2-AM
    MM-LP2-CM1-CM2-LP1-AM
    MM-LP2-CM2-CM1-LP1-AM
    AM-LP-CM1-CM2-MM
    AM-LP-CM2-CM1-MM
    AM-CM1-CM2-LP-MM
    AM-CM2-CM1-LP-MM
    AM-LP2-CM1-CM2-LP1-MM
    AM-LP2-CM2-CM1-LP1-MMAM-LP1-CM1-CM2-LP2-MM
    AM-LP1-CM2-CM1-LP2-MM wherein LP1 and LP2 are two linking peptides. In some aspects, a CM3 or a CM3 and a CM4 may also be provided between the AM and MM. In some examples, the LP1 and LP2 are identical to each other. In some examples, the LP1 and LP2 are not identical to each other. As used herein and unless otherwise stated, each dash (-) between the components of the activatable molecule represents either a direct linkage or indirect linkage via one or more linkers, or overlapping between the components.

In some embodiments, the substrate comprise more than two CMs. For example, the substrate may comprise a CM1 cleavable by a first protease, a CM2 cleavable by a second protease, and a CM3 cleavable by a third protease. Examples of the additional CM(s), e.g., CM3, in the substrate that are not the CM comprising the sequence of any of SEQ ID NOS: 9-24, 37-73, 83-353, 382-385, and 560-695 include those described in WO 2010/081173, WO2021207669, WO2021207657, WO2021142029, WO2021061867, WO2020252349, WO2020252358, WO2020236679, WO2020176672, WO2020118109, WO2020092881, WO2020086665, WO2019213444, WO2019183218, WO2019173771, WO2019165143, WO2019075405, WO2019046652, WO2019018828, WO2019014586, WO2018222949, WO2018165619, WO2018085555, WO2017011580, WO2016179335, WO2016179285, WO2016179257, WO2016149201, WO2016014974, which are incorporated herein by reference in their entireties for all purposes. In some examples, one or more of the additional CMs may be cleavable by legumain. In some examples, the CM cleavable by legumain may comprise a sequence of any of SEQ ID NO: 9-24, 37-73, 83-353, 383-385, and 560-695 and an Asparagine (Asn) residue at the N-terminus or C-terminus. In some examples, the CM cleavable by legumain may comprise a sequence of any of SEQ ID NO: 9-24, 37-73, 83-353, 383-385, and 560-683 and an Asparagine (Asn) residue at the N-terminus or C-terminus. For example, the CM cleavable by legumain may be PWGLRSN (SEQ ID NO: 9), RSPWGLN (SEQ ID NO: 10), or KPRGLN (SEQ ID NO: 23).

In some embodiments, the activatable molecule comprises a structural arrangement from N-terminus to C-terminus as follows: MM-CM1-CM2-AM, MM-CM2-CM1-AM, AM-CM1-CM2-MM, or AM-CM2-CM1-MM, MM-CM2-CM1-CM3-AM, MM-CM1-CM2-CM3-AM, MM-CM1-CM3-CM2-AM, MM-CM3-CM1-CM2-AM, or MM-CM3-CM2-CM1-AM. Likewise, a CM4 may be inserted any position between the MM and AM.

In some embodiments, the activatable molecule comprises a linking peptide (LP) and wherein the activatable molecule has a structural arrangement from N-terminus to C-terminus as follows: MM-LP-CM1-CM2-AM, MM-CM1-CM2-LP-AM, MM-LP-CM2-CM1-AM, MM-CM2-CM1-LP-AM, MM-LP-CM2-CM1-CM3-AM, MM-LP-CM1-CM2-CM3-AM, MM-LP-CM1-CM3-CM2-AM, MM-LP-CM3-CM1-CM2-AM, MM-LP-CM3-CM2-CM1-AM, MM-CM2-CM1-CM3-LP-AM, MM-CM1-CM2-CM3-LP-AM, MM-CM1-CM3-CM2-LP-AM, MM-CM3-CM1-CM2-LP-AM, or MM-CM3-CM2-CM1-LP-AM. Likewise, a CM4 may be inserted any position between the MM and AM.

In some embodiments, the activatable molecule comprises a first linking peptide (LP1) and a second linking peptide (LP2), and wherein the activatable molecule has a structural arrangement from N-terminus to C-terminus as follows: MM-LP1-CM1-CM2-LP2-AM, MM-LP1-CM2-CM1-LP2-AM, AM-LP2-CM1-CM2-LP1-MM, or AM-LP2-CM2-CM1-LP1-MM, MM-LP1-CM2-CM1-CM3-LP2-AM, MM-LP1-CM1-CM2-CM3-LP2-AM, MM-LP1-CM1-CM3-CM2-LP2-AM, MM-LP1-CM3-CM1-CM2-LP2-AM, MM-LP1-CM3-CM2-CM1-LP2-AM, MM-LP2-CM2-CM1-CM3-LP1-AM, MM-LP2-CM1-CM2-CM3-LP1-AM, MM-LP2-CM1-CM3-CM2-LP1-AM, MM-LP2-CM3-CM1-CM2-LP1-AM, or MM-LP2-CM3-CM2-CM1-LP1-AM. Likewise, a CM4 may be inserted any position between the MM and AM.

In some embodiments, the activatable molecule comprises an additional linking peptide (LP3) and wherein the activatable molecule has a structural arrangement from N-terminus to C-terminus as follows: MM-LP-CM1-LP3-CM2-AM, MM-CM1-LP3-CM2-LP-AM, MM-LP-CM2-LP3-CM1-AM, MM-CM2-LP3-CM1-LP-AM, MM-LP-CM2-LP3-CM1-CM3-AM, MM-LP-CM1-LP3-CM2-CM3-AM, MM-LP-CM1-LP3-CM3-CM2-AM, MM-LP-CM3-LP3-CM1-CM2-AM, MM-LP-CM3-LP3-CM2-CM1-AM, MM-CM2-LP3-CM1-CM3-LP-AM, MM-CM1-LP3-CM2-CM3-LP-AM, MM-CM1-LP3-CM3-CM2-LP-AM, MM-CM3-LP3-CM1-CM2-LP-AM, MM-CM3-LP3-CM2-CM1-LP-AM, MM-LP-CM2-CM1-LP3-CM3-AM, MM-LP-CM1-CM2-LP3-CM3-AM, MM-LP-CM1-CM3-LP3-CM2-AM, MM-LP-CM3-CM1-LP3-CM2-AM, MM-LP-CM3-CM2-LP3-CM1-AM, MM-CM2-CM1-LP3-CM3-LP-AM, MM-CM1-CM2-LP3-CM3-LP-AM, MM-CM1-CM3-LP3-CM2-LP-AM, MM-CM3-CM1-LP3-CM2-LP-AM, MM-CM3-CM2-LP3-CM1-LP-AM, MM-LP1-CM1-LP3-CM2-LP2-AM, MM-LP1-CM2-LP3-CM1-LP2-AM, AM-LP1-CM1-LP3-CM2-LP2-MM, or AM-LP1-CM2-LP3-CM1-LP2-MM, MM-LP1-CM2-LP3-CM1-CM3-LP2-AM, MM-LP1-CM1-LP3-CM2-CM3-LP2-AM, MM-LP1-CM1-LP3-CM3-CM2-LP2-AM, MM-LP1-CM3-LP3-CM1-CM2-LP2-AM, MM-LP1-CM3-LP3-CM2-CM1-LP2-AM, MM-LP2-CM2-LP3-CM1-CM3-LP1-AM, MM-LP2-CM1-LP3-CM2-CM3-LP1-AM, MM-LP2-CM1-LP3-CM3-CM2-LP1-AM, MM-LP2-CM3-LP3-CM1-CM2-LP1-AM, or MM-LP2-CM3-LP3-CM2-CM1-LP1-AM. Likewise, a CM4 may be inserted any position between the MM and AM.

In some embodiments, the activatable molecule has a structural arrangement from N-terminus to C-terminus as follows: MM-LP-CM2-LP3-CM1-LP4-CM3-AM, MM-LP-CM1-LP3-CM2-LP4-CM3-AM, MM-LP-CM1-LP3-CM3-LP4-CM2-AM, MM-LP-CM3-LP3-CM1-LP4-CM2-AM, MM-LP-CM3-LP3-CM2-LP4-CM1-AM, MM-CM2-LP3-CM1-LP4-CM3-LP-AM, MM-CM1-LP3-CM2-LP4-CM3-LP-AM, MM-CM1-LP3-CM3-LP4-CM2-LP-AM, MM-CM3-LP3-CM1-LP4-CM2-LP-AM, MM-CM3-LP3-CM2-LP4-CM1-LP-AM, MM-LP-CM2-LP4-CM1-LP3-CM3-AM, MM-LP-CM1-LP4-CM2-LP3-CM3-AM, MM-LP-CM1-LP4-CM3-LP3-CM2-AM, MM-LP-CM3-LP4-CM1-LP3-CM2-AM, MM-LP-CM3-LP4-CM2-LP3-CM1-AM, MM-CM2-LP4-CM1-LP3-CM3-LP-AM, MM-CM1-LP4-CM2-LP3-CM3-LP-AM, MM-CM1-LP4-CM3-LP3-CM2-LP-AM, MM-CM3-LP4-CM1-LP3-CM2-LP-AM, MM-CM3-LP4-CM2-LP3-CM1-LP-AM, MM-LP1-CM2-LP3-CM1-LP4-CM3-LP2-AM, MM-LP1-CM1-LP3-CM2-LP4-CM3-LP2-AM, MM-LP1-CM1-LP3-CM3-LP4-CM2-LP2-AM, MM-LP1-CM3-LP3-CM1-LP4-CM2-LP2-AM, MM-LP1-CM3-LP3-CM2-LP4-CM1-LP2-AM, MM-LP2-CM2-LP3-CM1-LP4-CM3-LP1-AM, MM-LP2-CM1-LP3-CM2-LP4-CM3-LP1-AM, MM-LP2-CM1-LP3-CM3-LP4-CM2-LP1-AM, MM-LP2-CM3-LP3-CM1-LP4-CM2-LP1-AM, or MM-LP2-CM3-LP3-CM2-LP4-CM1-LP1-AM. Likewise, a CM4 may be inserted any position between the MM and AM.

In some embodiments, two CMs, e.g., CM1 and CM2, in a substrate have a structural arrangement from N-terminus to C-terminus as CM1-CM2. In some embodiments, two CMs, e.g., CM1 and the CM2 in a substrate have a structural arrangement from N-terminus to C-terminus as CM2-CM1. As used herein, the CM1 and CM2 in the formula CM1-CM2 or CM2-CM1 may be overlapping CM1 and CM2, non-overlapping CM1 and CM2 coupled directly, or non-overlapping CM1 and CM2 coupled indirectly (e.g., via a linking peptide).

In some embodiments, two CMs, e.g., CM2 or CM4 and CM3 or CM4, in a substrate have a structural arrangement from N-terminus to C-terminus as CM2-CM3, CM2-CM4 or CM3-CM4. In some embodiments, two CMs, e.g., CM2 and the CM3 in a substrate have a structural arrangement from N-terminus to C-terminus as CM3-CM2 or CM4-CM2 or CM4-CM3. As used herein, the CM2 and CM3 in the formula CM2-CM3 or CM3-CM2 may be overlapping CM2 and CM3, non-overlapping CM2 and CM3 coupled directly, or non-overlapping CM2 and CM3 coupled indirectly (e.g., via a linking peptide). As used herein, the CM2 and CM4 in the formula CM2-CM4 or CM4-CM2 may be overlapping CM2 and CM4, non-overlapping CM2 and CM4 coupled directly, or non-overlapping CM2 and CM4 coupled indirectly (e.g., via a linking peptide). As used herein, the CM4 and CM3 in the formula CM4-CM3 or CM3-CM4 may be overlapping CM4 and CM3, non-overlapping CM4 and CM3 coupled directly, or non-overlapping CM4 and CM3 coupled indirectly (e.g., via a linking peptide).

Antibodies and Antigen-Binding Fragments

In some embodiments, the AM is an antibody or antigen-binding fragment thereof. The term "antibody" is used herein in its broadest sense and includes certain types of immunoglobulin molecules that include one or more target-binding domains that specifically bind an antigen or epitope. Examples of antibodies include intact antibodies (e.g., intact immunoglobulins), antibody fragments, bispecific, and multi-specific antibodies. One example of a target-binding domain is formed by a $V_H$-$V_L$ dimer. Additional examples of an antibody are described herein. Additional examples of an antibody are known in the art.

A "light chain" includes one variable domain (VL) and one constant domain (CL). There are two different light chains termed kappa or lambda. A "heavy chain" consists of one variable domain (VH) and three constant region domains (CH1, CH2, CH3). There are five main heavy-chain classes or isotypes, some of which have several subtypes, and these determine the functional activity of an antibody molecule. The five major classes of immunoglobulin are immunoglobulin M (IgM), immunoglobulin D (IgD), immunoglobulin G (IgG), immunoglobulin A (IgA), and immunoglobulin E (IgE). IgG is by far the most abundant immunoglobulin and has several subclasses (IgG1, IgG2, IgG3, and IgG4 in humans).

In some embodiments, the antigen-binding fragment is a Fab fragment, a F(ab') 2 fragment, a scFv, a scAb, a dAb, a single domain heavy chain antibody, or a single domain light chain antibody. Additional examples of the antigen-binding fragments include a VH domain, a VHH domain, a VNAR domain, and a single chain fragment variable (scFv), BiTE or a component thereof, a (scFv) 2, a NANOBODY®, a nanobody-HSA, VHH-scAb, a VHH-Fab, a Dual scFab, a F(ab')₂, a diabody, a CROSSMAB®, a DAF (two-in-one), a DAE (four-in-one), a DUTAMAB®, a DT-IgG, a knobs-in-holes common light chain, a knobs-in-holes assembly, a charge pair, a Fab-arm exchange, a SEEDbody, a LUZ-Y, a FcAb, a kI-body, an orthogonal Fab, a DVD-IgG, a IgG(H)-scFv, a scFv-(H) IgG, IgG(L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig, ZYBODY™, DVI-IgG, Diabody-CH3, a triple body, a miniantibody, a minibody, a TriBi minibody, scFv-CH3 KIH, Fab-scFv, a F(ab')₂-scFv2, a scFv-KIH, a Fab-scFv-Fc, a tetravaient HCAb, a scDiabody-Fc, a Diabody-Fc, a tandem scFv-Fc, a VHH-Fc, a tandem VHH-Fc, a L'HH-Fc KiH, a Fab-VHH-Fc, an Intrabody, a dock and lock, an ImmTAC® (immune-mobilizing monoclonal TCRs (T cell receptors) against cancer), an IgG-IgG conjugate, a Cov-X-Body, a scFv1-PEG-scFv2, an Adnectin, a DARPin®, a fibronectin, an IgG, an IgM, an IgA, an IgE, an IgD, a DEP conjugate, TMEA-body™, SAFEbody®, TRITAC®, or SHIELD antibody.

A "fragment antigen binding" (Fab) includes a complete light chain paired with the VH domain and the CH1 domain of a heavy chain. A F(ab')₂ fragment is formed when an antibody is cleaved by pepsin (or otherwise truncated) below the hinge region, in which case the two fragment target-binding domains (Fabs) of the antibody molecule remain linked. A F(ab')₂ fragment contains two complete light chains paired with the two VH and CH1 domains of the heavy chains joined together by the hinge region. A "fragment crystallizable" (Fc) fragment (also referred to herein as Fc domain) corresponds to the paired CH2 and CH3 domains and is the part of the antibody molecule that interacts with effector molecules and cells. The functional differences between heavy-chain isotypes lie mainly in the Fc fragment. A "single chain fragment variable" (scFv) contains only the variable domain of a light chain (VL) linked by a stretch of peptide to a variable domain of a heavy chain (VH). The name single-chain Fv is derived from Fragment variable. A "hinge region" or "interdomain" is flexible amino acid stretch that joins or links the Fab fragment to the Fc domain. A "synthetic hinge region" is an amino acid sequence that joins or links a Fab fragment to an Fc domain.

An "Fv" fragment includes a non-covalently-linked dimer of one heavy chain variable domain and one light chain variable domain. A "dual variable domain immunoglobulin G" or "DVD-IgG" refers to multivalent and multispecific target-binding proteins as described, e.g., in DiGiammarino et al., Methods Mol. Biol. 899:145-156, 2012, Jakob et al., MABs 5:358-363, 2013; and U.S. Pat. Nos. 7,612,181; 8,258,268; 8,586,714; 8,716,450; 8,722,855; 8,735,546; and 8,822,645, each of which is incorporated by reference in its entirety. Examples of DARTs are described in, e.g., Garber, Nature Reviews Drug Discovery 13:799-801, 2014.

A VHH domain is a single monomeric variable antibody domain that can be found in camelids. A VNAR domain is a single monomeric variable antibody domain that can be found in cartilaginous fish. Non-limiting aspects of VHH domains and VNAR domains are described in, e.g., Cromie et al., Curr. Top. Med. Chem. 15:2543-2557, 2016; De Genst et al. Dev. Comp. Immunol. 30:187-198, 2006; De Meyer et al, Trends Biotechnol 32:263-270, 2014; Kijanka et al., Nanomedicine 10:161-174, 2015; Kovaleva et al., Expert. Opin. Biol. Ther. 14:1527-1539, 2014; Krah et al., Immunopharmacol. Immunotoxicol. 38:21-28, 2016; Mujic-Delic et al., Trends Pharmacol. Sci. 35:247-255, 2014; Muyldermans, J. Biotechnol. 74:277-302, 2001, Muyldermans et al., Trends Biocheni. Sci. 26:230-235, 2001; Muyldermans, Ann. Rev. Biochem. 82:775-797, 2013; Rahbarizadeh et al., Immunol, invest. 40:299-338, 2011; Van Audenhove et al., EBioMedicine 8:40-48, 2016; Van Bockstaele et al., Curr. Opin. Investig. Drugs 10:1212-1224, 2009; Vincke et al. Methods Mol, Biol, 911:15-26, 2012; and Wesolowski et al. Med. Microbiol. Immunol. 198:157-174, 2009, each of which is incorporated by reference herein in its entirety.

In some embodiments, the AM may be a mouse, rat, rabbit, goat, camel, donkey, primate, human, or humanized or chimeric polypeptide. In one example, the AM may be a human polypeptide. In one example, the AM may be a humanized (e.g., fully humanized) polypeptide.

The term "humanized" refer to an AM having an amino acid sequence that includes VH and VL region sequences from a reference protein raised in a non-human species (e.g., a mouse), but also includes modifications in those sequences relative to the reference protein intended to render them more "human-like," i.e., more similar to human germline variable sequences. In some embodiments, a "humanized" AM is one that immunospecifically binds an antigen of interest and that has a framework (FR) region having substantially the amino acid sequence as that of a human protein, and a complementary determining region (CDR) having substantially the amino acid sequence as that of a non-human protein contains humanized VH and VL regions.

The term "human polypeptide" is intended to include AMs having variable and constant regions generated, assembled, or derived from human immunoglobulin sequences. In some embodiments, an AM may be considered to be "human" even though its amino acid sequence include residues or elements not encoded by human germline immunoglobulin sequences (e.g., include sequence variations, for example that may (originally) have been introduced by random or site-specific mutagenesis in vitro or by somatic mutation in vivo), e.g., in one or more CDRs.

Examples of antibodies and antigen-binding fragments include those binding to cell surface receptors and secreted binding proteins (e.g., growth factors), soluble enzymes, structural proteins (e.g. collagen, fibronectin) and the like, or an extracellular target (e.g., an extracellular protein target). In some embodiments, antibodies and antigen-binding fragments are designed for cellular uptake and are activatable inside a cell.

Examples of antibodies and antigen-binding fragments include those in Example 1, e.g., those comprising a light chain comprising a sequence selected from SEQ ID NOs: 354, 356, 358, 359, 361-366, and 368-381, and a heavy chain comprising a sequence selected from SEQ ID NOs: 355, 357, 360, and 367. In some examples, the polypeptide (e.g., isolated polypeptide) herein comprises a sequence selected from SEQ ID NOs: 354, 356, 358, 359, 361-366, and 368-381.

Multispecific Activatable Antibodies

In some embodiments, the activatable antibodies are multispecific activatable antibodies. In some examples, the multispecific activatable antibodies herein recognize two or more different antigens or epitopes and that include at least one masking moiety (MM) linked to at least one antigen- or epitope-binding domain of the multispecific antibody such that coupling of the MM reduces the ability of the antigen- or epitope-binding domain to bind its target. In some embodiments, the MM is coupled to the antigen- or epitope-binding domain of the multispecific antibody via a substrate cleavable by one or multiple proteases, e.g., MT-SP1 and/or an MMP. The activatable multispecific antibodies provided herein are stable in circulation, activated at intended sites of therapy and/or diagnosis but not in normal, i.e., healthy tissue, and, when activated, exhibit binding to a target that is at least comparable to the corresponding, unmodified multispecific antibody.

The multispecific activatable molecules may be used to target a first and a second target tissues. In one embodiment, the first and second target tissues are spatially separated, for example, at different sites in the organism. In one embodiment, the first and second target tissues are the same tissue temporally separated, for example the same tissue at two different points in time, for example the first time point is when the tissue is an early stage tumor, and the second time point is when the tissue is a late stage tumor.

In some embodiments, the multispecific activatable antibody includes a first antibody or antigen-binding fragment thereof (AB1) that binds a first target, where the AB1 is coupled to a masking moiety (MM1) such that coupling of the MM1 reduces the ability of the AB1 to bind the first target, and the multispecific activatable antibody includes a second antibody or antigen-binding fragment thereof (AB2) that binds a second target, where the AB2 is coupled to a masking moiety (MM2) such that coupling of the MM2 reduces the ability of the AB2 to bind the second target. In some embodiments, AB1 is coupled to MM1 via Substrate 1, and AB2 is coupled to MM2 via Substrate 2. In some embodiments, there are linking peptides between AB1 and Substrate 1, between Substrate 1 and MM1, between AB2 and Substrate 2, and/or between Substrate 2 and MM2. In some embodiments, AB1 is directly coupled to Substrate 1, Substrate 1 is directly coupled to MM1, AB2 is directly coupled to Substrate 2, and/or Substrate 2 is directly coupled to MM2.

For example, the multispecific activatable antibodies can be represented by the following formulas (in order from an amino (N) terminal region to carboxyl (C) terminal region):

MM1-Substrate 1-AB1: MM2-Substrate 2-AB2

AB1-Substrate 1-MM1: MM2-Substrate 2-AB2

AB1-Substrate 1-MM1: AB2-Substrate 2-MM2

MM1-Substrate 1-AB1: AB2-Substrate 2-MM2 wherein ":" separates two polypeptides, which may be two independent polypeptides on two different molecules, or two polypeptides on the same molecule (e.g., two polypeptide chains of the same protein). As used herein and unless otherwise stated, each dash (-) between the components of the activatable molecule represents either a direct linkage or indirect linkage via one or more linking peptides, or overlapping between the components.

In some embodiments, the multispecific activatable antibodies are designed to engage immune effector cells, also referred to herein as immune-effector cell engaging multispecific activatable antibodies. In some embodiments, the multispecific activatable antibodies are designed to engage leukocytes, also referred to herein as leukocyte engaging multispecific activatable antibodies. In some embodiments, the multispecific activatable antibodies are designed to engage T cells, also referred to herein as T-cell engaging multispecific activatable antibodies. In some embodiments, the multispecific activatable antibodies engage a surface antigen on a leukocyte, such as on a T cell, on a natural killer (NK) cell, on a myeloid mononuclear cell, on a macrophage, and/or on another immune effector cell. In some embodiments, the immune effector cell is a leukocyte. In some embodiments, the immune effector cell is a T cell. In some embodiments, the immune effector cell is a NK cell. In some embodiments, the immune effector cell is a mononuclear cell, such as a myeloid mononuclear cell. In some embodiments, the multispecific activatable antibodies are designed to bind or otherwise interact with more than one target and/or more than one epitope, also referred to herein as multi-antigen targeting activatable antibodies. As used herein, the terms "target" and "antigen" are used interchangeably.

In some embodiments, immune effector cell engaging multispecific activatable antibodies of the disclosure include a targeting antibody or antigen-binding fragment thereof and an immune effector cell engaging antibody or antigen-binding portion thereof, where at least one of the targeting antibody or antigen-binding fragment thereof and/or the immune effector cell engaging antibody or antigen-binding portion thereof is masked.

In some embodiments, the non-immune effector cell engaging antibody is a cancer targeting antibody. In some embodiments the non-immune cell effector antibody is an IgG. In some embodiments the immune effector cell engaging antibody is a scFv. In some embodiments the targeting antibody (e.g., non-immune cell effector antibody) is an IgG and the immune effector cell engaging antibody is a scFv. In some embodiments, the immune effector cell is a leukocyte. In some embodiments, the immune effector cell is a T cell. In some embodiments, the immune effector cell is a NK cell. In some embodiments, the immune effector cell is a myeloid mononuclear cell.

In some embodiments of an immune effector cell engaging multi-specific activatable antibody, one antigen is typically an antigen present on the surface of a tumor cell or other cell type associated with disease, and another antigen is typically a stimulatory or inhibitory receptor present on the surface of a T-cell, natural killer (NK) cell, myeloid mononuclear cell, macrophage, and/or other immune effector cell.

One embodiment of the disclosure is a multispecific activatable antibody that is activatable in a cancer microenvironment and that includes an antibody, for example an IgG or scFv, directed to a tumor target and an agonist antibody, for example an IgG or scFv, directed to a co-stimulatory receptor expressed on the surface of an activated T cell or NK cell, wherein at least one of the cancer target antibody and/or agonist antibody is masked. In this embodiment, the multispecific activatable antibody, once activated by tumor-associated proteases, effectively crosslinks and activates the T cell or NK cell expressed co-stimulatory receptors in a tumor-dependent manner to enhance the activity of T cells that are responding to any tumor antigen via their endogenous T cell antigen or NK-activating receptors. The activation-dependent nature of these T cell or NK cell costimulatory receptors focuses the activity of the activated multispecific activatable antibody to tumor-specific T cells, without activating all T cells independent of their antigen specificity. In one embodiment, at least the co-stimulatory receptor antibody of the multispecific activatable antibody is masked to prevent activation of auto-reactive T cells that may be present in tissues that also express the antigen recognized by the tumor target-directed antibody in the multispecific activatable antibody, but whose activity is restricted by lack of co-receptor engagement.

One embodiment of the disclosure is a multispecific activatable antibody that is activatable in a disease characterized by T cell overstimulation, such as an autoimmune disease or inflammatory disease microenvironment. Such a multispecific activatable antibody includes an antibody, for example an IgG or scFv, directed to a target comprising a surface antigen expressed in a tissue targeted by a T cell in autoimmune or inflammatory disease and an antibody, for example an IgG or scFv, directed to an inhibitory receptor expressed on the surface of a T cell or NK cell, wherein at least one of the disease tissue target antibody and/or T cell inhibitory receptor antibody is masked. Examples of a tissue antigen targeted by T cells in autoimmune disease include a surface antigen expressed on myelin or nerve cells in multiple sclerosis or a surface antigen expressed on pancreatic islet cells in Type 1 diabetes. In this embodiment, the multispecific activatable antibody when localized in the tissue under autoimmune attack or inflammation is activated and co-engages the T cell or NK cell inhibitory receptor to suppress the activity of autoreactive T cells responding to any disease tissue-targeted antigens via their endogenous TCR or activating receptors. In one embodiment, at least one or multiple antibodies are masked to prevent suppression of T cell responses in non-disease tissues where the target antigen may also be expressed.

In some embodiments, the multi-antigen targeting antibodies and/or multi-antigen targeting activatable antibodies include at least a first antibody or antigen-binding fragment thereof that binds a first target and/or first epitope and a second antibody or antigen-binding fragment thereof that binds a second target and/or a second epitope. In some embodiments, the multi-antigen targeting antibodies and/or multi-antigen targeting activatable antibodies bind two or more different targets. In some embodiments, the multi-antigen targeting antibodies and/or multi-antigen targeting activatable antibodies bind two or more different epitopes on the same target. In some embodiments, the multi-antigen targeting antibodies and/or multi-antigen targeting activatable antibodies bind a combination of two or more different targets and two or more different epitopes on the same target.

Masking Moieties (MMs)

The activatable molecules herein may comprise one or more masking moieties (MMs) capable of interfering with the binding of the AMs to the target. A masking moiety in an activatable molecule "masks" or reduces or otherwise inhibits the binding of the activatable molecule to its target. In some embodiments, the coupling of an AM (e.g., an antibody or fragment thereof, or other therapeutic or diagnostic protein) with an MM may inhibit the ability of the AM to specifically bind its target by means of inhibition known in the art (e.g., structural change, competition for antigen-binding domain, and the like). In some embodiments, the coupling of an AM with an MM may effect a structural change that reduces or inhibits the ability of the AM to specifically bind its target. In some embodiments, the coupling of a protein comprising an AM with an MM sterically blocks, reduces or inhibits the ability of the AM to specifically bind its target and or epitope. In some embodiments, when an activatable molecule is not activated, the MM prevents the AM from target binding; but when the activatable molecule is activated (when the substrate is cleaved by one or more proteases), the MM does not substantially or significantly interfere with the AM's binding to the target.

An MM may be coupled to an AM (e.g., an antibody or fragment thereof, or other therapeutic or diagnostic protein) via the substrate described herein, either directly or indirectly (e.g., via one or more linkers described herein). Alternatively, an MM interfering with the target binding of an AM may be coupled, either directly or indirectly, to a component of the activatable molecule that is not the AM. For example, the MM may be coupled, either directly or indirectly, to a different AM. In another example, the MM may be coupled, either directly or indirectly, with a half-life extending moiety (EM). In either case, in the tertiary or quaternary structure of the activatable structure, the MM may be in a position (e.g., proximal to the AM to be masked) that allows the MM to mask the AM.

In some embodiments, an MM interacts with the AM, thus reducing or inhibiting the interaction between the AM and its binding partner. In some embodiments, the MM comprises at least a partial or complete amino acid sequence of a naturally occurring binding partner of the AM. The term "naturally occurring" as used herein as applied to an object refers to the fact that an object can be found in nature. For example, a polypeptide or polynucleotide sequence that is present in an organism (including viruses or bacteria) that can be isolated from a source in nature and that has not been intentionally modified by man in the laboratory or otherwise is naturally occurring.

For example, the MM may be a fragment of a naturally occurring binding partner. The fragment may retain at least 95%, at least 90%, at least 80%, at least 75%, at least 70%, at least 60%, at least 50%, at least 40%, at least 30%, at least 25%, or at least 20% nucleic acid or amino acid sequence homology to the naturally occurring binding partner. In some embodiments, the MM is a cognate peptide of the AM. For example, the MM may comprise a sequence of the AM's epitope or a fragment thereof.

In some embodiments, the MM comprises an amino acid sequence that is not naturally occurring or does not contain the amino acid sequence of a naturally occurring binding partner or target protein. In certain embodiments, the MM is not a natural binding partner of the AM. In some embodiments, the MM does not comprise a subsequence of more than 4, 5, 6, 7, 8, 9 or 10 consecutive amino acid residues of a natural binding partner of the AM. The MM may be a modified binding partner for the AM which contains amino acid changes that decrease affinity and/or avidity of binding to the AM. In some embodiments, the MM contains no or substantially no nucleic acid or amino acid homology to the AM's natural binding partner. In other embodiments the MM has no more than 5%, 10%, 15%, 20%, 25%, 30%, 35%, 40%, 45%, 50%, 55%, 60%, 65%, 70%, 75%, or 80% homology to the natural binding partner of the AM.

In some embodiments, the MM is a polypeptide that binds to the AM. In some examples, the MM may be an antibody or antibody fragment (e.g., a Fab fragment, a F(ab') 2 fragment, a scFv, a scAb, a dAb, a single domain heavy chain antibody, and a single domain light chain antibody) that binds to the AM such that interrupts the AM's binding to its target. In some examples, the MM may be a ligand, a receptor, a fragment thereof (e.g., an extracellular domain of a receptor) of the AM that binds to the AM and interrupts the AM's binding to its target. In some examples, when the AM is an antibody or antibody fragment thereof, the MM may be an anti-idiotypic antibody or fragment thereof (e.g., scFv) that binds to the idiotype of the AM. In some examples, the MM may be a cytokine or a receptor for a cytokine. In some examples, the MM may have an amino acid sequence that is at least 85% identical to a cytokine or to a receptor for a cytokine.

In some embodiments, the MM does not bind the AM, but still interferes with AM's binding to its binding partner through non-specific interactions such as steric hindrance. For example, the MM may be positioned in the activatable molecule such that the tertiary or quaternary structure of the activatable molecule allows the MM to mask the AM through charge-based interaction, thereby holding the MM in place to interfere with binding partner access to the AM. Examples of such MMs include an albumin, e.g., human serum albumin (HSA), a fragment crystallizable (Fc) domain, an antibody constant domain (e.g., CH domains), a polymer (e.g., branched or multi-armed polyethylene glycol (PEG)), a latency associated protein (LAP), and any polypeptide or other moieties that sterically interfere AM-target interactions. In some examples, the MM may recruit a large protein binding partner that sterically interfere AM-target interactions. For example, the MM may be an antibody or a fragment thereof that binds to serum albumin.

Examples of suitable masking moieties include the full-length or a AM-binding fragment or mutein of a cognate receptor of the AM, and AM-binding antibodies and fragment thereof, e.g., a polyclonal antibody, a recombinant antibody, a human antibody, a humanized antibody a single chain variable fragment (scFv), single-domain antibody such as a heavy chain variable domain (VH), a light chain variable domain (VL), a variable domain of camelid-type nanobody (VHH), a dAb and the like. Other exemplary antigen-binding domain that bind the AM can also be used as an MM include non-immunoglobulin proteins that mimic antibody binding and/or structure such as, anticalins, affilins, affibody molecules, affimers, affitins, alphabodies, avimers, DARPins, fynomers, kunitz domain peptides, monobodies, and binding domains based on other engineered scaffolds such as SpA, GroEL, fibronectin, lipocallin and CTLA4 scaffolds. As another example, a peptide that is modified by conjugation to a water-soluble polymer, such as PEG, can sterically inhibit or prevent binding of the cytokine to its receptor. Antibodies and antigen-binding domains that bind to, for example, a protein with a long serum half-life such as HSA, immunoglobulin or transferrin, or to a receptor that is recycled to the plasma membrane, such as FcRn or transferrin receptor, can also inhibit the cytokine, particularly when bound to their antigen. In some embodiments, the MMs (e.g., those sterically interfere with the AM-target interaction) can also function as half-life extending elements.

In some embodiments, the MM may have a dissociation constant for binding to the AM that is no more than the dissociation constant of the AM to the target. In some embodiments, the MM does not interfere or compete with the AM for binding to the target in in the activated molecule (i.e., following cleavage of the substrate by a protease).

The structural properties of the MMs may be selected according to factors such as the minimum amino acid sequence required for interference with the AM binding to target, the target protein-protein binding pair of interest, the size of the AM, the presence or absence of linkers, and the like.

In some embodiments, the MM may be unique for the coupled AM. Examples of MMs include MMs that were specifically screened to bind a binding domain of the AM or fragment thereof (e.g., affinity masks). Methods for screening MMs to obtain MMs unique for the AM and those that specifically and/or selectively bind a binding domain of a binding partner/target are provided herein and can include protein display methods.

As used herein, the term "masking efficiency" refers to the activity (e.g., $EC_{50}$) of the activatable molecule divided by the activity of a control molecule, wherein the control molecule may be either cleavage product of the activatable molecule (i.e., the activated molecule) or the AM used in the activatable molecule. An activatable molecule having a reduced level of an AM activity may have a masking efficiency that is greater than 10. In some embodiments, the activatable molecules described herein have a masking efficiency that is greater than 10, 100, 1000, or 5000.

In some embodiments, the MM is a polypeptide of about 2 to 50 amino acids in length. For example, the MM may be a polypeptide of from 2 to 40, from 2 to 30, from 2 to 20, from 2 to 10, from 5 to 15, from 10 to 20, from 15 to 25, from 20 to 30, from 25 to 35, from 30 to 40, from 35 to 45, from 40 to 50 amino acids in length. For example, the MM may be a polypeptide with 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length. In some examples, the MM may be a polypeptide of more than 50 amino acids in length, e.g., 100, 200, 300, 400, 500, 600, 700, 800, or more amino acids. In some embodiments, the MM is a steric mask.

In some embodiments, in an activatable molecule with an AM and an interfering MM, in the presence of the target of an AM, there is no binding or substantially no binding of the AM to the target, or no more than 0.001%, 0.01%, 0.1%, 1%, 2%, 3%, 4%, 5%, 6%, 7%, 8%, 9%, 10%, 15%, 20%, 25%, 30%, 35%, 40%, or 50% binding of the AM to its target, as compared to the binding of an counterpart molecule without the interfering MM, for at least 0.1, 0.5, 1, 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months when measured in vitro immunoabsorbant assay, e.g., as described in US20200308243A1.

The binding affinity of the AM towards the target or binding partner with an interfering MM may be at least 5, 10, 25, 50, 100, 250, 500, 1,000, 2,500, 5,000, 10,000, 50,000, 100,000, 500,000, 1,000,000, 5,000,000, 10,000, 000, 50,000,000 times lower than the binding affinity of the AM towards its binding partner without an interfering MM, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AM towards its binding partner when there is no interfering MM.

The dissociation constant ($K_d$) of the MM towards the AM it masks, may be greater than the dissociation constant of the AM towards the target. The dissociation constant of the MM towards the masked AM may be at least 5, 10, 25, 50, 100, 250, 500, 1,000, 2,500, 5,000, 10,000, 100,000, 1,000,000 or even 10,000,000 times greater than the dissociation constant of the AM towards the target. Conversely, the binding affinity of the MM towards the masked AM may be lower than the binding affinity of the AM towards the target. The binding affinity of MM towards the AM may be at least 5, 10, 25, 50, 100, 250, 500, 1,000, 2,500, 5,000, 10,000, 100,000, 1,000,000 or even 10,000,000 times lower than the binding affinity of the AM towards the target.

In some embodiments, the $K_d$ of the activatable molecule comprising an MM and a substrate towards the AM's target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000, 000, 100-1,000, 100-10,000, 100-100,000, 100-1,000,000, 100-10,000,000, 1,000-10,000, 1,000-100,000, 1,000-1,000, 000, 1000-10,000,000, 10,000-100,000, 10,000-1,000,000, 10,000-10,000,000, 100,000-1,000,000, or 100,000-10,000, 000 times greater than the $K_d$ of a counterpart molecule that is substantially the same as the activatable molecule but does not comprise the MM or substrate towards the AM's target. Conversely, the binding affinity of the activatable molecule comprising an MM and a substrate towards the AM's target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000, 000, 100-1,000, 100-10,000, 100-100,000, 100-1,000,000, 100-10,000,000, 1,000-10,000, 1,000-100,000, 1,000-1,000, 000, 1000-10,000,000, 10,000-100,000, 10,000-1,000,000, 10,000-10,000,000, 100,000-1,000,000, or 100,000-10,000, 000 times lower than the binding affinity of a counterpart molecule that is substantially the same as the activatable molecule but does not comprise the MM or substrate towards the AM's target.

In some embodiments, when the AM is coupled with an MM and is in the presence of the target, the specific binding of the AM to its target is reduced or inhibited, as compared to the specific binding of the AM not coupled with the MM. When compared to the binding of the AM not coupled with the MM to the target, the target-binding ability of the AM coupled with the MM may be reduced by at least 50%, 60%, 70%, 80%, 90%, 92%, 93%, 94%, 95%, 96%, 97%, 98%, 99%, or 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or more when measured in vivo or in an in vitro assay.

In some embodiments, the MM comprises a non-binding steric moiety (NB) that does not bind the AM but is able to interfere the binding between the AM and its target via steric hindrance. In some embodiments, the MM comprises a binding partner (BP) for a NB, where the BP recruits or otherwise attracts the NB to the activatable molecule.

In some embodiments, the MM contains genetically encoded or genetically non-encoded amino acid(s). Examples of genetically non-encoded amino acids include D-amino acids, β-amino acids, and γ-amino acids. In specific embodiments, the MMs contain no more than 50%, 40%, 30%, 20%, 15%, 10%, 5% or 1% of genetically non-encoded amino acids.

In some embodiments, once released from the activatable molecule and in a free state, the MM may have a biological activity or a therapeutic effect, such as binding capability. For example, the free peptide may bind with the same or a different binding partner. In certain embodiments, the free MM may exert a therapeutic effect, providing a secondary function to the compositions disclosed herein. In some embodiments, once uncoupled from the activatable molecule and in a free state, the MM may advantageously not exhibit biological activity. For example, in some embodiments the MM after cleavage from the activatable molecule does not elicit an immune response in the subject.

Suitable MMs may be identified and/or further optimized through a screening procedure from a library of candidate activatable molecule having variable MMs. For example, an AM and a substrate may be selected to provide for a desired enzyme/target combination, and the amino acid sequence of the MM can be identified by the screening procedure described below to identify an MM that provides for an activatable phenotype. For example, a random peptide library (e.g., of peptides comprising 2 to 40 amino acids or more) may be used in the screening methods disclosed herein to identify a suitable MM.

In some embodiments, MMs with specific binding affinity for an AM may be identified through a screening procedure that includes providing a library of peptide scaffolds comprising candidate MMs wherein each scaffold is made up of a transmembrane protein and the candidate MM. The library may then be contacted with an entire or portion of a protein such as a full length protein, a naturally occurring protein fragment, or a non-naturally occurring fragment containing a protein (also capable of binding the binding partner of interest), and identifying one or more candidate MMs having detectably bound protein. The screening may be performed by one more rounds of magnetic-activated sorting (MACS) or fluorescence-activated sorting (FACS), as well as determination of the binding affinity of MM towards the AM and subsequent determination of the masking efficiency, e.g., as described in WO2009025846 and US20200308243A1, which are incorporated herein by reference in their entireties.

Examples of suitable MMs are disclosed in WO2021207657, WO2021142029, WO2021061867, WO2020252349, WO2020252358, WO2020236679, WO2020176672, WO2020118109, WO2020092881, WO2020086665, WO2019213444, WO2019183218, WO2019173771, WO2019165143, WO2019075405, WO2019046652, WO2019018828, WO2019014586, WO2018222949, WO2018165619, WO2018085555, WO2017011580, WO2016179335, WO2016179285, WO2016179257, WO2016149201, and WO2016014974, which are incorporated herein by reference in their entireties.

In some embodiments, the AM in an activatable molecule is an antibody or antigen-binding fragment that specifically binds EGFR. In some examples, such an activatable molecule comprises an MM that comprises the amino acid sequence of SEQ ID NO: 81. In some examples, such an activatable molecule comprises an MM that comprises the amino acid sequence of SEQ ID NO: 82. In some examples, such an activatable molecule comprises an MM that consists of the amino acid sequence of SEQ ID NO: 81. In some examples, such an activatable molecule comprises an MM that consists of the amino acid sequence of SEQ ID NO: 82.

In some aspects, the present disclosure includes an activatable antibody comprising an anti-EGFR antibody coupled directly or indirectly to a substrate, wherein the substrate is directly or indirectly coupled to an MM that comprises or consists of the amino acid sequence of SEQ ID NO: 82.

Linkers

The activatable molecules may comprise one or more linkers. The linkers may be linking peptides that comprise a stretch of amino acid sequence that link two components in the activatable molecule. The linkers may be non-cleavable by any protease. In some embodiments, one or more linkers may be introduced into the activatable molecule to provide flexibility at one or more of the junctions between domains, between moieties, between moieties and domains, or at any other junctions where a linker would be beneficial. In some embodiments, where the activatable molecule is provided as a conformationally constrained construct, a flexible linker may be inserted to facilitate formation and maintenance of a structure in the activatable molecule. Any of the linkers described herein may provide the desired flexibility to facilitate the inhibition of the binding of a target, or to facilitate cleavage of a substrate by a protease. In some embodiments, linkers included in the activatable molecule may be all or partially flexible, such that the linker can include a flexible linker as well as one or more portions that confer less flexible structure to provide for a desired activatable molecule. Some linkers may include cysteine residues, which may form disulfide bonds and reduce flexibility of the construct.

In some embodiments, a linker coupled to an MM may have a length that allows the MM to be in a position in the tertiary or quaternary to effectively mask an AM, (e.g., proximal to the AM to be masked) that allows the MM to mask the AM.

In most instances, the linker's length may be determined by counting, in a N- to C-direction, the number of amino acids from the N-terminus of the linker adjacent to the C-terminal amino acid of the preceding component, to the C-terminus of the linker adjacent to the N-terminal amino acid of the following component (i.e., where the linker length does not include either the C-terminal amino acid of the preceding component or the N-terminal amino acid of the following component).

In some embodiments, a linker may include a total of 1 to 50, 1 to 40, 1 to 30, 1 to 25 (e.g., 1 to 24, 1 to 22, 1 to 20, 1 to 18, 1 to 16, 1 to 15, 1 to 14, 1 to 12, 1 to 10, 1 to 8, 1 to 6, 1 to 5, 1 to 4, 1 to 3, 1 to 2, 2 to 25, 2 to 24, 2 to 22, 2 to 20, 2 to 18, 2 to 16, 2 to 15, 2 to 14, 2 to 12, 2 to 10, 2 to 8, 2 to 6, 2 to 5, 2 to 4, 2 to 3, 4 to 25, 4 to 24, 4 to 22, 4 to 20, 4 to 18, 4 to 16, 4 to 15, 4 to 14, 4 to 12, 4 to 10, 4 to 8, 4 to 6, 4 to 5, 5 to 25, 5 to 24, 5 to 22, 5 to 20, 5 to 18, 5 to 16, 5 to 15, 5 to 14, 5 to 12, 5 to 10, 5 to 8, 5 to 6, 6 to 25, 6 to 24, 6 to 22, 6 to 20, 6 to 18, 6 to 16, 6 to 15, 6 to 14, 6 to 12, 6 to 10, 6 to 8, 8 to 25, 8 to 24, 8 to 22, 8 to 20, 8 to 18, 8 to 16, 8 to 15, 8 to 14, 8 to 12, 8 to 10, 10 to 25, 10 to 24, 10 to 22, 10 to 20, 10 to 18, 10 to 16, 10 to 15, 10 to 14, 10 to 12, 12 to 25, 12 to 24, 12 to 22, 12 to 20, 12 to 18, 12 to 16, 12 to 15, 12 to 14, 14 to 25, 14 to 24, 14 to 22, 14 to 20, 14 to 18, 14 to 16, 14 to 15, 15 to 25, 15 to 24, 15 to 22, 15 to 20, 15 to 18, 15 to 16, 16 to 25, 16 to 24, 16 to 22, 16 to 20, 16 to 18, 18 to 25, 18 to 24, 18 to 22, 18 to 20, 20 to 25, 20 to 24, 20 to 22, 22 to 25, 22 to 24, or 24 to 25 amino acids). In some embodiments, the linker may include a total of 1, 2, 3, 4, 5, 6, 7, 8, 9, 10, 11, 12, 13, 14, 15, 16, 17, 18, 19, 20, 21, 22, 23, 24, or 25 amino acids.

In some embodiments, a linker may be rich in glycine (Gly or G) residues. In some embodiments, the linker may be rich in serine (Ser or S) residues. In some embodiments, the linker may be rich in glycine and serine residues. In some embodiments, the linker may have one or more glycine-serine residue pairs (GS) (e.g., 1, 2, 3, 4, 5, 6, 7, 8, 9, or 10 or more GS pairs).

In some embodiments, the linker may have one or more Gly-Gly-Gly-Ser (GGGS) (SEQ ID NO: 502) sequences (e.g., 1, 2, 3, 4, 5, 6, 7, 8, 9, or 10 or more GGGS sequences (SEQ ID NO: 502)). In some embodiments, the linker may have one or more Gly-Gly-Gly-Gly-Ser (GGGGS) (SEQ ID NO: 508) sequences (e.g., 1, 2, 3, 4, 5, 6, 7, 8, 9, or 10 or more GGGGS sequences (SEQ ID NO: 508)). In some embodiments, the linker may have one or more Gly-Gly-Ser-Gly (GGSG) (SEQ ID NO: 495) sequences (e.g., 1, 2, 3, 4, 5, 6, 7, 8, 9, or 10 or more GGSG sequences (SEQ ID NO: 495)). Examples of the linkers may include glycine polymers (G) n, glycine-serine polymers (including, for example, (GS) n, (GGS) n, (GSGGS) n (SEQ ID NO: 696) and (GGGS) n (SEQ ID NO: 502), where n is an integer of at least one), glycine-alanine polymers, alanine-serine polymers, and other flexible linkers known in the art. Glycine and glycine-serine polymers may be relatively unstructured, and therefore may be able to serve as a neutral link between components. Glycine accesses significantly more phi-psi space than even alanine, and is much less restricted than residues with longer side chains (see Scheraga, Rev. Computational Chem. 11173-142 (1992)). Exemplary flexible linkers include one of or a combination of one or more of: GGSG (SEQ ID NO: 495), GGSGG (SEQ ID NO: 496), GSGSG (SEQ ID NO: 497), GSGGG (SEQ ID NO: 498), GGGSG (SEQ ID NO: 499), GSSSG (SEQ ID NO: 500), GSSGGSGGSGG (SEQ ID NO: 501), GGGS (SEQ ID NO: 502), GGGSGGGS (SEQ ID NO: 503), GGGSGGGSGGGS (SEQ ID NO: 504), GGGGSGGGGSGGGGS (SEQ ID NO: 505), GGGGSGGGGSGGGGSGGGGSGGGGS (SEQ ID NO: 506), GGGGSGGGGS (SEQ ID NO: 507), GGGGS (SEQ ID NO: 508), GS, GGGGSGS (SEQ ID NO: 509), GGGGSGGGGSGGGGSGS (SEQ ID NO: 510), GGSLDPKGGGGS (SEQ ID NO: 511), PKSCDKTHTCPPCPAPELLG (SEQ ID NO: 512), SKYGPPCPPCPAPEFLG (SEQ ID NO: 513), GKSSGSGSESKS (SEQ ID NO: 514), GSTSGSGKSSEGKG (SEQ ID NO: 515), GSTSGSGKSSEGSGSTKG (SEQ ID NO: 516), GSTSGSGKPGSGEGSTKG (SEQ ID NO: 517), GSTSGSGKPGSSEGST (SEQ ID NO: 518), GGGSSGGS (SEQ ID NO: 519), GGGGSGGGSS (SEQ ID NO: 520), GGGSSGGSGGSSGGS (SEQ ID NO: 521), and GSTSGSGKPGSSEGST (SEQ ID NO: 522).

Examples of linkers may further include a sequence that is at least 70% identical (e.g., at least 72%, at least 74%, at least 75%, at least 76%, at least 78%, at least 80%, at least 82%, at least 84%, at least 85%, at least 86%, at least 88%, at least 90%, at least 92%, at least 94%, at least 95%, at least 96%, at least 97%, at least 98%, at least 99%, or 100% identical to the example linkers described herein. An ordinarily skilled artisan will recognize that design of an activatable molecules can include linkers that are all or partially flexible, such that the linker can include a flexible linker as well as one or more portions that confer less flexible structure to provide for a desired activatable molecules structure.

In some embodiments, an activatable molecule may include one, two, three, four, five, six, seven, eight, nine, or ten linker sequence(s) (e.g., the same or different linker sequences of any of the exemplary linker sequences described herein or known in the art). In some embodiments, a linker may comprise sulfo-SIAB, SMPB, and sulfo-SMPB, wherein the linkers react with primary amines sulf-hydryls.

Half-Life Extending Moieties (EMs)

The activatable molecule may further comprise a half-life extending moiety (EM). In some examples, the half-life extending moiety may be a serum half-life extending moiety, i.e., capable of extending the serum half-life of the molecule attached to the EM.

In some examples, the EM may comprise a fragment crystallizable region (Fc domain) of an antibody. For example, the EM may be the Fc domain of an IgG(e.g., IgG1, IgG2, IgG3, or IgG4). In some examples, the EM may comprise a dimer formed by two Fc domains. The Fc domain may be a wild type peptide or a mutant. For example, the EM may comprise a dimer formed by two Fc domain mutants. In such cases, the two Fc domain mutants may be a Fc domain hole mutant and a Fc domain knob mutant. The knob and hole mutants may interact with each other to facilitate the dimerization of the two Fc domains. In some embodiments, the knob and hole mutants may comprise one or more amino acid modifications within the interface between two Fc domains (e.g., in the CH3 domain). In one example, the modifications comprise amino acid substitution T366W and optionally the amino acid substitution S354C in one IgG Fc domain and the amino acid substitutions T366S, L368A, Y407V and optionally Y349C in the other IgG Fc domain (numbering according to EU numbering system). Example of Fc mutants also include SEQ ID NOs: 523-524.

Examples of the Fc domain mutants also include those described in U.S. Pat. No. 7,695,936, which is incorporated herein by reference in its entirety. In one example, the modifications comprise amino acid substitution T366Y in one IgG Fc domain, and the amino acid substitutions Y407T in the other IgG Fc domain. In one example, the modifications comprise amino acid substitution T366W in one IgG Fc domain, and the amino acid substitutions Y407A in the other IgG Fc domain. In one example, the modifications comprise amino acid substitution F405A in one IgG Fc domain, and the amino acid substitutions T394W in the other IgG Fc domain. In one example, the modifications comprise amino acid substitution T366Y and F405A in one IgG Fc domain, and the amino acid substitutions T394W and Y407T in the other IgG Fc domain. In one example, the modifications comprise amino acid substitution T366W and F405W in one IgG Fc domain, and the amino acid substitutions T394S and Y407A in the other IgG Fc domain. In one example, the modifications comprise amino acid substitution F405W and Y407A in one IgG Fc domain, and the amino acid substitutions T366W and T394S in the other IgG Fc domain. In one example, the modifications comprise amino acid substitution F405W in one IgG Fc domain, and the amino acid substitutions T394S in the other IgG Fc domain. The mutation positions in the Fc domains are numbered according to EU numbering system. The IgG Fc domain may be comprise a sequence of SEQ ID NOs: 525-528 (IgG1, IgG2, IgG3 or IgG4). In these sequences, amino acids 1-107 correspond to EU numbering 341-447.

In some examples, the Fc domains mutants may have reduced effector function. Examples of such Fc domains include those disclosed in in US20190135943, which incorporated herein by reference in its entirety.

Further examples of EMs include immunoglobulin (e.g., IgG), serum albumin (e.g., human serum albumin (HSA), hexa-hat GST (glutathione S-transferase) glutathione affinity, Calmodulin-binding peptide (CBP), Strep-tag, Cellulose Binding Domain, Maltose Binding Protein, S-Peptide Tag, Chitin Binding Tag, Immuno-reactive Epitopes, Epitope Tags, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, and VSV Epitope.

In some embodiments, the serum half-life of an activatable molecule comprising an EM is longer than that of a counterpart molecule that is substantially the same as the activatable molecule but does not comprise the EM, e.g., the pK of the activatable molecule is longer than that of the reference molecule. In some examples, the activatable molecule with an EM may have a serum half-life that is at least 10%, 20%, 30%, 40%, 50%, 60%, 70%, 80%, 90%, 2-fold, 4-fold, 6-fold, 8-fold, 10-fold, 20-fold, 30-fold, 40-fold, 50-fold, 60-fold, 70-fold, 80-fold, 90-fold, 100-fold longer than the serum half-life of the reference counterpart molecule. In some embodiments, the serum half-life of the activatable molecule with an EM may be at least 15 days, 12 days, 11 days, 10 days, 9 days, 8 days, 7 days, 6 days, 5 days, 4 days, 3 days, 2 days, 1 day, 20 hours, 18 hours, 16 hours, 14 hours, 12 hours, 10 hours, 8 hours, 6 hours, 4 hours, 3 hours, 2 hours, or 1 hour when administered to an organism.

Conjugation Agents

In some aspects, the present disclosure provides conjugated polypeptides. In some embodiments, a conjugated polypeptide comprises a substrate-containing polypeptide herein conjugated to one or more agent, e.g., a targeting moiety to facilitate delivery to a cell or tissue of interest, a therapeutic agent (e.g., an antineoplastic agent such as chemotherapeutic or anti-neoplastic agent), a toxin, or a fragment thereof. The agents may be conjugated to a component of the activatable molecules. In some embodiments, the conjugated polypeptide is an antibody-drug conjugate (ADC), which comprises an antibody or antigen-binding fragment thereof conjugated with a drug. In some examples, the antibody or antigen-binding fragment thereof may be conjugated with the drug via a substrate disclosed herein. In some examples, the antibody or antigen-binding fragment thereof may be an activatable antibody or antigen-binding fragment thereof (e.g., coupled with a MM via a substrate), which is further conjugated with a drug (e.g., via a cleavable or non-cleavable conjugating linker).

The term "agent" is used herein to denote a chemical compound, a mixture of chemical compounds, a biological macromolecule, or an extract made from biological materials. Examples of the agent include toxin, a microtubule inhibitor, a nucleic acid damaging agent, a dolastatin, an auristatin, a maytansinoid, a duocarmycin, a calicheamicin, or a combination thereof.

In some examples, the activatable molecule is conjugated to a cytotoxic agent, e.g., a toxin (e.g., an enzymatically active toxin of bacterial, fungal, plant, or animal origin, or fragments thereof) or a radioactive isotope.

Examples of cytotoxic agents include that can be conjugated to the activatable molecules dolastatins and derivatives thereof (e.g., auristatin E, AFP, monomethyl auristatin D (MMAD), monomethyl auristatin F (MMAF), monomethyl auristatin E (MMAE), desmethyl auristatin E (DMAE), auristatin F, desmethyl auristatin F (DMAF), dolastatin 16 (DmJ), dolastatin 16 (Dpv), auristatin derivatives (e.g., auristatin tyramine, auristatin quinolone), maytansinoids (e.g., DM-1, DM-4), maytansinoid derivatives, duocarmycin, alpha-amanitin, turbostatin, phenstatin, hydroxyphenstatin, spongistatin 5, spongistatin 7, halistatin 1, halistatin 2, halistatin 3, halocomstatin, pyrrolobenzimidazoles (PBI), cibrostatin6, doxaliform, cemadotin analogue (CemCH2-SH), *Pseudomonas* toxin A (PES8) variant, Pseudomonase toxin A (ZZ-PE38) variant, ZJ-101, anthracycline, doxorubicin, daunorubicin, bryostatin, camptothecin, 7-substituted campothecin, 11-difluoromethylenedioxycamptothecin, combretastatins, debromoaplysiatoxin, KahaMide-F, discodermolide, and Ecteinascidins. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine.

Examples of enzymatically active toxins that can be conjugated to the activatable molecules include diphtheria toxin, exotoxin A chain from *Pseudomonas aeruginosa*, ricin A chain, abrin A chain, modeccin A chain, alpha-sarcin, Aleuriies *fordii* proteins, dianfhin proteins, *Phytolaca Americana* proteins (e.g., PAPI, PAPII, and PAP-8), *Momordica charantia* inhibitor, curcin, crotirs, *Sapaonaria officinalis* inhibitor, geionin, mitogeliin, restrictocin, phenomycin, neomycin, and tricothecenes. A variety of radionuclides are available for the production of radioconjugated molecules. Examples of radionuclides include $^{212}$Bi, $^{131}$I, $^{131}$In, $^{90}$Y, and $^{186}$Re.

Examples of anti-neoplastics that can be conjugated to the activatable molecules include: adriamycin, cerubidine, bleomycin, alkeran, velban, oncovin, fluorouracil, methotrexate, thiotepa, bisantrene, novantrone, thioguanine, procarabizine, and cytarabine.

Examples of antivirals that can be conjugated to the activatable molecules include acyclovir, vira A, and symmetrel. Examples of antifungals that can be conjugated to the activatable molecules include: nystatin. Examples of detection reagents that can be conjugated to the activatable molecules include: fluorescein and derivatives thereof, fluorescein isothiocyanate (FITC). Examples of antibacterials that can be conjugated to the activatable molecules include: aminoglycosides, streptomycin, neomycin, kanamycin, amikacin, gentamicin, and tobramycin. Examples of 3beta, 16beta, 17alpha-trihydroxycholest-5-en-22-one16-O-(2-O-4-methoxybenzoyl-beta-D-xylopyranosyl)-(1->3)-(2-O-acetyl-alpha-L-arabinopyranoside) (OSW-1) that can be conjugated to the activatable molecules include: s-nitrobenzyloxycarbonyl derivatives of 06-benzylguanine, toposisomerase inhibitors, hemiasterlin, cephalotaxine, homoharringionine, pyrrol obenzodiazepine dimers (PBDs), functionalized pyrrolobenzodiazepenes, calcicheamicins, podophyiitoxins, taxanes, and *vinca* alkoids. Examples of radiopharmaceuticals that can be conjugated to the activatable molecules include: $^{123}$I, $^{89}$Zr, $^{125}$I, $^{131}$I, $^{201}$Tl, $^{62}$Cu, $^{18}$F, $^{68}$Ga, $^{13}$N, $^{15}$O, $^{38}$K, $^{82}$Rb, $^{111}$In, $^{133}$Xe, $^{11}$C, and $^{99m}$Tc (Technetium). Examples of heavy metals that can be conjugated to the activatable molecules include: barium, gold, and platinum. Examples of anti-mycoplasmals that can be conjugated to the activatable molecules include: tylosine, spectinomycin, streptomycin B, ampicillin, sulfanilamide, polymyxin, and chloramphenicol.

In some embodiments, the agent is a nucleic acid damaging agent, such as a DNA alkylator or DNA intercalator, or other DNA damaging agent.

Additional examples of the agents that can be conjugated include those in Table 1 below.

TABLE 1

| Exemplary Pharmaceutical Agents for Conjugation |
| --- |
| CYTOTOXIC AGENTS |
| Auristatins |
| Auristatin E |
| Monomethyl auristatin D (MMAD) |
| Monomethyl auristatin E (MMAE) |
| Desmethyl auristatin E (DMAE) |
| Auristatin F |
| Monomethyl auristatin F (MMAF) |
| Desmethyl auristatin F (DMAF) |
| Auristatin derivatives, e.g., amides thereof |
| Auristatin tyramine |
| Auristatin quinoline |
| Dolastatins |
| Dolastatin derivatives |
| Dolastatin 16 DmJ |
| Dolastatin 16 Dpv |
| Maytansinoids, e.g. DM-1; DM-4 |
| Maytansinoid derivatives |
| Duocarmycin |
| Duocarmycin derivatives |
| Alpha-amanitin |
| Anthracyclines |
| Doxorubicin |
| Daunorubicin |
| Bryostatins |
| Camptothecin |
| Camptothecin derivatives |
| 7-substituted Camptothecin |
| 10,11-Difluoromethylenedioxycamptothecin |
| Combretastatins |
| Debromoaplysiatoxin |
| Kahalalide-F |
| Discodermolide |
| Ecteinascidins |
| ANTIVIRALS |
| Acyclovir |
| Vira A |
| Symmetrel |
| ANTIFUNGALS |
| Nystatin |
| ADDITIONAL ANTI-NEOPLASTICS |
| Adriamycin |
| Cerubidine |
| Bleomycin |
| Alkeran |
| Velban |
| Oncovin |
| Fluorouracil |
| Methotrexate |
| Thiotepa |
| Bisantrene |
| Novantrone |
| Thioguanine |
| Procarabizine |
| Cytarabine |
| ANTI-BACTERIALS |
| Aminoglycosides |
| Streptomycin |
| Neomycin |
| Kanamycin |
| Amikacin |
| Gentamicin |
| Tobramycin |
| Streptomycin B |
| Spectinomycin |
| Ampicillin |
| Sulfanilamide |
| Polymyxin |
| Chloramphenicol |

TABLE 1-continued

| Exemplary Pharmaceutical Agents for Conjugation |
| --- |
| Turbostatin |
| Phenstatins |
| Hydroxyphenstatin |
| Spongistatin 5 |
| Spongistatin 7 |
| Halistatin 1 |
| Halistatin 2 |
| Halistatin 3 |
| Modified Bryostatins |
| Halocomstatins |
| Pyrrolobenzimidazoles (PBI) |
| Cibrostatin6 |
| Doxaliform |
| Anthracyclins analogues |
| Cemadotin analogue (CemCH2-SH) |
| *Pseudomonas* toxin A (PE38) variant |
| *Pseudomonas* toxin A (ZZ-PE38) variant |
| ZJ-101 |
| OSW-1 |
| 4-Nitrobenzyloxycarbonyl Derivatives of O6-Benzylguanine |
| Topoisomerase inhibitors |
| Hemiasterlin |
| Cephalotaxine |
| Homoharringtonine |
| Pyrrolobenzodiazepine dimers (PBDs) |
| Functionalized pyrrolobenzodiazepenes |
| Calicheamicins |
| Podophyllotoxins |
| Taxanes |
| Vinca alkaloids |
| CONJUGATABLE DETECTION REAGENTS |
| Fluorescein and derivatives thereof |
| Fluorescein isothiocyanate (FITC) |
| RADIOPHARMACEUTICALS |
| $^{125}$I |
| $^{131}$I |
| $^{89}$Zr |
| $^{111}$In |
| $^{123}$I |
| $^{131}$I |
| $^{99}$mTc (Technetium) |
| $^{201}$Tl |
| $^{133}$Xe |
| $^{11}$C |
| $^{62}$Cu |
| $^{18}$F |
| $^{68}$Ga |
| $^{13}$N |
| $^{15}$O |
| $^{38}$K |
| $^{82}$Rb |
| HEAVY METALS |
| Barium |
| Gold |
| Platinum |
| ANTI-MYCOPLASMALS |
| Tylosine |
| Spectinomycin |
| Nanoparticles |

In some embodiments, the activatable molecule comprises a signal peptide. If comprising multiple polypeptides, the activatable molecule may comprise multiple signal peptides, e.g., one signal peptide for each of the multiple polypeptides. A signal peptide may be a peptide (e.g., 10-30 amino acids long) present at a terminus (e.g., the N-terminus or C-terminus) of a newly synthesized proteins that are destined toward the secretory pathway. In some embodiments, the signal peptide may be conjugated to the activatable molecule via a spacer. In some embodiments, the spacer may be conjugated to the activatable molecule in the absence of a signal peptide.

Those of ordinary skill in the art will recognize that a large variety of possible agents may be conjugated to any of the activatable molecules described herein. The agents may be conjugated to another component of the activatable molecule by a conjugating linker. Conjugation may include any chemical reaction that binds the two molecules so long as the activatable molecule and the other moiety retain their respective activities. Conjugation may include many chemical mechanisms, e.g., covalent binding, affinity binding, intercalation, coordinate binding, and complexation. In some embodiments, the binding may be covalent binding. Covalent binding may be achieved either by direct condensation of existing side chains or by the incorporation of external bridging molecules. Many bivalent or polyvalent linking agents may be useful in conjugating any of the activatable molecules described herein. For example, conjugation may include organic compounds, such as thioesters, carbodiimides, succinimide esters, glutaraldehyde, diazobenzenes, and hexamethylene diamines. In some embodiments, the activatable molecules may include, or otherwise introduce, one or more non-natural amino acid residues to provide suitable sites for conjugation.

In some embodiments, an agent is attached by disulfide bonds (e.g., disulfide bonds on a cysteine molecule) to the activatable molecule. Since many cancers naturally release high levels of glutathione, a reducing agent, glutathione present in the cancerous tissue microenvironment can reduce the disulfide bonds, and subsequently release the agent at the site of delivery.

In some embodiments, when the agent binds its target in the presence of complement within the target site (e.g., diseased tissue (e.g., cancerous tissue)), the amide or ester bond attaching the agent to the linker is cleaved, resulting in the release of the agent in its activated form. These agents when administered to a subject, may accomplish delivery and release of the agent at the target site (e.g., diseased tissue (e.g., cancerous tissue)). These agents may be effective for the in vivo delivery of any of the agents described herein.

In some embodiments, the one or more agents is conjugated to a component of the activatable molecule (e.g., AM) via a conjugating linker. The conjugating linker may be a peptide or chemical moiety linking the agent and the activatable molecule. In some examples, the conjugating linker may be cleavable (e.g., by an enzyme such as a protease). In some examples, the conjugating linker may be non-cleavable (e.g., cannot be cleaved by an enzyme such as a protease). In some embodiments, the conjugating linker may be non-cleavable by enzymes of the complement system. In some embodiments, two or more conjugating linkers are present. The two or more conjugating linkers may be the same, i.e., cleavable or non-cleavable. The two or more conjugating linkers may be different, i.e., at least one cleavable and at least one non-cleavable. For example, the agent may be released without complement activation since complement activation ultimately lyses the target cell. In such embodiments, the conjugate and/or agent is to be delivered to the target cell (e.g., hormones, enzymes, corticosteroids, neurotransmitters, or genes). Furthermore, the conjugating linker may be mildly susceptible to cleavage by serum proteases, and the conjugate and/or agent is released slowly at the target site.

In some embodiments, the agent is conjugated to a component of the activatable molecule via a maleimide caproyl-valine-citrulline linker or a maleimide PEG-valine-citrulline linker. In some embodiments, the agent is conjugated to a component of the activatable molecule via a maleimide caproyl-valine-citrulline linker. In some embodiments, the agent is conjugated to a component of the activatable molecule via a maleimide PEG-valine-citrulline linker. In some embodiments, the agent is monomethyl auristatin D (MMAD) conjugated to a component of the activatable molecule via a maleimide PEG-valine-citrulline-para-aminobenzyloxycarbonyl linker, and this linker payload construct is vc-MMAD. In some embodiments, the agent is monomethyl auristatin E (MMAE) conjugated to a component of the activatable molecule via a maleimide PEG-valine-citrulline-para-aminobenzyloxycarbonyl linker, and this linker payload construct is vc-MMAE.

In some embodiments, the agent may be designed such that the agent is delivered to the target site (e.g., disease tissue (e.g., cancerous tissue)) but the conjugate and/or agent is not released.

In some embodiments, the agent may be attached to an AM either directly or via amino acids (e.g., D-amino acids), peptides, thiol-containing moieties, or other organic compounds that may be modified to include functional groups that can subsequently be utilized in attachment to AM by methods described herein.

In some embodiments, an activatable molecule includes at least one point of conjugation for an agent. In some embodiments, all possible points of conjugation are available for conjugation to an agent. In some embodiments, the one or more points of conjugation may include sulfur atoms involved in disulfide bonds, sulfur atoms involved in interchain disulfide bonds, sulfur atoms involved in interchain sulfide bonds but not sulfur atoms involved in intrachain disulfide bonds, and/or sulfur atoms of cysteine or other amino acid residues containing a sulfur atom. In such cases, residues may occur naturally in the protein construct structure or may be incorporated into the protein construct using methods including site-directed mutagenesis, chemical conversion, or mis-incorporation of non-natural amino acids.

The present disclosure also provides methods and materials for preparing an activatable molecule with one or more conjugated agents. In some embodiments, an activatable molecule may be modified to include one or more interchain disulfide bonds. For example, disulfide bonds may undergo reduction following exposure to a reducing agent such as, without limitation, TCEP, DTT, or β-mercaptoethanol. In some cases, the reduction of the disulfide bonds may be only partial. As used herein, the term partial reduction refers to situations where an activatable molecule is contacted with a reducing agent and a fraction of all possible sites of conjugation undergo reduction (e.g., not all disulfide bonds are reduced). In some embodiments, an activatable molecule may be partially reduced following contact with a reducing agent if less than 99%, (e.g., less than 98%, 97%, 96%, 95%, 90%, 85%, 80%, 75%, 70%, 65%, 60%, 55%, 50%, 45%, 40%, 35%, 30%, 25%, 20%, 15%, 10% or 5%) of all possible sites of conjugation are reduced. In some embodiments, the activatable molecule having a reduction in one or more interchain disulfide bonds may be conjugated to a drug reactive with free thiols.

The present disclosure also provides methods and materials for conjugating a therapeutic agent to a particular location on an activatable molecule. In some embodiments, an activatable molecule may be modified so that the therapeutic agents can be conjugated to the activatable molecule at particular locations on the activatable molecule. For example, an activatable molecule may be partially reduced in a manner that facilitates conjugation to the activatable molecule. In such cases, partial reduction of the activatable molecule may occur in a manner that conjugation sites in the activatable molecule are not reduced. In some embodiments, the conjugation site(s) on the activatable molecule may be selected to facilitate conjugation of an agent at a particular location on the protein construct. Various factors can influence the "level of reduction" of the activatable molecule upon treatment with a reducing agent. For example, without limitation, the ratio of reducing agent to activatable molecule, length of incubation, incubation temperature, and/or pH of the reducing reaction solution can require optimization in order to achieve partial reduction of the activatable molecule with the methods and materials described herein. Any appropriate combination of factors (e.g., ratio of reducing agent to activatable molecule, the length and temperature of incubation with reducing agent, and/or pH of reducing agent) may be used to achieve partial reduction of the activatable molecule (e.g., general reduction of possible conjugation sites or reduction at specific conjugation sites).

An effective ratio of reducing agent to activatable molecule can be any ratio that at least partially (i.e., partially or fully) reduces the activatable molecule in a manner that allows conjugation to an agent (e.g., general reduction of possible conjugation sites or reduction at specific conjugation sites). In some embodiments, the ratio of reducing agent to activatable molecule may be in a range from about 20:1 to 1:1, from 10:1 to 1:1, from 9:1 to 1:1, from 8:1 to 1:1, from 7:1 to 1:1, from 6:1 to 1:1, from 5:1 to 1:1, from 4:1 to 1:1, from 3:1 to 1:1, from 2:1 to 1:1, from 20:1 to 1:1.5, from 10:1 to 1:1.5, from 9:1 to 1:1.5, from 8:1 to 1:1.5, from 7:1 to 1:1.5, from 6:1 to 1:1.5, from 5:1 to 1:1.5, from 4:1 to 1:1.5, from 3:1 to 1:1.5, from 2:1 to 1:1.5, from 1.5:1 to 1:1.5, or from 1:1 to 1:1.5.

An effective incubation time and temperature for treating an activatable molecule with a reducing agent may be any time and temperature that at least partially reduces the activatable molecule in a manner that allows conjugation of an agent to an activatable molecule (e.g., general reduction of possible conjugation sites or reduction at specific conjugation sites). In some embodiments, the incubation time and temperature for treating an activatable molecule may be in a range from about 1 hour at 37° C. to about 12 hours at 37° C. (or any subranges therein).

An effective pH for a reduction reaction for treating an activatable molecule with a reducing agent can be any pH that at least partially reduces the activatable molecule in a manner that allows conjugation of the activatable molecule to an agent (e.g., general reduction of possible conjugation sites or reduction at specific conjugation sites).

When a partially-reduced activatable molecule is contacted with an agent containing thiols, the agent may conjugate to the interchain thiols in the activatable molecule. An agent can be modified in a manner to include thiols using a thiol-containing reagent (e.g., cysteine or N-acetyl cysteine). For example, the activatable molecule can be partially reduced following incubation with reducing agent (e.g., TEPC) for about 1 hour at about 37° C. at a desired ratio of reducing agent to activatable molecule. An effective ratio of reducing agent to activatable molecule may be any ratio that partially reduces at least two interchain disulfide bonds located in the activatable molecule in a manner that allows conjugation of a thiol-containing agent (e.g., general reduction of possible conjugation sites or reduction at specific conjugation sites).

In some embodiments, an activatable molecule may be reduced by a reducing agent in a manner that avoids reducing any intrachain disulfide bonds. In some embodiments of, an activatable molecule may be reduced by a reducing agent in a manner that avoids reducing any intrachain disulfide bonds and reduces at least one interchain disulfide bond.

In some embodiments, the agent may be a detectable moiety such as, for example, a label or other marker. For example, the agent may be or include a radiolabeled amino acid, one or more biotinyl moieties that can be detected by marked avidin (e.g., streptavidin containing a fluorescent marker or enzymatic activity that can be detected by optical or calorimetric methods), one or more radioisotopes or radionuclides, one or more fluorescent labels, one or more enzymatic labels, and/or one or more chemiluminescent agents. In some embodiments, detectable moieties may be attached by spacer molecules. In some embodiments, the detectable label may include an imaging agent, a contrasting agent, an enzyme, a fluorescent label, a chromophore, a dye, one or more metal ions, or a ligand-based label. In some embodiments, the imaging agent may comprise a radioisotope. In some embodiments, the radioisotope may be indium or technetium. In some embodiments, the contrasting agent may comprise iodine, gadolinium or iron oxide. In some embodiments, the enzyme may comprise horseradish peroxidase, alkaline phosphatase, or β-galactosidase. In some embodiments, the fluorescent label may comprise yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments, the luminescent label may comprise an N-methyl-acrydium derivative. In some embodiments, the label may comprise an Alexa Fluor® label, such as Alex Fluor® 680 or Alexa Fluor® 750. In some embodiments, the ligand-based label may comprise biotin, avidin, streptavidin or one or more haptens.

Further examples of detectable labels also include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^3H$.

In some embodiments, the agent may be conjugated to the activatable molecule using a carbohydrate moiety, sulfhydryl group, amino group, or carboxylate group. In some embodiments, the agent may be conjugated to the activatable molecule via a linker and/or a substrate described herein. In some embodiments, the agent may be conjugated to a cysteine or a lysine in the activatable molecule. In some embodiments, the agent may be conjugated to another residue of the activatable molecule, such as those residues disclosed herein.

In some embodiments, a variety of bifunctional protein-coupling agents may be used to conjugate the agent to the activatable molecule including N-succinimidyl-3-(2-pyridyldithiol) propionate (SPDP), iminothiolane (IT), bifunctional derivatives of imidoesters (e.g., dimethyl adipimidate HCL), active esters (e.g., disuccinimidyl suberate), aldehydes (e.g., glutareldehyde), bis-azido compounds (e.g., bis (p-azidobenzoyl) hexanediamine), bis-diazonium derivatives (e.g., bis-(p-diazoniumbenzoyl)-ethylenediamine), diisocyanates (e.g., tolyene 2,6-diisocyanate), and bis-active fluorine compounds (e.g., 1,5-difluoro-2,4-dinitrobenzene). For example, a ricin immunotoxin can be prepared as described in Vitetta et al., Science 238:1098 (1987). In some embodiments, a carbon-14-labeled 1-isothiocyanatobenzyl-3-methyldiethylene triaminepentaacetic acid (MX-DTPA) chelating agent can be used to conjugate a radionucleotide to the activatable molecule. (See, e.g., WO94/11026).

Suitable conjugating linkers also include those described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an activatable molecule by way of an oligopeptide. In some embodiments, suitable conjugating linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide]hexanoate (Pierce Chem. Co. Cat. #2165-G); and (v) sulfo-NHS (N-hydroxysulfo-succinimide: Pierce Chem. Co., Cat. #24510) conjugated to EDC. Additional example agents include SMCC, sulfo-SMCC, SPDB, and sulfo-SPDB.

Exemplary conjugating linkers for attachment to reduced activatable molecules include those having certain reactive groups capable of reaction with a sulfhydryl group of a reduced antibody or fragment. Such reactive groups include reactive haloalkyl groups (including, for example, haloacetyl groups), p-mercuribenzoate groups and groups capable of Michael-type addition reactions (including, for example, maleimides and groups of the type described by Mitra and Lawton, 1979, J. Amer. Chem. Soc. 101:3097-3110).

Exemplary conjugating linkers for attachment to neither oxidized nor reduced activatable molecules include those having certain functional groups capable of reaction with the primary amino groups present in unmodified lysine residues in the activatable molecules. Such reactive groups include NHS carboxylic or carbonic esters, sulfo-NHS carboxylic or carbonic esters, 4-nitrophenyl carboxylic or carbonic esters, pentafluorophenyl carboxylic or carbonic esters, acyl imidazoles, isocyanates, and isothiocyanates, and other dehydrating agents utilized for carboxamide formation. In these instances, the functional groups present in the suitable conjugating linkers include primary and secondary amines, hydrazines, hydroxylamines, and hydrazides.

The agent may be attached to the conjugating linker before or after the conjugating linker is attached to the activatable molecule. In certain applications it may be desirable to first produce an activatable molecule-conjugating linker intermediate in which the conjugating linker is free of an associated agent. Depending upon the particular application, a specific agent may then be covalently attached to the conjugating linker. In some embodiments, the AM is first attached to the MM, substrate and associated linking peptides and then attached to the conjugating linker for conjugation purposes.

In specific embodiments, branched conjugating linkers that have multiple sites for attachment of agents are utilized. For multiple site conjugating linkers, a single covalent attachment to an activatable molecule may result in an activatable molecule-linker intermediate capable of binding an agent at a number of sites. The sites may be aldehyde or sulfhydryl groups or any chemical site to which agents can be attached.

In some embodiments, higher specific activity (or higher ratio of agents to activatable molecule) can be achieved by attachment of a single site conjugating linker at a plurality of sites on the activatable molecule. This plurality of sites may be introduced into the activatable molecule by either of two methods. First, one may generate multiple aldehyde groups and/or sulfhydryl groups in the same activatable molecule. Second, one may attach to an aldehyde or sulfhydryl of the activatable molecule a branched conjugating linker having multiple functional sites for subsequent attachment to conjugating linkers. The functional sites of the branched conjugating linker or multiple site conjugating linker may be aldehyde or sulfhydryl groups, or may be any chemical site to which conjugating linkers may be attached. Still higher specific activities may be obtained by combining these two approaches, that is, attaching multiple site conjugating linkers at several sites on the activatable molecule.

Peptide conjugating linkers that are susceptible to cleavage by enzymes of the complement system, such as but not limited to u-plasminogen activator, tissue plasminogen activator, trypsin, plasmin, or another enzyme having proteolytic activity may be used in one embodiment of the present disclosure. According to one method of the present disclosure, an agent is attached via a conjugating linker susceptible to cleavage by complement. The antibody is selected from a class that can activate complement. The antibody-agent conjugate, thus, activates the complement cascade and releases the agent at the target site. According to another method of the present disclosure, an agent is attached via a conjugating linker susceptible to cleavage by enzymes having a proteolytic activity such as a u-plasminogen activator, a tissue plasminogen activator, plasmin, or trypsin. These cleavable conjugating linkers are useful in conjugated activatable molecules that include an extracellular toxin, e.g., by way of non-limiting example, any of the extracellular toxins shown in Table 1.

Non-limiting examples of cleavable linker sequences include any cleavable sequence disclosed herein or incorporated herein by reference as well as the exemplary sequences provided in Table 2.

TABLE 2

| Exemplary Conjugating Linker Sequences for Conjugation | |
|---|---|
| Types of Cleavable Sequences | Amino Acid Sequence |
| Plasmin cleavable sequences | |
| Pro-urokinase | PRFKIIGG (SEQ ID NO: 529) |
| | PRFRIIGG (SEQ ID NO: 530) |
| TGFβ | SSRHRRALD (SEQ ID NO: 531) |
| Plasminogen | RKSSIIIRMRDVVL (SEQ ID NO: 532) |
| Staphylokinase | SSSFDKGKYKKGDDA (SEQ ID NO: 533) |
| | SSSFDKGKYKRGDDA (SEQ ID NO: 534) |
| Factor Xa cleavable sequences | IEGR (SEQ ID NO: 535) |
| | IDGR (SEQ ID NO: 536) |
| | GGSIDGR (SEQ ID NO: 537) |
| MMP cleavable sequences | |
| Gelatinase A | PLGLWA (SEQ ID NO: 538) |
| Collagenase cleavable sequences | |
| Calf skin collagen (α1(I) chain) | GPQGIAGQ (SEQ ID NO: 539) |
| Calf skin collagen (α2(I) chain) | GPQGLLGA (SEQ ID NO: 540) |
| Bovine cartilage collagen (α1(II) chain) | GIAGQ (SEQ ID NO: 541) |
| Human liver collagen (α1(III) chain) | GPLGIAGI (SEQ ID NO: 542) |
| Human α2M | GPEGLRVG (SEQ ID NO: 543) |
| Human PZP | YGAGLGVV (SEQ ID NO:544 ) |
| | AGLGVVER (SEQ ID NO: 545) |
| | AGLGISST (SEQ ID NO: 546) |
| Rat α1M | EPQALAMS (SEQ ID NO: 547) |
| | QALAMSAI (SEQ ID NO: 548) |

TABLE 2-continued

| Exemplary Conjugating Linker Sequences for Conjugation | |
| --- | --- |
| Types of Cleavable Sequences | Amino Acid Sequence |
| Rat α2M | AAYHLVSQ (SEQ ID NO: 549) |
| | MDAFLESS (SEQ ID NO: 550) |
| Rat $\alpha_1 I_3$ (2J) | ESLPVVAV (SEQ ID NO: 551) |
| Rat $\alpha_1 I_3$ (27J) | SAPAVESE (SEQ ID NO: 552) |
| Human fibroblast collagenase | DVAQFVLT (SEQ ID NO: 553) |
| (autolytic cleavages) | VAQFVLTE (SEQ ID NO: 554) |
| | AQFVLTEG (SEQ ID NO: 555) |
| | PVQPIGPQ (SEQ ID NO:556) |

In addition, the agents may be attached via disulfide bonds (for example, the disulfide bonds on a cysteine molecule) to the activatable molecule. Since many tumors naturally release high levels of glutathione (a reducing agent) this can reduce the disulfide bonds with subsequent release of the agent at the site of delivery. In some embodiments, the reducing agent that would modify a substrate would also modify the conjugating linker of the conjugated activatable molecule.

In some embodiments, it may be necessary to construct the conjugating linker in such a way as to optimize the spacing between the agent and the activatable molecule. This may be accomplished by use of a conjugating linker of the general structure:

W—(CH$_2$)n-Q wherein

W is either —NH—CH$_2$— or —CH$_2$—;

Q is an amino acid, a polypeptide having between 2 to 20 amino acids; and n is an integer from 0 to 20.

In some embodiments, the conjugating linker may comprise a spacer element and a cleavable element. The spacer element serves to position the cleavable element away from the core of the activatable molecule such that the cleavable element is more accessible to the enzyme responsible for cleavage. Certain of the branched linkers described above may serve as spacer elements.

Throughout this discussion, it should be understood that attachment of the conjugating linker to the agent (or of spacer element to cleavable element, or cleavable element to agent) need not be by a particular mode of attachment or reaction. Any reaction providing a product of suitable stability and biological compatibility is acceptable.

In some embodiments, when release of an agent is desired, an activatable molecule that is an antibody of a class that can activate complement is used. The resulting conjugate retains both the ability to bind antigen and activate the complement cascade. Thus, according to this embodiment of the present disclosure, an agent is joined to one end of the cleavable conjugating linker or cleavable element and the other end of the conjugating linker group is attached to a specific site on the activatable molecule. For example, if the agent has a hydroxyl group or an amino group, it may be attached to the carboxyl terminus of a peptide, amino acid or other suitably chosen conjugating linker via an ester or amide bond, respectively. For example, such agents may be attached to the linker peptide via a carbodiimide reaction. If the agent contains functional groups that would interfere with attachment to the conjugating linker, these interfering functional groups can be blocked before attachment and deblocked once the product conjugate or intermediate is made. The opposite or amino terminus of the linker is then used either directly or after further modification for binding to an activatable molecule that is capable of activating complement.

Conjugating linkers (or spacer elements of conjugating linkers) may be of any desired length, one end of which can be covalently attached to specific sites on the activatable molecule. The other end of the conjugating linker or spacer element may be attached to an amino acid or peptide conjugating linker.

Thus when these conjugates bind antigen in the presence of complement the amide or ester bond that attaches the agent to the linker will be cleaved, resulting in release of the agent in its active form. These conjugates, when administered to a subject, will accomplish delivery and release of the agent at the target site, and are particularly effective for the in vivo delivery of pharmaceutical agents, antibiotics, antimetabolites, antiproliferative agents and the like.

In some embodiments, release of the agent without complement activation is desired since activation of the complement cascade will ultimately lyse the target cell. Hence, this approach is useful when delivery and release of the agent should be accomplished without killing the target cell. Such is the goal when delivery of cell mediators such as hormones, enzymes, corticosteroids, neurotransmitters, genes or enzymes to target cells is desired. These conjugates may be prepared by attaching the agent to an activatable molecule that is not capable of activating complement via a linker that is mildly susceptible to cleavage by serum proteases. When this conjugate is administered to an individual, antigen-antibody complexes will form quickly whereas cleavage of the agent will occur slowly, thus resulting in release of the compound at the target site.

In some embodiments, the activatable molecule may be conjugated to one or more therapeutic agents using certain biochemical cross-linkers. Cross-linking reagents form molecular bridges that tie together functional groups of two different molecules. To link two different proteins in a step-wise manner, hetero-bifunctional cross-linkers can be used that eliminate unwanted homopolymer formation.

Peptidyl conjugating linkers cleavable by lysosomal proteases are also useful, for example, Val-Cit, Val-Ala or other dipeptides. In addition, acid-labile conjugating linkers cleavable in the low-pH environment of the lysosome may be used, for example: bis-sialyl ether. Other suitable conjugating linkers include cathepsin-labile substrates, particularly those that show optimal function at an acidic pH.

Exemplary hetero-bifunctional cross-linkers are referenced in Table 3.

TABLE 3

Exemplary Hetero-Bifunctional Cross-Linkers
HETERO-BIFUNCTIONAL CROSS-LINKERS

| Linker | Reactive Toward | Advantages and Applications | Spacer Arm Length after cross-linking (Angstroms) |
|---|---|---|---|
| SMPT | Primary amines Sulfhydryls | Greater stability | 11.2 Å |
| SPDP | Primary amines Sulfhydryls | Thiolation Cleavable cross-linking | 6.8 Å |
| LC-SPDP | Primary amines Sulfhydryls | Extended spacer arm | 15.6 Å |
| Sulfo-LC-SPDP | Primary amines Sulfhydryls | Extender spacer arm Water-soluble | 15.6 Å |
| SMCC | Primary amines | Stable maleimide reactive group | 11.6 Å |
| | Sulfhydryls | Enzyme-antibody conjugation Hapten-carrier protein conjugation | |
| Sulfo-SMCC | Primary amines | Stable maleimide reactive group | 11.6 Å |
| | Sulfhydryls | Water-soluble Enzyme-antibody conjugation | |
| MBS | Primary amines | Enzyme-antibody conjugation | 9.9 Å |
| | Sulfhydryls | Hapten-carrier protein conjugation | |
| Sulfo-MBS | Primary amines Sulfhydryls | Water-soluble | 9.9 Å |
| SIAB | Primary amines | Enzyme-antibody conjugation | 10.6 Å |
| | Sulfhydryls | | |
| Sulfo-SIAB | Primary amines Sulfhydryls | Water-soluble | 10.6 Å |
| SMPB | Primary amines Sulfhydryls | Extended spacer arm Enzyme-antibody conjugation | 14.5 Å |
| Sulfo-SMPB | Primary amines Sulfhydryls | Extended spacer arm Water-soluble | 14.5 Å |
| EDE/Sulfo-NHS | Primary amines Carboxyl groups | Hapten-Carrier conjugation | 0 |
| ABH | Carbohydrates Nonselective | Reacts with sugar groups | 11.9 Å |

In some embodiments, the agent may be designed so that the agent is delivered to the target but not released. This may be accomplished by attaching an agent to an activatable molecule either directly or via a non-cleavable conjugating linker.

These non-cleavable conjugating linkers may include amino acids, peptides, D-amino acids or other organic compounds that may be modified to include functional groups that can subsequently be utilized in attachment to activatable molecules by the methods described herein.

In some embodiments, a compound may be attached to activatable molecules that do not activate complement. When using activatable molecules that are incapable of complement activation, this attachment may be accomplished using conjugating linkers that are susceptible to cleavage by activated complement or using linkers that are not susceptible to cleavage by activated complement.

The substrate-containing polypeptides disclosed herein can also be formulated as immunoliposomes. Liposomes containing the antibody are prepared by methods known in the art, such as described in Epstein et al., Proc. Natl. Acad. Sci. USA, 82:3688 (1985); Hwang et al., Proc. Natl Acad. Sci. USA, 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. A component of an activatable molecule can be conjugated to the liposomes as described in Martin et al., J. Biol. Chem., 257:286-288 (1982) via a disulfide-interchange reaction.

The agents described above may contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the SMPT contains a sterically-hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

Those of ordinary skill in the art will recognize that a large variety of possible agents can be conjugated to the activatable molecule of the disclosure. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference). In general, an effective conjugation of an agent (e.g., cytotoxic agent) to an activatable molecule can be accomplished by any chemical reaction that will bind the agent to the activatable molecule while also allowing the agent and the activatable molecule to retain functionality.

Nucleic Acids and Vectors

In some aspects, the present disclosure further provides nucleic acids comprising sequences that encode the substrate-containing polypeptides and polypeptide complexes (e.g., activatable molecules) herein, or components or fragment thereof. The nucleic acids may comprise coding sequences for the substrates. The nucleic acids may further comprise coding sequences for other components in an activatable molecule, e.g., the AMs, the MMs, the EM and/or the linker(s). In cases where the activatable molecule comprises multiple polypeptides, the nucleic acids may comprise coding sequences for the multiple polypeptides. In some examples, the coding sequence for one of the polypeptides is comprised in a nucleic acid molecule, and the coding sequence for another one of the polypeptides is comprised in another nucleic acid molecule. In some examples, the coding sequences for two or more of the multiple polypeptides are comprised in the same nucleic acid molecule.

Unless otherwise specified, a "nucleic acid sequence encoding a protein" includes all nucleotide sequences that are degenerate versions of each other and thus encode the same amino acid sequence. The term "nucleic acid" refers to a deoxyribonucleic acid (DNA) or ribonucleic acid (RNA), or a combination thereof, in either a single- or double-stranded form. Unless specifically limited, the term encompasses nucleic acids containing known analogues of natural nucleotides that have similar binding properties as the reference nucleotides. Unless otherwise indicated, a particular nucleic acid sequence also implicitly encompasses complementary sequences as well as the sequence explicitly indicated. In some embodiments, the nucleic acid is DNA. In some embodiments, the nucleic acid is RNA.

Modifications may be introduced into a nucleotide sequence by standard techniques known in the art, such as site-directed mutagenesis and polymerase chain reaction (PCR)-mediated mutagenesis. Conservative amino acid substitutions are ones in which the amino acid residue is replaced with an amino acid residue having a similar side chain. Families of amino acid residues having similar side chains have been defined in the art. These families include: amino acids with acidic side chains (e.g., aspartate and glutamate), amino acids with basic side chains (e.g., lysine, arginine, and histidine), non-polar amino acids (e.g., alanine, valine, leucine, isoleucine, proline, phenylalanine, methionine, and tryptophan), uncharged polar amino acids (e.g., glycine, asparagine, glutamine, cysteine, serine, threonine and tyrosine), hydrophilic amino acids (e.g., arginine, asparagine, aspartate, glutamine, glutamate, histidine, lysine, serine, and threonine), hydrophobic amino acids (e.g., alanine, cysteine, isoleucine, leucine, methionine, phenylalanine, proline, tryptophan, tyrosine, and valine). Other families of amino acids include: aliphatic-hydroxy amino acids (e.g., serine and threonine), amide family (e.g., asparagine and glutamine), alphatic family (e.g., alanine, valine, leucine and isoleucine), and aromatic family (e.g., phenylalanine, tryptophan, and tyrosine).

The present disclosure further provides vectors and sets of vectors comprising any of the nucleic acids described herein. One skilled in the art will be capable of selecting suitable vectors or sets of vectors (e.g., expression vectors) for making any of the activatable molecules described herein, and using the vectors or sets of vectors to express any of the activatable molecules described herein. For example, in selecting a vector or a set of vectors, the type of cell may be selected such that the vector(s) may need to be able to integrate into a chromosome of the cell and/or replicate in it. Example vectors that can be used to produce an activatable molecule are also described herein. As used herein, the term "vector" refers to a polynucleotide capable of inducing the expression of a recombinant protein (e.g., a first or second monomer) in a cell (e.g., any of the cells described herein). A "vector" is able to deliver nucleic acids and fragments thereof into a host cell, and includes regulatory sequences (e.g., promoter, enhancer, poly(A) signal). Exogenous polynucleotides may be inserted into the expression vector in order to be expressed. The term "vector" also includes artificial chromosomes, plasmids, retroviruses, and baculovirus vectors.

Methods for constructing suitable vectors that comprise any of the nucleic acids described herein, and suitable for transforming cells (e.g., mammalian cells) are well-known in the art. See, e.g., Sambrook et al., Eds. "Molecular Cloning: A Laboratory Manual," 2nd Ed., Cold Spring Harbor Press, 1989 and Ausubel et al., Eds. "Current Protocols in Molecular Biology," Current Protocols, 1993.

Examples of vectors include plasmids, transposons, cosmids, and viral vectors (e.g., any adenoviral vectors (e.g., pSV or pCMV vectors), adeno-associated virus (AAV) vectors, lentivirus vectors, and retroviral vectors), and any Gateway® vectors. A vector may, for example, include sufficient cis-acting elements for expression; other elements for expression may be supplied by the host mammalian cell or in an in vitro expression system. Skilled practitioners will be capable of selecting suitable vectors and mammalian cells for making any activatable molecule described herein.

In some embodiments, the substrate-containing polypeptides may be made biosynthetically using recombinant DNA technology and expression in eukaryotic or prokaryotic species.

Cells

In some aspects, the present disclosure provides recombinant host cells comprising any of the vectors or nucleic acids described herein. The cells may be used to produce the substrate-containing polypeptides (e.g., activatable molecules) described herein. In some embodiments, the cell may be an animal cell, a mammalian cell (e.g., a human cell), a rodent cell (e.g., a mouse cell, a rat cell, a hamster cell, or a guinea pig cell), a non-human primate cell, an insect cell, a bacterial cell, a fungal cell, or a plant cell. In some embodiments, the cell may be a eukaryotic cell. As used herein, the term "eukaryotic cell" refers to a cell having a distinct, membrane-bound nucleus. Such cells may include, for example, mammalian (e.g., rodent, non-human primate, or human), insect, fungal, or plant cells. In some embodiments, the eukaryotic cell is a yeast cell, such as *Saccharomyces cerevisiae*. In some embodiments, the eukaryotic cell is a higher eukaryote, such as mammalian, avian, plant, or insect cells. Non-limiting examples of mammalian cells include Chinese hamster ovary (CHO) cells and human embryonic kidney cells (e.g., HEK293 cells). In some embodiments, the cell may be a prokaryotic cell, e.g., an *E coli* cell.

Methods of introducing nucleic acids and vectors (e.g., any of the vectors or any of the sets of vectors described herein) into a cell are known in the art. Examples of methods that can be used to introducing a nucleic acid into a cell include: lipofection, transfection, calcium phosphate transfection, cationic polymer transfection, viral transduction (e.g., adenoviral transduction, lentiviral transduction), nanoparticle transfection, and electroporation.

In some embodiments, the introducing step includes introducing into a cell a vector (e.g., any of the vectors or sets of vectors described herein) including a nucleic acid encoding the monomers that make up any activatable molecule described herein.

Compositions and Kits

The present disclosure also provides compositions and kits comprising the substrate-containing polypeptides (e.g., activatable molecules or conjugated polypeptides) described herein. The compositions and kits may further comprise one or more excipients, carriers, reagents, instructions needed for the use of the activatable molecules.

In some embodiments, the compositions may be pharmaceutical compositions, which comprise the substrate-containing polypeptides, derivatives, fragments, analogs and homologs thereof. The pharmaceutical compositions may comprise the substrate-containing and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Suitable examples of such carriers or diluents include water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition may be formulated to be compatible with its intended route of administration. Examples of routes of administration include parenteral, e.g., intravenous, intradermal, subcutaneous, oral (e.g., inhalation), transdermal (e.g., topical), transmucosal, and rectal administration. Solutions or suspensions used for parenteral, intradermal, or subcutaneous application may include one or more of the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH may be adjusted with acids or bases, such as hydrochloric acid or sodium hydroxide. The parenteral preparation can be enclosed in ampoules, disposable syringes or multiple dose vials made of glass or plastic. In some, any of the activatable molecules described herein are prepared with carriers that protect against rapid elimination from the body, e.g., sustained and controlled release formulations, including implants and microencapsulated delivery systems. Biodegradable, biocompatible polymers can be used, e.g., ethylene vinyl acetate, polyanhydrides, polyglycolic acid, collagen, polyorthoesters, polylactic-co-glycolic acid, and polylactic acid. Methods for preparation of such pharmaceutical compositions and formulations are apparent to those skilled in the art. For example, the activatable molecules may be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

Sustained-release preparations may be prepared. Suitable examples of sustained-release preparations include semipermeable matrices of solid hydrophobic polymers containing the substrate-containing polypeptides, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides, copolymers of L-glutamic acid and y ethyl-L-glutamate, non-degradable ethylene-vinyl acetate, degradable lactic acid-glycolic acid copolymers (e.g., injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

In some embodiments, pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor® EL (CAS No. 61791-12-6) (BASF, Parsippany, N.J.), which is a mixture of polyoxyethylated triglycerides, by reacting castor oil with ethylene oxide in a molar ratio of 1:35, that acts as a nonionic surfactant, or phosphate buffered saline (PBS). The composition may be sterile and should be fluid and of a viscosity that facilitates easy syringeability. It may be stable under the conditions of manufacture and storage and preserved against the contaminating action of microorganisms such as bacteria and fungi. The carrier may be a solvent or dispersion medium containing, for example, water, ethanol, polyol (for example, glycerol, propylene glycol, and liquid polyethylene glycol, and the like), and suitable mixtures thereof. For dispersed particulate compositions, the proper fluidity can be maintained, for example, by the use of a coating on the particles such as lecithin, and by the maintenance of the required particle size in the case of dispersion and by the use of surfactants. In some embodiments, the pharmaceutical compositions may further comprise one or more antibacterial and/or antibacterial and antifungal agents, for example, parabens, chlorobutanol, phenol, ascorbic acid, thimerosal, and the like. In some embodiments, isotonic agents, for example, sugars, polyalcohols such as mannitol, sorbitol, and the like, as well as salts, such as, for example, sodium chloride and the like may be included in the composition. Prolonged absorption of the injectable compositions may be brought about by including in the composition an agent that delays absorption, for example, aluminum monostearate and gelatin.

In some embodiments, the pharmaceutical composition may comprise a sterile injectable solution. Sterile injectable solutions may be prepared by incorporating the active compound in the required amount in an appropriate solvent with one or a combination of ingredients enumerated above, as required, followed by filtered sterilization. Generally, dispersions may be prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

In some embodiments, the pharmaceutical composition may comprise an oral composition. Oral compositions may include an inert diluent or an edible carrier. They may be enclosed in gelatin capsules or compressed into tablets. For the purpose of oral therapeutic administration, the active compound may be incorporated with excipients and used in the form of tablets, troches, or capsules. Oral compositions may also be prepared using a fluid carrier for use as a mouthwash, wherein the compound in the fluid carrier is applied orally and swished and expectorated or swallowed. Pharmaceutically compatible binding agents, and/or adjuvant materials may be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primojel® (sodium starch glycolate), or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

In some embodiments, the pharmaceutical composition may be formulized for administration by inhalation. For example, the compounds may be delivered in the form of an aerosol spray from pressured container or dispenser that contains a suitable propellant, e.g., a gas such as carbon dioxide, or a nebulizer.

In some embodiments, the pharmaceutical composition may be formulized for systemic administration. For example, systemic administration may be by intravenous, as well by transmucosal or transdermal means. For transmucosal or transdermal administration, penetrants appropriate to the barrier to be permeated may be used in the formulation. Such penetrants are generally known in the art, and include, for example, for transmucosal administration, detergents, bile salts, and fusidic acid derivatives. Transmucosal administration may be accomplished through the use of nasal sprays or suppositories. For transdermal administration, the active compounds may be formulated into ointments, salves, gels, or creams as generally known in the art.

In some embodiments, the pharmaceutical composition may be prepared in the form of suppositories (e.g., with conventional suppository bases such as cocoa butter and other glycerides) or retention enemas for rectal delivery.

In one embodiment, the pharmaceutical composition may be prepared with carriers that protect the compound against rapid elimination from the body, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic-co-glycolic acid and polylactic acid. Methods for preparation of such formulations will be apparent to those skilled in the art.

It may be advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure may be dictated by and directly dependent on the unique characteristics of the active compound and the particular therapeutic effect to be achieved, and the limitations inherent in the art of compounding such an active compound for the treatment of individuals.

In some embodiments, the compositions (e.g., pharmaceutical compositions) may be included in a container, vial, syringe, injector pen, pack, or dispenser, optionally together with instructions for administration.

Also provided herein are kits that include any of the substrate-containing polypeptides (e.g., activatable molecules or conjugated polypeptides) described herein, any of the compositions that include any of the polypeptides described herein, or any of the pharmaceutical compositions that include any of the polypeptides described herein. Also provided are kits that include one or more second therapeutic agent(s) in addition to a polypeptide described herein. The second therapeutic agent(s) may be provided in a dosage administration form that is separate from the polypeptides herein. Alternatively, the second therapeutic agent(s) may be formulated together with the polypeptides herein.

Any of the kits described herein can include instructions for using any of the compositions (e.g., pharmaceutical compositions) and/or any of the substrate-containing polypeptides (e.g., activatable molecules or conjugated polypeptides) described herein. In some embodiments, the kits can include instructions for performing any of the methods described herein. In some embodiments, the kits can include at least one dose of any of the compositions (e.g., pharmaceutical compositions) described herein. In some embodiments, the kits can provide a syringe for administering any of the pharmaceutical compositions described herein.

Also provided herein are substrate-containing polypeptides (e.g., activatable molecules or conjugated polypeptides) produced by any of the methods described herein. Also provided are compositions (e.g., pharmaceutical compositions) that comprise any of the polypeptides produced by any of the methods described herein. Also provided herein are kits that include at least one dose of any of the compositions (e.g., pharmaceutical compositions) described herein.

Methods of Producing Substrate-Containing Polypeptides

Provided herein are methods of producing the substrate-containing polypeptides (e.g., activatable molecules or conjugated polypeptides) described herein that include: (a) culturing any of the recombinant host cells described herein in a liquid culture medium under conditions sufficient to produce the substrate-containing polypeptides; and (b) recovering the substrate-containing polypeptides from the host cell and/or the liquid culture medium.

Methods of culturing cells are well known in the art. In some embodiments, cells may be maintained in vitro under conditions that favor cell proliferation, cell differentiation and cell growth. For example, the recombinant cells may be cultured by contacting a cell (e.g., any of the cells described herein) with a cell culture medium that includes the necessary growth factors and supplements sufficient to support cell viability and growth.

In some embodiments, the method may further include isolating the recovered substrate-containing polypeptides (e.g., activatable molecules or conjugated polypeptides). The isolation of the substrate-containing polypeptides may be performed using any separation or purification technique for separating protein species, e.g., affinity tag-based protein purification (e.g., polyhistidine (His) tag, glutathione-S-transferase tag, and the like), ammonium sulfate precipitation, polyethylene glycol precipitation, size exclusion chromatography, ligand-affinity chromatography (e.g., Protein A chromatography), ion-exchange chromatography (e.g., anion or cation), hydrophobic interaction chromatography, and the like.

Compositions and methods described herein may involve use of non-reducing or partially-reducing conditions that allow disulfide bonds to form between the MM and the AM of the activatable molecules.

In some embodiments, the method further includes formulating the isolated polypeptides into a pharmaceutical composition. Various formulations are known in the art and are described herein. Any isolated polypeptides described herein can be formulated for any route of administration (e.g., intravenous, intratumoral, subcutaneous, intradermal, oral (e.g., inhalation), transdermal (e.g., topical), transmucosal, or intramuscular).

Methods of Using Substrate-Containing Polypeptides

In some aspects, the present disclosure further provides methods of using the substrate-containing polypeptides herein. In some embodiments, the present disclosure provides methods of the treating a disease (e.g., a cancer (e.g., any of the cancers described herein)) in a subject including administering a therapeutically effective amount of any of the polypeptides (e.g., activatable molecules or conjugated polypeptides) described herein to the subject. In some embodiments, the disclosure provides methods of preventing, delaying the progression of, treating, alleviating a symptom of, or otherwise ameliorating disease in a subject by administering a therapeutically effective amount of an polypeptides (e.g., activatable molecules or conjugated polypeptides) described herein to a subject in need thereof. The term "treatment" refers to ameliorating at least one symptom of a disorder. In some embodiments, the disorder being treated may be a cancer or autoimmune disease or to ameliorate at least one symptom of a cancer or autoimmune disease. As used herein, the term "subject" refers to any mammal. In some embodiments, the subject is a feline (e.g., a cat), a canine (e.g., a dog), an equine (e.g., a horse), a rabbit, a pig, a rodent (e.g., a mouse, a rat, a hamster or a guinea pig), a non-human primate (e.g., a simian (e.g., a monkey (e.g., a baboon, a marmoset), or an ape (e.g., a chimpanzee, a gorilla, an orangutan, or a gibbon)), or a human. In some embodiments, the subject is a human. The terms subject and patient are used interchangeably herein. In some embodiments, the subject has been previously identified or diagnosed as having the disease (e.g., cancer (e.g., any of the cancers described herein)).

A therapeutically effective amount of a substrate-containing polypeptide (e.g., activatable molecule or conjugated polypeptide) of the disclosure relates generally to the amount needed to achieve a therapeutic objective. As noted above, this may be a binding interaction between the AM and its target that, in certain cases, interferes with the functioning of the targets. The amount required to be administered will furthermore depend on the binding affinity of the polypeptides for its specific target, and will also depend on the rate at which an administered polypeptide is depleted from the free volume other subject to which it is administered. Common ranges for therapeutically effective dosing of a polypeptides of the disclosure may be, by way of non-limiting example, from about 0.001, 0.01, 0.1, 0.3, 0.5, 0.7, 0.8, 0.9, 1, 2, 3, 4, 5, 6, 7, 8, 9, 10, 15, 20, 25, 30, 35, 40, 45, or 50 mg/kg body weight or higher. The structure of the polypeptides of the present disclosure makes it possible to reduce the dosage of the polypeptide that is administered to a subject compared to conventional activatable molecules and compared to conventional antibodies. For example, the administered dose on a unit dosage basis or total dosage over a dosage regimen period may be reduced by 10, 20, 30, 40, or 50% compared to the corresponding dose of a corresponding conventional therapeutic molecules.

Common dosing frequencies may range, for example, from once or twice daily, weekly, biweekly, or monthly.

Efficaciousness of treatment is determined in association with any known method for diagnosing or treating the particular disorder. Methods for the screening of polypeptides that possess the desired specificity include, but are not limited to, enzyme linked immunosorbent assay (ELISA) and other immunologically mediated techniques known within the art.

In another embodiment, a polypeptide directed two or more targets are used in methods known within the art relating to the localization and/or quantitation of the targets (e.g., for use in measuring levels of one or more of the targets within appropriate physiological samples, for use in diagnostic methods, for use in imaging the protein, and the like). In a given embodiment, a polypeptide directed two or more targets, or a derivative, fragment, analog or homolog thereof, that contain the antibody derived antigen binding domain, are utilized as pharmacologically active compounds (referred to hereinafter as "Therapeutics").

The substrate-containing polypeptides used in any of the embodiments of these methods and uses may be administered at any stage of the disease. For example, such a polypeptide may be administered to a patient suffering cancer of any stage, from early to metastatic. In some embodiments, the substrate-containing polypeptides and formulations thereof may be administered to a subject suffering from or susceptible to a disease or disorder associated with aberrant target expression and/or activity.

A subject suffering from or susceptible to a disease or disorder associated with aberrant target expression and/or activity may be identified using any of a variety of methods known in the art. For example, subjects suffering from cancer or other neoplastic condition may be identified using any of a variety of clinical and/or laboratory tests such as, physical examination and blood, urine and/or stool analysis to evaluate health status. For example, subjects suffering from inflammation and/or an inflammatory disorder may be identified using any of a variety of clinical and/or laboratory tests such as physical examination and/or bodily fluid analysis, e.g., blood, urine and/or stool analysis, to evaluate health status.

In some embodiments, administration of a polypeptide to a patient suffering from a disease or disorder associated with aberrant target expression and/or activity may be considered successful if any of a variety of laboratory or clinical objectives is achieved. For example, administration of a polypeptide to a patient suffering from a disease or disorder associated with aberrant target expression and/or activity may be considered successful if one or more of the symptoms associated with the disease or disorder is alleviated, reduced, inhibited or does not progress to a further, i.e., worse, state. Administration of a polypeptide to a patient suffering from a disease or disorder associated with aberrant target expression and/or activity may be considered successful if the disease or disorder enters remission or does not progress to a further, i.e., worse, state.

As used herein, the term "treat" includes reducing the severity, frequency or the number of one or more (e.g., 1, 2, 3, 4, or 5) symptoms or signs of a disease (e.g., a cancer (e.g., any of the cancers described herein)) in the subject (e.g., any of the subjects described herein). In some embodiments where the disease is cancer, treating results in reducing cancer growth, inhibiting cancer progression, inhibiting cancer metastasis, or reducing the risk of cancer recurrence in a subject having cancer.

In some embodiments, the substrate comprises a substrate for a protease that is active, e.g., upregulated or otherwise unregulated, in a disease condition or diseased tissue. Exemplary disease conditions include, for example, a cancer (e.g., where the diseased tissue is a tumor tissue) and an inflammatory or autoimmune condition (e.g., where the diseased tissue is inflamed tissue). In some embodiments, the substrate comprises a substrate for an extracellular protease. In some embodiments, the substrate comprises a substrate for an intracellular protease. In some embodiments, the substrate is an intracellular protease and an extracellular protease. In some embodiments, the disease may be a cancer. In some embodiments, the subject may have been identified or diagnosed as having a cancer. Examples of cancer include: solid tumor, hematological tumor, sarcoma, a leukemia (e.g., hairy cell leukemia, chronic lymphocytic leukemia (CLL), acute myeloid leukemia (AML), chronic myeloid leukemia (CML), acute lymphocytic leukemia (ALL)), stomach cancer, urothelial carcinoma, lung cancer, renal cell carcinoma, gastric and esophageal cancer, pancreatic cancer, prostate cancer, brain cancer, colon cancer, bone cancer, lung cancer, breast cancer, colorectal cancer, ovarian cancer, non-small cell lung carcinoma (NSCLC), squamous cell head and neck carcinoma, endometrial cancer, bladder cancer, cervical cancer, and liver cancer. Metastases of the aforementioned cancers may also be treated or prevented in accordance with the methods described herein.

In some embodiments, the disease may be an autoimmune disease or condition. In some embodiments, the subject may have been identified or diagnosed as having an autoimmune disease or condition or is at heightened risk of developing an autoimmune disease or condition. Examples of autoimmune diseases include Type 1 diabetes, Rheumatoid arthritis (RA), Psoriasis/psoriatic arthritis, Multiple sclerosis, Systemic lupus erythematosus, Inflammatory bowel disease (e.g., Crohn's disease, ulcerative colitis), chronic inflammation, or transplant rejection (e.g., in kidney, liver, or heart transplantation), autoimmune diseases, infectious disease, chronic inflammation, or transplant rejection. In some embodiments, the disease is a cardiovascular disorder. In some embodiments, the disease is a neurodegenerative disorder.

In some embodiments, the methods herein may result in a reduction in the number, severity, or frequency of one or more symptoms of the cancer in the subject (e.g., as compared to the number, severity, or frequency of the one or more symptoms of the cancer in the subject prior to treatment).

The methods may further comprise administering to a subject one or more additional agents. In some embodiments, the substrate-containing polypeptides (e.g., activatable molecules or conjugated polypeptides) may be administered during and/or after treatment in combination with one or more additional agents. In some embodiments, the polypeptide may be formulated into a single therapeutic composition, and the polypeptide and additional agent(s) may be administered simultaneously. Alternatively, the polypeptide and additional agent(s) may be separate from each other, e.g., each is formulated into a separate therapeutic composition, and the polypeptide and the additional agent are administered simultaneously, or the polypeptide and the additional agent are administered at different times during a treatment regimen. For example, the polypeptide may be administered prior to the administration of the additional agent, subsequent to the administration of the additional agent, or in an alternating fashion. The polypeptide and additional agent(s) may be administered in single doses or in multiple doses.

One of more of the polypeptides herein may be co-formulated with, and/or co-administered with, one or more anti-inflammatory drugs, immunosuppressants, or metabolic or enzymatic inhibitors. In some embodiments, one or more polypeptides herein may be combined with one or more polypeptides of other types.

The present disclosure also provides methods of detecting presence or absence of a cleaving agent and/or the target in a subject or a sample. Such methods may comprise (i) contacting a subject or biological sample with an activatable molecule, wherein the activatable molecule includes a detectable label that is positioned on a portion of the activatable molecule that is released following cleavage of the substrate and (ii) measuring a level of activated molecule in the subject or biological sample, wherein a detectable level of activated molecule in the subject or biological sample indicates that the cleaving agent, the target or both the cleaving agent and the target are absent and/or not sufficiently present in the subject or biological sample, such that the target binding and/or protease cleavage of the activatable molecule cannot be detected in the subject or biological sample, and wherein a reduced detectable level of activated molecule in the subject or biological sample indicates that the cleaving agent and the target are present in the subject or biological sample.

Such detection methods may be adapted to also provide for detection of the presence or absence of a target that is capable of binding the AM of the activatable molecules when cleaved. Thus, the assays can be adapted to assess the presence or absence of a cleaving agent and the presence or absence of a target of interest. The presence or absence of the cleaving agent can be detected by the presence of and/or an increase in detectable label of the activatable molecules as described above, and the presence or absence of the target can be detected by detection of a target-AM complex e.g., by use of a detectably labeled anti-target antibody.

In some embodiments, activatable molecules are also useful in in situ imaging for the validation of activatable molecule activation, e.g., by protease cleavage, and binding to a particular target. In situ imaging is a technique that enables localization of proteolytic activity and target in biological samples such as cell cultures or tissue sections. Using this technique, it is possible to confirm both binding to a given target and proteolytic activity based on the presence of a detectable label (e.g., a fluorescent label).

These techniques are useful with any frozen cells or tissue derived from a disease site (e.g. tumor tissue) or healthy tissues. These techniques are also useful with fresh cell or tissue samples.

In these techniques, an activatable molecule may be labeled with a detectable label. The detectable label may be a fluorescent dye, (e.g. a fluorophore, Fluorescein Isothiocyanate (FITC), Rhodamine Isothiocyanate (TRITC), an Alexa Fluor® label), a near infrared (NIR) dye (e.g., Qdot® nanocrystals), a colloidal metal, a hapten, a radioactive marker, biotin and an amplification reagent such as streptavidin, or an enzyme (e.g. horseradish peroxidase or alkaline phosphatase).

Detection of the label in a sample that has been incubated with the labeled, activatable molecule indicates that the sample contains the target and contains a protease that is specific for the substrate of the activatable molecule. In some embodiments, the presence of the protease can be confirmed using broad spectrum protease inhibitors such as those described herein, and/or by using an agent that is specific for the protease, for example, an antibody such as A11, which is specific for the protease matriptase and inhibits the proteolytic activity of matriptase; see e.g., International Publication Number WO 2010/129609, published 11 Nov. 2010. The same approach of using broad spectrum protease inhibitors such as those described herein, and/or by using a more selective inhibitory agent can be used to identify a protease that is specific for the substrate of the activatable molecule. In some embodiments, the presence of the target can be confirmed using an agent that is specific for the target, e.g., another antibody, or the detectable label can be competed with unlabeled target. In some embodiments, unlabeled activatable molecule may be used, with detection by a labeled secondary antibody or more complex detection system.

Similar techniques are also useful for in vivo imaging where detection of the fluorescent signal in a subject, e.g., a mammal, including a human, indicates that the disease site contains the target and contains a protease that is specific for the substrate of the activatable molecule.

These techniques are also useful in kits and/or as reagents for the detection, identification or characterization of protease activity in a variety of cells, tissues, and organisms based on the protease-specific substrate in the activatable molecule.

A reduced level of detectable label may be, for example, a reduction of at least 5%, 10%, 15%, 20%, 25%, 30%, 35%, 40%, 45%, 50%, 55%, 60%, 65%, 70%, 75%, 80%, 85%, 90%, or 95%, or a reduction of substantially 100%. In some embodiments, the detectable label may be conjugated to a component of the polypeptide, e.g., the AM. In some embodiments, measuring the level of polypeptide in the subject or sample may be accomplished using a secondary reagent that specifically binds the activated protein, wherein the reagent comprises a detectable label. The secondary reagent may be an antibody comprising a detectable label.

In some embodiments, the substrate-containing polypeptides may also be useful in the detection of the target in patient samples and accordingly are useful as diagnostics. For example, the polypeptides may be used in in vitro assays, e.g., ELISA, to detect target levels in a patient sample. For example, a polypeptide may be immobilized on a solid support (e.g., the well(s) of a microtiter plate). The immobilized polypeptide may serve as a capture protein for any target that may be present in a test sample. Prior to contacting the immobilized polypeptide with a patient sample, the solid support may be rinsed and treated with a blocking agent such as milk protein or albumin to prevent nonspecific adsorption of the analyte.

In some embodiments, based on the results obtained using the polypeptides in an in vitro diagnostic assay, the stage of a disease in a subject may be determined based on expression levels of the target protein (e.g., antigen). For a given disease, samples of blood may be taken from subjects diagnosed as being at various stages in the progression of the disease, and/or at various points in the therapeutic treatment of the disease. Using a population of samples that provides statistically significant results for each stage of progression or therapy, a range of concentrations of the target protein (e.g., antigen) that may be considered characteristic of each stage is designated.

Polypeptides herein may also be used in diagnostic and/or imaging methods. In some embodiments, such methods may be in vitro methods. In some embodiments, such methods may be in vivo methods. In some embodiments, such methods may be in situ methods. In some embodiments, such methods may be ex vivo methods. For example, polypeptides having a substrate may be used to detect the presence or absence of an enzyme capable of cleaving the substrate. Such polypeptides may be used in diagnostics, which can include in vivo detection (e.g., qualitative or quantitative) of enzyme activity (or, in some embodiments, an environment of increased reduction potential such as that which can provide for reduction of a disulfide bond) through measured accumulation of activated antibodies (i.e., antibodies resulting from cleavage of a polypeptide) in a given cell or tissue of a given host organism. Such accumulation of activated proteins indicates not only that the tissue expresses enzymatic activity (or an increased reduction potential depending on the nature of the substrate) but also that the tissue expresses target to which the activated protein binds. In some examples, the polypeptides may be used for detecting protease activity with an assay that does not rely on target binding, e.g., a quantitative ex vivo zymography (QZ) assay as described in Howng et al., "Novel Ex Vivo Zymography Approach for Assessment of Protease Activity in Tissues with Activatable Antibodies," Pharmaceutics. 2021 Sep. 2; 13 (9): 1390, which is incorporated by reference herein in its entirety.

For example, the substrate may be selected to be a protease substrate for a protease found at the site of a tumor, at the site of a viral or bacterial infection at a biologically confined site (e.g., such as in an abscess, in an organ, and the like), and the like. The AM may be one that binds a target protein (e.g., antigen). Using methods familiar to one skilled in the art, a detectable label (e.g., a fluorescent label or radioactive label or radiotracer) may be conjugated to an AM or other region of a polypeptide. Suitable detectable labels may be discussed in the context of the above screening methods and additional specific examples are provided below. Using an AM specific to a protein or peptide of the disease state, along with a protease whose activity is elevated in the disease tissue of interest, polypeptides may exhibit an increased rate of binding to disease tissue relative to tissues where the substrate specific enzyme is not present at a detectable level or is present at a lower level than in disease tissue or is inactive (e.g., in zymogen form or in complex with an inhibitor). Since small proteins and peptides are rapidly cleared from the blood by the renal filtration system, and because the enzyme specific for the substrate is not present at a detectable level (or is present at lower levels in non-disease tissues or is present in inactive conformation), accumulation of activated protein in the disease tissue may be enhanced relative to non-disease tissues.

In some embodiments, the substrate-containing polypeptides may be useful for in vivo imaging where detection of the fluorescent signal in a subject, e.g., a mammal, including a human, indicates that the disease site contains the target and contains a protease that is specific for the substrate of the polypeptide. The in vivo imaging may be used to identify or otherwise refine a patient population suitable for treatment with a polypeptide of the disclosure. For example, patients that test positive for both the target and a protease that cleaves the substrate in the substrate of the polypeptide being tested (e.g., accumulate activated proteins at the disease site) are identified as suitable candidates for treatment with such a polypeptide comprising such a substrate. Likewise, patients that test negative may be identified as suitable candidates for another form of therapy (i.e., not suitable for treatment with the polypeptide being tested). In some embodiments, such patients that test negative with respect to a first polypeptide can be tested with other polypeptides comprising different substrates until a suitable polypeptide for treatment is identified (e.g., a polypeptide comprising a substrate that is cleaved by the patient at the site of disease).

In some embodiments, in situ imaging may be useful in methods to identify which patients to treat. For example, in in situ imaging, the polypeptides may be used to screen patient samples to identify those patients having the appropriate protease(s) and target(s) at the appropriate location, e.g., at a tumor site. In some embodiments, in situ imaging is used to identify or otherwise refine a patient population suitable for treatment with a polypeptide of the disclosure. For example, patients that test positive for both the target and a protease that cleaves the substrate in the substrate of the polypeptide being tested (e.g., accumulate activated antibodies at the disease site) are identified as suitable candidates for treatment with such a polypeptide comprising such a substrate. Likewise, patients that test negative for either or both of the target and the protease that cleaves the substrate used in the polypeptide being tested using these methods are identified as suitable candidates for another form of therapy (i.e., not suitable for treatment with the polypeptide being tested). In some embodiments, such patients that test negative with respect to a first polypeptide can be tested with other polypeptides comprising different substrates until a suitable polypeptide for treatment is identified (e.g., a polypeptide comprising a substrate that is cleaved by the patient at the site of disease).

The present application also provides aspects and embodiments as set forth in the following numbered Statements:

Statement 1. An isolated polypeptide comprising a substrate, wherein the substrate comprises a first cleavable moiety (CM1) cleavable by a first protease and a second cleavable moiety (CM2) cleavable by a second protease, and wherein the CM1 comprises the amino acid sequence of PXGL, wherein X is W, Y, F, R, K, Q, A, or M, optionally wherein the CM1 comprises the amino acid sequence of PXGL, wherein X is W, Y, F, R, K, Q, or M. In certain aspects, the present disclosure may include substitution of any alanine in the disclosed CM sequences with a valine. According to some embodiments of the present disclosures, the isolated polypeptide is a molecule in which cleavage of the CM by a protease results in a part or component of the molecule being separated from the remainder of the molecule. In some aspects of the present disclosure, cleavage of the CM by a protease activates the molecule. In some aspects, the isolated polypeptide is a molecule in which multiple proteases cleave the CM. In some aspects, the isolated polypeptide is a molecule in which MMP2 cleaves the CM. In some aspects, the isolated polypeptide is a molecule in which MMP9 cleaves the CM. In some aspects, the isolated polypeptide is a molecule in which MMP14 cleaves the CM. In some aspects, the isolated polypeptide is a molecule in which MT-SP1 cleaves the CM. In some aspects, the isolated polypeptide is a molecule in which uPA cleaves the CM. In some aspects, the isolated polypeptide is a molecule in which two, three, four, or all of MMP2, MMP9, MMP14, MT-SP1, and uPA cleave the CM. In some aspects, the isolated polypeptide is a molecule in which the % cleavability of the CM is at least 50%, at least 60%, at least 70%, at least 80%, at least 90%, or at least 95%, or 100%, e.g., at least 50%, at least 60%, at least 70%, at least 80%, at least 90%, or at least 95%, or 100% cleavable by any one of MMP2, MMP9, MMP14, MT-SP1, and uPA, or any two of MMP2, MMP9, MMP14, MT-SP1, and uPA, or any three of MMP2, MMP9, MMP14, MT-SP1, and uPA, or any four of MMP2, MMP9, MMP14, MT-SP1, and uPA, or each of MMP2, MMP9, MMP14, MT-SP1. In some aspects, the isolated polypeptide is a molecule in which the % cleavability of the CM is improved by 1.5×, 2×, 2.5×, 3×, 4×, 5×, 7×, 8×, or 10× or more over the % cleavability of SEQ ID NO: 78 (see, e.g., Example 2). According to some embodiments of the present disclosures, the isolated polypeptide is a molecule that has high in vivo stability such that it is not cleaved in plasma as demonstrated by less than 50%, less than 40%, less than 30%, or less than 25% in vivo activation following 7 days of administration in vivo (see, e.g., Example 3). According to embodiments of the present disclosures, the isolated polypeptide is a molecule comprising a CM that has a $k_{cat}/K_M$ ($M^{-1}$ s" 1) of greater than $1\times10^2$ $M^{-1}$ $s^{-1}$. According to some embodiments of the present disclosures, the isolated polypeptide is a molecule comprising a CM that has a $k_{cat}/K_M$ ($M^{-1}$ $s^{-1}$) of greater than $1\times10^3$ $M^{-1}$ $s^{-1}$. According to some embodiments of the present disclosures, the isolated polypeptide is a molecule comprising a CM that has a $k_{cat}/K_M$ ($M^{-1}$ $s^{-1}$) of greater than $1\times10^4$ $M^{-1}$ $s^{-1}$. According to some embodiments of the present disclosures, the isolated polypeptide is a molecule comprising a CM that has a $k_{cat}/K_M$ ($M^{-1}$ $s^{-1}$) of greater than $1\times10^5$ $M^{-1}$ $s^{-1}$.

Statement 2. The isolated polypeptide of Statement 1, wherein the CM2 comprises the amino acid sequence of RS (SEQ ID NO: 36).

Statement 3. The isolated polypeptide of Statement 2, wherein the CM1 comprises the amino acid sequence of PWGL (SEQ ID NO: 2).

Statement 4. The isolated polypeptide of Statement 3, wherein the substrate comprises the amino acid sequence of RSPWGLN (SEQ ID NO: 10), RSPWGL (SEQ ID NO: 90), PWGLRS (SEQ ID NO: 48), PWGLSGKS (SEQ ID NO: 150), LSGRSPWGLS (SEQ ID NO: 695), or PWGLRSN (SEQ ID NO: 9), optionally wherein the substrate comprises the amino acid sequence of RSPWGLN (SEQ ID NO: 10), RSPWGL (SEQ ID NO: 90), PWGLRS (SEQ ID NO: 48), PWGLSGKS (SEQ ID NO: 150), or PWGLRSN (SEQ ID NO: 9); or the isolated polypeptide of Statement 1, wherein the substrate comprises the amino acid sequence of PYGLSGRS (SEQ ID NO: 151), PFGLSGRS (SEQ ID NO: 152), PRGLSGRS (SEQ ID NO: 153), PAGLSGRS (SEQ ID NO: 687), LSGRSPWGL (SEQ ID NO: 177), PWGLSARS (SEQ ID NO: 163), LSGKSPWGL (SEQ ID NO: 178), PWGLAGRS (SEQ ID NO: 690), PWGLSARS (SEQ ID NO: 691), PWGLSGAS (SEQ ID NO: 692), PWGLSGRA (SEQ ID NO: 693), or LSGRSPAGL (SEQ ID NO: 694).

Statement 5. The isolated polypeptide of Statement 2, wherein the CM2 comprises the amino acid sequence of GRS.

Statement 6. The isolated polypeptide of Statement 5, wherein the CM2 comprises the amino acid sequence of SGRS (SEQ ID NO: 31), SGRSNI (SEQ ID NO: 32), or LSGRSNI (SEQ ID NO: 26).

Statement 7. The isolated polypeptide of Statement 5 or 6, wherein the CM1 comprises the amino acid sequence of PWGL (SEQ ID NO: 2).

Statement 8. The isolated polypeptide of Statement 5 or 6, wherein the substrate comprises the amino acid sequence of GPWGLSGRSNI (SEQ ID NO: 11), PWGLSGRS (SEQ ID NO: 12), GRSPWGLL (SEQ ID NO: 13), APMGLKHLSGRSNI (SEQ ID NO: 14), or GPYGLSGRSNI (SEQ ID NO: 15).

Statement 9. The isolated polypeptide of Statement 2, wherein the CM2 comprises the amino acid sequence of PRS.

Statement 10. The isolated polypeptide of Statement 9, wherein the CM2 comprises the amino acid sequence of APRS (SEQ ID NO: 34).

Statement 11. The isolated polypeptide of Statement 9 or 10, wherein the CM1 comprises the amino acid sequence of PWGL (SEQ ID NO: 2).

Statement 12. The isolated polypeptide of Statement 9 or 10, wherein the substrate comprises an amino acid sequence of APRSPWGL (SEQ ID NO: 16), PWGLPRS (SEQ ID NO: 17), PRSPWGL (SEQ ID NO: 313), or PRSPWGLL (SEQ ID NO: 18).

Statement 13. The isolated polypeptide of Statement 2, wherein the CM2 comprises the amino acid sequence of SRS.

Statement 14. The isolated polypeptide of Statement 13, wherein the CM2 comprises the amino acid sequence of HQSRS (SEQ ID NO: 28).

Statement 15. The isolated polypeptide of Statement 13, wherein the substrate comprises the amino acid sequence of PWGLSRS (SEQ ID NO: 19), PFGLSRS (SEQ ID NO: 20), APMGLKHDHQSRS (SEQ ID NO: 21) or DHQSRSAPMGLKH (SEQ ID NO: 22)

Statement 16. The isolated polypeptide of Statement 1, wherein the substrate comprises the amino acid sequence of KPRGL (SEQ ID NO: 664).

Statement 17. The isolated polypeptide of Statement 16, wherein the substrate comprises the amino acid sequence of KPRGLN (SEQ ID NO: 23) or KPRGLF (SEQ ID NO: 24)

Statement 18. The isolated polypeptide of any one or combination of Statements 1-3, 5-7, 9-11, 13, 14, 16, and 17, wherein the N-terminal to C-terminal arrangement of the substrate is CM1-CM2.

Statement 19. The isolated polypeptide of Statements 1-3, 5-7, 9-11, 13, 14, 16, and 17, wherein the N-terminal to C-terminal arrangement of the substrate is CM2-CM1.

Statement 20. The isolated polypeptide of Statement 18 or 19, wherein the CM1 and CM2 are indirectly coupled via a linking peptide.

Statement 21. The isolated polypeptide of Statement 18 or 19, wherein the CM1 and CM2 are directly coupled to each other.

Statement 22. The isolated polypeptide of any one or combination of Statements 1-3, 5-7, 9-11, 13, 14, 16, and 17, wherein at least a portion of the CM1 overlaps with at least a portion of the CM2.

Statement 23. The isolated polypeptide of any one or combination of Statements 1-22, wherein the isolated polypeptide is an activatable molecule and further comprises an active moiety (AM) that specifically binds a target. According to some embodiments of the present disclosures, the isolated polypeptide is an activatable molecule that has high in vivo stability such that it is not cleaved in plasma as demonstrated by less than 50%, less than 40%, less than 30%, or less than 25% in vivo activation following 7 days of administration in vivo (e.g., as exemplified in Example 3). According to some embodiments of the present disclosures, the isolated polypeptide is an activatable molecule that has masking efficiency of 18×, 26×, 30×, 33×, 50×, 60×, 70×, 77×, 95×, 100×, 112×, 123×, 135×, 139×, 150×, 200×, 234×, 300×, or higher (e.g., as exemplified in Example 4). According to some embodiments of the present disclosures, the activatable molecule is activated by one, two, three, four, or all of MMP2, MMP9, MMP14, MT-SP1, and uPA. According to some embodiments of the present disclosures, the activatable molecule is activated to an extent of having a cleavability percentage of at least 40%, at least 50%, at least 60%, at least 70%, at least 80%, at least 90%, or at least 95%, or 100%, e.g., at least 50%, at least 60%, at least 70%, at least 80%, at least 90%, or at least 95%, or 100% cleavable by any one of MMP2, MMP9, MMP14 and MT-SP1, or any two of MMP2, MMP9, MMP14, MT-SP1, and uPA, or any three of MMP2, MMP9, MMP14, MT-SP1, and uPA, or any four of MMP2, MMP9, MMP14, MT-SP1, and uPA, or each of MMP2, MMP9, MMP14, MT-SP1. According to some embodiments of the present disclosures, the activatable molecule exhibits attenuated binding to a target as compared to the binding of a counterpart "activated" molecule comprising the same active moiety (AM) to the same target.

Statement 24. The isolated polypeptide of Statement 23, wherein the AM is coupled to the CM1.

Statement 25. The isolated polypeptide of Statement 24, wherein the AM is linked coupled to the CM1.

Statement 26. The isolated polypeptide of Statement 24, wherein the AM is coupled to the CM1 via a linking peptide.

Statement 27. The isolated polypeptide of any one or combination of Statements 23-26, wherein the AM is coupled to the CM2.

Statement 28. The isolated polypeptide of Statement 27, wherein the AM is directly coupled to the CM2.

Statement 29. The isolated polypeptide of Statement 27, wherein the AM is indirectly coupled to the CM2 via a linking peptide.

Statement 30. The isolated polypeptide of any one or combination of Statements 23-29, further comprising a masking moiety (MM).

Statement 31. The isolated polypeptide of Statement 30, wherein the MM has a dissociation constant for binding to the AM that is greater than the dissociation constant of the AM for binding to the target.

Statement 32. The isolated polypeptide of Statement 30 or 31, wherein the MM is 2 to 40 amino acids in length.

Statement 33. The isolated polypeptide of any one or combination of Statements 30-32, wherein the MM is coupled to the substrate such that the isolated polypeptide comprises a structural arrangement from N-terminus to C-terminus as follows: MM-CM1-CM2-AM, MM-CM2-CM1-AM, AM-CM1-CM2-MM, or AM-CM2-CM1-MM.

Statement 34. The isolated polypeptide of Statement 33, wherein the MM is directly coupled to the CM1.

Statement 35. The isolated polypeptide of Statement 33, wherein the MM is indirectly coupled to the CM1 via a linking peptide.

Statement 36. The isolated polypeptide of Statement 35, wherein the MM is directly coupled to the CM2.

Statement 37. The isolated polypeptide of Statement 35, wherein the MM is indirectly coupled to the CM2 via a linking peptide.

Statement 38. The isolated polypeptide of any one or combination of Statements 30-37, wherein the isolated polypeptide comprises a linking peptide (LP), and wherein the isolated polypeptide has a structural arrangement from N-terminus to C-terminus as follows: MM-LP-CM1-CM2-AM, MM-LP-CM2-CM1-AM, AM-CM1-CM2-LP-MM, or AM-CM2-CM1-LP-MM, MM-CM1-CM2-LP-AM, MM-CM2-CM1-LP-AM, AM-LP-CM1-CM2-MM, or AM-LP-CM2-CM1-MM.

Statement 39. The isolated polypeptide of any one or combination of Statements 30-37, wherein the isolated polypeptide comprises a first linking peptide (LP1) and a second linking peptide (LP2), and wherein the isolated polypeptide has a structural arrangement from N-terminus to C-terminus as follows: MM-LP1-CM1-CM2-LP2-AM, MM-LP1-CM2-CM1-LP2-AM, AM-LP1-CM1-CM2-LP2-MM, or AM-LP1-CM2-CM1-LP2-MM.

Statement 40. The isolated polypeptide of Statement 39, wherein the LP1 and LP2 are not identical to each other.

Statement 41. The isolated polypeptide of Statement 39, wherein the LP1 and LP2 are identical to each other.

Statement 42. The isolated polypeptide of any one of Statements 38-40, wherein each of the LP1 and LP2 is a peptide of 1 to 20 amino acids in length.

Statement 43. The isolated polypeptide of any one or combination of Statements 1-41, wherein the first protease is a matrix metalloproteinase (MMP).

Statement 44. The isolated polypeptide of Statement 42, wherein the MMP is MMP2, MMP9, or MMP14.

Statement 45. The isolated polypeptide of Statement 44, wherein the $k_{cat}/K_M$ of the substrate by MMP2 cleavage is at least $1 \times 10^3$ $M^{-1}$ $s^{-1}$, optionally at 37° C. in 50 mM Tris-HCl (pH 7.5), 10 mM $CaCl_2$), 150 mM NaCl, 0.05% (w/v) Brij-35.

Statement 46. The isolated polypeptide of Statement 44, wherein the $k_{cat}/K_M$ of the substrate by MMP2 cleavage is at least $1 \times 10^4$ $M^{-1}$ $s^{-1}$, optionally at 37° C. in 50 mM Tris-HCl (pH 7.5), 10 mM $CaCl_2$), 150 mM NaCl, 0.05% (w/v) Brij-35.

Statement 47. The isolated polypeptide of any one of Statements 44-46, wherein the $k_{cat}/K_M$ of the substrate by MMP9 cleavage is at least $1 \times 10^3$ $M^{-1}$ $s^{-1}$, optionally at 37° C. in 50 mM Tris-HCl (pH 7.5), 10 mM $CaCl_2$), 150 mM NaCl, 0.05% (w/v) Brij-35.

Statement 48. The isolated polypeptide of any one of Statements 44-46, wherein the $k_{cat}/K_M$ of the substrate by MMP9 cleavage is at least $1 \times 10^4$ $M^{-1}$ $s^{-1}$, optionally at 37° C. in 50 mM Tris-HCl (pH 7.5), 10 mM $CaCl_2$), 150 mM NaCl, 0.05% (w/v) Brij-35.

Statement 49. The isolated polypeptide of any one of Statements 44-48, wherein the $k_{cat}/K_M$ of the substrate by MMP14 cleavage is at least $1 \times 10^3$ $M^{-1}$ $s^{-1}$, optionally at 37° C. in 50 mM Tris-HCl (pH 7.5), 10 mM $CaCl_2$), 150 mM NaCl, 0.05% (w/v) Brij-35.

Statement 50. The isolated polypeptide of any one of Statements 44-48, wherein the $k_{cat}/K_M$ of the substrate by MMP14 cleavage is at least $1 \times 10^4$ $M^{-1}$ $s^{-1}$, optionally at 37° C. in 50 mM Tris-HCl (pH 7.5), 10 mM $CaCl_2$), 150 mM NaCl, 0.05% (w/v) Brij-35.

Statement 51. The isolated polypeptide of any one or combination of Statements 1-50, wherein the second protease is a serine protease.

Statement 52. The isolated polypeptide of Statement 51, wherein the serine protease is membrane type serine protease 1 (MT-SP1).

Statement 53. The isolated polypeptide of Statement 51, wherein the $k_{cat}/K_M$ of the substrate by MT-SP1 cleavage is at least $1 \times 10^3$ $M^{-1}$ $s^{-1}$, optionally at 37° C. in 50 mM TRIS-HCl (pH 7.4), 150 mM NaCl, 0.05% Tween 20.

Statement 54. The isolated polypeptide of Statement 51, wherein the $k_{cat}/K_M$ of the substrate by MT-SP1 cleavage is at least $1 \times 10^4$ $M^{-1}$ $s^{-1}$, optionally at 37° C. in 50 mM TRIS-HCl (pH 7.4), 150 mM NaCl, 0.05% Tween 20.

Statement 55. An isolated polypeptide comprising a substrate, wherein the substrate comprises: APRG (SEQ ID NO: 382), or a first cleavable moiety (CM1) cleavable by a first protease and a second cleavable moiety (CM2) cleavable by a second protease, and wherein the substrate comprises an APR core and the substrate comprises the amino acid sequence of APRSL (SEQ ID NO: 669), APRSY (SEQ ID NO: 39), APRSM (SEQ ID NO: 383), APRGL (SEQ ID NO: 672), APRGY (SEQ ID NO: 384), or APRGM. (SEQ ID NO: 385).

Statement 56. The isolated polypeptide of Statement 55, wherein the substrate comprises the amino acid sequence of APRSL (SEQ ID NO: 669), APRSY (SEQ ID NO: 39), or APRSM (SEQ ID NO: 383).

Statement 57. The isolated polypeptide of Statement 55, wherein the substrate comprises the amino acid sequence of APRGL (SEQ ID NO: 672), APRGY (SEQ ID NO: 384), or APRGM (SEQ ID NO: 385).

Statement 58. The isolated polypeptide of Statement 55, wherein the substrate comprises the amino acid sequence of APRSLL (SEQ ID NO: 37), APRGLL (SEQ ID NO: 38), APRSY (SEQ ID NO: 39), or VAPRSMR (SEQ ID NO: 40).

Statement 59. The isolated polypeptide of any one or combination of Statements 55-58, wherein the isolated polypeptide is an activatable molecule and further comprises an active moiety (AM) that specifically binds to a target.

Statement 60. The isolated polypeptide of Statement 59, wherein the AM is coupled to the substrate.

Statement 61. The isolated polypeptide of Statement 59, wherein the AM is directly coupled to the substrate.

Statement 62. The isolated polypeptide of Statement 59, wherein the AM is indirectly coupled to the substrate via a linking peptide.

Statement 63. The isolated polypeptide of any one or combination of Statements 55-62, wherein the AM is coupled to an N-terminus of the substrate.

Statement 64. The isolated polypeptide of any one or combination of Statements 55-62, wherein the AM is coupled to a C-terminus of the substrate.

Statement 65. The isolated polypeptide of any one or combination of Statements 55-62, further comprising a masking moiety (MM).

Statement 66. The isolated polypeptide of Statement 65, wherein the MM has a dissociation constant for binding to the AM that is greater than the dissociation constant of the AM for binding to the target.

Statement 67. The isolated polypeptide of Statement 65 or 66, wherein the MM is 2 to 40 amino acids in length.

Statement 68. The isolated polypeptide of any one or combination of Statements 65-67, wherein the MM is coupled to the substrate such that the isolated polypeptide comprises a structural arrangement from N-terminus to C-terminus as follows: MM-substrate-AM or AM-substrate-MM.

Statement 69. The isolated polypeptide of Statement 68, wherein the MM is directly coupled to the substrate.

Statement 70. The isolated polypeptide of Statement 68, wherein the MM is indirectly coupled to the substrate via a linking peptide.

Statement 71. The isolated polypeptide of Statement 70, wherein the isolated polypeptide comprises a first linking peptide (LP1) and a second linking peptide (LP2), and wherein the isolated polypeptide has a structural arrangement from N-terminus to C-terminus as follows: MM-LP1-substrate-LP2-AM, or AM-LP1-substrate-LP2-MM.

Statement 72. The isolated polypeptide of Statement 71, wherein the LP1 and LP2 are not identical to each other.

Statement 73. The isolated polypeptide of Statement 71, wherein the LP1 and LP2 are identical to each other.

Statement 74. The isolated polypeptide of any one of Statements 71-73, wherein each of the LP1 and LP2 is a peptide of 1 to 20 amino acids in length.

Statement 75. The isolated polypeptide of any one or combination of Statements 55-75, wherein the first protease is a serine protease.

Statement 76. The isolated polypeptide of Statement 75, wherein the serine protease is membrane type serine protease 1 (MT-SP1).

Statement 77. The isolated polypeptide of Statement 76, wherein the $k_{cat}/K_M$ of the substrate by MT-SP1 cleavage is at least $1 \times 10^3$ $M^{-1}$ $s^{-1}$, optionally at 37° C. in 50 mM TRIS-HCl (pH 7.4), 150 mM NaCl, 0.05% Tween 20.

Statement 78. The isolated polypeptide of Statement 76, wherein the $k_{cat}/K_M$ of the substrate by MT-SP1 cleavage is at least $1 \times 10^4$ $M^{-1}$ $s^{-1}$, optionally at 37° C. in 50 mM TRIS-HCl (pH 7.4), 150 mM NaCl, 0.05% Tween 20.

Statement 79. The isolated polypeptide of any one or combination of Statements 55-78, wherein the second protease is a matrix metalloproteinase (MMP). The isolated polypeptide of Statement 79, wherein the MMP is MMP2, MMP9, or MMP14. The isolated polypeptide of Statement 33, wherein the MMP is MMP2. The isolated polypeptide of Statement 33, wherein the MMP is MMP9. The isolated polypeptide of Statement 33, wherein the MMP is MMP14.

Statement 80. The isolated polypeptide of Statement 79, wherein the MMP is MMP2, MMP9, or MMP14.

Statement 81. The isolated polypeptide of Statement 80, wherein the $k_{cat}/K_M$ of the substrate by MMP2 cleavage is at least $1\times10^3$ $M^{-1}$ $s^{-1}$, optionally at 37° C. in 50 mM Tris-HCl (pH 7.5), 10 mM $CaCl_2$, 150 mM NaCl, 0.05% (w/v) Brij-35.

Statement 82. The isolated polypeptide of Statement 80, wherein the $k_{cat}/K_M$ of the substrate by MMP2 cleavage is at least $1\times10^4$ $M^{-1}$ $s^{-1}$, optionally at 37° C. in 50 mM Tris-HCl (pH 7.5), 10 mM $CaCl_2$, 150 mM NaCl, 0.05% (w/v) Brij-35.

Statement 83. The isolated polypeptide of any one of Statements 80-82, wherein the $k_{cat}/K_M$ of the substrate by MMP9 cleavage is at least $1\times10^3$ $M^{-1}$ $s^{-1}$, optionally at 37° C. in 50 mM Tris-HCl (pH 7.5), 10 mM $CaCl_2$, 150 mM NaCl, 0.05% (w/v) Brij-35.

Statement 84. The isolated polypeptide of any one of Statements 80-82, wherein the $k_{cat}/K_M$ of the substrate by MMP9 cleavage is at least $1\times10^4$ $M^{-1}$ $s^{-1}$, optionally at 37° C. in 50 mM Tris-HCl (pH 7.5), 10 mM $CaCl_2$), 150 mM NaCl, 0.05% (w/v) Brij-35.

Statement 85. The isolated polypeptide of any one of Statements 80-84, wherein the $k_{cat}/K_M$ of the substrate by MMP14 cleavage is at least $1\times10^3$ $M^{-1}$ $s^{-1}$, optionally at 37° C. in 50 mM HEPES (pH 6.8), 10 mM $CaCl_2$, 0.5 mM $MgCl_2$, 0.05% (w/v) Brij-35.

Statement 86. The isolated polypeptide of any one of Statements 80-84, wherein the $k_{cat}/K_M$ of the substrate by MMP14 cleavage is at least $1\times10^4$ $M^{-1}$ $s^{-1}$, optionally at 37° C. in 50 mM HEPES (pH 6.8), 10 mM $CaCl_2$, 0.5 mM $MgCl_2$, 0.05% (w/v) Brij-35.

Statement 87. The isolated of polypeptide of any one of Statements 75, 79-86, wherein the serine protease is urokinase-type plasminogen activator (uPA), optionally at 37° C. in 50 mM TRIS-HCl (pH 7.4), 150 mM NaCl, 0.05% Tween 20.

Statement 88. The isolated polypeptide of Statement 87, wherein the $k_{cat}/K_M$ of the substrate by uPA cleavage is at least $1\times10^3$ $M^{-1}$ $s^{-1}$, optionally at 37° C. in 50 mM TRIS-HCl (pH 7.4), 150 mM NaCl, 0.05% Tween 20.

Statement 89. The isolated polypeptide of Statement 87, wherein the $k_{cat}/K_M$ of the substrate by uPA cleavage is at least $1\times10^4$ $M^{-1}$ $s^{-1}$, optionally at 37° C. in 50 mM TRIS-HCl (pH 7.4), 150 mM NaCl, 0.05% Tween 20.

Statement 90. An isolated polypeptide comprising a substrate cleavable an MMP and a serine protease, wherein the substrate comprises an amino acid sequence selected from SEQ ID NOs: 9-24, 37-73, 83-353, 383-385, and 560-695, optionally selected from SEQ ID NOs: 9-24, 37-73, 83-353, 383-385, and 560-683.

Statement 91. An isolated polypeptide comprising a substrate, wherein the substrate comprises a first cleavable moiety (CM1) cleavable by a first protease and a second cleavable moiety (CM2) cleavable by a second protease, and wherein the substrate comprises an amino acid sequence with one-amino acid mutation of any one of SEQ ID NOs: 9-24, 37-73, 83-353, and 383-385.

Statement 92. An isolated polypeptide comprising a substrate, wherein the substrate comprises a first cleavable moiety (CM1) cleavable by a first protease and a second cleavable moiety (CM2) cleavable by a second protease, and wherein the substrate comprises an amino acid sequence with two-amino acid mutations of any one of SEQ ID NOs: 9-24, 37-73, 83-353, and 383-385.

Statement 93. An isolated polypeptide comprising a substrate, wherein the substrate comprises a first cleavable moiety (CM1) cleavable by a first protease and a second cleavable moiety (CM2) cleavable by a second protease, and wherein the substrate comprises an amino acid sequence with three-amino acid mutations of any one of SEQ ID NOs: 9-24, 37-73, 83-353, and 383-385.

Statement 94. An isolated polypeptide comprising a substrate, wherein the substrate comprises a first cleavable moiety (CM1) cleavable by a first protease and a second cleavable moiety (CM2) cleavable by a second protease, and wherein the substrate comprises an amino acid sequence with four-amino acid mutations of any one of SEQ ID NOs: 9-24, 37-73, 83-353, and 383-385.

Statement 95. An isolated polypeptide comprising a cleavable moiety (CM) comprising an amino acid sequence with one-amino acid mutation of any one of SEQ ID NO: 382, wherein the CM is a substrate for a protease.

Statement 96. An isolated polypeptide comprising a cleavable moiety (CM) comprising an amino acid sequence with two-amino acid mutations of any one of SEQ ID NO: 382, wherein the CM is a substrate for a protease.

Statement 97. The isolated polypeptide of any one or combination of Statements 91-96, wherein the isolated polypeptide is an activatable molecule and further comprises an active moiety (AM) that specifically binds to a target.

Statement 98. The isolated polypeptide of Statement 97, wherein the AM is coupled to the substrate.

Statement 99. The isolated polypeptide of Statement 98, wherein the AM is directly coupled to the substrate.

Statement 100. The isolated polypeptide of Statement 98, wherein the AM is indirectly coupled to the substrate via a linking peptide.

Statement 101. The isolated polypeptide of any one or combination of Statements 91-100, wherein the AM is coupled to an N-terminus of the substrate.

Statement 102. The isolated polypeptide of any one or combination of Statements 91-100, wherein the AM is coupled to a C-terminus of the substrate.

Statement 103. The isolated polypeptide of any one or combination of Statements 91-102, further comprising a masking moiety (MM).

Statement 104. The isolated polypeptide of Statement 103, wherein the MM has a dissociation constant for binding to the AM that is greater than the dissociation constant of the AM for binding to the target.

Statement 105. The isolated polypeptide of Statement 103 or 104, wherein the MM is 2 to 40 amino acids in length.

Statement 106. The isolated polypeptide of any one or combination of Statements 103-105, wherein the MM is coupled to the substrate such that the isolated polypeptide comprises a structural arrangement from N-terminus to C-terminus as follows: MM-substrate-AM or AM-substrate-MM.

Statement 107. The isolated polypeptide of Statement 106, wherein the MM is directly coupled to the substrate.

Statement 108. The isolated polypeptide of Statement 106, wherein the MM is indirectly coupled to the substrate via a linking peptide.

Statement 109. The isolated polypeptide of Statement 108, wherein the isolated polypeptide comprises a first linking peptide (LP1) and a second linking peptide (LP2), and wherein the isolated polypeptide has a structural arrangement from N-terminus to C-terminus as follows: MM-LP1-substrate-LP2-AM, or AM-LP1-substrate-LP2-MM.

Statement 110. The isolated polypeptide of Statement 109, wherein the LP1 and LP2 are not identical to each other.

Statement 111. The isolated polypeptide of Statement 109, wherein the LP1 and LP2 are identical to each other.

Statement 112. The isolated polypeptide of any one of Statements 109-111, wherein each of the LP1 and LP2 is a peptide of 1 to 20 amino acids in length.

Statement 113. The isolated polypeptide of any one or combination of Statements 55-112, wherein the first protease is a serine protease.

Statement 114. The isolated polypeptide of Statement 113, wherein the serine protease is membrane type serine protease 1 (MT-SP1) or uPA.

Statement 115. The isolated polypeptide of any one or combination of Statements 55-114, wherein the second protease is a matrix metalloproteinase (MMP).

Statement 116. The isolated polypeptide of Statement 115, wherein the MMP is MMP2, MMP9, or MMP14.

Statement 117. The isolated polypeptide of any one or combination of Statements 23-54, 59-90, and 97-116, wherein the AM is an antibody or antigen binding fragment thereof.

Statement 118. The isolated polypeptide of Statement 117, wherein the antigen binding fragment thereof is selected from the group consisting of a Fab fragment, a F(ab') 2 fragment, a scFv, a scAb, a dAb, a single domain heavy chain antibody, and a single domain light chain antibody.

Statement 119. The isolated polypeptide of any one or combination of Statements 23-54, 59-90, and 97-116, wherein the AM is a therapeutic macromolecule.

Statement 120. The isolated polypeptide of any one or combination of Statements 23-54, 59-90, and 97-116, wherein the AM is a cytokine.

Statement 121. The isolated polypeptide of any one or combination of Statements 23-54, 59-90, and 97-116, wherein the AM is a chimeric antigen receptor.

Statement 122. The isolated polypeptide of any one or combination of Statements 30-54, 65-90, and 103-120, wherein the MM interferes with AM's binding to its binding partner through non-specific interactions such as steric hindrance, optionally wherein the MM is positioned in the activatable molecule such that the tertiary or quaternary structure of the activatable molecule allows the MM to mask the AM through charge-based interaction, optionally wherein the MM is an albumin, e.g., human serum albumin (HSA), a fragment crystallizable (Fc) domain, an antibody constant domain (e.g., CH domains), a polymer (e.g., branched or multi-armed polyethylene glycol (PEG)), a latency associated protein (LAP), and any polypeptide or other moieties that sterically interfere AM-target interactions, optionally wherein the MM may recruit a large protein binding partner that sterically interfere AM-target interactions, optionally wherein the MM is an antibody or a fragment thereof that binds to an albumin, optionally wherein the MM comprises a full-length or a AM-binding fragment or mutein of a cognate receptor of the AM, and AM-binding antibodies and fragment thereof, e.g., a polyclonal antibody, a recombinant antibody, a human antibody, a humanized antibody a single chain variable fragment (scFv), single-domain antibody such as a heavy chain variable domain (VH), a light chain variable domain (VL), a variable domain of camelid-type nanobody (VHH), or a dAb, optionally wherein the MM is a non-immunoglobulin proteins that mimic antibody binding and/or structure such as, anticalins, affilins, affibody molecules, affimers, affitins, alphabodies, avimers, DARPins, fynomers, kunitz domain peptides, monobodies, and binding domains based on other engineered scaffolds such as SpA, GroEL, fibronectin, lipocallin and CTLA4 scaffolds, optionally wherein the MM is a peptide that is modified by conjugation to a water-soluble polymer, such as a polyalkylene glycol, e.g., a polyethylene glycol (PEG), optionally wherein the MM is an antibody or antigen-binding domain that binds to a protein with a long serum half-life such as HSA, immunoglobulin or transferrin, or to a receptor that is recycled to the plasma membrane, such as FcRn or a transferrin receptor.

Statement 123. The isolated polypeptide of any one or combination of Statements 1-122, wherein the isolated polypeptide is resistant to cleavage in situ in human bone marrow, optionally resistant to cleavage in situ in human bone marrow compared to a CM of SEQ ID NO: 78, optionally resistant to cleavage in situ in human bone marrow compared to a CM of SEQ ID NO: 79, or optionally resistant to cleavage in situ in human bone marrow compared to a CM of SEQ ID NO: 80.

Statement 124. The isolated polypeptide of any one or combination of Statements 1-122, wherein the isolated polypeptide is resistant to cleavage in vivo in human bone marrow, optionally resistant to cleavage in situ in human bone marrow compared to a CM of SEQ ID NO: 78, optionally resistant to cleavage in situ in human bone marrow compared to a CM of SEQ ID NO: 79, or optionally resistant to cleavage in situ in human bone marrow compared to a CM of SEQ ID NO: 80.

Statement 125. The isolated polypeptide of any one or combination of Statements 23-54, 59-90, 97-116, wherein the AM is an antibody or antigen-binding fragment that binds EGFR and the MM comprises the amino acid sequence of SEQ ID NO: 82.

Statement 126. An isolated polypeptide comprising an antibody or antigen-binding fragment thereof that binds EGFR (AB), a masking moiety (MM) comprising the SEQ ID NO: 82, and a cleavable moiety (CM), wherein AB is coupled with the MM via the CM.

Statement 127. The isolated polypeptide of any one or combination of Statements 1-126, further comprising one or more additional CMs, optionally wherein at least a portion of a first CM overlaps with at least a portion of a second CM in the substrate, such that one or more amino acids belong to both CMs.

Statement 128. A polypeptide complex comprising one or more of the isolated polypeptides of any one or combination of Statements 1-127 bound to a second isolated polypeptide.

Statement 129. A conjugated polypeptide comprising the isolated polypeptide of any one or combination of Statements 1-127 conjugated to an agent.

Statement 130. The conjugated polypeptide of Statement 129, wherein the agent is conjugated to the AM via a linker.

Statement 131. The conjugated polypeptide of Statement 130, wherein the linker is a cleavable linker.

Statement 132. The conjugated polypeptide of Statement 130, wherein the linker is a non-cleavable linker.

Statement 133. The conjugated polypeptide of Statement 131, wherein the conjugating linker comprises an amino acid sequence selected from SEQ ID NOs: 9-24, 37-73, 83-353, 382-385, and 560-695, optionally selected from SEQ ID NOs: 9-24, 37-73, 83-353, 382-385, and 560-683.

Statement 134. The conjugated polypeptide of any one or combination of Statements 129-133, wherein the agent is a toxin, a microtubule inhibitor, a nucleic acid damaging agent, a dolastatin, an auristatin, a maytansinoid, a duocarmycin, a calicheamicin, or a combination thereof.

Statement 135. A composition comprising the isolated polypeptide of any one or combination of Statements 1-127, the polypeptide complex of Statement 128, or the conjugated activatable molecule of any one or combination of Statements 129-134, and a carrier.

Statement 136. The composition of Statement 135, wherein the carrier is a pharmaceutically acceptable carrier.

Statement 137. The composition of Statement 135 or 136, comprising an additional agent.

Statement 138. The composition of Statement 137, wherein the additional agent is a therapeutic agent.

Statement 139. An isolated nucleic acid molecule encoding the isolated polypeptide of any one or combination of Statements 1-127.

Statement 140. A vector comprising the isolated nucleic acid molecule of Statement 139.

Statement 141. A cell comprising the isolated polypeptide of any one or combination of Statements 1-127 or the isolated nucleic acid molecule of Statement 139 or the vector of Statement 140.

Statement 142. A method of manufacturing an isolated polypeptide or an activatable molecule that contains a substrate, the method comprising expressing and recovering a polypeptide comprising the isolated polypeptide of any one or combination of Statements 1-127, optionally wherein the polypeptide is an activatable molecule.

Statement 143. A method of treating, alleviating a symptom of, or delaying the progression of a disease or disorder in a subject, comprising administering a therapeutically effective amount of the isolated polypeptide of any one or combination of Statements 1-127, the polypeptide complex of Statement 128, the conjugated activatable molecule of any one or combination of Statements 129-134, the composition of any one of Statements 135-138, the nucleic acid molecule of Statement 139, the vector of Statement 140, or the cell of Statement 141 to the subject. The isolated polypeptide of any one or combination of Statements 1-127, the polypeptide complex of Statement 128, the conjugated polypeptide of any one or combination of Statements 129-134, the composition of any one of Statements 135-138, the nucleic acid molecule of Statement 139, the vector of Statement 140, or the cell of Statement 141 for use as a medicament or for use in therapy, optionally for treating a cancer, an infection, an inflammatory disorder, a cardiovascular disorder, a neurodegenerative disorder, or an autoimmune disorder, optionally with an additional agent which is optionally a therapeutic agent. The isolated polypeptide of any one or combination of Statements 1-127, the polypeptide complex of Statement 128, the conjugated polypeptide of any one or combination of Statements 129-134, the composition of any one of Statements 135-138, the nucleic acid molecule of Statement 139, the vector of Statement 140, or the cell of Statement 141 for treating a cancer. The isolated polypeptide of any one or combination of Statements 1-127, the polypeptide complex of Statement 128, the conjugated polypeptide of any one or combination of Statements 129-134, the composition of any one of Statements 135-138, the nucleic acid molecule of Statement 139, the vector of Statement 140, or the cell of Statement 141 for treating an infection. The isolated polypeptide of any one or combination of Statements 1-127, the polypeptide complex of Statement 128, the conjugated polypeptide of any one or combination of Statements 129-134, the composition of any one of Statements 135-138, the nucleic acid molecule of Statement 139, the vector of Statement 140, or the cell of Statement 141 for treating an inflammatory disorder. The isolated polypeptide of any one or combination of Statements 1-127, the polypeptide complex of Statement 128, the conjugated polypeptide of any one or combination of Statements 129-134, the composition of any one of Statements 135-138, the nucleic acid molecule of Statement 139, the vector of Statement 140, or the cell of Statement 141 for treating a cardiovascular disorder. The isolated polypeptide of any one or combination of Statements 1-127, the polypeptide complex of Statement 128, the conjugated polypeptide of any one or combination of Statements 129-134, the composition of any one of Statements 135-138, the nucleic acid molecule of Statement 139, the vector of Statement 140, or the cell of Statement 141 for treating a neurodegenerative disorder. The isolated polypeptide of any one or combination of Statements 1-127, the polypeptide complex of Statement 128, the conjugated polypeptide of any one or combination of Statements 129-134, the composition of any one of Statements 135-138 to the subject, the nucleic acid molecule of Statement 139, the vector of Statement 140, or the cell of Statement 141 for treating an autoimmune disorder.

Statement 144. The method of Statement 143, wherein the disease is a cancer, an infection, an inflammatory disorder, a cardiovascular disorder, a neurodegenerative disorder, or an autoimmune disorder.

Statement 145. A kit comprising the isolated polypeptide of any one or combination of Statements 1-127, the polypeptide complex of Statement 128, the conjugated activatable molecule of any one or combination of Statements 129-134, or the composition of any one of Statements 135-138.

Statement 146. The use of the isolated polypeptide of any one or combination of Statements 1-127, the polypeptide complex of Statement 128, the conjugated activatable molecule of any one or combination of Statements 129-134, the composition of any one of Statements 135-138, the nucleic acid molecule of Statement 139, the vector of Statement 140, or the cell of Statement 141 for the manufacture of a medicament for the treatment of a disease or disorder.

Statement 147. The use of Statement 146, wherein the disease or disorder is a cancer, an infection, an inflammatory disorder, a cardiovascular disorder, a neurodegenerative disorder, or an autoimmune disorder.

Statement 148. A method of detecting or diagnosing a disease or health condition of a subject, comprising: contacting the isolated polypeptide of any one or combination of Statements 1-127, the polypeptide complex of Statement 128, the conjugated activatable molecule of any one or combination of Statements 129-134, or the composition of any one of Statements 135-138 with a sample from the subject; and measuring a level of cleavage of the isolated polypeptide, thereby detecting or diagnosing the disease or health condition of the subject.

Statement 149. The method of Statement 148, wherein the disease is a cancer, an infection, an inflammatory disorder, a cardiovascular disorder, a neurodegenerative disorder, or an autoimmune disorder.

EXAMPLES

Example 1: Exemplary Activatable Antibodies and Protease Cleavable Substrates

The studies provided herein describe exemplary protease cleavable substrates of the present disclosure that include at least one cleavable moiety cleavable by a matrix metalloprotease (MMP) and/or at least one cleavable moiety cleavable by a matriptase (MT-SP1).

Exemplary activatable antibodies were constructed such that each one includes one of the substrates listed in Table 4. The exemplary activatable antibodies, the sequences of which are listed in Table 5, include an antibody or antigen binding fragment thereof (AB) that is based on a mouse/ human chimeric monoclonal antibody that specifically binds to epidermal growth factor receptor (EGFR). The exemplary activatable antibodies also include a prodomain coupled to the N-terminus of the light chain of the AB. Each prodomain includes a masking moiety (MM) and a substrate, and the substrate includes at least one sequence of Table 4.

TABLE 4

MMP/MT-SP1 Substrates

| Name | Sequence | SEQ ID NO: |
|------|----------|------------|
| 8050 | PWGLRSN | 9 |
| 8051 | RSPWGLN | 10 |
| 8052 | GPWGLSGRSNI | 11 |
| 8053 | PWGLSGRS | 12 |
| 8054 | GRSPWGLL | 13 |
| 8055 | APMGLKHLSGRSNI | 14 |
| 8056 | GPYGLSGRSNI | 15 |
| 8057 | APRSPWGL | 16 |
| 8058 | PWGLPRS | 17 |

TABLE 4-continued

MMP/MT-SP1 Substrates

| Name | Sequence | SEQ ID NO: |
|------|----------|------------|
| 8059 | PRSPWGLL | 18 |
| 8060 | PWGLSRS | 19 |
| 8061 | PFGLSRS | 20 |
| 8062 | APMGLKHDHQSRS | 21 |
| 8063 | DHQSRSAPMGLKH | 22 |
| 8064 | KPRGLN | 23 |
| 8065 | KPRGLF | 24 |
| 8066 | APRSLL | 37 |
| 8067 | APRGLL | 38 |
| 8068 | APRSY | 39 |
| 8069 | VAPRSMR | 40 |

TABLE 5

Activatable Antibody Sequences

| Molecule Name | Light chain EGFR Mask | Light chain substrate | Protein description (Light chain /Heavy chain) |
|---------------|-----------------------|-----------------------|------------------------------------------------|
| CX-122 | CISPRGCPDGPYVMY (SEQ ID NO: 81) | 2001 (SEQ ID NO: 78) | C225v5 3954 2001 (SEQ ID NO: 354/SEQ ID NO: 355) |
| AA w/5007 | CISPRGCPDGPYVMY (SEQ ID NO: 81) | 5007 (SEQ ID NO: 80) | C225v5 3954 5007 (SEQ ID NO: 356/SEQ ID NO: 357) |
| CX-229 | CISPRGCLDGPYVMY (SEQ ID NO: 82) | 3001 (SEQ ID NO: 79) | C225v5 3954 3001 (SEQ ID NO: 358/SEQ ID NO: 355) |
| CTX-028 | CISPRGCPDGPYVMY (SEQ ID NO: 81) | 1001 (SEQ ID NO: 75) | C225v5 3954 1001 (SEQ ID NO: 359/SEQ ID NO: 360) |
| ProC795 | CISPRGCPDGPYVMY (SEQ ID NO: 81) | 8055 (SEQ ID NO: 14) | C225v5 3954 8055 (SEQ ID NO: 361/SEQ ID NO: 355) |
| ProC902 | CISPRGCPDGPYVMY (SEQ ID NO: 81) | 8052 (SEQ ID NO: 11) | C225v5 3954 8052 (SEQ ID NO: 362/SEQ ID NO: 355) |
| ProC903 | CISPRGCPDGPYVMY (SEQ ID NO: 81) | 8056 (SEQ ID NO: 15) | C225v5 3954 8056 (SEQ ID NO: 363/SEQ ID NO: 355) |
| ProC904 | CISPRGCPDGPYVMY (SEQ ID NO: 81) | 8063 (SEQ ID NO: 22) | C225v5 3954 8063 (SEQ ID NO: 364/SEQ ID NO: 355) |
| ProC906 | CISPRGCPDGPYVMY (SEQ ID NO: 81) | 8062 (SEQ ID NO: 21) | C225v5 3954 8062 ((SEQ ID NO: 365/SEQ ID NO: 355) |

TABLE 5-continued

Activatable Antibody Sequences

| Molecule Name | Light chain EGFR Mask | Light chain substrate | Protein description (Light chain /Heavy chain) |
|---|---|---|---|
| ProC1260 | CISPRGCPDGPYVMY (SEQ ID NO: 81) | 8057 (SEQ ID NO: 16) | C225v5 3954 8057 (SEQ ID NO: 366/SEQ ID NO: 367) |
| ProC1261 | CISPRGCPDGPYVMY (SEQ ID NO: 81) | 8058 (SEQ ID NO: 17) | C225v5 3954 8058 (SEQ ID NO: 368/SEQ ID NO: 367) |
| ProC1264 | CISPRGCPDGPYVMY (SEQ ID NO: 81) | 8064 (SEQ ID NO: 23) | C225v5 3954 8064 (SEQ ID NO: 369/SEQ ID NO: 367) |
| ProC1265 | CISPRGCPDGPYVMY (SEQ ID NO: 81) | 8050 (SEQ ID NO: 9) | C225v5 3954 8050 (SEQ ID NO: 370/SEQ ID NO: 367) |
| ProC1266 | CISPRGCPDGPYVMY (SEQ ID NO: 81) | 8051 (SEQ ID NO: 10) | C225v5 3954 8051 (SEQ ID NO: 371/SEQ ID NO: 367) |
| ProC1750 | CISPRGCPDGPYVMY (SEQ ID NO: 81) | 8065 (SEQ ID NO: 24) | C225v5 3954 8065 (SEQ ID NO: 372/SEQ ID NO: 355) |
| ProC1754 | CISPRGCPDGPYVMY (SEQ ID NO: 81) | 8053 (SEQ ID NO: 12) | C225v5 3954 8053 (SEQ ID NO: 373/SEQ ID NO: 355) |
| ProC1755 | CISPRGCPDGPYVMY (SEQ ID NO: 81) | 8060 (SEQ ID NO: 19) | C225v5 3954 8060 (SEQ ID NO: 374/SEQ ID NO: 355) |
| ProC1756 | CISPRGCPDGPYVMY (SEQ ID NO: 81) | 8061 (SEQ ID NO: 20) | C225v5 3954 8061 (SEQ ID NO: 375/SEQ ID NO: 355) |
| ProC1757 | CISPRGCPDGPYVMY (SEQ ID NO: 81) | 8059 (SEQ ID NO: 18) | C225v5 3954 8059 (SEQ ID NO: 376/SEQ ID NO: 355) |
| ProC1758 | CISPRGCPDGPYVMY (SEQ ID NO: 81) | 8054 (SEQ ID NO: 13) | C225v5 3954 8054 (SEQ ID NO: 377/SEQ ID NO: 355) |
| ProC900 | CISPRGCPDGPYVMY (SEQ ID NO: 81) | 8066 (SEQ ID NO: 37) | C225v5 3954 8066 (SEQ ID NO: 378/SEQ ID NO: 355) |
| ProC901 | CISPRGCPDGPYVMY (SEQ ID NO: 81) | 8067 (SEQ ID NO: 38) | C225v5 3954 8067 (SEQ ID NO: 379/SEQ ID NO: 355) |
| ProC1259 | CISPRGCPDGPYVMY (SEQ ID NO: 81) | 8068 (SEQ ID NO: 39) | C225v5 3954 8068 (SEQ ID NO: 380/SEQ ID NO: 367) |
| ProC1752 | CISPRGCPDGPYVMY (SEQ ID NO: 81) | 8069 (SEQ ID NO: 40) | C225v5 3954 8069 (SEQ ID NO: 381/SEQ ID NO: 355) |

Example 2: In Vitro Cleavability of Exemplary Activatable Antibodies with Protease Cleavable Substrates The studies provided herein evaluate the in vitro cleavability of activatable antibodies containing exemplary substrates that include at least one cleavable moiety cleavable by a matrix metalloprotease (MMP) and/or at least one cleavable moiety cleavable by matriptase (MT-SP1).

The cleavability of the activatable antibodies having the substrates of the present disclosure, along with control substrate 2001 (WO2016/118629) was measured in the presence of MT-SP1, urokinase-type plasminogen activator (uPA), MMP2, MMP9, and/or MMP14. Each activatable antibody (500 nM) was incubated with 10 nM of a single protease for 1.5 and 4 hours at 37° C. as indicated in the tables below. Human recombinant proteases were purchased from R&D Systems: MMP2 (catalog No: 902-MP), MMP9 (catalog No: 911-MP), MMP14 (catalog No: 918-MP), MT-SP1 (catalog No: 3946-SEB) and uPA (catalog No: 1310-SE). MMPs were activated according to the manufacturer's instructions. Protease concentrations were determined by active site titration. Activity assays for MMP2 and MMP9 were performed in the buffer: 50 mM Tris-HCl (pH 7.5), 10 mM CaCl$_2$, 150 mM NaCl, 0.05% (w/v) Brij-35. Activity assays were performed for MMP14 using 50 mM HEPES (pH 6.8), 10 mM CaCl$_2$, 0.5 mM MgCl$_2$. Activity assays were performed for MT-SP1 and uPA using buffer 50 mM TRIS-HCl (pH 7.4), 150 mM NaCl, 0.05% Tween 20. Following incubation, the presence of cleavage product was determined by capillary electrophoresis using a LabChip GXII Touch system (Perkin Elmer) with the HT Protein Express 100 protocol (Perkin Elmer). LabChip GXII Touch HT Chips (Perkin Elmer #760499) were set up using the protocol of the Protein Express Assay Reagent Kit (Perkin Elmer #CLS960008). The fraction of cleaved activatable antibody was determined by quantifying the fraction of the higher mobility polypeptide corresponding to the cleaved activatable antibody using the LabChip GX Reviewer software (Perkin Elmer). The fraction of activatable antibody, and hence, substrate that is cleaved by each particular protease is presented as a "cleavability percentage" in Tables 6A-6F. These exemplary results show that the exemplary substrates showed a range of cleavability by the indicated proteases. The results in Tables 6A-6F indicate that substrates 8052 (GPWGLSGRSNI; SEQ ID NO: 11), 8053 (PWGLSGRS; SEQ ID NO: 12), 8055 (APMGLKHLS-GRSNI; SEQ ID NO: 14), 8056 (GPYGLSGRSNI; SEQ ID NO: 15), 8060 (PWGLSRS; SEQ ID NO: 19), 8065 (KPR-GLF; SEQ ID NO: 24), 8062 (APMGLKHDHQSRS; SEQ ID NO: 21), 8063 (DHQSRSAPMGLKH; SEQ ID NO: 22), 8066 (APRSLL; SEQ ID NO: 37), and 8069 (VAPRSMR; SEQ ID NO: 40) were each substantially cleaved by MT-SP1 at cleavability percentages of greater than 40%.

The results in Tables 6A-6F indicate that the group of substrates 8065 (KPRGLF; SEQ ID NO: 24), 8053 (PWGLSGRS; SEQ ID NO: 12), 8052 (GPWGLSGRSNI; SEQ ID NO: 11), 8056 (GPYGLSGRSNI; SEQ ID NO: 15), 8063 (DHQSRSAPMGLKH; SEQ ID NO: 22), 8066 (APRSLL; SEQ ID NO: 37), and 8069 (VAPRSMR; SEQ ID NO: 40) were all substantially cleaved by MT-SP1, MMP9, and MMP2 at cleavability percentages of greater than 40%.

The results in Tables 6A-6F indicate that the group of substrates 8065 (KPRGLF; SEQ ID NO: 24), 8055 (APMGLKHLSGRSNI; SEQ ID NO: 14), 8063 (DHQSR-SAPMGLKH; SEQ ID NO: 22), and 8062 (APMGLKHDHQSRS; SEQ ID NO: 21) were all substantially cleaved by MT-SP1 and MMP14, MMP2 at cleavability percentages of greater than 50%.

The results of Tables 6A-6F indicate that the group of substrates 8062 (APMGLKHDHQSRS; SEQ ID NO: 21), 8063 (DHQSRSAPMGLKH; SEQ ID NO: 22), 8056 (GPYGLSGRSNI; SEQ ID NO: 15), 8052 (GPWGLS-GRSNI; SEQ ID NO: 11), 8065 (KPRGLF; SEQ ID NO: 24), 8053 (PWGLSGRS; SEQ ID NO: 12), 8066 (APRSLL; SEQ ID NO: 37), 8069 (VAPRSMR; SEQ ID NO: 40), and 8055 (APMGLKHLSGRSNI; SEQ ID NO: 14) were each substantially cleaved by MT-SP1 and MMP2 at a cleavability percentage of greater than 50%.

The results in Tables 6A-6F indicate that the group of substrates 8050 (PWGLRSN; SEQ ID NO: 9), 8065 (KPR- GLF; SEQ ID NO: 24), 8062 (APMGLKHDHQSRS; SEQ ID NO: 21), 8063 (DHQSRSAPMGLKH; SEQ ID NO: 22), 8056 (GPYGLSGRSNI; SEQ ID NO: 15), 8052 (GPWGLS-GRSNI; SEQ ID NO: 11), 8066 (APRSLL; SEQ ID NO: 37), 8069 (VAPRSMR; SEQ ID NO: 40), 8055 (APMGLKHLSGRSNI; SEQ ID NO: 14), and 8067 (APR-GLL; SEQ ID NO: 38) were each substantially cleaved by MMP2 at cleavability percentages of greater than 70%.

The results in Table 6A-6F indicate that the group of substrates 8058 (PWGLPRS; SEQ ID NO: 17), 8064 (KPR-GLN; SEQ ID NO: 23) were cleaved substantially by MT-SP1 at cleavability percentage between 20% and 40%.

The results in Tables 6A-6F indicate that the group of substrates 8057 APRSPWGL (SEQ ID NO: 16), 8064 (KPR-GLN; SEQ ID NO: 23), 8051 RSPWGLN (SEQ ID NO: 10), 8055 (APMGLKHLSGRSNI; SEQ ID NO: 14), and 8062 (APMGLKHDHQSRS; SEQ ID NO: 21) were each substantially cleaved by MMP9 at cleavability percentage between 10% and 40%.

The results in Tables 6A-6F indicate that the group of substrates 8050 (PWGLRSN; SEQ ID NO: 9), 8065 (KPR-GLF; SEQ ID NO: 24), 8059 (PRSPWGLL; SEQ ID NO: 18), 8054 (GRSPWGLL; SEQ ID NO: 13), and 8067 (APRGLL; SEQ ID NO: 38) were cleaved substantially by MMP14, MMP9, and MMP2 at cleavability percentages of greater than 50%.

In addition, an exemplary study to determine the cleavability kinetics (i.e., $k_{cat}/K_M$ ($M^{-1}$ $s^{-1}$)) of the indicated substrates with the indicated proteases. The exemplary results of this in vitro study are summarized in Table 6G.

These exemplary results of Table 6G also show that the exemplary substrates 8064 (KPRGLN; SEQ ID NO: 23) and 8053 (PWGLSGRS; SEQ ID NO: 12) had a $k_{cat}/K_M$ ($M^{-1}$ $s^{-1}$) of greater than $1 \times 10^3$ $M^{-1}$ $s^{-1}$ for in vitro cleavability with MT-SP1.

These exemplary results of Table 6G also show that the exemplary substrates 8064 (KPRGLN; SEQ ID NO: 23) and 8053 (PWGLSGRS; SEQ ID NO: 12) had a $k_{cat}/K_M$ ($M^{-1}$ $s^{-1}$) of greater than $1 \times 10^4$ $M^{-1}$ $s^{-1}$ for in vitro cleavability with MT-SP1.

These exemplary results of Table 6G also show that the exemplary substrates 8064 (KPRGLN; SEQ ID NO: 23) and 8053 (PWGLSGRS; SEQ ID NO: 12) had a $k_{cat}/K_M$ ($M^{-1}$ $s^{-1}$) of greater than $1 \times 10^3$ $M^{-1}$ $s^{-1}$ for in vitro cleavability with MMP14

These exemplary results of Table 6G also show that the exemplary substrates 8064 (KPRGLN; SEQ ID NO: 23) and 8053 (PWGLSGRS; SEQ ID NO: 12) had a $k_{cat}/K_M$ ($M^{-1}$ $s^{-1}$) of greater than $1 \times 10^3$ $M^{-1}$ $s^{-1}$ for in vitro cleavability with MMP9.

These exemplary results of Table 6G also show that the exemplary substrate 8053 (PWGLSGRS; SEQ ID NO: 12) had a $k_{cat}/K_M$ ($M^{-1}$ $s^{-1}$) of greater than $1 \times 10^4$ $M^{-1}$ $s^{-1}$ for in vitro cleavability with MMP9.

These exemplary results of Table 6G also show that the exemplary substrates 8064 (KPRGLN; SEQ ID NO: 23) and 8053 (PWGLSGRS; SEQ ID NO: 12) had a $k_{cat}/K_M$ ($M^{-1}$ $s^{-1}$) of greater than $1 \times 10^3$ $M^{-1}$ $s^{-1}$ for in vitro cleavability with MMP2.

These exemplary results of Table 6G also show that the exemplary substrate 8053 (PWGLSGRS; SEQ ID NO: 12) had a $k_{cat}/K_M$ ($M^{-1}$ $s^{-1}$) of greater than $1 \times 10^4$ $M^{-1}$ $s^{-1}$ for in vitro cleavability with MMP2.

TABLE 6A

In Vitro Activation of Activatable Antibodies
with Exemplary Protease Cleavable Substrates

| Substrate of Activatable Antibody | Substrate | MT-SP1 1.5 hours | MMP2 1.5 hours | MMP9 1.5 hours | MMP14 1.5 hours |
|---|---|---|---|---|---|
| 2001 | ISSGLLS GRSDNH (SEQ ID NO: 78) | 6 | 28 | — | 61 |
| 8057 | APRSPWG L (SEQ ID NO: 16) | 24 | 18 | 10 | — |
| 8058 | PWGLPRS (SEQ ID NO: 17) | 24 | — | — | — |

TABLE 6A-continued

In Vitro Activation of Activatable Antibodies
with Exemplary Protease Cleavable Substrates

| Substrate of Activatable Antibody | Substrate | MT-SP1 1.5 hours | MMP2 1.5 hours | MMP9 1.5 hours | MMP14 1.5 hours |
|---|---|---|---|---|---|
| 8064 | KPRGLN (SEQ ID NO: 23) | 35 | 57 | 10 | 6 |
| 8050 | PWGLRSN (SEQ ID NO: 9) | — | 92 | 82 | 52 |
| 8051 | RSPWGLN (SEQ ID NO: 10) | — | 20 | 21 | — |

Note:
"—" indicates below limit of quantification

TABLE 6B

In Vitro Activation of Activatable Antibodies with Exemplary Protease
Cleavable Substrates

| Substrate of Activatable Antibody | Substrate | MT-SP1 1.5 hours | uPA 1.5 hours | MMP2 1.5 hours | MMP9 1.5 hours | MMP14 1.5 hours |
|---|---|---|---|---|---|---|
| 2001 | ISSGLLSGRSD NH (SEQ ID NO: 78) | 16 | 11 | 36 | — | 64 |
| 8057 | APRSPWGL (SEQ ID NO: 16) | 7 | — | 25 | 16 | — |
| 8065 | KPRGLF (SEQ ID NO: 24) | 64 | — | 94 | 64 | 83 |
| 8053 | PWGLSGRS (SEQ ID NO: 12) | 76 | 13 | 60 | 59 | 30 |
| 8060 | PWGLSRS (SEQ ID NO: 19) | 64 | — | 10 | 8 | 16 |
| 8059 | PRSPWGLL (SEQ ID NO: 18) | 12 | — | 63 | 73 | 56 |
| 8054 | GRSPWGLL (SEQ ID NO: 13) | 7 | 4 | 64 | 74 | 53 |

Note:
"—" indicates below limit of quantification

TABLE 6C

In Vitro Activation of Activatable Antibodies with Exemplary Protease
Cleavable Substrates

| Substrate of Activatable Antibody | Substrate (SEQ ID NO) | MT-SP1 4 hours | MMP2 1.5 hours | MMP9 1.5 hours | MMP14 1.5 hours |
|---|---|---|---|---|---|
| 2001 | ISSGLLSGRSDNH (SEQ ID NO: 78) | 30 | 14 | — | 85 |

TABLE 6C-continued

In Vitro Activation of Activatable Antibodies with Exemplary Protease
Cleavable Substrates

| Substrate of Activatable Antibody | Substrate (SEQ ID NO) | Cleavability (%) | | | |
|---|---|---|---|---|---|
| | | MT-SP1 4 hours | MMP2 1.5 hours | MMP9 1.5 hours | MMP14 1.5 hours |
| 8055 | APMGLKHLSGRS NI (SEQ ID NO: 14) | 100 | 100 | 20 | 100 |

Note:
"—" indicates below limit of quantification

15

TABLE 6D

In Vitro Activation of Activatable Antibodies with Exemplary Protease
Cleavable Substrates

| Substrate of Activatable Antibody | Substrate (SEQ ID NO) | Cleavability (%) | | | |
|---|---|---|---|---|---|
| | | MT-SP1 1.5 hours | MMP2 1.5 hours | MMP9 1.5 hours | MMP14 1.5 hours |
| 2001 | ISSGLLSGRSDNH (SEQ ID NO: 78) | 9 | 25 | — | 58 |
| 8052 | GPWGLSGRSNI (SEQ ID NO: 11) | 88 | 86 | 93 | 49 |
| 8056 | GPYGLSGRSNI (SEQ ID NO: 15) | 94 | 97 | 97 | 30 |
| 8063 | DHQSRSAPMGLK H (SEQ ID NO: 22) | 78 | 96 | 47 | 69 |
| 8062 | APMGLKHDHQSR S (SEQ ID NO: 21) | 62 | 80 | 18 | 56 |

Note:
"—" indicates below limit of quantification

TABLE 6E

In Vitro Activation of Activatable Antibodies with Exemplary
Protease Cleavable Substrates

| Ex p# | Substrate of Activatable Antibody | Substrate | MT-SP1 1.5 hours | MMP2 1.5 hours | MMP9 1.5 hours | MMP14 1.5 hours |
|---|---|---|---|---|---|---|
| 1 | 2001 | ISSGLLSGRSDNH (SEQ ID NO: 78) | 9 | 25 | — | 58 |
| | 8066 | APRSLL (SEQ ID NO: 37) | 57 | 95 | 48 | 25 |
| | 8067 | APRGLL (SEQ ID NO: 38) | 11 | 100 | 75 | 89 |

Note:
"—" indicates below limit of quantification

TABLE 6F

In Vitro Activation of Activatable Antibodies with Exemplary
Protease Cleavable Substrates

| Substrate of Activatable Antibody | Substrate | MT-SP1 1.5 hours | MMP2 1.5 hours | MMP9 1.5 hours | MMP14 1.5 hours |
|---|---|---|---|---|---|
| 2001 | ISSGLLSGRSDNH (SEQ ID NO: 78) | 16 | 36 | — | 64 |
| 8069 | VAPRSMR (SEQ ID NO: 40) | 94 | 95 | 74 | 39 |

Note:
"—" indicates below limit of quantification

TABLE 6G

In Vitro Activation of Activatable Antibodies with Exemplary Protease
Cleavable Substrates

| Substrate of Activatable Antibody | Substrate | $K_{cat}/K_M$ $(M^{-1} s^{-1})$ | | | | |
|---|---|---|---|---|---|---|
| | | MT-SP1 | uPA | MMP2 | MMP9 | MMP14 |
| 2001 | ISSGLLSGRSDN H (SEQ ID NO: 78) | 1.60E+03 | 6.78E+02 | 5.08E+03 | — | 1.21E+04 |
| 8064 | KPRGLN (SEQ ID NO: 23) | 1.02E+04 | — | 9.40E+03 | 3.51E+03 | 1.79E+03 |
| 8053 | PWGLSGRS (SEQ ID NO: 12) | 2.22E+04 | 2.45E+03 | 1.33E+04 | 2.50E+04 | 5.42E+03 |

Note:
"—" indicates below limit of quantification

Example 3: In Vivo Stability of Activatable Antibodies with Exemplary Protease Cleavable Substrates The study provided herein evaluates the in vivo stability of activatable antibodies with the exemplary protease cleavable substrates, that include matrix metalloprotease (MMP) and/or matriptase (MT-SP1) substrates.

This exemplary study measured the stability of activatable antibodies containing exemplary substrates by administering a dose of the activatable antibodies to mice, and then measuring the cleaved activatable antibody in the plasma by a capillary electrophoresis immunoassay. The stability was compared to activatable antibodies with control substrates 3001 (AVGLLAPPGGLSGRSDNH; SEQ ID NO: 79) (WO2016/118629) or 5007 (APRSALAHGLF; SEQ ID NO: 80) (WO2020118109).

In this study, nu/nu mice of about 7-8 weeks of age were administered intraperitoneally with the indicated test article at a dosage of 10 mg/kg. After 7 days following the administration, terminal blood was collected by cardiac puncture and processed to plasma within 1 hour of collec-tion. The collected sample was diluted 1:50 in phosphate-buffered saline solution and denatured and analyzed using the Wes™ Western Blot protocol (Protein Simple) using the A110UK goat anti-human IgG antibody (American Qualex) and an anti-goat secondary antibody (Jackson ImmunoResearch). The fraction of cleaved activatable antibody was determined by quantifying the fraction of the higher mobility polypeptide corresponding to the cleaved activatable antibody using the Compass software (Protein Simple). The results of these exemplary assays are summarized in Table 7.

These exemplary results showed that activatable antibodies with exemplary substrates 8052, 8053, 8054, 8057, 8058, 8059, 8060, 8062, 8063, and 8064 demonstrate a higher or comparable in vivo stability than activatable antibodies that have the control substrates 3001 (AVGLLAPPGGLS-GRSDNH; SEQ ID NO: 79) or 5007 (APRSALAHGLF; SEQ ID NO: 80).

TABLE 7

In Vivo Stability of Activatable Antibodies with Exemplary
Substrates

| Substrate of Activatable Antibody | Substrate | In Vivo % Activation (nu/nu, day 7) |
|---|---|---|
| 3001 | AVGLLAPPGGLSGRSD NH (SEQ ID NO: 79) | 63.0 |
| 5007 | APRSALAHGLF (SEQ ID NO: 80) | 56.0 |
| 8052 | GPWGLSGRSNI (SEQ ID NO: 11) | 51.8 |
| 8053 | PWGLSGRS (SEQ ID NO: 12) | 39.5 |
| 8054 | GRSPWGLL (SEQ ID NO: 13) | 46.2 |
| 8057 | APRSPWGL (SEQ ID NO: 16) | 24.8 |
| 8058 | PWGLPRS (SEQ ID NO: 17) | 36.7 |
| 8059 | PRSPWGLL SEQ ID NO: 18) | 47.7 |
| 8060 | PWGLSRS (SEQ ID NO: 19) | 37.9 |
| 8062 | APMGLKHDHOSRS (SEQ ID NO: 21) | 41.5 |
| 8063 | DHOSRSAPMGLKH (SEQ ID NO: 22) | 53.1 |
| 8064 | KPRGLN (SEQ ID NO: 23) | 31.7 |

Example 4: Masking Efficiency of Activatable Antibodies with Exemplary Substrates The studies provided herein evaluate the in vitro masking efficiency of activatable antibodies that include exemplary substrates cleavable by matrix metalloprotease (MMP) and/or matriptase (MT-SP1).

Figure 1B:
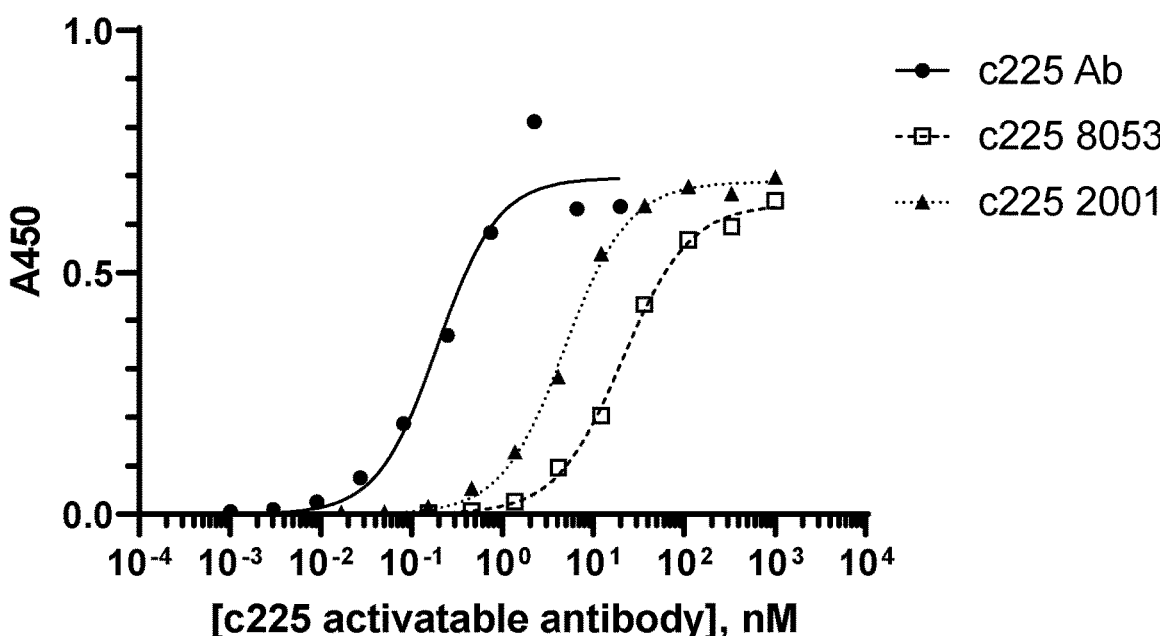

In these studies, a solid-phase binding assay (ELISA) was used to demonstrate the binding affinity of anti-EGFR activatable antibodies that include substrates cleavable by MMP and/or matriptase (MT-SP1) to recombinant EGFR. The binding affinity to EGFR of the activatable antibodies with the indicated substrates was measured and compared to the unmasked control c225v5 antibody. A summary of these exemplary results is shown in FIGS. 1A-1B and Table 8.

These exemplary results showed that the substrates had an effect by increasing the apparent masking efficiency of the masking moiety in the activatable antibody.

TABLE 8

In Vitro Binding Activity and Masking
Efficiency of Activatable Antibodies

| Test Article | $K_D$ in nM | Masking Efficiency |
|---|---|---|
| Unmasked control C225v5 antibody | 0.096 | 1x |

TABLE 8-continued

In Vitro Binding Activity and Masking
Efficiency of Activatable Antibodies

| Test Article | $K_D$ in nM | Masking Efficiency |
|---|---|---|
| C225v5-3954-2001 | 1.77 | 18x |
| C225v5-3954-8062 | 7.70 | 80x |
| C225v5-3954-8063 | 7.35 | 77x |
| C225v5-3954-8056 | 12.92 | 135x |
| C225v5-3954-8052 | 11.77 | 123x |
| C225v5-3954-8066 | 6.62 | 70x |
| C225v5-3954-8067 | 13.35 | 139x |
| Unmasked control C225v5 antibody | 0.19 | 1x |
| C225v5-3954-2001 | 4.89 | 26x |
| C225v5-3954-8053 | 21.23 | 112x |

Example 5: In Vivo Efficacy of Anti-EGFR Activatable Antibodies with Exemplary Substrates The studies provided herein evaluate the in vivo efficacy of activatable antibodies that include exemplary substrates cleavable by matrix metalloprotease (MMP) and matriptase (MT-SP1) using the H292 (human lung cancer cell line) xenograft model and using the SUM149 (human triple negative breast cancer cell line) xenograft model.

Figure 2A:
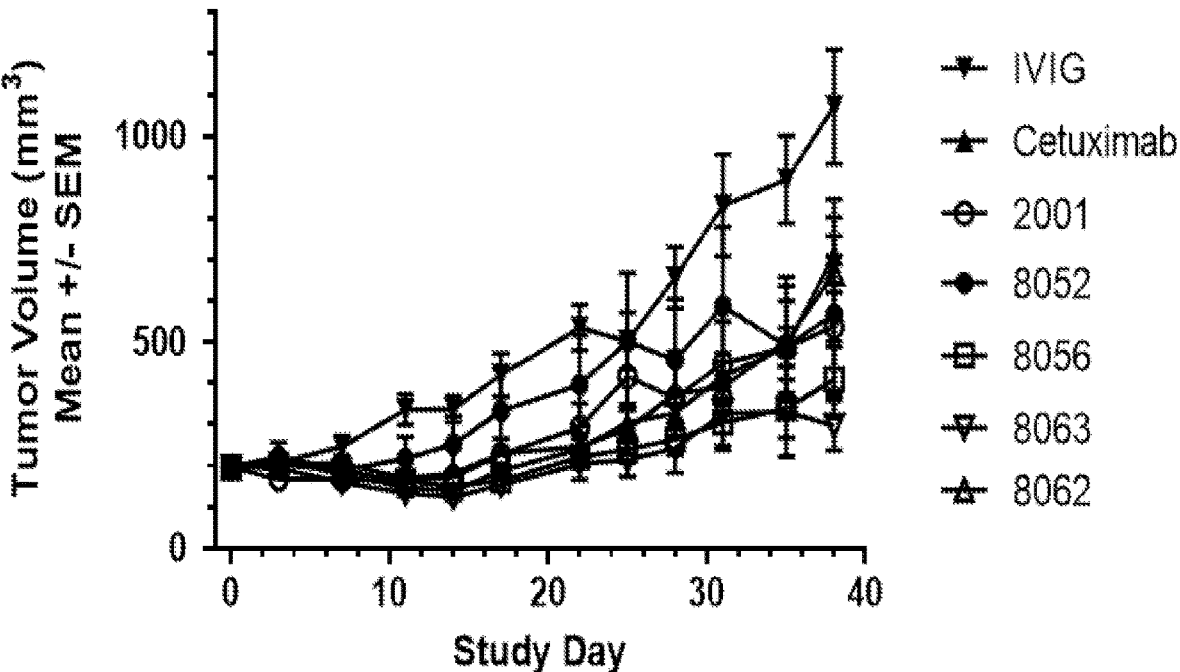
FIGS. 2A-2D show the effects of activatable antibodies with exemplary substrates on H292 xenograft tumors.
Figure 2B:
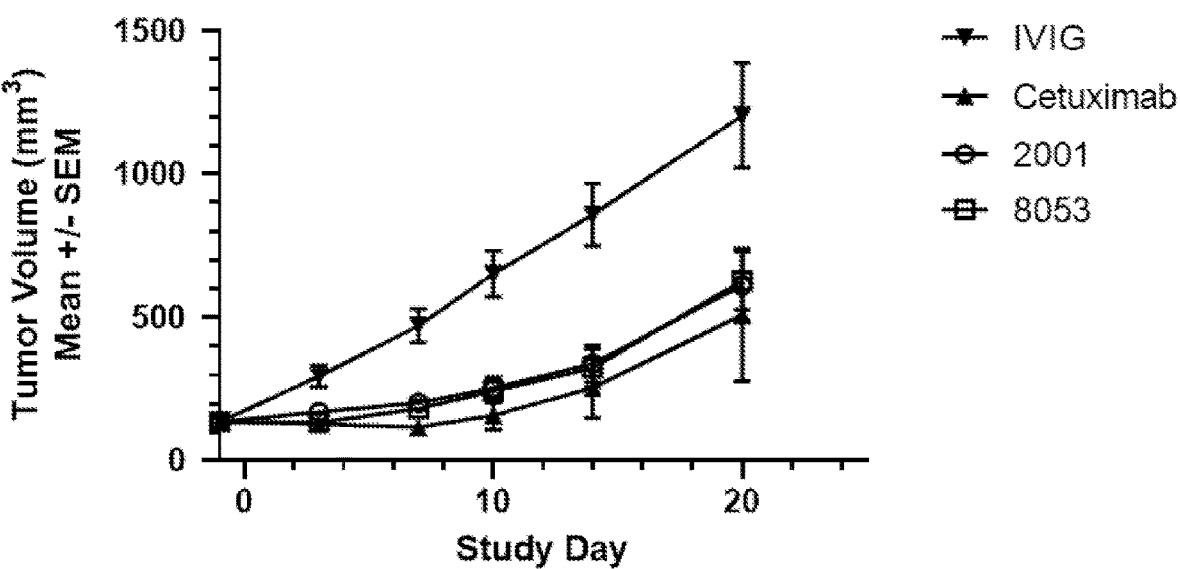
Figure 2C:
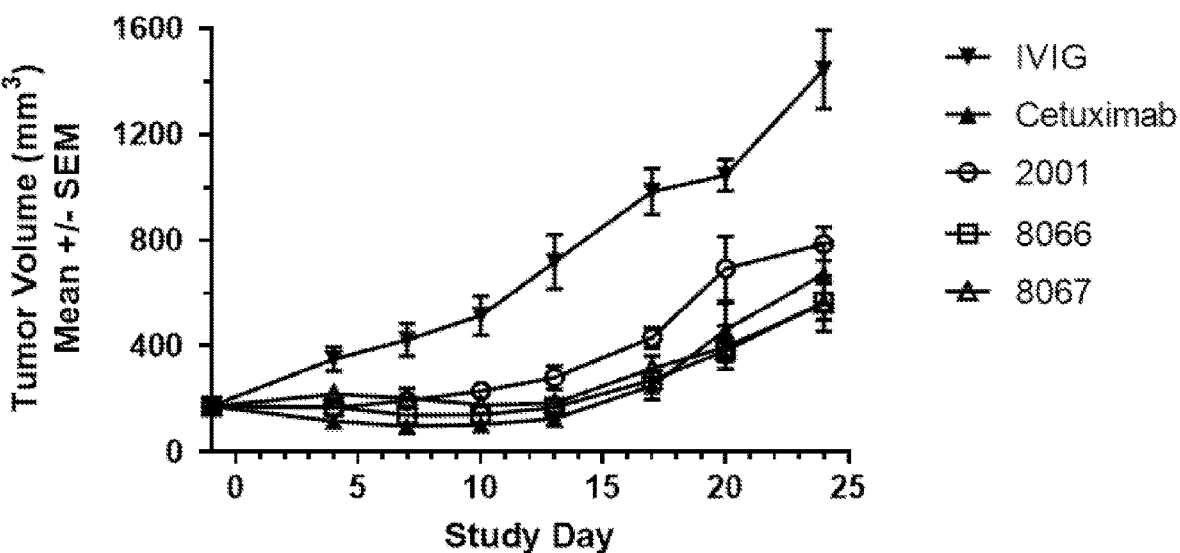

In these studies, H292 (human lung cancer-derived cell line) subcutaneous xenograft tumors in female nu/nu mice of 6-8 weeks of age were grown to an average volume of 90-249 mm³. The H292 cell line is responsive to the anti-EGFR antibody cetuximab. The mice were then randomized into groups of 8 mice each and each group was dosed intraperitoneally on day 1 with 7.5 mg/kg of the indicated test article as noted on the Figures. The mean tumor volume±SEM was plotted for each time point following administration of the test article, as shown in FIGS. 2A-2C. Each mouse was treated with activated antibodies with the indicated substrates, or with cetuximab or immunoglobulin (IVIG) control. The efficacy was determined with activatable antibodies that having control substrate e.g. 2001 (ISSGLLSGRSDNH; SEQ ID NO: 78).

Figure 2D:
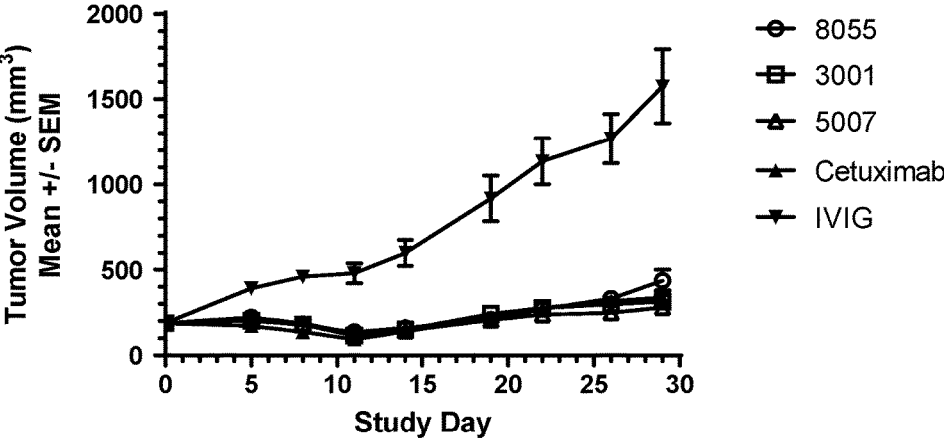

In addition, one study was preformed using SUM149 (human triple negative breast cancer-derived cell line) subcutaneous tumors in female nu/nu mice of 6-8 weeks of age grown to an average volume of 158-219 mm³. The SUM149 cell line is responsive to the anti-EGFR antibody cetuximab. The mice were then randomized into groups of 8 mice each and each group was dosed intraperitoneally on day 1 with 5 mg/kg of the indicated test article. The mean tumor volume±SEM was plotted for each time point following administration of the test article, as shown in FIG. 2D. Each mouse was treated with activated antibodies with the indicated substrates, or with cetuximab or immunoglobulin (IVIG) control. The efficacy was determined with activatable antibodies that have the control substrates 3001 (AVGLLAPPGGLSGRSDNH; SEQ ID NO: 79) and 5007 (APRSALAHGLE; SEQ ID NO: 80).

Figure 2E:
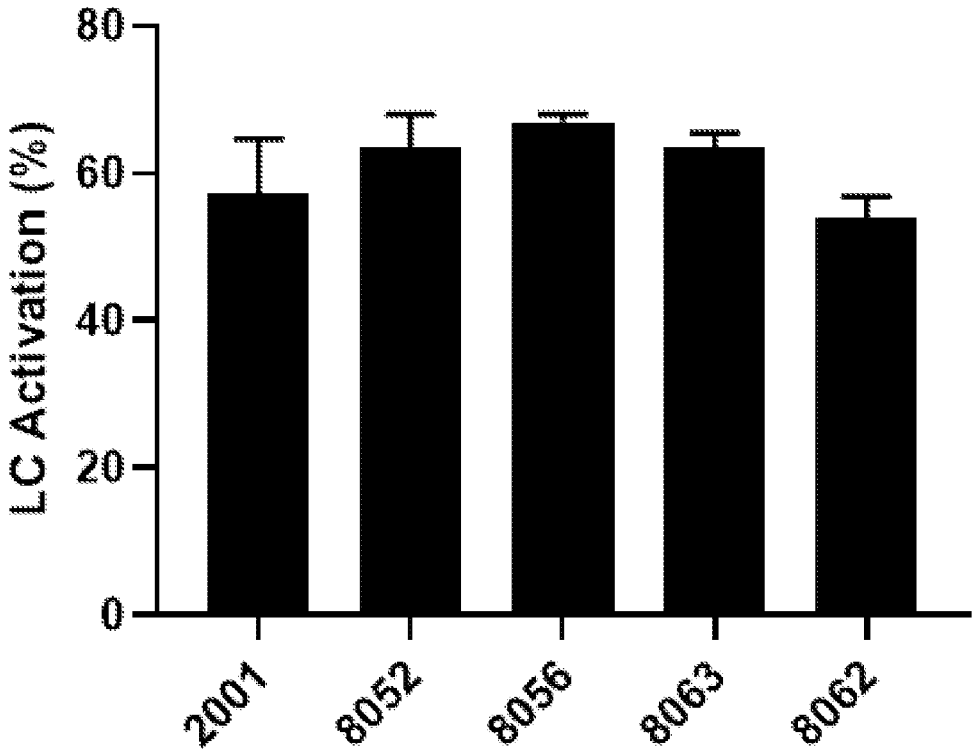
FIGS. 2E-2F show results of in vivo intratumoral activation assays using activatable antibodies with exemplary substrates.
Figure 2F:
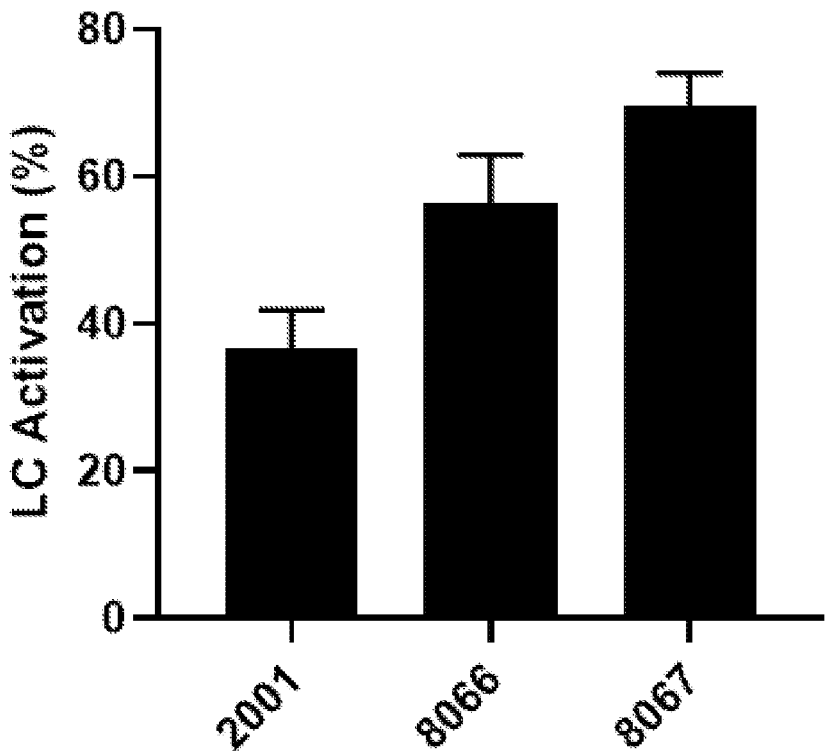

In addition to the in vivo efficacy study, an intra-tumoral activation assay was performed using the indicated activatable antibodies as shown in FIGS. 2E-2F. Tumors were collected from the mice at days 7 or 8 as indicated after dosing. The tumor tissue was lysed with immunoprecipitation buffer (Pierce) containing HALT protease inhibitor cocktail (Thermo Fisher) and EDTA and lysed using the Barocycler (Pressure Bioscience). The sample was analyzed using the Wes™ Western Blot protocol (Protein Simple) using the A110UK goat anti-human IgG antibody (American Qualex) and an anti-goat secondary antibody (Jackson ImmunoResearch). The fraction of cleaved activatable antibody was determined by quantifying the fraction of the higher mobility polypeptide corresponding to the cleaved activatable antibody. The results of these exemplary assays are summarized in FIGS. 2E-2F.

As shown in FIGS. 2A-2D, the activatable antibodies with substrates 8055 (APMGLKHLSGRSNI; SEQ ID NO: 14), 8056 (GPYGLSGRSNI; SEQ ID NO: 15), 8063 (DHQSR-SAPMGLKH; SEQ ID NO: 22), 8062 (APMGLKHDHQSRS; SEQ ID NO: 21), 8053 (PWGLS-GRS; SEQ ID NO: 12), 8066 (APRSLL; SEQ ID NO: 37) and 8067 (APRGLL; SEQ ID NO: 38) demonstrated an in vivo efficacy that was comparable or higher than with cetuximab, which lacks a prodomain.

As shown in FIGS. 2E-F, the activatable antibodies with substrates 8052 (GPWGLSGRSNI; SEQ ID NO: 11), 8056 (GPYGLSGRSNI; SEQ ID NO: 15), 8062 (APMGLKHDHQSRS; SEQ ID NO: 21), 8063 (DHQSR-SAPMGLKH; SEQ ID NO: 22), 8066 (APRSLL; SEQ ID NO: 37), and 8067 (APRGLL; SEQ ID NO: 38) demonstrated light chain activation in the H292 xenograft model that was comparable with the activatable antibody with the control substrate 2001 (ISSGLLSGRSDNH; SEQ ID NO: 78).

Example 6: In Situ Stability of Anti-EGFR Activatable Antibodies in Human Bone Marrow Aspirates The study provided herein evaluates the in situ stability of activatable antibodies with the exemplary substrates 8055 (APMGLKHLSGRSNI; SEQ ID NO: 14), 8052 (GPWGLS-GRSNI; SEQ ID NO: 11), 8056 (GPYGLSGRSNI; SEQ ID NO: 15), 8063 (DHQSRSAPMGLKH; SEQ ID NO: 22), 8062 (APMGLKHDHQSRS; SEQ ID NO: 21), 8066 (APRSLL; SEQ ID NO: 37), 8067 (APRGLL; SEQ ID NO: 38), and 8053 (PWGLSGRS; SEQ ID NO: 12) by human bone marrow aspirates. Fresh human bone marrow aspirates from healthy donors were purchased from Stemcell Technology Inc. (Catalog No. 70502) and AllCells Inc. and were processed to lyse red blood cells and washed 5 times with buffer or serum-free media. The cells were plated at a density of 250,000 cells or 28,000 cells per well in serum-free RPMI media and incubated for 30 min at room temperature with an equal volume of 80 µg/mL unmasked control c225 antibody prepared in serum-free RPMI media. An equal volume of AF647-labeled c225 antibodies prepared at 40 µg/mL in serum-free RPMI media were then added to form a mixture and incubated at a final concentration of 20 µg/mL at 37° C. for 21 or 24 hours. Cells were pelleted through centrifugation for 5 min at 300×g. Supernatants were collected from each incubated mixture and transferred into a well of a 96-well PCR plate for assay by capillary electrophoresis. Each supernatant sample was mixed with Pico Sample Buffer (Perkin Elmer) containing 2-beta-mercaptoethanol at four parts sample and one part of Pico Sample Buffer and then heated at 95° C. for 10 minutes. Substrate cleavage was measured by capillary electrophoresis using a LabChip GXII Touch system (Perkin Elmer) with the HT Pico Protein Express 100 protocol (Perkin Elmer). Protein Express Assay LabChips (Perkin Elmer #760499) were set up using the protocol of the Protein Pico Assay Reagent Kit (Perkin Elmer #760498). The fraction of cleaved activatable antibody in bone marrow cell supernatants was determined by quantifying the fraction of the higher mobility polypeptide corresponding to the cleaved activatable antibody using the LabChip GX Reviewer software (Perkin Elmer). Data was averaged from N=2-4 donors and normalized to the 2001 substrate cleavage measured by each donor.

Figure 3A:
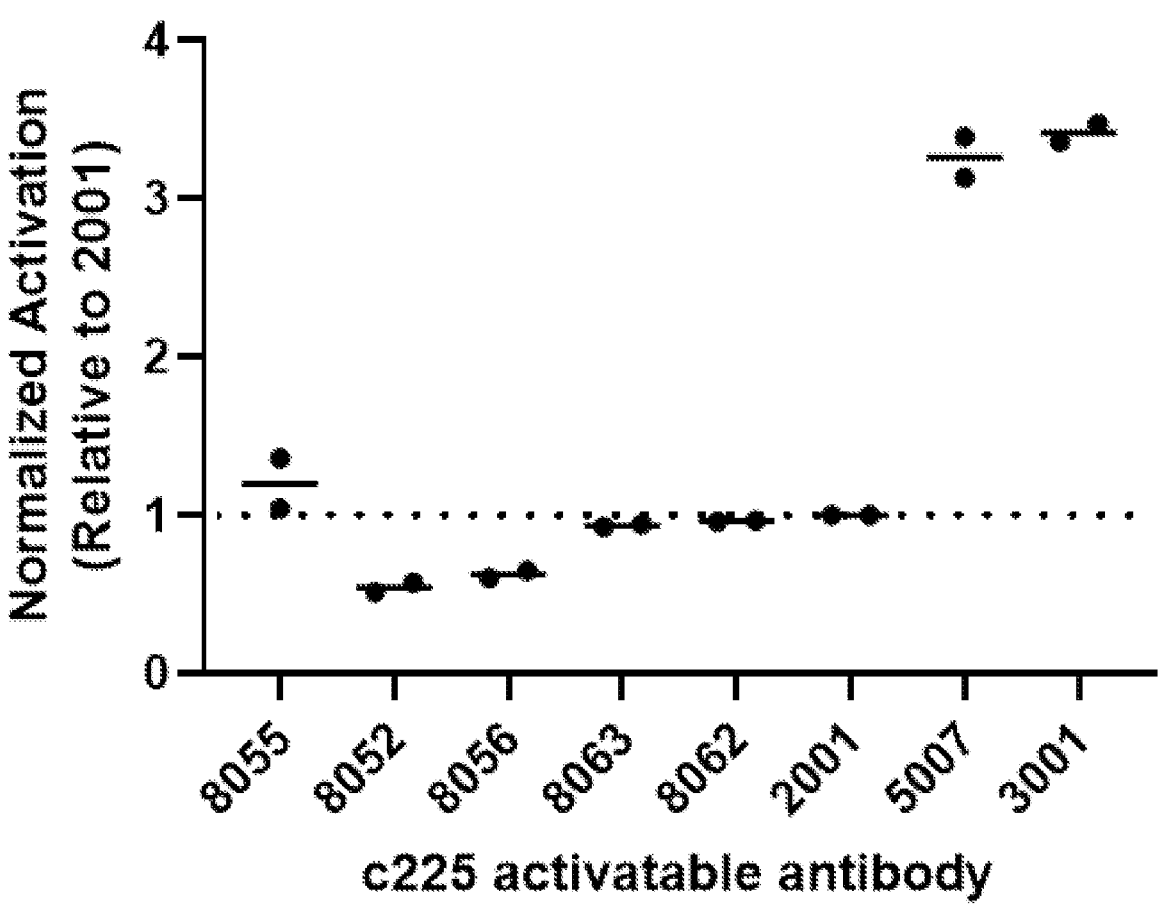
FIGS. 3A-3C show the in situ stability of activatable antibodies with exemplary substrates in human bone marrow aspirates.
Figure 3B:
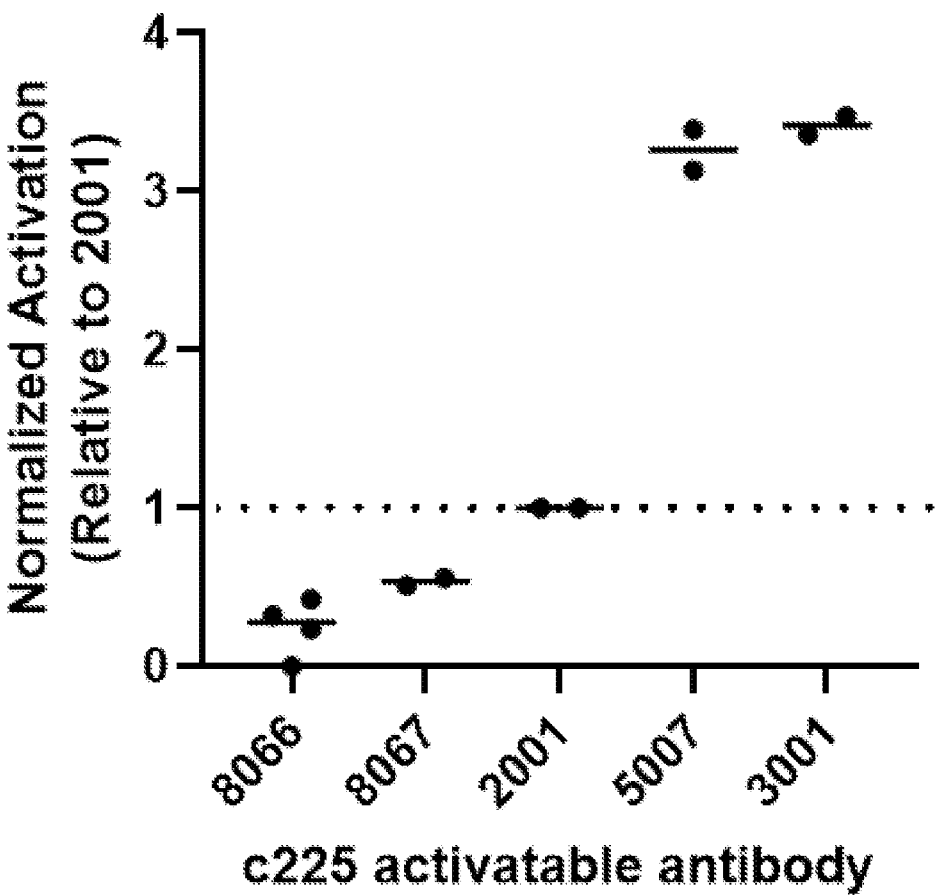
Figure 3C:
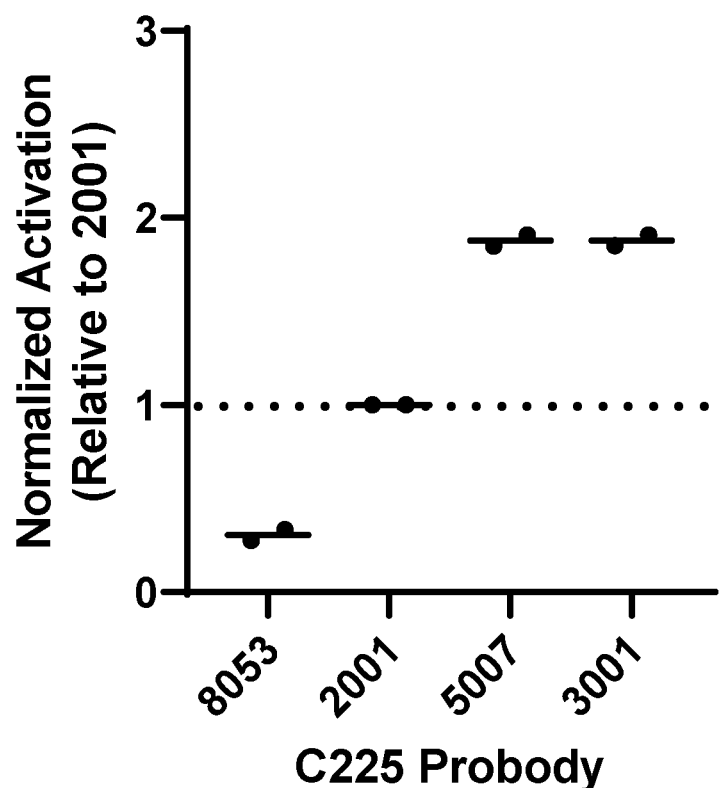

As shown in FIGS. 3, 3B, and 3C, activatable antibodies with substrates 8055 (APMGLKHLSGRSNI; SEQ ID NO: 14), 8052 (GPWGLSGRSNI; SEQ ID NO: 11), 8056 (GPYGLSGRSNI; SEQ ID NO: 15), 8063 (DHQSR-SAPMGLKH; SEQ ID NO: 22), 8062 (APMGLKHDHQSRS; SEQ ID NO: 21), 8066 (APRSLL; SEQ ID NO: 37), 8067 (APRGLL; SEQ ID NO: 38) and 8053 (PWGLSGRS; SEQ ID NO: 12) demonstrate a resistance to cleavage in situ in the bone marrow that is comparable or more resistant as compared to the control substrate 2001 (ISSGLLSGRSDNH; SEQ ID NO: 78) and more resistant than the control substrates 5007 (APR-SALAHGLF; SEQ ID NO: 80) and 3001 (AVGLLAPPG-GLSGRSDNH; SEQ ID NO: 79).

Example 7: In Vitro Cleavability of Exemplary CMs in a Peptide Probe Cleavage Assay The study provided herein evaluated the cleavability kinetics (i.e., pM/s and $k_{cat}/K_M$ (M⁻¹ s⁻¹)) of CMs with membrane type serine protease 1 (MT-SP1), urokinase-type plasminogen activator (uPA), matrix metalloprotease (MMP) 2, MMP9, and MMP14. The CMs listed in Table 9 below were presented in an internally quenched peptide probe format, rather than included in an activatable antibody format. In the internally quenched probes, the CM sequence was positioned between a 7-methoxycoumarin-4-acetyl (MCA) fluorophore and a 2,4-dinitrophenyl (DNP) quencher such that cleavage of the CM sequence produced a fluorescence signal. The probes were of the following designs: (MCA)-Ser-Pro-Trp-Gly-Leu-Ser-Gly-$X_1$-Ser-Gly-Lys (DNP)-D-Arg (SEQ ID NO: 697) where $X_1$ is Arg or Lys and (MCA)-Gly-Ser-$X_1$-$X_2$-Pro-$X_3$-Gly-Leu-$X_4$-$X_5$-Gly-Ser-Lys (DNP)-D-Arg (SEQ ID NO: 698) where $X_1$ is Arg or is absent, $X_2$ is Ser or is absent, $X_3$ is Trp, $X_4$ is Arg or is absent, and $X_5$ is Ser or is absent, as indicated in Table 9. The cleavage rates (pM/s) were measured using 20 μM internally quenched peptide probe and 20 nM MT-SP1, uPA, MMP2, MMP9, or MMP14. Cleavability kinetics (i.e., pM/s and $k_{cat}/K_M$ ($M^{-1}$ $s^{-1}$)) were determined in 96- or 384-well plate

TABLE 9

| CMs tested in peptide format | |
| --- | --- |
| Sequence | SEQ ID NO: |
| PWGLSGRS | 12 |
| PWGLSGKS | 150 |
| PWGLRS | 48 |
| RSPWGL | 90 |

Table 10 provides exemplary probe cleavage rates (pM/s) of the exemplary CMs of Table 9 with MT-SP1, uPA, MMP2, MMP9, and MMP14. Table 11 provides exemplary $K_{cat}/K_M$ ($M^{-1}$ $s^{-1}$) values of the exemplary CMs of Table 9 with MT-SP1, uPA, MMP2, MMP9, and MMP14.

TABLE 10

In Vitro Activation of Peptide Probes with Exemplary CMs (pM/s)

| Probe CM Sequence | Probe Cleavage (pM/s) | | | | |
| --- | --- | --- | --- | --- | --- |
| | MT-SP1 | uPA | MMP2 | MMP9 | MMP14 |
| PWGLSGRS (SEQ ID NO: 12) | 7810 | 429 | 2920 | 7620 | 3120 |
| PWGLSGKS (SEQ ID NO: 150) | 2330 | 15.2 | 1620 | 5360 | 2010 |
| PWGLRS (SEQ ID No: 48) | 1230 | — | 3800 | 3830 | 4380 |
| RSPWGL (SEQ ID No: 90) | 2390 | 3210 | 11700 | 25500 | 9580 |

Note:
"—" indicates below limit of quantification.

TABLE 11

In Vitro Activation of Peptide Probes with Exemplary CMs ($k_{cat}/K_M$)

| Probe CM Sequence | Probe Cleavage ($k_{cat}/K_M$ ($M^{-1}$ $s^{-1}$)) | | | | |
| --- | --- | --- | --- | --- | --- |
| | MT-SP1 | uPA | MMP2 | MMP9 | MMP14 |
| PWGLSGRS (SEQ ID NO: 12) | $1.5 \times 10^5$ | $5.3 \times 10^3$ | $7.8 \times 10^4$ | $1.5 \times 10^5$ | $3.7 \times 10^4$ |
| PWGLSGKS (SEQ ID NO: 150) | $8.0 \times 10^4$ | — | $5.9 \times 10^4$ | $1.3 \times 10^5$ | $2.4 \times 10^4$ |
| PWGLRS (SEQ ID No: 48) | $3.1 \times 10^4$ | — | $1.4 \times 10^5$ | $1.5 \times 10^5$ | $8.1 \times 10^4$ |
| RSPWGL (SEQ ID No: 90) | $4.8 \times 10^4$ | $6.6 \times 10^4$ | $2.6 \times 10^5$ | $8.7 \times 10^5$ | $8.5 \times 10^4$ |

Note:
"—" indicates not determined.

format at 37° C. in the following buffers: 50 mM TRIS-HCl (pH 7.4), 150 mM NaCl, 0.05% Tween 20 for MT-SP1 and uPA, 50 mM Tris-HCl (pH 7.5), 10 mM $CaCl_2$, 150 mM NaCl, 0.05% (w/v) Brij-35 for MMP2 and MMP9, and 50 mM HEPES (pH 6.8), 10 mM $CaCl_2$), 0.5 mM $MgCl_2$, 0.05% (w/v) Brij-35 for MMP14. Cleavability kinetics were determined on an Infinite 200 PRO (Tecan) multimode plate reader using a fluorescence excitation wavelength of 320 nm and an emission wavelength of 405 nm.

These exemplary results show that CM PWGLSGRS (SEQ ID NO: 12), CM PWGLSGKS (SEQ ID NO: 150), CM PWGLRS (SEQ ID No: 48), and CM RSPWGL (SEQ ID No: 90) are cleavable by the MMPs MMP2, MMP9, and MMP14 with a $k_{cat}/K_M$ ($M^{-1}$ $s^{-1}$) of greater than $1 \times 10^4$ $M^{-1}$ $s^{-1}$. These exemplary results show that CM PWGLSGRS (SEQ ID NO: 12), CM PWGLSGKS (SEQ ID NO: 150), CM PWGLRS (SEQ ID No: 48), and CM RSPWGL (SEQ ID No: 90) are cleavable by MMP9 with a $k_{cat}/K_M$ ($M^{-1}$ $s^{-1}$)

of greater than $1 \times 10^5$ $M^{-1}$ $s^{-1}$. These exemplary results show that CM PWGLRS (SEQ ID No: 48) and CM RSPWGL (SEQ ID No: 90) are cleavable by MMP2 and MMP9 with a $k_{cat}/K_M$ ($M^{-1}$ $s^{-1}$) of greater than $1 \times 10^5$ $M^{-1}$ $s^{-1}$.

These exemplary results show that CM PWGLSGRS (SEQ ID NO: 12), CM PWGLSGKS (SEQ ID NO: 150), CM PWGLRS (SEQ ID No: 48), and CM RSPWGL (SEQ ID No: 90) are cleavable by MT-SP1 with a $k_{cat}/K_M$ ($M^{-1}$ $s^{-1}$) of greater than $1 \times 10^4$ $M^{-1}$ $s^{-1}$. These exemplary results show that CM PWGLSGRS (SEQ ID NO: 12) is cleavable by MT-SP1 with a $k_{cat}/K_M$ ($M^{-1}$ $s^{-1}$) of greater than $1 \times 10^5$ $M^{-1}$ $s^{-1}$.

These exemplary results show that CM PWGLSGRS (SEQ ID NO: 12) and CM RSPWGL (SEQ ID No: 90) are cleavable by uPA with a $k_{cat}/K_M$ ($M^{-1}$ $s^{-1}$) of greater than $1 \times 10^3$ $M^{-1}$ $s^{-1}$. These exemplary results show that CM RSPWGL (SEQ ID No: 90) is cleavable by uPA with a $k_{cat}/K_M$ ($M^{-1}$ $s^{-1}$) of greater than $1 \times 10^4$ $M^{-1}$ $s^{-1}$.

Example 8: In Vitro Cleavability of Additional Exemplary CMs in a Peptide Probe Cleavage Assay The study provided herein evaluated the cleavability kinetics (i.e., pM/s and $k_{cat}/K_M$ ($M^{-1}$ $s^{-1}$)) of CMs with membrane type serine protease 1 (MT-SP1), urokinase-type plasminogen activator (uPA), matrix metalloprotease (MMP) 2, MMP9, and MMP14. The CMs listed in Table 12 below were presented in an internally quenched peptide probe format, rather than included in an activatable antibody format. In the internally quenched probes, the CM sequence was positioned between a 7-methoxycoumarin-4-acetyl (MCA) fluorophore and a 2,4-dinitrophenyl (DNP) quencher such that cleavage of the CM sequence produced a fluorescence signal. The probes were of the following designs: (MCA)-Ser-Pro-Trp-Gly-Leu-Ser-Gly-Arg-Ser-Gly-Lys (DNP)-D-Arg (SEQ ID NO: 699); (MCA)-Ser-Pro-Trp-Gly-Leu-Ser-Gly-Arg-Gly-Ser-Lys (DNP)-D-Arg (SEQ ID NO: 700); (MCA)-Ser-Pro-Trp-Gly-Leu-Ser-Gly-Gly-Gly-Ser-Lys (DNP)-D-Arg (SEQ ID NO: 701); (MCA)-Gly-Ser-Trp-Gly-Leu-Ser-Gly-Arg-Ser-Gly-Lys (DNP)-D-Arg (SEQ ID NO: 702); (MCA)-Ser-Pro-Trp-Gly-Leu-Ser-Gly-Arg-Ser-Gly-Lys (DNP)-D-Arg (SEQ ID NO: 699) where any single amino acid in the sequence Pro-Trp-Gly-Leu-Ser-Gly-Arg-Ser (SEQ ID NO: 12) is replace with Ala; (MCA)-Ser-Leu-Ser-Gly-$X_1$-Ser-Pro-$X_2$-Gly-Leu-Gly-Lys (DNP)-D-Arg (SEQ ID NO: 703) were $X_1$ is Arg or Lys and $X_2$ is Trp or Ala, as shown in Table 12. The cleavage rates (pM/s) were measured using 20 µM internally quenched peptide probe and 20 nM MT-SP1, uPA, MMP2, MMP9, or MMP14. Cleavability kinetics (i.e., pM/s) were determined in 96- or 384-well plate format at 37° C. in the following buffers: 50 mM TRIS-HCl (pH 7.4), 150 mM NaCl, 0.05% Tween 20 for MT-SP1 and uPA, 50 mM Tris-HCl (pH 7.5), 10 mM $CaCl_2$, 150 mM NaCl, 0.05% (w/v) Brij-35 for MMP2 and MMP9, and 50 mM HEPES (pH 6.8), 10 mM $CaCl_2$, 0.5 mM $MgCl_2$, 0.05% (w/v) Brij-35 for MMP14. Cleavability kinetics were determined on an Infinite 200 PRO (Tecan) multimode plate reader using a fluorescence excitation wavelength of 320 nm and an emission wavelength of 405 nm.

TABLE 12

| CMs tested in peptide format | |
| --- | --- |
| Sequence | SEQ ID NO: |
| PWGLSGRS | 12 |
| PWGLSGR | 163 |
| PWGLSG | 684 |
| WGLSGRS | 685 |
| AWGLSGRS | 686 |
| PAGLSGRS | 687 |
| PWALSGRS | 688 |
| PWGASGRS | 689 |
| PWGLAGRS | 690 |
| PWGLSARS | 691 |
| PWGLSGAS | 692 |
| PWGLSGRA | 693 |
| LSGRSPWGL | 177 |
| LSGKSPWGL | 178 |
| LSGRSPAGL | 694 |

Table 13 provides exemplary probe cleavage rates (pM/s) of the exemplary CMs of Table 9 with MT-SP1, uPA, MMP2, MMP9, and MMP14.

TABLE 13

| In Vitro Activation of Peptide Probes with Exemplary CMs (pM/s) | | | | | |
| --- | --- | --- | --- | --- | --- |
| Probe CM | Probe Cleavage (pM/s) | | | | |
| Sequence | MT-SP1 | uPA | MMP2 | MMP9 | MMP14 |
| PWGLSGRS (SEQ ID NO: 12) | 7810 | 429 | 2920 | 7620 | 3120 |
| PWGLSGR (SEQ ID NO: 163) | 1290 | 48.3 | 6540 | 17200 | 1280 |
| PWGLSG (SEQ ID NO: 684) | 5.10 | 12.9 | 3100 | 13000 | 705 |
| WGLSGRS (SEQ ID NO: 685) | 10600 | 548 | 66.4 | 581 | — |

TABLE 13-continued

| In Vitro Activation of Peptide Probes with Exemplary CMs (pM/s) | | | | | |
|---|---|---|---|---|---|
| Probe CM | Probe Cleavage (pM/s) | | | | |
| Sequence | MT-SP1 | uPA | MMP2 | MMP9 | MMP14 |
| AWGLSGRS (SEQ ID NO: 686) | 17000 | 832 | 816 | 2070 | 224 |
| PAGLSGRS (SEQ ID NO: 687) | 16500 | 1570 | Above the limit of quantification | 16200 | 1380 |
| PWALSGRS (SEQ ID NO: 688) | 15300 | 1130 | 4890 | 12800 | 612 |
| PWGASGRS (SEQ ID NO: 689) | 18000 | 1310 | 202 | 456 | 29.7 |
| PWGLAGRS (SEQ ID NO: 690) | 15800 | 126 | 4870 | 13700 | 692 |
| PWGLSARS (SEQ ID NO: 691) | 13100 | 1520 | 9580 | 17500 | 1230 |
| PWGLSGAS (SEQ ID NO: 692) | 13.0 | 1.80 | 4370 | 16400 | 933 |
| PWGLSGRA (SEQ ID NO: 693) | 7620 | 380 | 6100 | 17500 | 1130 |
| LSGRSPWGL (SEQ ID NO: 177) | 812 | 668 | 48.9 | 1070 | 61.0 |
| LSGKSPWGL (SEQ ID NO: 178) | 595 | 117 | 37.1 | 630 | 36.8 |
| LSGRSPAGL (SEQ ID NO: 694) | 1520 | 620 | 2080 | 1630 | 190 |

Note:
"—" indicates below limit of quantification.

These exemplary results show that CM PWGLSGRS (SEQ ID NO: 12), CM PWGLSGR (SEQ ID NO: 163), CM PWGLSG (SEQ ID NO: 684), CM AWGLSGRS (SEQ ID NO: 686), CM PAGLSGRS (SEQ ID NO: 687), CM PWALSGRS (SEQ ID NO: 688), CM PWGLAGRS (SEQ ID NO: 690), CM PWGLSARS (SEQ ID NO: 691), CM PWGLSGAS (SEQ ID NO: 692), CM PWGLSGRA (SEQ ID NO: 693), CM LSGRSPWGL (SEQ ID NO: 177), CM LSGRSPAGL (SEQ ID NO: 694) have high MMP9 cleavage with a cleavage rate of greater than 1000 pM/s for MMP9. These exemplary results show that CM PWGLS-GRS (SEQ ID NO: 12), CM PWGLSGR (SEQ ID NO: 163), CM PWGLSG (SEQ ID NO: 684), CM PAGLSGRS (SEQ ID NO: 687), CM PWALSGRS (SEQ ID NO: 688), CM PWGLAGRS (SEQ ID NO: 690), CM PWGLSARS (SEQ ID NO: 691), CM PWGLSGAS (SEQ ID NO: 692), and CM PWGLSGRA (SEQ ID NO: 693) have high MMP9 cleavage with a cleavage rate of greater than 7000 pM/s for MMP9. These exemplary results show that CM PWGLSGRS (SEQ ID NO: 12), CM PWGLSGR (SEQ ID NO: 163), CM PWGLSG (SEQ ID NO: 684), CM PAGLSGRS (SEQ ID NO: 687), CM PWALSGRS (SEQ ID NO: 688), CM PWGLAGRS (SEQ ID NO: 690), CM PWGLSARS (SEQ ID NO: 691), CM PWGLSGAS (SEQ ID NO: 692), CM PWGLSGRA (SEQ ID NO: 693), and CM LSGRSPAGL (SEQ ID NO: 694) have high MMP2 cleavage with a cleavage rate of greater than 1500 pM/s or above the limit of quantification for MMP2. These exemplary results show that CM PWGLSGRS (SEQ ID NO: 12), CM PWGLSGR (SEQ ID NO: 163), CM PWGLSG (SEQ ID NO: 684), CM PAGLSGRS (SEQ ID NO: 687), CM PWALSGRS (SEQ ID NO: 688), CM PWGLAGRS (SEQ ID NO: 690), CM PWGLSARS (SEQ ID NO: 691), CM PWGLSGAS (SEQ ID NO: 692), and CM PWGLSGRA (SEQ ID NO: 693) have high MMP14 cleavage with a cleavage rate of greater than 500 pM/s for MMP14.

These exemplary results show that CM PWGLSGRS (SEQ ID NO: 12), CM PWGLSGR (SEQ ID NO: 163), CM WGLSGRS (SEQ ID NO: 685), CM AWGLSGRS (SEQ ID NO: 686), CM PAGLSGRS (SEQ ID NO: 687), CM PWALSGRS (SEQ ID NO: 688), PWGASGRS (SEQ ID NO: 689), CM PWGLAGRS (SEQ ID NO: 690), CM PWGLSARS (SEQ ID NO: 691), CM PWGLSGRA (SEQ ID NO: 693), CM LSGRSPWGL (SEQ ID NO: 177), CM LSGKSPWGL (SEQ ID NO: 178), and CM LSGRSPAGL (SEQ ID NO: 694) have high MT-SP1 cleavage with a cleavage rate of greater than 500 pM/s for MT-SP1. These exemplary results show that CM PWGLSGRS (SEQ ID NO: 12), CM WGLSGRS (SEQ ID NO: 685), CM AWGLSGRS (SEQ ID NO: 686), CM PAGLSGRS (SEQ ID NO: 687), CM PWALSGRS (SEQ ID NO: 688), CM PWGASGRS (SEQ ID NO: 689), CM PWGLAGRS (SEQ ID NO: 690), CM PWGLSARS (SEQ ID NO: 691), and CM PWGLS-GRA (SEQ ID NO: 693) have high MT-SP1 cleavage with a cleavage rate of greater than 7000 pM/s for MT-SP1. These exemplary results show that CM PWGLSGRS (SEQ ID NO: 12), CM WGLSGRS (SEQ ID NO: 685), CM AWGLSGRS (SEQ ID NO: 686), CM PAGLSGRS (SEQ ID NO: 687), CM PWALSGRS (SEQ ID NO: 688), PWGASGRS (SEQ ID NO: 689), CM PWGLSARS (SEQ ID NO: 691), CM LSGRSPWGL (SEQ ID NO: 177) and CM LSGRSPAGL (SEQ ID NO: 694) have high uPA cleavage with a cleavage rate of greater than 400 pM/s for uPA.

Example 9: Additional Exemplary Activatable Antibodies and Protease Cleavable Substrates The studies provided herein describe additional exemplary substrates that include at least one cleavable moiety cleavable by a matrix metalloprotease (MMP), and at least one cleavable moiety cleavable by a matriptase (MT-SP1).

Exemplary activatable antibodies were constructed such that each one includes one of the substrates listed in Table 14. The exemplary activatable antibodies, the sequences of which are listed in Table 15, include an antibody or antigen binding fragment thereof (AB) that is based on a mouse/human chimeric monoclonal antibody that specifically binds to epidermal growth factor receptor (EGFR). The exemplary activatable antibodies also include a prodomain coupled to the N-terminus of the light chain of the AB. Each prodomain includes a masking moiety (MM) and a substrate, and the substrate includes at least one sequence of Table 14.

TABLE 14

| Exemplary MMP/MT-SP1 Substrates | |
|---|---|
| Sequence | SEQ ID NO: |
| PWGLSGRS | 12 |
| PWGLSGKS | 150 |
| PYGLSGRS | 151 |
| PFGLSGRS | 152 |
| PRGLSGRS | 153 |
| PAGLSGRS | 687 |
| LSGRSPWGL | 177 |
| LSGKSPWGL | 178 |
| LSGRSPWGLS | 695 |

TABLE 15

| Activatable Antibody Sequences | | | |
|---|---|---|---|
| Molecule Name | Light chain EGFR Mask | Light chain substrate | Protein description (Light chain/Heavy chain) |
| ProC1754 | CISPRGCPDGPYVMY (SEQ ID NO: 81) | PWGLSGRS (SEQ ID NO: 12) | C225v5 3954 9820 (SEQ ID NO: 373/SEQ ID NO: 355) |
| ProC3625 | CISPRGCPDGPYVMY (SEQ ID NO: 81) | PWGLSGKS (SEQ ID NO: 150) | C225v5 3954 2198 (SEQ ID NO: 386/SEQ ID NO: 355) |
| ProC3626 | CISPRGCPDGPYVMY (SEQ ID NO: 81) | PYGLSGRS (SEQ ID NO: 151) | C225v5 3954 2298 (SEQ ID NO: 387/SEQ ID NO: 355) |
| ProC3627 | CISPRGCPDGPYVMY (SEQ ID NO: 81) | PFGLSGRS (SEQ ID NO: 152) | C225v5 3954 9822 (SEQ ID NO: 388/SEQ ID NO: 355) |
| ProC3628 | CISPRGCPDGPYVMY (SEQ ID NO: 81) | PRGLSGRS (SEQ ID NO: 153) | C225v5 3954 9823 (SEQ ID NO: 389/SEQ ID NO: 355) |
| ProC3629 | CISPRGCPDGPYVMY (SEQ ID NO: 81) | PAGLSGRS (SEQ ID NO: 687) | C225v5 3954 9824 (SEQ ID NO: 390/SEQ ID NO: 355) |
| ProC3630 | CISPRGCPDGPYVMY (SEQ ID NO: 81) | LSGRSPWGL (SEQ ID NO: 177) | C225v5 3954 9827 (SEQ ID NO: 391/SEQ ID NO: 355) |
| ProC3631 | CISPRGCPDGPYVMY (SEQ ID NO: 81) | LSGKSPWGL (SEQ ID NO: 178) | C225v5 3954 9828 (SEQ ID NO: 392/SEQ ID NO: 355) |
| ProC3632 | CISPRGCPDGPYVMY (SEQ ID NO: 81) | LSGRSPWGLS (SEQ ID NO: 695) | C225v5 3954 9829 (SEQ ID NO: 393/SEQ ID NO: 355) |

Example 10: In Vitro Cleavability of Activatable
Antibodies with Additional Exemplary Substrates The studies provided herein evaluate the in vitro cleavability of activatable antibodies containing additional exemplary substrates that include at least one cleavable moiety cleavable by a matrix metalloprotease (MMP) and/or at least one cleavable moiety cleavable by matriptase (MT-SP1).

The cleavability of the activatable antibodies was measured in the presence of the indicated recombinant proteases was determined by quantifying the fraction of the higher mobility polypeptide corresponding to the cleaved activatable antibody using the LabChip GX Reviewer software (Perkin Elmer). The fraction of activatable antibody, and hence the CM that is cleaved by each particular protease, is presented as a "cleavability percentage" in Table 16.

These exemplary results show that the substrates showed a range of cleavability by the indicated proteases. These exemplary results show that the substrates showed a range of cleavability by uPA, MT-SP1, MMP2, MMP9, and/or MMP14.

TABLE 16

In Vitro Activation of Activatable Antibodies with Exemplary Substrates

| Substrate | Cleavability (%) | | | | |
| --- | --- | --- | --- | --- | --- |
| | uPA | MT-SP1 | MMP2 | MMP9 | MMP14 |
| PWGLSGRS (SEQ ID NO: 12) | 11.3 | 100 | 76.7 | 100 | 37.4 |
| PWGLSGKS (SEQ ID NO: 150) | 3.60 | 88.6 | 68.9 | 100 | 30.1 |
| PYGLSGRS (SEQ ID NO: 151) | 13.2 | 100 | 90.4 | 100 | 20.9 |
| PFGLSGRS (SEQ ID NO: 152) | 12.5 | 100 | 78.1 | 100 | 18.1 |
| PRGLSGRS (SEQ ID NO: 153) | 10.0 | 100 | 100 | 100 | 63.7 |
| PAGLSGRS (SEQ ID NO: 687) | 9.20 | 100 | 100 | 87 | 76.4 |
| LSGRSPWGL (SEQ ID NO: 177) | 4.40 | 17.3 | 39 | 61.4 | 16.5 |
| LSGKSPWGL (SEQ ID NO: 178) | — | 15.6 | 38.7 | 53.8 | 16.5 |
| LSGRSPWGLS (SEQ ID NO: 695) | 3.10 | 20.6 | 62.2 | 100 | 40.1 |

Note:
"—" indicates below limit of quantification.

(MT-SP1, uPA, MMP2, MMP9, and MMP14). Each activatable antibody (500 nM) was incubated with 10 nM of the indicated protease for 4 hours at 37° C. Human recombinant proteases were purchased from R&D Systems: MMP2 (catalog No: 902-MP), MMP9 (catalog No: 911-MP), MMP14 (catalog No: 918-MP), MT-SP1 (catalog No: 3946-SEB), and uPA (catalog No: 1310-SE). MMPs were activated according to the manufacturer's instructions. Protease concentrations were determined by active site titration. Activity assays for MMP2 and MMP9 were performed in the following buffer: 50 mM Tris-HCl (pH 7.5), 10 mM CaCl$_2$), 150 mM NaCl, 0.05% (w/v) Brij-35. Activity assays were performed for MMP14 using 50 mM HEPES (pH 6.8), 10 mM CaCl$_2$, 0.5 mM MgCl$_2$, and for MT-SP1 and uPA, activity assays used 50 mM TRIS-HCl (pH 7.4), 150 mM NaCl, 0.05% Tween 20. Following incubation, the presence of cleavage product was determined at 4 hours by capillary electrophoresis for each protease enzyme using a LabChip GXII Touch system (Perkin Elmer). For capillary electrophoresis assays, the HT Protein Express 100 protocol (Perkin Elmer) was used. LabChip GXII Touch HT Chips (Perkin Elmer #760499) were set up using the protocol of the Protein Express Assay Reagent Kit (Perkin Elmer #CLS960008). The fraction of cleaved activatable antibody These exemplary results show a group of substrates in which cleavage by uPA is at least 20%. Such substrates include those having the amino acid sequence of PWGLSGRS (SEQ ID NO: 12), PYGLSGRS (SEQ ID NO: 151), PFGLSGRS (SEQ ID NO: 152), PRGLSGRS (SEQ ID NO: 153), and PAGLSGRS (SEQ ID NO: 687).

These exemplary results show a group of substrates in which cleavage by MT-SP1 is at least 50%. Such substrates include those having the amino acid sequence of PWGLSGRS (SEQ ID NO: 12), PWGLSGKS (SEQ ID NO: 150), PYGLSGRS (SEQ ID NO: 151), PFGLSGRS (SEQ ID NO: 152), PRGLSGRS (SEQ ID NO: 153), and PAGLSGRS (SEQ ID NO: 687).

These exemplary results also show a group of substrates in which cleavage by MT-SP1 is at least 70%. Such substrates include those having the amino acid sequence of PWGLSGRS (SEQ ID NO: 12), PWGLSGKS (SEQ ID NO: 150), PYGLSGRS (SEQ ID NO: 151), PFGLSGRS (SEQ ID NO: 152), PRGLSGRS (SEQ ID NO: 153), and PAGLSGRS (SEQ ID NO: 687).

These exemplary results also show a group of substrates in which cleavage by MT-SP1, MMP9, and MMP2 is at least 60%. Such substrates include those having the amino acid sequence of PWGLSGRS (SEQ ID NO: 12), PYGLSGRS (SEQ ID NO: 151), PFGLSGRS (SEQ ID NO: 152), PRGLSGRS (SEQ ID NO: 153), and PAGLSGRS (SEQ ID NO: 687). These exemplary results also show a group of substrates in which cleavage by MT-SP1, MMP9, and MMP2 is at least 60%. Such substrates include those having the amino acid sequence of PWGLSGRS (SEQ ID NO: 12), PWGLSGKS (SEQ ID NO: 150), PYGLSGRS (SEQ ID NO: 151), PFGLSGRS (SEQ ID NO: 152), PRGLSGRS (SEQ ID NO: 153), and PAGLSGRS (SEQ ID NO: 687).

These exemplary results also show a group of substrates in which cleavage by MT-SP1, MMP9, and MMP2 is at least 60% and uPA cleavage is at least 20%. Such substrates include those having the amino acid sequence of PWGLS-GRS (SEQ ID NO: 12), PYGLSGRS (SEQ ID NO: 151), PFGLSGRS (SEQ ID NO: 152), PRGLSGRS (SEQ ID NO: 153), and PAGLSGRS (SEQ ID NO: 687).

These exemplary results also show a group of substrates in which cleavage by MT-SP1 and MMP14, MMP2 is at least 50%. These exemplary results also show a group of substrates in which cleavage by MT-SP1, MMP14, MMP9, and MMP2 is at least 50% and uPA cleavage is at least 20%. Such substrates include those having the amino acid sequence of PRGLSGRS (SEQ ID NO: 153) and PAGLS-GRS (SEQ ID NO: 687).

These exemplary results also show a group of substrates in which cleavage by MT-SP1 and MMP2 is at least 50%. Such substrates include those having the amino acid sequence of PWGLSGRS (SEQ ID NO: 12), PWGLSGKS (SEQ ID NO: 150), PYGLSGRS (SEQ ID NO: 151), PFGLSGRS (SEQ ID NO: 152), PRGLSGRS (SEQ ID NO: 153), and PAGLSGRS (SEQ ID NO: 687).

These exemplary results also show a group of substrates in which cleavage by MT-SP1 and MMP2 is at least 50% and uPA cleavage is at least 20%. Such substrates include those having the amino acid sequence of PWGLSGRS (SEQ ID NO: 12), PYGLSGRS (SEQ ID NO: 151), PFGLSGRS (SEQ ID NO: 152), PRGLSGRS (SEQ ID NO: 153), and PAGLSGRS (SEQ ID NO: 687).

These exemplary results also show a group of substrates in which cleavage by MMP2 is at least 70%. Such substrates include those having the amino acid sequence of PWGLS-GRS (SEQ ID NO: 12), PYGLSGRS (SEQ ID NO: 151), PFGLSGRS (SEQ ID NO: 152), PRGLSGRS (SEQ ID NO: 153), and PAGLSGRS (SEQ ID NO: 687).

These exemplary results also show a group of substrates in which cleavage by MMP9 is at least 50%. Such substrates include those having the amino acid sequence of PWGLS-GRS (SEQ ID NO: 12), PWGLSGKS (SEQ ID NO: 150), PYGLSGRS (SEQ ID NO: 151), PFGLSGRS (SEQ ID NO: 152), PRGLSGRS (SEQ ID NO: 153), PAGLSGRS (SEQ ID NO: 687), LSGRSPWGL (SEQ ID NO: 177), LSGK-SPWGL (SEQ ID NO: 178), and LSGRSPWGLS (SEQ ID NO: 695).

These exemplary results also show a group of substrates in which cleavage by MMP14 is at least 50%. Such substrates include those having the amino acid sequence of PRGLSGRS (SEQ ID NO: 153) and PAGLSGRS (SEQ ID NO: 687).

These exemplary results also show a group of substrates in which cleavage by MMP14, MMP9, and MMP2 is greater than 50%. Such substrates include those having the amino acid sequence of PRGLSGRS (SEQ ID NO: 153), and PAGLSGRS (SEQ ID NO: 687).

These exemplary results also show a group of substrates in which cleavage by MMP9 and MMP2 is greater than 50%. PWGLSGRS (SEQ ID NO: 12), PWGLSGKS (SEQ ID NO: 150), PYGLSGRS (SEQ ID NO: 151), PFGLSGRS (SEQ ID NO: 152), PRGLSGRS (SEQ ID NO: 153), PAGLSGRS (SEQ ID NO: 687), and LSGRSPWGLS (SEQ ID NO: 695).

Example 11: In Situ Stability of Additional Exemplary CMs in a Peptide Probe Format in Supernatant from Human Bone Marrow Aspirates The study provided herein evaluates the in situ stability of peptide probes comprising the exemplary substrates PAGLSGRS (SEQ ID NO: 687) and LSGRSPWGL (SEQ ID NO: 177) in human bone marrow aspirates. The probes were of the following designs: (MCA)-Ser-Pro-Ala-Gly-Leu-Ser-Gly-Arg-Ser-Gly-Lys (DNP)-D-Arg (SEQ ID NO: 704) and (MCA)-Ser-Leu-Ser-Gly-Arg-Ser-Pro-Trp-Gly-Leu-Gly-Lys (DNP)-D-Arg (SEQ ID NO: 705).

Fresh human bone marrow aspirates from healthy donors were purchased from Stemcell Technology Inc. (Catalog No. 70502) and were processed to lyse red blood cells and washed 5 times with serum-free media. The cells were plated at a density of 250,000 cells per well in serum-free RPMI media and incubated at 37° C. for 24 hours. Cells were pelleted through centrifugation for 5 min at 300×g and bone marrow supernatant was collected. Collected supernatant was cleared of any cellular debris with centrifugation for 10 min at 15,000×g. Stability assays were performed by mixing the probe in serum-free media with an equal volume of bone marrow supernatant to a final probe concentration of 20 µM. Cleavability kinetics (i.e., pM/s) were determined in 384-well plate format at 37° C. on an Infinite 200 PRO (Tecan) multimode plate reader using a fluorescence excitation wavelength of 320 nm and an emission wavelength of 405 nm.

The substrate LSGRSPWGL (SEQ ID NO: 177) demonstrates resistance to cleavage in supernatant from human bone marrow aspirates, with a cleavage rate of only 154 pM/s. The substrate PAGLSGRS (SEQ ID NO: 687) demonstrates reduced stability in supernatant from human bone marrow, with a cleavage rate of 2190 pM/s.

TABLE 17

| Exemplary sequences | | |
|---|---|---|
| SEQ ID NO | Note | Sequence |
| | 7040 | PXGL where X is W, Y, F, R, K, Q, or M |
| | | PXGL where X is W, Y, F, R, K, Q, A, or M |
| 2 | 7041 | PWGL |

TABLE 17-continued

| | | Exemplary sequences |
|---|---|---|
| SEQ ID NO | Note | Sequence |
| 3 | 7049 | PFGL |
| 4 | 7047 | PYGL |
| 5 | 7051 | PMGL |
| 6 | 7050 | PRGL |
| 7 | 7054 | PKGL |
| 8 | 7053 | PQGL |
| 9 | 8050 | PWGLRSN |
| 10 | 8051 | RSPWGLN |
| 11 | 8052 | GPWGLSGRSNI |
| 12 | 8053 | PWGLSGRS |
| 13 | 8054 | GRSPWGLL |
| 14 | 8055 | APMGLKHLSGRSNI |
| 15 | 8056 | GPYGLSGRSNI |
| 16 | 8057 | APRSPWGL |
| 17 | 8058 | PWGLPRS |
| 18 | 8059 | PRSPWGLL |
| 19 | 8060 | PWGLSRS |
| 20 | 8061 | PFGLSRS |
| 21 | 8062 | APMGLKHDHQSRS |
| 22 | 8063 | DHQSRSAPMGLKH |
| 23 | 8064 | KPRGLN |
| 24 | 8065 | KPRGLF |
| 25 | 7046 | APMGLKH |
| 26 | | LSGRSNI |
| 27 | 6005 | DHQSRS |
| 28 | 6001 | HQSRS |
| | | GRS |
| 30 | | LSGRS |
| 31 | | SGRS |
| 32 | | SGRSNI |
| | | PRS |
| 34 | | APRS |
| | | SRS |
| | | RS |
| 37 | 8066 | APRSLL |
| 38 | 8067 | APRGLL |
| 39 | 8068 | APRSY |
| 40 | 8069 | VAPRSMR |

TABLE 17-continued

| Exemplary sequences | | |
| --- | --- | --- |
| SEQ ID NO | Note | Sequence |
| 41 | 10200 | PWGLKSN |
| 42 | 10201 | PYGLRSN |
| 43 | 10202 | PFGLRSN |
| 44 | 10203 | PRGLRSN |
| 45 | 10204 | PMGLRSN |
| 46 | 10205 | PKGLRSN |
| 47 | 10206 | PQGLRSN |
| 48 | 10207 | PWGLRS |
| 49 | 10208 | PWGLR |
| 50 | 10209 | PWGLKS |
| 51 | 10210 | PWGLK |
| 52 | 10211 | PYGLRS |
| 53 | 10212 | PYGLR |
| 54 | 10213 | PYGLKS |
| 55 | 10214 | PYGLK |
| 56 | 10215 | PFGLRS |
| 57 | 10216 | PFGLR |
| 58 | 10217 | PFGLKS |
| 59 | 10218 | PFGLK |
| 60 | 10219 | PMGLRS |
| 61 | 10220 | PMGLR |
| 62 | 10221 | PRGLRS |
| 63 | 10222 | PRGLR |
| 64 | 10223 | PRGLKS |
| 65 | 10224 | PRGLK |
| 66 | 10225 | PKGLRS |
| 67 | 10226 | PKGLR |
| 68 | 10227 | PKGLKS |
| 69 | 10228 | PKGLK |
| 70 | 10229 | PQGLRS |
| 71 | 10230 | PQGLR |
| 72 | 10231 | PQGLKS |
| 73 | 10232 | PQGLK |
| 74 | 1401 | ALAHGLF |
| 75 | 1001 | ISSGLLSS |
| 76 | 1004 | AVGLLAPP |
| 77 | 0001 | LSGRSDNH |

TABLE 17-continued

Exemplary sequences

| SEQ ID NO | Note | Sequence |
|---|---|---|
| 78 | 2001 | ISSGLLSGRSDNH |
| 79 | 3001 | AVGLLAPPGGLSGRSDNH |
| 80 | 5007 | APRSALAHGLF |
| 81 | EGFR Mask | CISPRGCPDGPYVMY |
| 82 | EGFR Mask | CISPRGCLDGPYVMY |
| 83 | 10233 | KSPWGLN |
| 84 | 10234 | RSPYGLN |
| 85 | 10235 | RSPFGLN |
| 86 | 10236 | RSPRGLN |
| 87 | 10237 | RSPMGLN |
| 88 | 10238 | RSPKGLN |
| 89 | 10239 | RSPQGLN |
| 90 | 10240 | RSPWGL |
| 91 | 10241 | KSPWGL |
| 92 | 10242 | RPWGL |
| 93 | 10243 | KPWGL |
| 94 | 10244 | RSPYGL |
| 95 | 10245 | KSPYGL |
| 96 | 10246 | RPYGL |
| 97 | 10247 | KPYGL |
| 98 | 10248 | RSPFGL |
| 99 | 10249 | KSPFGL |
| 100 | 10250 | RPFGL |
| 101 | 10251 | KPFGL |
| 102 | 10252 | RSPMGL |
| 103 | 10253 | KSPMGL |
| 104 | 10254 | RPMGL |
| 105 | 10255 | KPMGL |
| 106 | 10256 | RSPRGL |
| 107 | 10257 | KSPRGL |
| 108 | 10258 | RSPKGL |
| 109 | 10259 | KSPKGL |
| 110 | 10260 | RSPQGL |
| 111 | 10261 | KSPQGL |
| 112 | 10262 | RPQGL |
| 113 | 10263 | KPQGL |
| 114 | 10264 | GPWGLSGKSNI |

TABLE 17-continued

Exemplary sequences

| SEQ ID NO | Note | Sequence |
|---|---|---|
| 115 | 10265 | GPFGLSGRSNI |
| 116 | 10266 | GPRGLSGRSNI |
| 117 | 10267 | GPMGLSGRSNI |
| 118 | 10268 | GPKGLSGRSNI |
| 119 | 10269 | GPQGLSGRSNI |
| 120 | 10270 | PWGLSGRSNI |
| 121 | 10271 | PWGLSGKSNI |
| 122 | 10272 | PFGLSGRSNI |
| 123 | 10273 | PFGLSGKSNI |
| 124 | 10274 | PMGLSGRSNI |
| 125 | 10275 | PMGLSGKSNI |
| 126 | 10276 | PRGLSGRSNI |
| 127 | 10277 | PRGLSGKSNI |
| 128 | 10278 | PKGLSGRSNI |
| 129 | 10279 | PKGLSGKSNI |
| 130 | 10280 | PQGLSGRSNI |
| 131 | 10281 | PQGLSGKSNI |
| 132 | 10282 | GPWGLSGRSAN |
| 133 | 10283 | GPFGLSGRSAN |
| 134 | 10284 | GPRGLSGRSAN |
| 135 | 10285 | GPMGLSGRSAN |
| 136 | 10286 | GPKGLSGRSAN |
| 137 | 10287 | GPQGLSGRSAN |
| 138 | 10288 | GPWGLSGRSA |
| 139 | 10289 | GPFGLSGRSA |
| 140 | 10290 | GPRGLSGRSA |
| 141 | 10291 | GPMGLSGRSA |
| 142 | 10292 | GPKGLSGRSA |
| 143 | 10293 | GPQGLSGRSA |
| 144 | 10294 | GPWGLSGRSNA |
| 145 | 10295 | GPFGLSGRSNA |
| 146 | 10296 | GPRGLSGRSNA |
| 147 | 10297 | GPMGLSGRSNA |
| 148 | 10298 | GPKGLSGRSNA |
| 149 | 10299 | GPQGLSGRSNA |
| 150 | 10300 | PWGLSGKS |
| 151 | 10301 | PYGLSGRS |

TABLE 17-continued

Exemplary sequences

| SEQ ID NO | Note | Sequence |
|---|---|---|
| 152 | 10302 | PFGLSGRS |
| 153 | 10303 | PRGLSGRS |
| 154 | 10304 | PMGLSGRS |
| 155 | 10305 | PKGLSGRS |
| 156 | 10306 | PQGLSGRS |
| 157 | 10307 | PYGLSGKS |
| 158 | 10308 | PFGLSGKS |
| 159 | 10309 | PRGLSGKS |
| 160 | 10310 | PMGLSGKS |
| 161 | 10311 | PKGLSGKS |
| 162 | 10312 | PQGLSGKS |
| 163 | 10313 | PWGLSGR |
| 164 | 10314 | PWGLSGK |
| 165 | 10315 | PYGLSGR |
| 166 | 10316 | PYGLSGK |
| 167 | 10317 | PFGLSGR |
| 168 | 10318 | PFGLSGK |
| 169 | 10319 | PRGLSGR |
| 170 | 10320 | PRGLSGK |
| 171 | 10321 | PMGLSGR |
| 172 | 10322 | PMGLSGK |
| 173 | 10323 | PKGLSGR |
| 174 | 10324 | PKGLSGK |
| 175 | 10325 | PQGLSGR |
| 176 | 10326 | PQGLSGK |
| 177 | 10327 | LSGRSPWGL |
| 178 | 10328 | LSGKSPWGL |
| 179 | 10329 | LSGRSPYGL |
| 180 | 10330 | LSGKSPYGL |
| 181 | 10331 | LSGRSPFGL |
| 182 | 10332 | LSGKSPFGL |
| 183 | 10333 | LSGRSPRGL |
| 184 | 10334 | LSGKSPRGL |
| 185 | 10335 | LSGRSPMGL |
| 186 | 10336 | LSGKSPMGL |
| 187 | 10337 | LSGRSPKGL |
| 188 | 10338 | LSGKSPKGL |
| 189 | 10339 | LSGRSPQGL |

TABLE 17-continued

| SEQ ID NO | Note | Sequence |
|---|---|---|
| 190 | 10340 | LSGKSPQGL |
| 191 | 10341 | RSPWGLL |
| 192 | 10342 | KSPWGLL |
| 193 | 10343 | GKSPWGLL |
| 194 | 10344 | GRSPYGLL |
| 195 | 10345 | GKSPYGLL |
| 196 | 10346 | GRSPFGLL |
| 197 | 10347 | GKSPFGLL |
| 198 | 10348 | GRSPRGLL |
| 199 | 10349 | GKSPRGLL |
| 200 | 10350 | GRSPMGLL |
| 201 | 10351 | GKSPMGLL |
| 202 | 10352 | GRSPKGLL |
| 203 | 10353 | GKSPKGLL |
| 204 | 10354 | GRSPQGLL |
| 205 | 10355 | GKSPQGLL |
| 206 | 10356 | APWGLKHLSGRSNI |
| 207 | 10357 | PWGLKHLSGRSNI |
| 208 | 10358 | APWGLKHLSGKSNI |
| 209 | 10359 | PWGLKHLSGKSNI |
| 210 | 10360 | APMGLKHLSGKSNI |
| 211 | 10361 | PMGLKHLSGKSNI |
| 212 | 10362 | PMGLKHLSGRSNI |
| 213 | 10363 | APMGLKLSGRSNI |
| 214 | 10364 | PMGLKLSGRSNI |
| 215 | 10365 | APMGLLSGRSNI |
| 216 | 10366 | PMGLLSGRSNI |
| 217 | 10367 | PWGLLSGRSNI |
| 218 | 10368 | PWGLLSGKSNI |
| 219 | 10369 | PWGLLSGRSAN |
| 220 | 10370 | PWGLLSGRSA |
| 221 | 10371 | PWGLLSGRSNA |
| 222 | 10372 | PWGLSGRSANI |
| 223 | 10373 | PWGLSGRSAN |
| 224 | 10374 | PWGLSGRSA |
| 225 | 10375 | APWGLKHLSGRSAN |
| 226 | 10376 | PWGLKHLSGRSAN |

TABLE 17-continued

Exemplary sequences

| SEQ ID NO | Note | Sequence |
|---|---|---|
| 227 | 10377 | APMGLKLSGRSAN |
| 228 | 10378 | PMGLKLSGRSAN |
| 229 | 10379 | APMGLLSGRSAN |
| 230 | 10380 | PMGLLSGRSAN |
| 231 | 10381 | APWGLKHLSGRSA |
| 232 | 10382 | PWGLKHLSGRSA |
| 233 | 10383 | APMGLKLSGRSA |
| 234 | 10384 | PMGLKLSGRSA |
| 235 | 10385 | APMGLLSGRSA |
| 236 | 10386 | PMGLLSGRSA |
| 237 | 10387 | APWGLKHLSGRSNA |
| 238 | 10388 | PWGLKHLSGRSNA |
| 239 | 10389 | APMGLKLSGRSNA |
| 240 | 10390 | PMGLKLSGRSNA |
| 241 | 10391 | APMGLLSGRSNA |
| 242 | 10392 | PMGLLSGRSNA |
| 243 | 10393 | GPYGLSGKSNI |
| 244 | 10394 | PYGLSGKSNI |
| 245 | 10395 | PYGLSGRSNI |
| 246 | 10396 | GPYGLLSGRSNI |
| 247 | 10397 | GPYGLLSGKSNI |
| 248 | 10398 | PYGLLSGRSNI |
| 249 | 10399 | PYGLLSGKSNI |
| 250 | 10400 | GPYGLSGRSAN |
| 251 | 10401 | PYGLSGRSAN |
| 252 | 10402 | GPYGLLSGRSAN |
| 253 | 10403 | PYGLLSGRSAN |
| 254 | 10404 | GPYGLSGRSA |
| 255 | 10405 | PYGLSGRSA |
| 256 | 10406 | GPYGLLSGRSA |
| 257 | 10407 | PYGLLSGRSA |
| 258 | 10408 | GPYGLSGRSNA |
| 259 | 10409 | PYGLSGRSNA |
| 260 | 10410 | GPYGLLSGRSNA |
| 261 | 10411 | PYGLLSGRSNA |
| 262 | 10412 | AAPRSPWGL |
| 263 | 10413 | AAPKSPWGL |
| 264 | 10414 | APRSPWGLL |

TABLE 17-continued

Exemplary sequences

| SEQ ID NO | Note | Sequence |
|---|---|---|
| 265 | 10415 | APKSPWGLL |
| 266 | 10416 | APRSPYGL |
| 267 | 10417 | APKSPWGL |
| 268 | 10418 | APKSPYGL |
| 269 | 10419 | APRSPFGL |
| 270 | 10420 | APKSPFGL |
| 271 | 10421 | APRSPRGL |
| 278 | 10422 | APKSPRGL |
| 279 | 10423 | APRSPMGL |
| 280 | 10424 | APKSPMGL |
| 281 | 10425 | APRSPKGL |
| 282 | 10426 | APKSPKGL |
| 283 | 10427 | APRSPQGL |
| 284 | 10428 | APKSPQGL |
| 285 | 10429 | PYGLPRS |
| 286 | 10430 | PFGLPRS |
| 287 | 10431 | PRGLPRS |
| 288 | 10432 | PMGLPRS |
| 289 | 10433 | PKGLPRS |
| 290 | 10434 | PQGLPRS |
| 291 | 10435 | PWGLPKS |
| 292 | 10436 | PYGLPKS |
| 293 | 10437 | PFGLPKS |
| 294 | 10438 | PRGLPKS |
| 295 | 10439 | PMGLPKS |
| 296 | 10440 | PKGLPKS |
| 297 | 10441 | PQGLPKS |
| 298 | 10442 | PWGLPR |
| 299 | 10443 | PYGLPR |
| 300 | 10444 | PFGLPR |
| 301 | 10445 | PRGLPR |
| 302 | 10446 | PMGLPR |
| 303 | 10447 | PKGLPR |
| 304 | 10448 | PQGLPR |
| 305 | 10449 | PWGLPK |
| 306 | 10450 | PYGLPK |
| 307 | 10451 | PFGLPK |

TABLE 17-continued

Exemplary sequences

| SEQ ID NO | Note | Sequence |
|---|---|---|
| 308 | 10452 | PRGLPK |
| 309 | 10453 | PMGLPK |
| 310 | 10454 | PKGLPK |
| 311 | 10455 | PQGLPK |
| 312 | 10456 | PKSPWGLL |
| 313 | 10457 | PRSPWGL |
| 314 | 10458 | PKSPWGL |
| 315 | 10459 | PRSPYGL |
| 316 | 10460 | PKSPYGL |
| 317 | 10461 | PRSPFGL |
| 318 | 10462 | PKSPFGL |
| 319 | 10463 | PRSPMGL |
| 320 | 10464 | PKSPMGL |
| 321 | 10465 | PRSPRGL |
| 322 | 10466 | PKSPRGL |
| 323 | 10467 | PRSPKGL |
| 324 | 10468 | PKSPKGL |
| 325 | 10469 | PRSPQGL |
| 326 | 10470 | PKSPQGL |
| 327 | 10471 | PRSPYGLL |
| 328 | 10472 | PRSPFGLL |
| 329 | 10473 | PRSPRGLL |
| 330 | 10474 | PRSPMGLL |
| 331 | 10475 | PRSPKGLL |
| 332 | 10476 | PRSPQGLL |
| 333 | 10477 | PYGLSRS |
| 334 | 10478 | PFGLSRS |
| 335 | 10479 | PRGLSRS |
| 336 | 10480 | PMGLSRS |
| 337 | 10481 | PKGLSRS |
| 338 | 10482 | PQGLSRS |
| 339 | 10483 | PWGLSKS |
| 340 | 10484 | PYGLSKS |
| 341 | 10485 | PFGLSKS |
| 342 | 10486 | PRGLSKS |
| 343 | 10487 | PMGLSKS |
| 344 | 10488 | PKGLSKS |
| 345 | 10489 | PQGLSKS |

TABLE 17-continued

| | | Exemplary sequences |
| --- | --- | --- |
| SEQ ID NO | Note | Sequence |
| 346 | 10490 | PWGLSR |
| 347 | 10491 | PYGLSR |
| 348 | 10492 | PFGLSR |
| 349 | 10493 | PRGLSR |
| 350 | 10494 | PMGLSR |
| 351 | 10495 | PKGLSR |
| 352 | 10496 | PQGLSR |
| 353 | 10497 | PWGLSK |
| 559 | | Intentionally left blank |
| 560 | 10498 | PYGLSK |
| 561 | 10499 | PFGLSK |
| 562 | 10500 | PRGLSK |
| 563 | 10501 | PMGLSK |
| 564 | 10502 | PKGLSK |
| 565 | 10503 | PQGLSK |
| 566 | 10504 | APMGLKHDHQSKS |
| 567 | 10505 | PMGLKHDHQSRS |
| 568 | 10506 | PMGLKHDHQSKS |
| 569 | 10507 | APMGLKHDHQSR |
| 570 | 10508 | APMGLKHDHQSK |
| 571 | 10509 | PMGLKHDHQSR |
| 572 | 10510 | PMGLKHDHQSK |
| 573 | 10511 | PMGLKDHQSRS |
| 574 | 10512 | PMGLKDHQSKS |
| 575 | 10513 | PMGLKHHQSRS |
| 576 | 10514 | PMGLKHHQSKS |
| 577 | 10515 | PMGLKHQSRS |
| 578 | 10516 | PMGLKHQSKS |
| 579 | 10517 | PMGLKDHQSR |
| 580 | 10518 | PMGLKDHQSK |
| 581 | 10519 | PMGLKHHQSR |
| 582 | 10520 | PMGLKHHQSK |
| 583 | 10521 | PMGLKHQSR |
| 584 | 10522 | PMGLKHQSK |
| 585 | 10523 | PYGLKHQSR |
| 586 | 10524 | PFGLKHQSR |
| 587 | 10525 | PRGLKHQSR |

TABLE 17-continued

| Exemplary sequences | | |
| --- | --- | --- |
| SEQ ID NO | Note | Sequence |
| 588 | 10526 | PWGLKHQSR |
| 589 | 10527 | PKGLKHQSR |
| 590 | 10528 | PQGLKHQSR |
| 591 | 10529 | PYGLKHQSK |
| 592 | 10530 | PFGLKHQSK |
| 593 | 10531 | PRGLKHQSK |
| 594 | 10532 | PWGLKHQSK |
| 595 | 10533 | PKGLKHQSK |
| 596 | 10534 | PQGLKHQSK |
| 597 | 10535 | HQSRSAPMGLKH |
| 598 | 10536 | DHQSRSPMGLKH |
| 599 | 10537 | HQSRSPMGLKH |
| 600 | 10538 | DHQSKSAPMGLKH |
| 601 | 10539 | HQSKSAPMGLKH |
| 602 | 10540 | DHQSKSPMGLKH |
| 603 | 10541 | HQSKSPMGLKH |
| 604 | 10542 | DHQSRSAPMGLK |
| 605 | 10543 | HQSRSAPMGLK |
| 606 | 10544 | DHQSRSPMGLK |
| 607 | 10545 | HQSRSPMGLK |
| 608 | 10546 | DHQSKSAPMGLK |
| 609 | 10547 | HQSKSAPMGLK |
| 610 | 10548 | DHQSKSPMGLK |
| 611 | 10549 | HQSKSPMGLK |
| 612 | 10550 | DHQSRSAPMGL |
| 613 | 10551 | HQSRSAPMGL |
| 614 | 10552 | DHQSRSPMGL |
| 615 | 10553 | HQSRSPMGL |
| 616 | 10554 | DHQSKSAPMGL |
| 617 | 10555 | HQSKSAPMGL |
| 618 | 10556 | DHQSKSPMGL |
| 619 | 10557 | HQSKSPMGL |
| 620 | 10558 | HQSRSPRGL |
| 621 | 10559 | HQSRSPKGL |
| 622 | 10560 | HQSRSPQGL |
| 623 | 10561 | HQSKSPRGL |
| 624 | 10562 | HQSKSPKGL |
| 625 | 10563 | HQSKSPQGL |

TABLE 17-continued

| Exemplary sequences | | |
| --- | --- | --- |
| SEQ ID NO | Note | Sequence |
| 626 | 10564 | HQSRPMGL |
| 627 | 10565 | HQSRPRGL |
| 628 | 10566 | HQSRPKGL |
| 629 | 10567 | HQSRPQGL |
| 630 | 10568 | HQSKPMGL |
| 631 | 10569 | HQSKPRGL |
| 632 | 10570 | HQSKPKGL |
| 633 | 10571 | HQSKPQGL |
| 634 | 10572 | PMGLHQSRS |
| 635 | 10573 | PYGLHQSRS |
| 636 | 10574 | PFGLHQSRS |
| 637 | 10575 | PRGLHQSRS |
| 638 | 10576 | PKGLHQSRS |
| 639 | 10577 | PQGLHQSRS |
| 640 | 10578 | PMGLHQSKS |
| 641 | 10579 | PYGLHQSKS |
| 642 | 10580 | PFGLHQSKS |
| 643 | 10581 | PRGLHQSKS |
| 644 | 10582 | PKGLHQSKS |
| 645 | 10583 | PQGLHQSKS |
| 646 | 10584 | PMGLHQSR |
| 647 | 10585 | PYGLHQSR |
| 648 | 10586 | PFGLHQSR |
| 649 | 10587 | PRGLHQSR |
| 650 | 10588 | PKGLHQSR |
| 651 | 10589 | PQGLHQSR |
| 652 | 10590 | PMGLHQSK |
| 653 | 10591 | PYGLHQSK |
| 654 | 10592 | PFGLHQSK |
| 655 | 10593 | PRGLHQSK |
| 656 | 10594 | PKGLHQSK |
| 657 | 10595 | PQGLHQSK |
| 658 | 10596 | RPRGLN |
| 659 | 10597 | RPKGLN |
| 660 | 10598 | KPKGLN |
| 661 | 10599 | RPRGLF |
| 662 | 10600 | RPKGLF |

TABLE 17-continued

| SEQ ID NO | Note | Sequence |
|---|---|---|
| 663 | 10601 | KPKGLF |
| 664 | 10602 | KPRGL |
| 665 | 10603 | RPRGL |
| 666 | 10604 | RPKGL |
| 667 | 10605 | KPKGL |
| 668 | 10606 | APKSLL |
| 669 | 10607 | APRSL |
| 670 | 10608 | APKSL |
| 671 | 10609 | APKGLL |
| 672 | 10610 | APRGL |
| 673 | 10611 | APKGL |
| 674 | 10612 | AAPRSY |
| 675 | 10613 | AAPKSY |
| 676 | 10614 | APKSY |
| 677 | 10615 | AAPRSMR |
| 678 | 10616 | VAPRSMK |
| 679 | 10617 | VAPKSMR |
| 680 | 10618 | VAPKSMK |
| 681 | 10619 | AAPKSMR |
| 682 | 10620 | AAPRSMK |
| 683 | 10621 | AAPKSMK |
| 684 | | PWGLSG |
| 685 | | WGLSGRS |
| 686 | | AWGLSGRS |
| 687 | | PAGLSGRS |
| 688 | | PWALSGRS |
| 689 | | PWGASGRS |
| 690 | | PWGLAGRS |
| 691 | | PWGLSARS |
| 692 | | PWGLSGAS |
| 693 | | PWGLSGRA |
| 694 | | LSGRSPAGL |
| 695 | | LSGRSPWGLS |
| 354 | CX-122 LC | QGQSGQCISPRGCPDGPYVMYGSSGGSGGSGGSGISS GLLSGRSDNHGSSGTQILLTQSPVILSVSPGERVSFSCR ASQSIGTNIHWYQQRTNGSPRLLIKYASESISGIPSRFSG SGSGTDFTLSINSVESEDIADYYCQQNNNWPTTFGAGT KLELKRTVAAPSVFIFPPSDEQLKSGTASVVCLLNNFYP REAKVQWKVDNALQSGNSQESVTEQDSKDSTYSLSST LTLSKADYEKHKVYACEVTHQGLSSPVTKSFNRGEC |

TABLE 17-continued

Exemplary sequences

| SEQ ID NO | Note | Sequence |
|---|---|---|
| 355 | CX-122 HC | QVQLKQSGPGLVQPSQSLSITCTVSGFSLTNYGVHWVR QSPGKGLEWLGVIWSGGNTDYNTPFTSRLSINKDNSKS QVFFKMNSLQSQDTAIYYCARALTYYDYEFAYWGQG TLVTVSSASTKGPSVFPLAPSSKSTSGGTAALGCLVKD YFPEPVTVSWNSGALTSGVHTFPAVLQSSGLYSLSSVV TVPSSSLGTQTYICNVNHKPSNTKVDKKVEPKSCDKTH TCPPCPAPELLGGPSVFLFPPKPKDTLMISRTPEVTCVV VDVSHEDPEVKFNWYVDGVEVHNAKTKPREEQYNST YRVVSVLTVLHQDWLNGKEYKCKVSNKALPAPIEKTIS KAKGQPREPQVYTLPPSREEMTKNQVSLTCLVKGFYPS DIAVEWESNGQPENNYKTTPPVLDSDGSFFLYSKLTVD KSRWQQGNVFSCSVMHEALHNHYTQKSLSLSPGK |
| 356 | AA w/5007 LC | QGQSGQCISPRGCPDGPYVMYGGGSSGGSAPRSALA HGLFGGGSQILLTQSPVILSVSPGERVSFSCRASQSIGTN IHWYQQRTNGSPRLLIKYASESISGIPSRFSGSGSGTDFT LSINSVESEDIADYYCQQNNNWPTTFGAGTKLELKRTV AAPSVFIFPPSDEQLKSGTASVVCLLNNFYPREAKVQW KVDNALQSGNSQESVTEQDSKDSTYSLSSTLTLSKADY EKHKVYACEVTHQGLSSPVTKSFNRGEC |
| 357 | AA w/5007 HC | QVQLKQSGPGLVQPSQSLSITCTVSGFSLTNYGVHWVR QSPGKGLEWLGVIWSGGNTDYNTPFTSRLSINKDNSKS QVFFKMNSLQSQDTAIYYCARALTYYDYEFAYWGQG TLVTVSSASTKGPSVFPLAPSSKSTSGGTAALGCLVKD YFPEPVTVSWNSGALTSGVHTFPAVLQSSGLYSLSSVV TVPSSSLGTQTYICNVNHKPSNTKVDKKVEPKSCDKTH TCPPCPAPELLGGPSVFLFPPKPKDTLMISRTPEVTCVV VDVSHEDPEVKFNWYVDGVEVHNAKTKPREEQYNST YRVVSVLTVLHQDWLNGKEYKCKVSNKALPAPIEKTIS KAKGQPREPQVYTLPPSRDELTKNQVSLTCLVKGFYPS DIAVEWESNGQPENNYKTTPPVLDSDGSFFLYSKLTVD KSRWQQGNVFSCSVMHEALHNHYTQKSLSLSPGK |
| 358 | CX-229 LC | QGQSGQCISPRGCLDGPYVMYGSSGGSGGSGGSGAV GLLAPPGGLSGRSDNHGSSGTQILLTQSPVILSVSPGER VSFSCRASQSIGTNIHWYQQRTNGSPRLLIKYASESISGI PSRFSGSGSGTDFTLSINSVESEDIADYYCQQNNNWPTT FGAGTKLELKRTVAAPSVFIFPPSDEQLKSGTASVVCLL NNFYPREAKVQWKVDNALQSGNSQESVTEQDSKDSTY SLSSTLTLSKADYEKHKVYACEVTHQGLSSPVTKSFNR GEC |
| | CX-229 HC | Same as CX-122 HC SEQ ID NO: 355 above |
| 359 | CTX-028- light chain | QGQSGQCISPRGCPDGPYVMYGSSGGSGGSGGSGISS GLLSSGSSGTQILLTQSPVILSVSPGERVSFSCRASQSIG TNIHWYQQRTNGSPRLLIKYASESISGIPSRFSGSGSGTD FTLSINSVESEDIADYYCQQNNNWPTTFGAGTKLELKR TVAAPSVFIFPPSDEQLKSGTASVVCLLNNFYPREAKVQ WKVDNALQSGNSQESVTEQDSKDSTYSLSSTLTLSKAD YEKHKVYACEVTHQGLSSPVTKSFNRGEC |
| 360 | CTX-028- heavy chain | QGQSGQCISPRGCPDGPYVMYGSSGGSGGSGGSGISSG LLSSGSSGTQILLTQSPVILSVSPGERVSFSCRASQSIGTN IHWYQQRTNGSPRLLIKYASESISGIPSRFSGSGSGTDFT LSINSVESEDIADYYCQQNNNWPTTFGAGTKLELKRTV AAPSVFIFPPSDEQLKSGTASVVCLLNNFYPREAKVQW KVDNALQSGNSQESVTEQDSKDSTYSLSSTLTLSKADY EKHKVYACEVTHQGLSSPVTKSFNRGEC |
| 361 | ProC795 LC | QGQSGQGCISPRGCPDGPYVMYGGGSSGGSAPMGLK HLSGRSNIGGGSQILLTQSPVILSVSPGERVSFSCRASQS IGTNIHWYQQRTNGSPRLLIKYASESISGIPSRFSGSGSG TDFTLSINSVESEDIADYYCQQNNNWPTTFGAGTKLEL KRTVAAPSVFIFPPSDEQLKSGTASVVCLLNNFYPREAK VQWKVDNALQSGNSQESVTEQDSKDSTYSLSSTLTLSK ADYEKHKVYACEVTHQGLSSPVTKSFNRGEC |
| | ProC795 HC | Same as CX-122 HC SEQ ID NO: 355 above |

TABLE 17-continued

<hr>

Exemplary sequences

<hr>

| SEQ ID NO | Note | Sequence |
|---|---|---|
| 362 | ProC902 LC | QGQSGQGCISPRGCPDGPYVMYGGGSSGGSGPWGLS GRSNIGGGSQILLTQSPVILSVSPGERVSFSCRASQSIGT NIHWYQQRTNGSPRLLIKYASESISGIPSRFSGSGSGTDF TLSINSVESEDIADYYCQQNNNWPTTFGAGTKLELKRT VAAPSVFIFPPSDEQLKSGTASVVCLLNNFYPREAKVQ WKVDNALQSGNSQESVTEQDSKDSTYSLSSTLTLSKAD YEKHKVYACEVTHQGLSSPVTKSFNRGEC |
| | ProC902 HC | Same as CX-122 HC SEQ ID NO: 355 above |
| 363 | ProC903 LC | QGQSGQGCISPRGCPDGPYVMYGGGSSGGSGPYGLS GRSNIGGGSQILLTQSPVILSVSPGERVSFSCRASQSIGT NIHWYQQRTNGSPRLLIKYASESISGIPSRFSGSGSGTDF TLSINSVESEDIADYYCQQNNNWPTTFGAGTKLELKRT VAAPSVFIFPPSDEQLKSGTASVVCLLNNFYPREAKVQ WKVDNALQSGNSQESVTEQDSKDSTYSLSSTLTLSKAD YEKHKVYACEVTHQGLSSPVTKSFNRGEC |
| | ProC903 HC | Same as CX-122 HC SEQ ID NO: 355 above |
| 364 | ProC904 LC | QGQSGQGCISPRGCPDGPYVMYGGGSSGGSDHQSRS APMGLKHGGGSQILLTQSPVILSVSPGERVSESCRASQS IGTNIHWYQQRTNGSPRLLIKYASESISGIPSRESGSGSG TDFTLSINSVESEDIADYYCQQNNNWPTTFGAGTKLEL KRTVAAPSVFIFPPSDEQLKSGTASVVCLLNNFYPREAK VQWKVDNALQSGNSQESVTEQDSKDSTYSLSSTLTLSK ADYEKHKVYACEVTHQGLSSPVTKSFNRGEC |
| | ProC904 HC | Same as CX-122 HC SEQ ID NO: 355 above |
| 365 | ProC906 LC | QGQSGQGCISPRGCPDGPYVMYGGGSSGGSAPMGLK HDHQSRSGGGSQILLTQSPVILSVSPGERVSFSCRASQSI GTNIHWYQQRTNGSPRLLIKYASESISGIPSRFSGSGSGT DFTLSINSVESEDIADYYCQQNNNWPTTFGAGTKLELK RTVAAPSVFIFPPSDEQLKSGTASVVCLLNNFYPREAKV QWKVDNALQSGNSQESVTEQDSKDSTYSLSSTLTLSKA DYEKHKVYACEVTHQGLSSPVTKSFNRGEC |
| | ProC906 HC | Same as CX-122 HC SEQ ID NO: 355 above |
| 366 | ProC1260 LC | QGQSGQGCISPRGCPDGPYVMYGGGSSGGSAPRSPW GLGGGSQILLTQSPVILSVSPGERVSFSCRASQSIGTNIH WYQQRTNGSPRLLIKYASESISGIPSRFSGSGSGTDFTLS INSVESEDIADYYCQQNNNWPTTFGAGTKLELKRTVA APSVFIFPPSDEQLKSGTASVVCLLNNFYPREAKVQWK VDNALQSGNSQESVTEQDSKDSTYSLSSTLTLSKADYE KHKVYACEVTHQGLSSPVTKSFNRGEC |
| 367 | ProC1260 HC | QVQLKQSGPGLVQPSQSLSITCTVSGFSLTNYGVHWVR QSPGKGLEWLGVIWSGGNTDYNTPFTSRLSINKDNSKS QVFFKMNSLQSQDTAIYYCARALTYYDYEFAYWGQG TLVTVSAASTKGPSVFPLAPSSKSTSGGTAALGCLVKD YFPEPVTVSWNSGALTSGVHTFPAVLQSSGLYSLSSVV TVPSSSLGTQTYICNVNHKPSNTKVDKKVEPKSCDKTH TCPPCPAPELLGGPSVFLFPPKPKDTLMISRTPEVTCVV VDVSHEDPEVKFNWYVDGVEVHNAKTKPREEQYNST YRVVSVLTVLHQDWLNGKEYKCKVSNKALPAPIEKTIS KAKGQPREPQVYTLPPSRDELTKNQVSLTCLVKGFYPS DIAVEWESNGQPENNYKTTPPVLDSDGSFFLYSKLTVD KSRWQQGNVFSCSVMHEALHNHYTQKSLSLSPGK |
| 368 | ProC1261 LC | QGQSGQGCISPRGCPDGPYVMYGGGSSGGSPWGLPR SGGGSQILLTQSPVILSVSPGERVSFSCRASQSIGTNIHW YQQRTNGSPRLLIKYASESISGIPSRFSGSGSGTDFTLSIN SVESEDIADYYCQQNNNWPTTFGAGTKLELKRTVAAP SVFIFPPSDEQLKSGTASVVCLLNNFYPREAKVQWKVD NALQSGNSQESVTEQDSKDSTYSLSSTLTLSKADYEKH KVYACEVTHQGLSSPVTKSFNRGEC |
| | ProC1261 HC | Same as HC SEQ ID NO: 367 above |

TABLE 17-continued

| SEQ ID NO | Note | Sequence |
|---|---|---|
| 369 | ProC1264 LC | QGQSGQGCISPRGCPDGPYVMYGGGSSGGKPRGLNGGGSQILLTQSPVILSVSPGERVSFSCRASQSIGTNIHWYQQRTNGSPRLLIKYASESISGIPSRFSGSGSGTDFTLSINSVESEDIADYYCQQNNNWPTTFGAGTKLELKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | ProC1264 HC | Same as HC SEQ ID NO: 367 above |
| 370 | ProC1265 LC | QGQSGQGCISPRGCPDGPYVMYGGGSSGGSPWGLRSNGGGSQILLTQSPVILSVSPGERVSFSCRASQSIGTNIHWYQQRTNGSPRLLIKYASESISGIPSRFSGSGSGTDFTLSINSVESEDIADYYCQQNNNWPTTFGAGTKLELKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | ProC1265 HC | Same as HC SEQ ID NO: 367 above |
| 371 | ProC1266 LC | QGQSGQGCISPRGCPDGPYVMYGGGSSGGSRSPWGLNGGGSQILLTQSPVILSVSPGERVSFSCRASQSIGTNIHWYQQRTNGSPRLLIKYASESISGIPSRFSGSGSGTDFTLSINSVESEDIADYYCQQNNNWPTTFGAGTKLELKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | ProC1266 HC | Same as HC SEQ ID NO: 367 above |
| 372 | ProC1750 LC | QGQSGQGCISPRGCPDGPYVMYGGGSSGGSKPRGLFGGGSQILLTQSPVILSVSPGERVSFSCRASQSIGTNIHWYQQRTNGSPRLLIKYASESISGIPSRESGSGSGTDFTLSINSVESEDIADYYCQQNNNWPTTFGAGTKLELKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | ProC1750 HC | Same as CX-122 HC SEQ ID NO: 355 above |
| 373 | ProC1754 LC | QGQSGQGCISPRGCPDGPYVMYGGGSSGGSPWGLSGRSGGGSQILLTQSPVILSVSPGERVSFSCRASQSIGTNIHWYQQRTNGSPRLLIKYASESISGIPSRFSGSGSGTDFTLSINSVESEDIADYYCQQNNNWPTTFGAGTKLELKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | ProC1754 HC | Same as CX-122 HC SEQ ID NO: 355 above |
| 374 | ProC1755 LC | QGQSGQGCISPRGCPDGPYVMYGGGSSGGSPWGLSRSGGGSQILLTQSPVILSVSPGERVSFSCRASQSIGTNIHWYQQRTNGSPRLLIKYASESISGIPSRFSGSGSGTDFTLSINSVESEDIADYYCQQNNNWPTTFGAGTKLELKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | ProC1755 HC | Same as CX-122 HC SEQ ID NO: 355 above |
| 375 | ProC1756 LC | QGQSGQGCISPRGCPDGPYVMYGGGSSGGSPFGLSRSGGGSQILLTQSPVILSVSPGERVSFSCRASQSIGTNIHWYQQRTNGSPRLLIKYASESISGIPSRFSGSGSGTDFTLSINSVESEDIADYYCQQNNNWPTTFGAGTKLELKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

TABLE 17-continued

Exemplary sequences

| SEQ ID NO | Note | Sequence |
|---|---|---|
| | ProC1756 HC | Same as CX-122 HC SEQ ID NO: 355 above |
| 376 | ProC1757 LC | QGQSGQGCISPRGCPDGPYVMYGGGSSGGSPRSPWG LLGGGSQILLTQSPVILSVSPGERVSFSCRASQSIGTNIH WYQQRTNGSPRLLIKYASESISGIPSRFSGSGSGTDFTLS INSVESEDIADYYCQQNNNWPTTFGAGTKLELKRTVA APSVFIFPPSDEQLKSGTASVVCLLNNFYPREAKVQWK VDNALQSGNSQESVTEQDSKDSTYSLSSTLTLSKADYE KHKVYACEVTHQGLSSPVTKSFNRGEC |
| | ProC1757 HC | Same as CX-122 HC SEQ ID NO: 355 above |
| 377 | ProC1758 LC | QGQSGQGCISPRGCPDGPYVMYGGGSSGGSGRSPWG LLGGGSQILLTQSPVILSVSPGERVSFSCRASQSIGTNIH WYQQRTNGSPRLLIKYASESISGIPSRFSGSGSGTDFTLS INSVESEDIADYYCQQNNNWPTTFGAGTKLELKRTVA APSVFIFPPSDEQLKSGTASVVCLLNNFYPREAKVQWK VDNALQSGNSQESVTEQDSKDSTYSLSSTLTLSKADYE KHKVYACEVTHQGLSSPVTKSFNRGEC |
| | ProC1758 HC | Same as CX-122 HC SEQ ID NO: 355 above |
| 378 | ProC900 LC | QGQSGQGCISPRGCPDGPYVMYGGGSSGGSAPRSLL GGGSQILLTQSPVILSVSPGERVSFSCRASQSIGTNIHWY QQRTNGSPRLLIKYASESISGIPSRFSGSGSGTDFTLSINS VESEDIADYYCQQNNNWPTTFGAGTKLELKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC |
| | ProC900 HC | Same as CX-122 HC SEQ ID NO: 355 above |
| 379 | ProC901 LC | QGQSGQGCISPRGCPDGPYVMYGGGSSGGSAPRGLL GGGSQILLTQSPVILSVSPGERVSFSCRASQSIGTNIHWY QQRTNGSPRLLIKYASESISGIPSRFSGSGSGTDFTLSINS VESEDIADYYCQQNNNWPTTFGAGTKLELKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC |
| | ProC901 HC | Same as CX-122 HC SEQ ID NO: 355 above |
| 380 | ProC1259 LC | QGQSGQGCISPRGCPDGPYVMYGGGSSGGSAPRSYG GGSQILLTQSPVILSVSPGERVSFSCRASQSIGTNIHWYQ QRTNGSPRLLIKYASESISGIPSRFSGSGSGTDFTLSINSV ESEDIADYYCQQNNNWPTTFGAGTKLELKRTVAAPSV FIFPPSDEQLKSGTASVVCLLNNFYPREAKVQWKVDNA LQSGNSQESVTEQDSKDSTYSLSSTLTLSKADYEKHKV YACEVTHQGLSSPVTKSFNRGEC |
| | ProC1259 HC | Same as HC SEQ ID NO: 367 above |
| 381 | ProC1752 LC | QGQSGQGCISPRGCPDGPYVMYGGGSSGGSVAPRSM RGGGSQILLTQSPVILSVSPGERVSFSCRASQSIGTNIHW YQQRTNGSPRLLIKYASESISGIPSRFSGSGSGTDFTLSIN SVESEDIADYYCQQNNNWPTTFGAGTKLELKRTVAAP SVFIFPPSDEQLKSGTASVVCLLNNFYPREAKVQWKVD NALQSGNSQESVTEQDSKDSTYSLSSTLTLSKADYEKH KVYACEVTHQGLSSPVTKSFNRGEC |
| | ProC1752 HC | Same as CX-122 HC SEQ ID NO: 355 above |
| 382 | | APRG |
| 383 | | APRSM |
| 384 | | APRGY |

TABLE 17-continued

Exemplary sequences

| SEQ ID NO | Note | Sequence |
|---|---|---|
| 385 | | APRGM |
| 386 | ProC3625 LC | QGQSGQGCISPRGCPDGPYVMYGGGSSGGSPWGLSGK SGGGSQILLTQSPVILSVSPGERVSFSCRASQSIGTNIHW YQQRTNGSPRLLIKYASESISGIPSRFSGSGSGTDFTLSIN SVESEDIADYYCQQNNNWPTTFGAGTKLELKRTVAAP SVFIFPPSDEQLKSGTASVVCLLNNFYPREAKVQWKVD NALQSGNSQESVTEQDSKDSTYSLSSTLTLSKADYEKH KVYACEVTHQGLSSPVTKSFNRGEC |
| | ProC3625 HC | Same as SEQ ID NO: 355 above |
| 387 | ProC3626 LC | QGQSGQGCISPRGCPDGPYVMYGGGSSGGSPYGLSGRS GGGSQILLTQSPVILSVSPGERVSFSCRASQSIGTNIHWY QQRTNGSPRLLIKYASESISGIPSRFSGSGSGTDFTLSINS VESEDIADYYCQQNNNWPTTFGAGTKLELKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC |
| | ProC3626 HC | Same as SEQ ID NO: 355 above |
| 388 | ProC3627 LC | QGQSGQGCISPRGCPDGPYVMYGGGSSGGSPFGLSGRS GGGSQILLTQSPVILSVSPGERVSFSCRASQSIGTNIHWY QQRTNGSPRLLIKYASESISGIPSRFSGSGSGTDFTLSINS VESEDIADYYCQQNNNWPTTFGAGTKLELKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC |
| | ProC3627 HC | Same as SEQ ID NO: 355 above |
| 389 | ProC3628 LC | QGQSGQGCISPRGCPDGPYVMYGGGSSGGSPRGLSGRS GGGSQILLTQSPVILSVSPGERVSFSCRASQSIGTNIHWY QQRTNGSPRLLIKYASESISGIPSRFSGSGSGTDFTLSINS VESEDIADYYCQQNNNWPTTFGAGTKLELKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC |
| | ProC3628 HC | Same as SEQ ID NO: 355 above |
| 390 | ProC3629 LC | QGQSGQGCISPRGCPDGPYVMYGGGSSGGSPAGLSGRS GGGSQILLTQSPVILSVSPGERVSFSCRASQSIGTNIHWY QQRTNGSPRLLIKYASESISGIPSRFSGSGSGTDFTLSINS VESEDIADYYCQQNNNWPTTFGAGTKLELKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC |
| | ProC3629 HC | Same as SEQ ID NO: 355 above |
| 391 | ProC3630 LC | QGQSGQGCISPRGCPDGPYVMYGGGSSGGSLSGRSPW GLGGGSQILLTQSPVILSVSPGERVSFSCRASQSIGTNIH WYQQRTNGSPRLLIKYASESISGIPSRFSGSGSGTDFTLS INSVESEDIADYYCQQNNNWPTTFGAGTKLELKRTVA APSVFIFPPSDEQLKSGTASVVCLLNNFYPREAKVQWK VDNALQSGNSQESVTEQDSKDSTYSLSSTLTLSKADYE KHKVYACEVTHQGLSSPVTKSFNRGEC |
| | ProC3630 HC | Same as SEQ ID NO: 355 above |
| 392 | ProC3631 LC | QGQSGQGCISPRGCPDGPYVMYGGGSSGGSLSGKSPW GLGGGSQILLTQSPVILSVSPGERVSFSCRASQSIGTNIH WYQQRTNGSPRLLIKYASESISGIPSRFSGSGSGTDFTLS INSVESEDIADYYCQQNNNWPTTFGAGTKLELKRTVA APSVFIFPPSDEQLKSGTASVVCLLNNFYPREAKVQWK VDNALQSGNSQESVTEQDSKDSTYSLSSTLTLSKADYE KHKVYACEVTHQGLSSPVTKSFNRGEC |

TABLE 17-continued

| Exemplary sequences | | |
| --- | --- | --- |
| SEQ ID NO | Note | Sequence |
| | ProC3631 HC | Same as SEQ ID NO: 355 above |
| 393 | ProC3632 LC | QGQSGQGCISPRGCPDGPYVMYGGGSSGGSLSGRSPW GLSGGGSQILLTQSPVILSVSPGERVSFSCRASQSIGTNI HWYQQRTNGSPRLLIKYASESISGIPSRFSGSGSGTDFTL SINSVESEDIADYYCQQNNNWPTTFGAGTKLELKRTVA APSVFIFPPSDEQLKSGTASVVCLLNNFYPREAKVQWK VDNALQSGNSQESVTEQDSKDSTYSLSSTLTLSKADYE KHKVYACEVTHQGLSSPVTKSFNRGEC |
| | ProC3632 HC | Same as SEQ ID NO: 355 above |
| 394-494 | | Intentionally left blank |
| 495 | Linking peptide | GGSG |
| 496 | Linking peptide | GGSGG |
| 497 | Linking peptide | GSGSG |
| 498 | Linking peptide | GSGGG |
| 499 | Linking peptide | GGGSG |
| 500 | Linking peptide | GSSSG |
| 501 | Linking peptide | GSSGGSGGSGG |
| 502 | Linking peptide | GGGS |
| 503 | Linking peptide | GGGSGGGS |
| 504 | Linking peptide | GGGSGGGSGGGS |
| 505 | Linking peptide | GGGGSGGGGSGGGGS |
| 506 | Linking peptide | GGGGSGGGGSGGGGSGGGGSGGGGSGGGGS |
| 507 | Linking peptide | GGGGSGGGGS |
| 508 | Linking peptide | GGGGS |
| 509 | Linking peptide | GGGGSGS |
| 510 | Linking peptide | GGGGSGGGGSGGGGSGS |
| 511 | Linking peptide | GGSLDPKGGGGS |
| 512 | Linking peptide | PKSCDKTHTCPPCPAPELLG |
| 513 | Linking peptide | SKYGPPCPPCPAPEFLG |

TABLE 17-continued

Exemplary sequences

| SEQ ID NO | Note | Sequence |
|---|---|---|
| 514 | Linking peptide | GKSSGSGSESKS |
| 515 | Linking peptide | GSTSGSGKSSEGKG |
| 516 | Linking peptide | GSTSGSGKSSEGSGSTKG |
| 517 | Linking peptide | GSTSGSGKPGSGEGSTKG |
| 518 | Linking peptide | GSTSGSGKPGSSEGST |
| 519 | Linking peptide | GGGSSGGS |
| 520 | Linking peptide | GGGGSGGGGSS |
| 521 | Linking peptide | GGGSSGGSGGSSGGS |
| 522 | Linking peptide | GSTSGSGKPGSSEGST |
| 523 | Fc domain hole mutant | ESKYGPPCPPCPAPEFEGGPSVFLFPPKPKDTLMISRTPE VTCVVVDVSQEDPEVQFNWYVDGVEVHNAKTKPREE QFNSTYRVVSVLTVLHQDWLNGKEYKCKVSNKGLPSS IEKTISKAKGQPREPQVCTLPPSQEEMTKNQVSLSCAVK GFYPSDIA VEWESNGQPENNYKTTPPVLDSDGSFFLVS RLTVDKSRWQEGNVFSCSVMHEALHNHYTQKSLSLSL G *Note: the Fc may further comprise a lysine residue (K) at the C-terminus. |
| 524 | Fc domain knob mutant | GSSKYGPPCPPCPAPEFEGGPSVFLFPPKPKDTLMISRTP EVTCVVVDVSQEDPEVQFNWYVDGVEVHNAKTKPRE EQFNSTYRVVSVLTVLHQDWLNGKEYKCKVSNKGLPS SIEKTISKAKGQPREPQVYTLPPCQEEMTKNQVSLWCL VKGFYPSDIA VEWESNGQPENNYKTTPPVLDSDGSFFL YSRLTVDKSRWQEGNVFSCSVMHEALHNHYTQKSLSL SLG* *Note: the Fc may further comprise a lysine residue (K) at the C-terminus. |
| 525 | Human IgG1 | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSCDKTHTCPPCPAPE LLGGPSVFLFPPKPKDTLMISRTPEVTCVVVDVSHEDPE VKFNWYVDGVEVHNAKTKPREEQYNSTYRVVSVLTV LHQDWLNGKEYKCKVSNKALPAPIEKTISKAKGQPREP QVYTLPPSREEMTKNQVSLTCLVKGFYPSDIA VEWESN GQPENNYKTTPPVLDSDGSFFLYSKLTVDKSRWQQGN VFSCSVMHEALHNHYTQKSLSLSPG* *Note: the Fc may further comprise a lysine residue (K) at the C-terminus. |
| 526 | Human IgG2 | ASTKGPSVFPLAPCSRSTSESTAALGCLVKDYFPEPVTV SWNSGALTSGVHTFPAVLQSSGLYSLSSVVTVPSSNFG TQTYTCNVDHKPSNTKVDKTVERKCCVECPPCPAPPV AGPSVFLFPPKPKDTLMISRTPEVTCVVVDVSHEDPEV QFNWYVDGVEVHNAKTKPREEQFNSTFRVVSVLTVVH QDWLNGKEYKCKVSNKGLPAPIEKTISKTKGQPREPQV YTLPPSREEMTKNQVSLTCLVKGFYPSDISVEWESNGQ PENNYKTTPPMLDSDGSFFLYSKLTVDKSRWQQGNVF SCSVMHEALHNHYTQKSLSLSPG* *Note: the Fc may further comprise a lysine residue (K) at the C-terminus. |
| 527 | Human IgG3 | ASTKGPSVFPLAPCSRSTSGGTAALGCLVKDYFPEPVT VSWNSGALTSGVHTFPAVLQSSGLYSLSSVVTVPSSSL GTQTYTCNVNHKPSNTKVDKRVELKTPLGDTTHTCPR CPEPKSCDTPPPCPRCPEPKSCDTPPPCPRCPEPKSCDTP |

TABLE 17-continued

Exemplary sequences

| SEQ ID NO | Note | Sequence |
|---|---|---|
| | | PPCPRCPAPELLGGPSVFLFPPKPKDTLMISRTPEVTCVV VDVSHEDPEVQFKWYVDGVEVHNAKTKPREEQYNST FRVVSVLTVLHQDWLNGKEYKCKVSNKALPAPIEKTIS KTKGQPREPQVYTLPPSREEMTKNQVSLTCLVKGFYPS DIA VEWESSGQPENNYNTTPPMLDSDGSFFLYSKLTVD KSRWQQGNIFSCSVMHEALHNRFTQKSLSLSPG* *Note: the Fc may further comprise a lysine residue (K) at the C-terminus. |
| 528 | Human IgG4 | ASTKGPSVFPLAPCSRSTSESTAALGCLVKDYFPEPVTV SWNSGALTSGVHTFPAVLQSSGLYSLSSVVTVPSSSLGT KTYTCNVDHKPSNTKVDKRVESKYGPPCPSCPAPEFLG GPSVFLFPPKPKDTLMISRTPEVTCVVVDVSQEDPEVQF NWYVDGVEVHNAKTKPREEQFNSTYRVVSVLTVLHQ DWLNGKEYKCKVSNKGLPSSIEKTISKAKGQPREPQVY TLPPSQEEMTKNQVSLTCLVKGFYPSDIA VEWESNGQP ENNYKTTPPVLDSDGSFFLYSRLTVDKSRWQEGNVFSC SVMHEALHNHYTQKSLSLSLG* *Note: the Fc may further comprise a lysine residue (K) at the C-terminus. |
| 529 | | PRFKIIGG |
| 530 | | PRFRIIGG |
| 531 | | SSRHRRALD |
| 532 | | RKSSIIIRMRDVVL |
| 533 | | SSSFDKGKYKKGDDA |
| 534 | | SSSFDKGKYKRGDDA |
| 535 | | IEGR |
| 536 | | IDGR |
| 537 | | GGSIDGR |
| 538 | | PLGLWA |
| 539 | | GPQGIAGQ |
| 540 | | GPQGLLGA |
| 541 | | GIAGQ |
| 542 | | GPLGIAGI |
| 543 | | GPEGLRVG |
| 544 | | YGAGLGVV |
| 545 | | AGLGVVER |
| 546 | | AGLGISST |
| 547 | | EPQALAMS |
| 548 | | QALAMSAI |
| 549 | | AAYHLVSQ |
| 550 | | MDAFLESS |
| 551 | | ESLPVVAV |
| 552 | | SAPAVESE |
| 553 | | DVAQFVLT |
| 554 | | VAQFVLTE |
| 555 | | AQFVLTEG |

TABLE 17-continued

Exemplary sequences

| SEQ ID NO | Note | Sequence |
|---|---|---|
| 556 | | PVQPIGPQ |
| 557 | Unmasked control c225v5 antibody heavy chain | QVQLKQSGPGLVQPSQSLSITCTVSGFSLTNYGVHWVR QSPGKGLEWLGVIWSGGNTDYNTPFTSRLSINKDNSKS QVFFKMNSLQSQDTAIYYCARALTYYDYEFAYWGQG TLVTVSAASTKGPSVFPLAPSSKSTSGGTAALGCLVKD YFPEPVTVSWNSGALTSGVHTFPAVLQSSGLYSLSSVV TVPSSSLGTQTYICNVNHKPSNTKVDKKVEPKSCDKTH TCPPCPAPELLGGPSVFLFPPKPKDTLMISRTPEVTCVV VDVSHEDPEVKFNWYVDGVEVHNAKTKPREEQYNST YRVVSVLTVLHQDWLNGKEYKCKVSNKALPAPIEKTIS KAKGQPREPQVYTLPPSRDELTKNQVSLTCLVKGFYPS DIAVEWESNGQPENNYKTTPPVLDSDGSFFLYSKLTVD KSRWQQGNVFSCSVMHEALHNHYTQKSLSLSPGK |
| 558 | Unmasked control c225v5 antibody light chain | QILLTQSPVILSVSPGERVSFSCRASQSIGTNIHWYQQRT NGSPRLLIKYASESISGIPSRFSGSGSGTDFTLSINSVESE DIADYYCQQNNNWPTTFGAGTKLELKRTVAAPSVFIFP PSDEQLKSGTASVVCLLNNFYPREAKVQWKVDNALQS GNSQESVTEQDSKDSTYSLSSTLTLSKADYEKHKVYAC EVTHQGLSSPVTKSFNRGEC |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

All publications, patent applications, patents, and other references mentioned herein are incorporated by reference in their entirety. In case of conflict, the present specification, including definitions, will control. In addition section headings, the materials, methods, and examples are illustrative only and not intended to be limiting.

What is claimed is:

1. An isolated polypeptide comprising a substrate, wherein the substrate comprises a sequence selected from the group consisting of SEQ ID NOs: 13, 163, 164, 177, 178, 191-193, 690, and 691, wherein the isolated polypeptide comprises a first linking peptide (LP1) N-terminal to the sequence, and a second linking peptide (LP2) C-terminal to the sequence.

2. The isolated polypeptide of claim 1, wherein the substrate comprises SEQ ID NO: 12.

3. The isolated polypeptide of claim 1, wherein the substrate comprises SEQ ID NO: 11.

4. The isolated polypeptide of claim 1, wherein the substrate comprises SEQ ID NO: 223.

5. The isolated polypeptide of claim 1, wherein the substrate comprises SEQ ID NO: 120.

6. The isolated polypeptide of claim 1, wherein the substrate comprises SEQ ID NO: 121.

7. The isolated polypeptide of claim 1, wherein the substrate comprises SEQ ID NO: 132.

8. The isolated polypeptide of claim 1, wherein the substrate comprises SEQ ID NO: 138.

9. The isolated polypeptide of claim 1, wherein the substrate comprises SEQ ID NO: 144.

10. The isolated polypeptide of claim 1, wherein the substrate comprises SEQ ID NO: 150.

11. The isolated polypeptide of claim 1, wherein the substrate comprises SEQ ID NO: 693.

12. The isolated polypeptide of claim 1, wherein the substrate comprises SEQ ID NO: 695.

13. An isolated polypeptide comprising an amino acid sequence selected from the group consisting of SEQ ID NO: 12, 13, 163, 164, 177, 178, 191-193, 690, and 691, wherein the isolated polypeptide is an activatable molecule and further comprises an active moiety (AM) that specifically binds a target.

14. The isolated polypeptide of claim 13, wherein the AM is coupled to the substrate.

15. The isolated polypeptide of claim 14, wherein the AM is coupled directly to the substrate.

16. The isolated polypeptide of claim 14, wherein the AM is coupled indirectly to the substrate via a linking peptide.

17. The isolated polypeptide of claim 13, wherein the AM is a therapeutic macromolecule.

18. The isolated polypeptide of claim 13, wherein the AM is a cytokine or a chimeric antigen receptor.

19. The isolated polypeptide of claim 13, wherein the substrate comprises SEQ ID NO: 12.

20. The isolated polypeptide of claim 13, wherein the substrate comprises SEQ ID NO: 11.

21. The isolated polypeptide of claim 13, wherein the substrate comprises SEQ ID NO: 223.

22. The isolated polypeptide of claim 13, wherein the substrate comprises SEQ ID NO: 120.

23. The isolated polypeptide of claim 13, wherein the substrate comprises SEQ ID NO: 121.

24. The isolated polypeptide of claim 13, wherein the substrate comprises SEQ ID NO: 132.

25. The isolated polypeptide of claim 13, wherein the substrate comprises SEQ ID NO: 138.

26. The isolated polypeptide of claim 13, wherein the substrate comprises SEQ ID NO: 144.

27. The isolated polypeptide of claim 13, wherein the substrate comprises SEQ ID NO: 150.

28. The isolated polypeptide of claim 13, wherein the substrate comprises SEQ ID NO: 693.

29. The isolated polypeptide of claim 13, wherein the substrate comprises SEQ ID NO: 695.

30. An isolated polypeptide comprising a substrate, wherein the substrate comprises a sequence selected from the group consisting of SEQ ID NOs: 11, 120, 132, 138, 144, 222 and 223.

* * * * *

SEQUENCE LISTING

```
Sequence total quantity: 705
SEQ ID NO: 1          moltype =   length =
SEQUENCE: 1
000

SEQ ID NO: 2          moltype = AA  length = 4
FEATURE               Location/Qualifiers
source                1..4
                      mol_type = protein
                      organism = synthetic construct
SEQUENCE: 2
PWGL                                                          4

SEQ ID NO: 3          moltype = AA  length = 4
FEATURE               Location/Qualifiers
source                1..4
                      mol_type = protein
                      organism = synthetic construct
SEQUENCE: 3
PFGL                                                          4

SEQ ID NO: 4          moltype = AA  length = 4
FEATURE               Location/Qualifiers
source                1..4
                      mol_type = protein
                      organism = synthetic construct
SEQUENCE: 4
PYGL                                                          4

SEQ ID NO: 5          moltype = AA  length = 4
FEATURE               Location/Qualifiers
source                1..4
                      mol_type = protein
                      organism = synthetic construct
SEQUENCE: 5
```

```
PMGL                                                                4

SEQ ID NO: 6            moltype = AA  length = 4
FEATURE                 Location/Qualifiers
source                  1..4
                        mol_type = protein
                        organism = synthetic construct SEQUENCE: 6
PRGL                                                                4

SEQ ID NO: 7            moltype = AA  length = 4
FEATURE                 Location/Qualifiers
source                  1..4
                        mol_type = protein
                        organism = synthetic construct SEQUENCE: 7
PKGL                                                                4

SEQ ID NO: 8            moltype = AA  length = 4
FEATURE                 Location/Qualifiers
source                  1..4
                        mol_type = protein
                        organism = synthetic construct SEQUENCE: 8
PQGL                                                                4

SEQ ID NO: 9            moltype = AA  length = 7
FEATURE                 Location/Qualifiers
source                  1..7
                        mol_type = protein
                        organism = synthetic construct SEQUENCE: 9
PWGLRSN                                                             7

SEQ ID NO: 10           moltype = AA  length = 7
FEATURE                 Location/Qualifiers
source                  1..7
                        mol_type = protein
                        organism = synthetic construct SEQUENCE: 10
RSPWGLN                                                             7

SEQ ID NO: 11           moltype = AA  length = 11
FEATURE                 Location/Qualifiers
source                  1..11
                        mol_type = protein
                        organism = synthetic construct SEQUENCE: 11
GPWGLSGRSN I                                                        11

SEQ ID NO: 12           moltype = AA  length = 8
FEATURE                 Location/Qualifiers
source                  1..8
                        mol_type = protein
                        organism = synthetic construct SEQUENCE: 12
PWGLSGRS                                                            8

SEQ ID NO: 13           moltype = AA  length = 8
FEATURE                 Location/Qualifiers
source                  1..8
                        mol_type = protein
                        organism = synthetic construct SEQUENCE: 13
GRSPWGLL                                                            8

SEQ ID NO: 14           moltype = AA  length = 14
FEATURE                 Location/Qualifiers
source                  1..14
                        mol_type = protein
                        organism = synthetic construct SEQUENCE: 14
APMGLKHLSG RSNI                                                     14

SEQ ID NO: 15           moltype = AA  length = 11
FEATURE                 Location/Qualifiers
source                  1..11
                        mol_type = protein
                        organism = synthetic construct
```

```
SEQUENCE: 15
GPYGLSGRSN I                                                         11

SEQ ID NO: 16         moltype = AA   length = 8
FEATURE               Location/Qualifiers
source                1..8
                      mol_type = protein
                      organism = synthetic construct
SEQUENCE: 16
APRSPWGL                                                             8

SEQ ID NO: 17         moltype = AA   length = 7
FEATURE               Location/Qualifiers
source                1..7
                      mol_type = protein
                      organism = synthetic construct
SEQUENCE: 17
PWGLPRS                                                              7

SEQ ID NO: 18         moltype = AA   length = 8
FEATURE               Location/Qualifiers
source                1..8
                      mol_type = protein
                      organism = synthetic construct
SEQUENCE: 18
PRSPWGLL                                                             8

SEQ ID NO: 19         moltype = AA   length = 7
FEATURE               Location/Qualifiers
source                1..7
                      mol_type = protein
                      organism = synthetic construct
SEQUENCE: 19
PWGLSRS                                                              7

SEQ ID NO: 20         moltype = AA   length = 7
FEATURE               Location/Qualifiers
source                1..7
                      mol_type = protein
                      organism = synthetic construct
SEQUENCE: 20
PFGLSRS                                                              7

SEQ ID NO: 21         moltype = AA   length = 13
FEATURE               Location/Qualifiers
source                1..13
                      mol_type = protein
                      organism = synthetic construct
SEQUENCE: 21
APMGLKHDHQ SRS                                                       13

SEQ ID NO: 22         moltype = AA   length = 13
FEATURE               Location/Qualifiers
source                1..13
                      mol_type = protein
                      organism = synthetic construct
SEQUENCE: 22
DHQSRSAPMG LKH                                                       13

SEQ ID NO: 23         moltype = AA   length = 6
FEATURE               Location/Qualifiers
source                1..6
                      mol_type = protein
                      organism = synthetic construct
SEQUENCE: 23
KPRGLN                                                               6

SEQ ID NO: 24         moltype = AA   length = 6
FEATURE               Location/Qualifiers
source                1..6
                      mol_type = protein
                      organism = synthetic construct
SEQUENCE: 24
KPRGLF                                                               6

SEQ ID NO: 25         moltype = AA   length = 7
FEATURE               Location/Qualifiers
source                1..7
                      mol_type = protein
```

```
                         organism = synthetic construct
SEQUENCE: 25
APMGLKH                                                          7

SEQ ID NO: 26           moltype = AA   length = 7
FEATURE                 Location/Qualifiers
source                  1..7
                        mol_type = protein
                        organism = synthetic construct
SEQUENCE: 26
LSGRSNI                                                          7

SEQ ID NO: 27           moltype = AA   length = 6
FEATURE                 Location/Qualifiers
source                  1..6
                        mol_type = protein
                        organism = synthetic construct
SEQUENCE: 27
DHQSRS                                                           6

SEQ ID NO: 28           moltype = AA   length = 5
FEATURE                 Location/Qualifiers
source                  1..5
                        mol_type = protein
                        organism = synthetic construct
SEQUENCE: 28
HQSRS                                                            5

SEQ ID NO: 29           moltype =    length =
SEQUENCE: 29
000

SEQ ID NO: 30           moltype = AA   length = 5
FEATURE                 Location/Qualifiers
source                  1..5
                        mol_type = protein
                        organism = synthetic construct
SEQUENCE: 30
LSGRS                                                            5

SEQ ID NO: 31           moltype = AA   length = 4
FEATURE                 Location/Qualifiers
source                  1..4
                        mol_type = protein
                        organism = synthetic construct
SEQUENCE: 31
SGRS                                                             4

SEQ ID NO: 32           moltype = AA   length = 6
FEATURE                 Location/Qualifiers
source                  1..6
                        mol_type = protein
                        organism = synthetic construct
SEQUENCE: 32
SGRSNI                                                           6

SEQ ID NO: 33           moltype =    length =
SEQUENCE: 33
000

SEQ ID NO: 34           moltype = AA   length = 4
FEATURE                 Location/Qualifiers
source                  1..4
                        mol_type = protein
                        organism = synthetic construct
SEQUENCE: 34
APRS                                                             4

SEQ ID NO: 35           moltype =    length =
SEQUENCE: 35
000

SEQ ID NO: 36           moltype =    length =
SEQUENCE: 36
000

SEQ ID NO: 37           moltype = AA   length = 6
FEATURE                 Location/Qualifiers
source                  1..6
```

```
                          mol_type = protein
                          organism = synthetic construct
SEQUENCE: 37
APRSLL                                                        6

SEQ ID NO: 38            moltype = AA  length = 6
FEATURE                  Location/Qualifiers
source                   1..6
                         mol_type = protein
                         organism = synthetic construct
SEQUENCE: 38
APRGLL                                                        6

SEQ ID NO: 39            moltype = AA  length = 5
FEATURE                  Location/Qualifiers
source                   1..5
                         mol_type = protein
                         organism = synthetic construct
SEQUENCE: 39
APRSY                                                         5

SEQ ID NO: 40            moltype = AA  length = 7
FEATURE                  Location/Qualifiers
source                   1..7
                         mol_type = protein
                         organism = synthetic construct
SEQUENCE: 40
VAPRSMR                                                       7

SEQ ID NO: 41            moltype = AA  length = 7
FEATURE                  Location/Qualifiers
source                   1..7
                         mol_type = protein
                         organism = synthetic construct
SEQUENCE: 41
PWGLKSN                                                       7

SEQ ID NO: 42            moltype = AA  length = 7
FEATURE                  Location/Qualifiers
source                   1..7
                         mol_type = protein
                         organism = synthetic construct
SEQUENCE: 42
PYGLRSN                                                       7

SEQ ID NO: 43            moltype = AA  length = 7
FEATURE                  Location/Qualifiers
source                   1..7
                         mol_type = protein
                         organism = synthetic construct
SEQUENCE: 43
PFGLRSN                                                       7

SEQ ID NO: 44            moltype = AA  length = 7
FEATURE                  Location/Qualifiers
source                   1..7
                         mol_type = protein
                         organism = synthetic construct
SEQUENCE: 44
PRGLRSN                                                       7

SEQ ID NO: 45            moltype = AA  length = 7
FEATURE                  Location/Qualifiers
source                   1..7
                         mol_type = protein
                         organism = synthetic construct
SEQUENCE: 45
PMGLRSN                                                       7

SEQ ID NO: 46            moltype = AA  length = 7
FEATURE                  Location/Qualifiers
source                   1..7
                         mol_type = protein
                         organism = synthetic construct
SEQUENCE: 46
PKGLRSN                                                       7

SEQ ID NO: 47            moltype = AA  length = 7
FEATURE                  Location/Qualifiers
```

-continued

```
source                  1..7
                        mol_type = protein
                        organism = synthetic construct
SEQUENCE: 47
PQGLRSN                                                                    7

SEQ ID NO: 48           moltype = AA   length = 6
FEATURE                 Location/Qualifiers
source                  1..6
                        mol_type = protein
                        organism = synthetic construct
SEQUENCE: 48
PWGLRS                                                                     6

SEQ ID NO: 49           moltype = AA   length = 5
FEATURE                 Location/Qualifiers
source                  1..5
                        mol_type = protein
                        organism = synthetic construct
SEQUENCE: 49
PWGLR                                                                      5

SEQ ID NO: 50           moltype = AA   length = 6
FEATURE                 Location/Qualifiers
source                  1..6
                        mol_type = protein
                        organism = synthetic construct
SEQUENCE: 50
PWGLKS                                                                     6

SEQ ID NO: 51           moltype = AA   length = 5
FEATURE                 Location/Qualifiers
source                  1..5
                        mol_type = protein
                        organism = synthetic construct
SEQUENCE: 51
PWGLK                                                                      5

SEQ ID NO: 52           moltype = AA   length = 6
FEATURE                 Location/Qualifiers
source                  1..6
                        mol_type = protein
                        organism = synthetic construct
SEQUENCE: 52
PYGLRS                                                                     6

SEQ ID NO: 53           moltype = AA   length = 5
FEATURE                 Location/Qualifiers
source                  1..5
                        mol_type = protein
                        organism = synthetic construct
SEQUENCE: 53
PYGLR                                                                      5

SEQ ID NO: 54           moltype = AA   length = 6
FEATURE                 Location/Qualifiers
source                  1..6
                        mol_type = protein
                        organism = synthetic construct
SEQUENCE: 54
PYGLKS                                                                     6

SEQ ID NO: 55           moltype = AA   length = 5
FEATURE                 Location/Qualifiers
source                  1..5
                        mol_type = protein
                        organism = synthetic construct
SEQUENCE: 55
PYGLK                                                                      5

SEQ ID NO: 56           moltype = AA   length = 6
FEATURE                 Location/Qualifiers
source                  1..6
                        mol_type = protein
                        organism = synthetic construct
SEQUENCE: 56
PFGLRS                                                                     6

SEQ ID NO: 57           moltype = AA   length = 5
```

-continued

```
FEATURE               Location/Qualifiers
source                1..5
                      mol_type = protein
                      organism = synthetic construct
SEQUENCE: 57
PFGLR                                                              5

SEQ ID NO: 58         moltype = AA  length = 6
FEATURE               Location/Qualifiers
source                1..6
                      mol_type = protein
                      organism = synthetic construct
SEQUENCE: 58
PFGLKS                                                             6

SEQ ID NO: 59         moltype = AA  length = 5
FEATURE               Location/Qualifiers
source                1..5
                      mol_type = protein
                      organism = synthetic construct
SEQUENCE: 59
PFGLK                                                              5

SEQ ID NO: 60         moltype = AA  length = 6
FEATURE               Location/Qualifiers
source                1..6
                      mol_type = protein
                      organism = synthetic construct
SEQUENCE: 60
PMGLRS                                                            6

SEQ ID NO: 61         moltype = AA  length = 5
FEATURE               Location/Qualifiers
source                1..5
                      mol_type = protein
                      organism = synthetic construct
SEQUENCE: 61
PMGLR                                                             5

SEQ ID NO: 62         moltype = AA  length = 6
FEATURE               Location/Qualifiers
source                1..6
                      mol_type = protein
                      organism = synthetic construct
SEQUENCE: 62
PRGLRS                                                            6

SEQ ID NO: 63         moltype = AA  length = 5
FEATURE               Location/Qualifiers
source                1..5
                      mol_type = protein
                      organism = synthetic construct
SEQUENCE: 63
PRGLR                                                             5

SEQ ID NO: 64         moltype = AA  length = 6
FEATURE               Location/Qualifiers
source                1..6
                      mol_type = protein
                      organism = synthetic construct
SEQUENCE: 64
PRGLKS                                                            6

SEQ ID NO: 65         moltype = AA  length = 5
FEATURE               Location/Qualifiers
source                1..5
                      mol_type = protein
                      organism = synthetic construct
SEQUENCE: 65
PRGLK                                                             5

SEQ ID NO: 66         moltype = AA  length = 6
FEATURE               Location/Qualifiers
source                1..6
                      mol_type = protein
                      organism = synthetic construct
SEQUENCE: 66
PKGLRS                                                            6
```

-continued

```
SEQ ID NO: 67          moltype = AA   length = 5
FEATURE                Location/Qualifiers
source                 1..5
                       mol_type = protein
                       organism = synthetic construct
SEQUENCE: 67
PKGLR                                                                    5

SEQ ID NO: 68          moltype = AA   length = 6
FEATURE                Location/Qualifiers
source                 1..6
                       mol_type = protein
                       organism = synthetic construct
SEQUENCE: 68
PKGLKS                                                                   6

SEQ ID NO: 69          moltype = AA   length = 5
FEATURE                Location/Qualifiers
source                 1..5
                       mol_type = protein
                       organism = synthetic construct
SEQUENCE: 69
PKGLK                                                                    5

SEQ ID NO: 70          moltype = AA   length = 6
FEATURE                Location/Qualifiers
source                 1..6
                       mol_type = protein
                       organism = synthetic construct
SEQUENCE: 70
PQGLRS                                                                   6

SEQ ID NO: 71          moltype = AA   length = 5
FEATURE                Location/Qualifiers
source                 1..5
                       mol_type = protein
                       organism = synthetic construct
SEQUENCE: 71
PQGLR                                                                    5

SEQ ID NO: 72          moltype = AA   length = 6
FEATURE                Location/Qualifiers
source                 1..6
                       mol_type = protein
                       organism = synthetic construct
SEQUENCE: 72
PQGLKS                                                                   6

SEQ ID NO: 73          moltype = AA   length = 5
FEATURE                Location/Qualifiers
source                 1..5
                       mol_type = protein
                       organism = synthetic construct
SEQUENCE: 73
PQGLK                                                                    5

SEQ ID NO: 74          moltype = AA   length = 7
FEATURE                Location/Qualifiers
source                 1..7
                       mol_type = protein
                       organism = synthetic construct
SEQUENCE: 74
ALAHGLF                                                                  7

SEQ ID NO: 75          moltype = AA   length = 8
FEATURE                Location/Qualifiers
source                 1..8
                       mol_type = protein
                       organism = synthetic construct
SEQUENCE: 75
ISSGLLSS                                                                 8

SEQ ID NO: 76          moltype = AA   length = 8
FEATURE                Location/Qualifiers
source                 1..8
                       mol_type = protein
                       organism = synthetic construct
SEQUENCE: 76
AVGLLAPP                                                                 8
```

```
SEQ ID NO: 77              moltype = AA   length = 8
FEATURE                    Location/Qualifiers
source                     1..8
                           mol_type = protein
                           organism = synthetic construct
SEQUENCE: 77
LSGRSDNH                                                              8

SEQ ID NO: 78              moltype = AA   length = 13
FEATURE                    Location/Qualifiers
source                     1..13
                           mol_type = protein
                           organism = synthetic construct
SEQUENCE: 78
ISSGLLSGRS DNH                                                        13

SEQ ID NO: 79              moltype = AA   length = 18
FEATURE                    Location/Qualifiers
source                     1..18
                           mol_type = protein
                           organism = synthetic construct
SEQUENCE: 79
AVGLLAPPGG LSGRSDNH                                                   18

SEQ ID NO: 80              moltype = AA   length = 11
FEATURE                    Location/Qualifiers
source                     1..11
                           mol_type = protein
                           organism = synthetic construct
SEQUENCE: 80
APRSALAHGL F                                                          11

SEQ ID NO: 81              moltype = AA   length = 15
FEATURE                    Location/Qualifiers
source                     1..15
                           mol_type = protein
                           organism = synthetic construct
SEQUENCE: 81
CISPRGCPDG PYVMY                                                      15

SEQ ID NO: 82              moltype = AA   length = 15
FEATURE                    Location/Qualifiers
source                     1..15
                           mol_type = protein
                           organism = synthetic construct
SEQUENCE: 82
CISPRGCLDG PYVMY                                                      15

SEQ ID NO: 83              moltype = AA   length = 7
FEATURE                    Location/Qualifiers
source                     1..7
                           mol_type = protein
                           organism = synthetic construct
SEQUENCE: 83
KSPWGLN                                                               7

SEQ ID NO: 84              moltype = AA   length = 7
FEATURE                    Location/Qualifiers
source                     1..7
                           mol_type = protein
                           organism = synthetic construct
SEQUENCE: 84
RSPYGLN                                                               7

SEQ ID NO: 85              moltype = AA   length = 7
FEATURE                    Location/Qualifiers
source                     1..7
                           mol_type = protein
                           organism = synthetic construct
SEQUENCE: 85
RSPFGLN                                                               7

SEQ ID NO: 86              moltype = AA   length = 7
FEATURE                    Location/Qualifiers
source                     1..7
                           mol_type = protein
                           organism = synthetic construct
SEQUENCE: 86
```

-continued

```
RSPRGLN                                                           7

SEQ ID NO: 87          moltype = AA  length = 7
FEATURE                Location/Qualifiers
source                 1..7
                       mol_type = protein
                       organism = synthetic construct

SEQUENCE: 87
RSPMGLN                                                           7

SEQ ID NO: 88          moltype = AA  length = 7
FEATURE                Location/Qualifiers
source                 1..7
                       mol_type = protein
                       organism = synthetic construct

SEQUENCE: 88
RSPKGLN                                                           7

SEQ ID NO: 89          moltype = AA  length = 7
FEATURE                Location/Qualifiers
source                 1..7
                       mol_type = protein
                       organism = synthetic construct

SEQUENCE: 89
RSPQGLN                                                           7

SEQ ID NO: 90          moltype = AA  length = 6
FEATURE                Location/Qualifiers
source                 1..6
                       mol_type = protein
                       organism = synthetic construct

SEQUENCE: 90
RSPWGL                                                            6

SEQ ID NO: 91          moltype = AA  length = 6
FEATURE                Location/Qualifiers
source                 1..6
                       mol_type = protein
                       organism = synthetic construct

SEQUENCE: 91
KSPWGL                                                            6

SEQ ID NO: 92          moltype = AA  length = 5
FEATURE                Location/Qualifiers
source                 1..5
                       mol_type = protein
                       organism = synthetic construct

SEQUENCE: 92
RPWGL                                                             5

SEQ ID NO: 93          moltype = AA  length = 5
FEATURE                Location/Qualifiers
source                 1..5
                       mol_type = protein
                       organism = synthetic construct

SEQUENCE: 93
KPWGL                                                             5

SEQ ID NO: 94          moltype = AA  length = 6
FEATURE                Location/Qualifiers
source                 1..6
                       mol_type = protein
                       organism = synthetic construct

SEQUENCE: 94
RSPYGL                                                            6

SEQ ID NO: 95          moltype = AA  length = 6
FEATURE                Location/Qualifiers
source                 1..6
                       mol_type = protein
                       organism = synthetic construct

SEQUENCE: 95
KSPYGL                                                            6

SEQ ID NO: 96          moltype = AA  length = 5
FEATURE                Location/Qualifiers
source                 1..5
                       mol_type = protein
                       organism = synthetic construct
```

```
SEQUENCE: 96
RPYGL                                                          5

SEQ ID NO: 97          moltype = AA   length = 5
FEATURE                Location/Qualifiers
source                 1..5
                       mol_type = protein
                       organism = synthetic construct
SEQUENCE: 97
KPYGL                                                          5

SEQ ID NO: 98          moltype = AA   length = 6
FEATURE                Location/Qualifiers
source                 1..6
                       mol_type = protein
                       organism = synthetic construct
SEQUENCE: 98
RSPFGL                                                         6

SEQ ID NO: 99          moltype = AA   length = 6
FEATURE                Location/Qualifiers
source                 1..6
                       mol_type = protein
                       organism = synthetic construct
SEQUENCE: 99
KSPFGL                                                         6

SEQ ID NO: 100         moltype = AA   length = 5
FEATURE                Location/Qualifiers
source                 1..5
                       mol_type = protein
                       organism = synthetic construct
SEQUENCE: 100
RPFGL                                                          5

SEQ ID NO: 101         moltype = AA   length = 5
FEATURE                Location/Qualifiers
source                 1..5
                       mol_type = protein
                       organism = synthetic construct
SEQUENCE: 101
KPFGL                                                          5

SEQ ID NO: 102         moltype = AA   length = 6
FEATURE                Location/Qualifiers
source                 1..6
                       mol_type = protein
                       organism = synthetic construct
SEQUENCE: 102
RSPMGL                                                         6

SEQ ID NO: 103         moltype = AA   length = 6
FEATURE                Location/Qualifiers
source                 1..6
                       mol_type = protein
                       organism = synthetic construct
SEQUENCE: 103
KSPMGL                                                         6

SEQ ID NO: 104         moltype = AA   length = 5
FEATURE                Location/Qualifiers
source                 1..5
                       mol_type = protein
                       organism = synthetic construct
SEQUENCE: 104
RPMGL                                                          5

SEQ ID NO: 105         moltype = AA   length = 5
FEATURE                Location/Qualifiers
source                 1..5
                       mol_type = protein
                       organism = synthetic construct
SEQUENCE: 105
KPMGL                                                          5

SEQ ID NO: 106         moltype = AA   length = 6
FEATURE                Location/Qualifiers
source                 1..6
                       mol_type = protein
```

```
SEQUENCE: 106
RSPRGL                                                                       6

SEQ ID NO: 107         moltype = AA  length = 6
FEATURE                Location/Qualifiers
source                 1..6
                       mol_type = protein
                       organism = synthetic construct
SEQUENCE: 107
KSPRGL                                                                       6

SEQ ID NO: 108         moltype = AA  length = 6
FEATURE                Location/Qualifiers
source                 1..6
                       mol_type = protein
                       organism = synthetic construct
SEQUENCE: 108
RSPKGL                                                                       6

SEQ ID NO: 109         moltype = AA  length = 6
FEATURE                Location/Qualifiers
source                 1..6
                       mol_type = protein
                       organism = synthetic construct
SEQUENCE: 109
KSPKGL                                                                       6

SEQ ID NO: 110         moltype = AA  length = 6
FEATURE                Location/Qualifiers
source                 1..6
                       mol_type = protein
                       organism = synthetic construct
SEQUENCE: 110
RSPQGL                                                                       6

SEQ ID NO: 111         moltype = AA  length = 6
FEATURE                Location/Qualifiers
source                 1..6
                       mol_type = protein
                       organism = synthetic construct
SEQUENCE: 111
KSPQGL                                                                       6

SEQ ID NO: 112         moltype = AA  length = 5
FEATURE                Location/Qualifiers
source                 1..5
                       mol_type = protein
                       organism = synthetic construct
SEQUENCE: 112
RPQGL                                                                        5

SEQ ID NO: 113         moltype = AA  length = 5
FEATURE                Location/Qualifiers
source                 1..5
                       mol_type = protein
                       organism = synthetic construct
SEQUENCE: 113
KPQGL                                                                        5

SEQ ID NO: 114         moltype = AA  length = 11
FEATURE                Location/Qualifiers
source                 1..11
                       mol_type = protein
                       organism = synthetic construct
SEQUENCE: 114
GPWGLSGKSN I                                                                11

SEQ ID NO: 115         moltype = AA  length = 11
FEATURE                Location/Qualifiers
source                 1..11
                       mol_type = protein
                       organism = synthetic construct
SEQUENCE: 115
GPFGLSGRSN I                                                                11

SEQ ID NO: 116         moltype = AA  length = 11
FEATURE                Location/Qualifiers
source                 1..11
```

-continued

```
                              mol_type = protein
                              organism = synthetic construct
SEQUENCE: 116
GPRGLSGRSN I                                                     11

SEQ ID NO: 117                moltype = AA  length = 11
FEATURE                       Location/Qualifiers
source                        1..11
                              mol_type = protein
                              organism = synthetic construct
SEQUENCE: 117
GPMGLSGRSN I                                                     11

SEQ ID NO: 118                moltype = AA  length = 11
FEATURE                       Location/Qualifiers
source                        1..11
                              mol_type = protein
                              organism = synthetic construct
SEQUENCE: 118
GPKGLSGRSN I                                                     11

SEQ ID NO: 119                moltype = AA  length = 11
FEATURE                       Location/Qualifiers
source                        1..11
                              mol_type = protein
                              organism = synthetic construct
SEQUENCE: 119
GPQGLSGRSN I                                                     11

SEQ ID NO: 120                moltype = AA  length = 10
FEATURE                       Location/Qualifiers
source                        1..10
                              mol_type = protein
                              organism = synthetic construct
SEQUENCE: 120
PWGLSGRSNI                                                       10

SEQ ID NO: 121                moltype = AA  length = 10
FEATURE                       Location/Qualifiers
source                        1..10
                              mol_type = protein
                              organism = synthetic construct
SEQUENCE: 121
PWGLSGKSNI                                                       10

SEQ ID NO: 122                moltype = AA  length = 10
FEATURE                       Location/Qualifiers
source                        1..10
                              mol_type = protein
                              organism = synthetic construct
SEQUENCE: 122
PFGLSGRSNI                                                       10

SEQ ID NO: 123                moltype = AA  length = 10
FEATURE                       Location/Qualifiers
source                        1..10
                              mol_type = protein
                              organism = synthetic construct
SEQUENCE: 123
PFGLSGKSNI                                                       10

SEQ ID NO: 124                moltype = AA  length = 10
FEATURE                       Location/Qualifiers
source                        1..10
                              mol_type = protein
                              organism = synthetic construct
SEQUENCE: 124
PMGLSGRSNI                                                       10

SEQ ID NO: 125                moltype = AA  length = 10
FEATURE                       Location/Qualifiers
source                        1..10
                              mol_type = protein
                              organism = synthetic construct
SEQUENCE: 125
PMGLSGKSNI                                                       10

SEQ ID NO: 126                moltype = AA  length = 10
FEATURE                       Location/Qualifiers
```

```
source                     1..10
                           mol_type = protein
                           organism = synthetic construct
SEQUENCE: 126
PRGLSGRSNI                                                                    10

SEQ ID NO: 127             moltype = AA  length = 10
FEATURE                    Location/Qualifiers
source                     1..10
                           mol_type = protein
                           organism = synthetic construct
SEQUENCE: 127
PRGLSGKSNI                                                                    10

SEQ ID NO: 128             moltype = AA  length = 10
FEATURE                    Location/Qualifiers
source                     1..10
                           mol_type = protein
                           organism = synthetic construct
SEQUENCE: 128
PKGLSGRSNI                                                                    10

SEQ ID NO: 129             moltype = AA  length = 10
FEATURE                    Location/Qualifiers
source                     1..10
                           mol_type = protein
                           organism = synthetic construct
SEQUENCE: 129
PKGLSGKSNI                                                                    10

SEQ ID NO: 130             moltype = AA  length = 10
FEATURE                    Location/Qualifiers
source                     1..10
                           mol_type = protein
                           organism = synthetic construct
SEQUENCE: 130
PQGLSGRSNI                                                                    10

SEQ ID NO: 131             moltype = AA  length = 10
FEATURE                    Location/Qualifiers
source                     1..10
                           mol_type = protein
                           organism = synthetic construct
SEQUENCE: 131
PQGLSGKSNI                                                                    10

SEQ ID NO: 132             moltype = AA  length = 11
FEATURE                    Location/Qualifiers
source                     1..11
                           mol_type = protein
                           organism = synthetic construct
SEQUENCE: 132
GPWGLSGRSA N                                                                  11

SEQ ID NO: 133             moltype = AA  length = 11
FEATURE                    Location/Qualifiers
source                     1..11
                           mol_type = protein
                           organism = synthetic construct
SEQUENCE: 133
GPFGLSGRSA N                                                                  11

SEQ ID NO: 134             moltype = AA  length = 11
FEATURE                    Location/Qualifiers
source                     1..11
                           mol_type = protein
                           organism = synthetic construct
SEQUENCE: 134
GPRGLSGRSA N                                                                  11

SEQ ID NO: 135             moltype = AA  length = 11
FEATURE                    Location/Qualifiers
source                     1..11
                           mol_type = protein
                           organism = synthetic construct
SEQUENCE: 135
GPMGLSGRSA N                                                                  11

SEQ ID NO: 136             moltype = AA  length = 11
```

-continued

```
FEATURE              Location/Qualifiers
source               1..11
                     mol_type = protein
                     organism = synthetic construct
SEQUENCE: 136
GPKGLSGRSA N                                                      11

SEQ ID NO: 137       moltype = AA  length = 11
FEATURE              Location/Qualifiers
source               1..11
                     mol_type = protein
                     organism = synthetic construct
SEQUENCE: 137
GPQGLSGRSA N                                                      11

SEQ ID NO: 138       moltype = AA  length = 10
FEATURE              Location/Qualifiers
source               1..10
                     mol_type = protein
                     organism = synthetic construct
SEQUENCE: 138
GPWGLSGRSA                                                        10

SEQ ID NO: 139       moltype = AA  length = 10
FEATURE              Location/Qualifiers
source               1..10
                     mol_type = protein
                     organism = synthetic construct
SEQUENCE: 139
GPFGLSGRSA                                                        10

SEQ ID NO: 140       moltype = AA  length = 10
FEATURE              Location/Qualifiers
source               1..10
                     mol_type = protein
                     organism = synthetic construct
SEQUENCE: 140
GPRGLSGRSA                                                        10

SEQ ID NO: 141       moltype = AA  length = 10
FEATURE              Location/Qualifiers
source               1..10
                     mol_type = protein
                     organism = synthetic construct
SEQUENCE: 141
GPMGLSGRSA                                                        10

SEQ ID NO: 142       moltype = AA  length = 10
FEATURE              Location/Qualifiers
source               1..10
                     mol_type = protein
                     organism = synthetic construct
SEQUENCE: 142
GPKGLSGRSA                                                        10

SEQ ID NO: 143       moltype = AA  length = 10
FEATURE              Location/Qualifiers
source               1..10
                     mol_type = protein
                     organism = synthetic construct
SEQUENCE: 143
GPQGLSGRSA                                                        10

SEQ ID NO: 144       moltype = AA  length = 11
FEATURE              Location/Qualifiers
source               1..11
                     mol_type = protein
                     organism = synthetic construct
SEQUENCE: 144
GPWGLSGRSN A                                                      11

SEQ ID NO: 145       moltype = AA  length = 11
FEATURE              Location/Qualifiers
source               1..11
                     mol_type = protein
                     organism = synthetic construct
SEQUENCE: 145
GPFGLSGRSN A                                                      11
```

-continued

```
SEQ ID NO: 146            moltype = AA   length = 11
FEATURE                   Location/Qualifiers
source                    1..11
                          mol_type = protein
                          organism = synthetic construct
SEQUENCE: 146
GPRGLSGRSN A                                                     11

SEQ ID NO: 147            moltype = AA   length = 11
FEATURE                   Location/Qualifiers
source                    1..11
                          mol_type = protein
                          organism = synthetic construct
SEQUENCE: 147
GPMGLSGRSN A                                                     11

SEQ ID NO: 148            moltype = AA   length = 11
FEATURE                   Location/Qualifiers
source                    1..11
                          mol_type = protein
                          organism = synthetic construct
SEQUENCE: 148
GPKGLSGRSN A                                                     11

SEQ ID NO: 149            moltype = AA   length = 11
FEATURE                   Location/Qualifiers
source                    1..11
                          mol_type = protein
                          organism = synthetic construct
SEQUENCE: 149
GPQGLSGRSN A                                                     11

SEQ ID NO: 150            moltype = AA   length = 8
FEATURE                   Location/Qualifiers
source                    1..8
                          mol_type = protein
                          organism = synthetic construct
SEQUENCE: 150
PWGLSGKS                                                         8

SEQ ID NO: 151            moltype = AA   length = 8
FEATURE                   Location/Qualifiers
source                    1..8
                          mol_type = protein
                          organism = synthetic construct
SEQUENCE: 151
PYGLSGRS                                                         8

SEQ ID NO: 152            moltype = AA   length = 8
FEATURE                   Location/Qualifiers
source                    1..8
                          mol_type = protein
                          organism = synthetic construct
SEQUENCE: 152
PFGLSGRS                                                         8

SEQ ID NO: 153            moltype = AA   length = 8
FEATURE                   Location/Qualifiers
source                    1..8
                          mol_type = protein
                          organism = synthetic construct
SEQUENCE: 153
PRGLSGRS                                                         8

SEQ ID NO: 154            moltype = AA   length = 8
FEATURE                   Location/Qualifiers
source                    1..8
                          mol_type = protein
                          organism = synthetic construct
SEQUENCE: 154
PMGLSGRS                                                         8

SEQ ID NO: 155            moltype = AA   length = 8
FEATURE                   Location/Qualifiers
source                    1..8
                          mol_type = protein
                          organism = synthetic construct
SEQUENCE: 155
PKGLSGRS                                                         8
```

-continued

```
SEQ ID NO: 156            moltype = AA  length = 8
FEATURE                   Location/Qualifiers
source                    1..8
                          mol_type = protein
                          organism = synthetic construct
SEQUENCE: 156
PQGLSGRS                                                             8

SEQ ID NO: 157            moltype = AA  length = 8
FEATURE                   Location/Qualifiers
source                    1..8
                          mol_type = protein
                          organism = synthetic construct
SEQUENCE: 157
PYGLSGKS                                                             8

SEQ ID NO: 158            moltype = AA  length = 8
FEATURE                   Location/Qualifiers
source                    1..8
                          mol_type = protein
                          organism = synthetic construct
SEQUENCE: 158
PFGLSGKS                                                             8

SEQ ID NO: 159            moltype = AA  length = 8
FEATURE                   Location/Qualifiers
source                    1..8
                          mol_type = protein
                          organism = synthetic construct
SEQUENCE: 159
PRGLSGKS                                                             8

SEQ ID NO: 160            moltype = AA  length = 8
FEATURE                   Location/Qualifiers
source                    1..8
                          mol_type = protein
                          organism = synthetic construct
SEQUENCE: 160
PMGLSGKS                                                             8

SEQ ID NO: 161            moltype = AA  length = 8
FEATURE                   Location/Qualifiers
source                    1..8
                          mol_type = protein
                          organism = synthetic construct
SEQUENCE: 161
PKGLSGKS                                                             8

SEQ ID NO: 162            moltype = AA  length = 8
FEATURE                   Location/Qualifiers
source                    1..8
                          mol_type = protein
                          organism = synthetic construct
SEQUENCE: 162
PQGLSGKS                                                             8

SEQ ID NO: 163            moltype = AA  length = 7
FEATURE                   Location/Qualifiers
source                    1..7
                          mol_type = protein
                          organism = synthetic construct
SEQUENCE: 163
PWGLSGR                                                              7

SEQ ID NO: 164            moltype = AA  length = 7
FEATURE                   Location/Qualifiers
source                    1..7
                          mol_type = protein
                          organism = synthetic construct
SEQUENCE: 164
PWGLSGK                                                              7

SEQ ID NO: 165            moltype = AA  length = 7
FEATURE                   Location/Qualifiers
source                    1..7
                          mol_type = protein
                          organism = synthetic construct
SEQUENCE: 165
```

-continued

```
PYGLSGR                                                       7

SEQ ID NO: 166          moltype = AA  length = 7
FEATURE                 Location/Qualifiers
source                  1..7
                        mol_type = protein
                        organism = synthetic construct
SEQUENCE: 166
PYGLSGK                                                       7

SEQ ID NO: 167          moltype = AA  length = 7
FEATURE                 Location/Qualifiers
source                  1..7
                        mol_type = protein
                        organism = synthetic construct
SEQUENCE: 167
PFGLSGR                                                       7

SEQ ID NO: 168          moltype = AA  length = 7
FEATURE                 Location/Qualifiers
source                  1..7
                        mol_type = protein
                        organism = synthetic construct
SEQUENCE: 168
PFGLSGK                                                       7

SEQ ID NO: 169          moltype = AA  length = 7
FEATURE                 Location/Qualifiers
source                  1..7
                        mol_type = protein
                        organism = synthetic construct
SEQUENCE: 169
PRGLSGR                                                       7

SEQ ID NO: 170          moltype = AA  length = 7
FEATURE                 Location/Qualifiers
source                  1..7
                        mol_type = protein
                        organism = synthetic construct
SEQUENCE: 170
PRGLSGK                                                       7

SEQ ID NO: 171          moltype = AA  length = 7
FEATURE                 Location/Qualifiers
source                  1..7
                        mol_type = protein
                        organism = synthetic construct
SEQUENCE: 171
PMGLSGR                                                       7

SEQ ID NO: 172          moltype = AA  length = 7
FEATURE                 Location/Qualifiers
source                  1..7
                        mol_type = protein
                        organism = synthetic construct
SEQUENCE: 172
PMGLSGK                                                       7

SEQ ID NO: 173          moltype = AA  length = 7
FEATURE                 Location/Qualifiers
source                  1..7
                        mol_type = protein
                        organism = synthetic construct
SEQUENCE: 173
PKGLSGR                                                       7

SEQ ID NO: 174          moltype = AA  length = 7
FEATURE                 Location/Qualifiers
source                  1..7
                        mol_type = protein
                        organism = synthetic construct
SEQUENCE: 174
PKGLSGK                                                       7

SEQ ID NO: 175          moltype = AA  length = 7
FEATURE                 Location/Qualifiers
source                  1..7
                        mol_type = protein
                        organism = synthetic construct
```

```
SEQUENCE: 175
PQGLSGR                                                              7

SEQ ID NO: 176            moltype = AA  length = 7
FEATURE                   Location/Qualifiers
source                    1..7
                          mol_type = protein
                          organism = synthetic construct
SEQUENCE: 176
PQGLSGK                                                              7

SEQ ID NO: 177            moltype = AA  length = 9
FEATURE                   Location/Qualifiers
source                    1..9
                          mol_type = protein
                          organism = synthetic construct
SEQUENCE: 177
LSGRSPWGL                                                            9

SEQ ID NO: 178            moltype = AA  length = 9
FEATURE                   Location/Qualifiers
source                    1..9
                          mol_type = protein
                          organism = synthetic construct
SEQUENCE: 178
LSGKSPWGL                                                            9

SEQ ID NO: 179            moltype = AA  length = 9
FEATURE                   Location/Qualifiers
source                    1..9
                          mol_type = protein
                          organism = synthetic construct
SEQUENCE: 179
LSGRSPYGL                                                            9

SEQ ID NO: 180            moltype = AA  length = 9
FEATURE                   Location/Qualifiers
source                    1..9
                          mol_type = protein
                          organism = synthetic construct
SEQUENCE: 180
LSGKSPYGL                                                            9

SEQ ID NO: 181            moltype = AA  length = 9
FEATURE                   Location/Qualifiers
source                    1..9
                          mol_type = protein
                          organism = synthetic construct
SEQUENCE: 181
LSGRSPFGL                                                            9

SEQ ID NO: 182            moltype = AA  length = 9
FEATURE                   Location/Qualifiers
source                    1..9
                          mol_type = protein
                          organism = synthetic construct
SEQUENCE: 182
LSGKSPFGL                                                            9

SEQ ID NO: 183            moltype = AA  length = 9
FEATURE                   Location/Qualifiers
source                    1..9
                          mol_type = protein
                          organism = synthetic construct
SEQUENCE: 183
LSGRSPRGL                                                            9

SEQ ID NO: 184            moltype = AA  length = 9
FEATURE                   Location/Qualifiers
source                    1..9
                          mol_type = protein
                          organism = synthetic construct
SEQUENCE: 184
LSGKSPRGL                                                            9

SEQ ID NO: 185            moltype = AA  length = 9
FEATURE                   Location/Qualifiers
source                    1..9
                          mol_type = protein
```

```
                          organism = synthetic construct
SEQUENCE: 185
LSGRSPMGL                                                             9

SEQ ID NO: 186            moltype = AA   length = 9
FEATURE                   Location/Qualifiers
source                    1..9
                          mol_type = protein
                          organism = synthetic construct
SEQUENCE: 186
LSGKSPMGL                                                             9

SEQ ID NO: 187            moltype = AA   length = 9
FEATURE                   Location/Qualifiers
source                    1..9
                          mol_type = protein
                          organism = synthetic construct
SEQUENCE: 187
LSGRSPKGL                                                             9

SEQ ID NO: 188            moltype = AA   length = 9
FEATURE                   Location/Qualifiers
source                    1..9
                          mol_type = protein
                          organism = synthetic construct
SEQUENCE: 188
LSGKSPKGL                                                             9

SEQ ID NO: 189            moltype = AA   length = 9
FEATURE                   Location/Qualifiers
source                    1..9
                          mol_type = protein
                          organism = synthetic construct
SEQUENCE: 189
LSGRSPQGL                                                             9

SEQ ID NO: 190            moltype = AA   length = 9
FEATURE                   Location/Qualifiers
source                    1..9
                          mol_type = protein
                          organism = synthetic construct
SEQUENCE: 190
LSGKSPQGL                                                             9

SEQ ID NO: 191            moltype = AA   length = 7
FEATURE                   Location/Qualifiers
source                    1..7
                          mol_type = protein
                          organism = synthetic construct
SEQUENCE: 191
RSPWGLL                                                               7

SEQ ID NO: 192            moltype = AA   length = 7
FEATURE                   Location/Qualifiers
source                    1..7
                          mol_type = protein
                          organism = synthetic construct
SEQUENCE: 192
KSPWGLL                                                               7

SEQ ID NO: 193            moltype = AA   length = 8
FEATURE                   Location/Qualifiers
source                    1..8
                          mol_type = protein
                          organism = synthetic construct
SEQUENCE: 193
GKSPWGLL                                                              8

SEQ ID NO: 194            moltype = AA   length = 8
FEATURE                   Location/Qualifiers
source                    1..8
                          mol_type = protein
                          organism = synthetic construct
SEQUENCE: 194
GRSPYGLL                                                              8

SEQ ID NO: 195            moltype = AA   length = 8
FEATURE                   Location/Qualifiers
source                    1..8
```

```
                                 mol_type = protein
                                 organism = synthetic construct
SEQUENCE: 195
GKSPYGLL                                                             8

SEQ ID NO: 196      moltype = AA   length = 8
FEATURE             Location/Qualifiers
source              1..8
                    mol_type = protein
                    organism = synthetic construct
SEQUENCE: 196
GRSPFGLL                                                             8

SEQ ID NO: 197      moltype = AA   length = 8
FEATURE             Location/Qualifiers
source              1..8
                    mol_type = protein
                    organism = synthetic construct
SEQUENCE: 197
GKSPFGLL                                                             8

SEQ ID NO: 198      moltype = AA   length = 8
FEATURE             Location/Qualifiers
source              1..8
                    mol_type = protein
                    organism = synthetic construct
SEQUENCE: 198
GRSPRGLL                                                             8

SEQ ID NO: 199      moltype = AA   length = 8
FEATURE             Location/Qualifiers
source              1..8
                    mol_type = protein
                    organism = synthetic construct
SEQUENCE: 199
GKSPRGLL                                                             8

SEQ ID NO: 200      moltype = AA   length = 8
FEATURE             Location/Qualifiers
source              1..8
                    mol_type = protein
                    organism = synthetic construct
SEQUENCE: 200
GRSPMGLL                                                             8

SEQ ID NO: 201      moltype = AA   length = 8
FEATURE             Location/Qualifiers
source              1..8
                    mol_type = protein
                    organism = synthetic construct
SEQUENCE: 201
GKSPMGLL                                                             8

SEQ ID NO: 202      moltype = AA   length = 8
FEATURE             Location/Qualifiers
source              1..8
                    mol_type = protein
                    organism = synthetic construct
SEQUENCE: 202
GRSPKGLL                                                             8

SEQ ID NO: 203      moltype = AA   length = 8
FEATURE             Location/Qualifiers
source              1..8
                    mol_type = protein
                    organism = synthetic construct
SEQUENCE: 203
GKSPKGLL                                                             8

SEQ ID NO: 204      moltype = AA   length = 8
FEATURE             Location/Qualifiers
source              1..8
                    mol_type = protein
                    organism = synthetic construct
SEQUENCE: 204
GRSPQGLL                                                             8

SEQ ID NO: 205      moltype = AA   length = 8
FEATURE             Location/Qualifiers
```

-continued

```
source                  1..8
                        mol_type = protein
                        organism = synthetic construct
SEQUENCE: 205
GKSPQGLL                                                             8

SEQ ID NO: 206          moltype = AA  length = 14
FEATURE                 Location/Qualifiers
source                  1..14
                        mol_type = protein
                        organism = synthetic construct
SEQUENCE: 206
APWGLKHLSG RSNI                                                      14

SEQ ID NO: 207          moltype = AA  length = 13
FEATURE                 Location/Qualifiers
source                  1..13
                        mol_type = protein
                        organism = synthetic construct
SEQUENCE: 207
PWGLKHLSGR SNI                                                       13

SEQ ID NO: 208          moltype = AA  length = 14
FEATURE                 Location/Qualifiers
source                  1..14
                        mol_type = protein
                        organism = synthetic construct
SEQUENCE: 208
APWGLKHLSG KSNI                                                      14

SEQ ID NO: 209          moltype = AA  length = 13
FEATURE                 Location/Qualifiers
source                  1..13
                        mol_type = protein
                        organism = synthetic construct
SEQUENCE: 209
PWGLKHLSGK SNI                                                       13

SEQ ID NO: 210          moltype = AA  length = 14
FEATURE                 Location/Qualifiers
source                  1..14
                        mol_type = protein
                        organism = synthetic construct
SEQUENCE: 210
APMGLKHLSG KSNI                                                      14

SEQ ID NO: 211          moltype = AA  length = 13
FEATURE                 Location/Qualifiers
source                  1..13
                        mol_type = protein
                        organism = synthetic construct
SEQUENCE: 211
PMGLKHLSGK SNI                                                       13

SEQ ID NO: 212          moltype = AA  length = 13
FEATURE                 Location/Qualifiers
source                  1..13
                        mol_type = protein
                        organism = synthetic construct
SEQUENCE: 212
PMGLKHLSGR SNI                                                       13

SEQ ID NO: 213          moltype = AA  length = 13
FEATURE                 Location/Qualifiers
source                  1..13
                        mol_type = protein
                        organism = synthetic construct
SEQUENCE: 213
APMGLKLSGR SNI                                                       13

SEQ ID NO: 214          moltype = AA  length = 12
FEATURE                 Location/Qualifiers
source                  1..12
                        mol_type = protein
                        organism = synthetic construct
SEQUENCE: 214
PMGLKLSGRS NI                                                        12

SEQ ID NO: 215          moltype = AA  length = 12
```

-continued

```
FEATURE             Location/Qualifiers
source              1..12
                    mol_type = protein
                    organism = synthetic construct
SEQUENCE: 215
APMGLLSGRS NI                                                      12

SEQ ID NO: 216      moltype = AA  length = 11
FEATURE             Location/Qualifiers
source              1..11
                    mol_type = protein
                    organism = synthetic construct
SEQUENCE: 216
PMGLLSGRSN I                                                       11

SEQ ID NO: 217      moltype = AA  length = 11
FEATURE             Location/Qualifiers
source              1..11
                    mol_type = protein
                    organism = synthetic construct
SEQUENCE: 217
PWGLLSGRSN I                                                       11

SEQ ID NO: 218      moltype = AA  length = 11
FEATURE             Location/Qualifiers
source              1..11
                    mol_type = protein
                    organism = synthetic construct
SEQUENCE: 218
PWGLLSGKSN I                                                       11

SEQ ID NO: 219      moltype = AA  length = 11
FEATURE             Location/Qualifiers
source              1..11
                    mol_type = protein
                    organism = synthetic construct
SEQUENCE: 219
PWGLLSGRSA N                                                       11

SEQ ID NO: 220      moltype = AA  length = 10
FEATURE             Location/Qualifiers
source              1..10
                    mol_type = protein
                    organism = synthetic construct
SEQUENCE: 220
PWGLLSGRSA                                                         10

SEQ ID NO: 221      moltype = AA  length = 11
FEATURE             Location/Qualifiers
source              1..11
                    mol_type = protein
                    organism = synthetic construct
SEQUENCE: 221
PWGLLSGRSN A                                                       11

SEQ ID NO: 222      moltype = AA  length = 11
FEATURE             Location/Qualifiers
source              1..11
                    mol_type = protein
                    organism = synthetic construct
SEQUENCE: 222
PWGLSGRSAN I                                                       11

SEQ ID NO: 223      moltype = AA  length = 10
FEATURE             Location/Qualifiers
source              1..10
                    mol_type = protein
                    organism = synthetic construct
SEQUENCE: 223
PWGLSGRSAN                                                         10

SEQ ID NO: 224      moltype = AA  length = 9
FEATURE             Location/Qualifiers
source              1..9
                    mol_type = protein
                    organism = synthetic construct
SEQUENCE: 224
PWGLSGRSA                                                          9
```

-continued

```
SEQ ID NO: 225        moltype = AA   length = 14
FEATURE               Location/Qualifiers
source                1..14
                      mol_type = protein
                      organism = synthetic construct
SEQUENCE: 225
APWGLKHLSG RSAN                                               14

SEQ ID NO: 226        moltype = AA   length = 13
FEATURE               Location/Qualifiers
source                1..13
                      mol_type = protein
                      organism = synthetic construct
SEQUENCE: 226
PWGLKHLSGR SAN                                                13

SEQ ID NO: 227        moltype = AA   length = 13
FEATURE               Location/Qualifiers
source                1..13
                      mol_type = protein
                      organism = synthetic construct
SEQUENCE: 227
APMGLKLSGR SAN                                                13

SEQ ID NO: 228        moltype = AA   length = 12
FEATURE               Location/Qualifiers
source                1..12
                      mol_type = protein
                      organism = synthetic construct
SEQUENCE: 228
PMGLKLSGRS AN                                                 12

SEQ ID NO: 229        moltype = AA   length = 12
FEATURE               Location/Qualifiers
source                1..12
                      mol_type = protein
                      organism = synthetic construct
SEQUENCE: 229
APMGLLSGRS AN                                                 12

SEQ ID NO: 230        moltype = AA   length = 11
FEATURE               Location/Qualifiers
source                1..11
                      mol_type = protein
                      organism = synthetic construct
SEQUENCE: 230
PMGLLSGRSA N                                                  11

SEQ ID NO: 231        moltype = AA   length = 13
FEATURE               Location/Qualifiers
source                1..13
                      mol_type = protein
                      organism = synthetic construct
SEQUENCE: 231
APWGLKHLSG RSA                                                13

SEQ ID NO: 232        moltype = AA   length = 12
FEATURE               Location/Qualifiers
source                1..12
                      mol_type = protein
                      organism = synthetic construct
SEQUENCE: 232
PWGLKHLSGR SA                                                 12

SEQ ID NO: 233        moltype = AA   length = 12
FEATURE               Location/Qualifiers
source                1..12
                      mol_type = protein
                      organism = synthetic construct
SEQUENCE: 233
APMGLKLSGR SA                                                 12

SEQ ID NO: 234        moltype = AA   length = 11
FEATURE               Location/Qualifiers
source                1..11
                      mol_type = protein
                      organism = synthetic construct
SEQUENCE: 234
PMGLKLSGRS A                                                  11
```

```
SEQ ID NO: 235          moltype = AA  length = 11
FEATURE                 Location/Qualifiers
source                  1..11
                        mol_type = protein
                        organism = synthetic construct
SEQUENCE: 235
APMGLLSGRS A                                                          11

SEQ ID NO: 236          moltype = AA  length = 10
FEATURE                 Location/Qualifiers
source                  1..10
                        mol_type = protein
                        organism = synthetic construct
SEQUENCE: 236
PMGLLSGRSA                                                            10

SEQ ID NO: 237          moltype = AA  length = 14
FEATURE                 Location/Qualifiers
source                  1..14
                        mol_type = protein
                        organism = synthetic construct
SEQUENCE: 237
APWGLKHLSG RSNA                                                       14

SEQ ID NO: 238          moltype = AA  length = 13
FEATURE                 Location/Qualifiers
source                  1..13
                        mol_type = protein
                        organism = synthetic construct
SEQUENCE: 238
PWGLKHLSGR SNA                                                        13

SEQ ID NO: 239          moltype = AA  length = 13
FEATURE                 Location/Qualifiers
source                  1..13
                        mol_type = protein
                        organism = synthetic construct
SEQUENCE: 239
APMGLKLSGR SNA                                                        13

SEQ ID NO: 240          moltype = AA  length = 12
FEATURE                 Location/Qualifiers
source                  1..12
                        mol_type = protein
                        organism = synthetic construct
SEQUENCE: 240
PMGLKLSGRS NA                                                         12

SEQ ID NO: 241          moltype = AA  length = 12
FEATURE                 Location/Qualifiers
source                  1..12
                        mol_type = protein
                        organism = synthetic construct
SEQUENCE: 241
APMGLLSGRS NA                                                         12

SEQ ID NO: 242          moltype = AA  length = 11
FEATURE                 Location/Qualifiers
source                  1..11
                        mol_type = protein
                        organism = synthetic construct
SEQUENCE: 242
PMGLLSGRSN A                                                          11

SEQ ID NO: 243          moltype = AA  length = 11
FEATURE                 Location/Qualifiers
source                  1..11
                        mol_type = protein
                        organism = synthetic construct
SEQUENCE: 243
GPYGLSGKSN I                                                          11

SEQ ID NO: 244          moltype = AA  length = 10
FEATURE                 Location/Qualifiers
source                  1..10
                        mol_type = protein
                        organism = synthetic construct
SEQUENCE: 244
```

```
PYGLSGKSNI                                                  10

SEQ ID NO: 245          moltype = AA  length = 10
FEATURE                 Location/Qualifiers
source                  1..10
                        mol_type = protein
                        organism = synthetic construct
SEQUENCE: 245
PYGLSGRSNI                                                  10

SEQ ID NO: 246          moltype = AA  length = 12
FEATURE                 Location/Qualifiers
source                  1..12
                        mol_type = protein
                        organism = synthetic construct
SEQUENCE: 246
GPYGLLSGRS NI                                               12

SEQ ID NO: 247          moltype = AA  length = 12
FEATURE                 Location/Qualifiers
source                  1..12
                        mol_type = protein
                        organism = synthetic construct
SEQUENCE: 247
GPYGLLSGKS NI                                               12

SEQ ID NO: 248          moltype = AA  length = 11
FEATURE                 Location/Qualifiers
source                  1..11
                        mol_type = protein
                        organism = synthetic construct
SEQUENCE: 248
PYGLLSGRSN I                                                11

SEQ ID NO: 249          moltype = AA  length = 11
FEATURE                 Location/Qualifiers
source                  1..11
                        mol_type = protein
                        organism = synthetic construct
SEQUENCE: 249
PYGLLSGKSN I                                                11

SEQ ID NO: 250          moltype = AA  length = 11
FEATURE                 Location/Qualifiers
source                  1..11
                        mol_type = protein
                        organism = synthetic construct
SEQUENCE: 250
GPYGLSGRSA N                                                11

SEQ ID NO: 251          moltype = AA  length = 10
FEATURE                 Location/Qualifiers
source                  1..10
                        mol_type = protein
                        organism = synthetic construct
SEQUENCE: 251
PYGLSGRSAN                                                  10

SEQ ID NO: 252          moltype = AA  length = 12
FEATURE                 Location/Qualifiers
source                  1..12
                        mol_type = protein
                        organism = synthetic construct
SEQUENCE: 252
GPYGLLSGRS AN                                               12

SEQ ID NO: 253          moltype = AA  length = 11
FEATURE                 Location/Qualifiers
source                  1..11
                        mol_type = protein
                        organism = synthetic construct
SEQUENCE: 253
PYGLLSGRSA N                                                11

SEQ ID NO: 254          moltype = AA  length = 10
FEATURE                 Location/Qualifiers
source                  1..10
                        mol_type = protein
                        organism = synthetic construct
```

-continued

```
SEQUENCE: 254
GPYGLSGRSA                                                              10

SEQ ID NO: 255              moltype = AA  length = 9
FEATURE                     Location/Qualifiers
source                      1..9
                            mol_type = protein
                            organism = synthetic construct
SEQUENCE: 255
PYGLSGRSA                                                               9

SEQ ID NO: 256              moltype = AA  length = 11
FEATURE                     Location/Qualifiers
source                      1..11
                            mol_type = protein
                            organism = synthetic construct
SEQUENCE: 256
GPYGLLSGRS A                                                            11

SEQ ID NO: 257              moltype = AA  length = 10
FEATURE                     Location/Qualifiers
source                      1..10
                            mol_type = protein
                            organism = synthetic construct
SEQUENCE: 257
PYGLLSGRSA                                                              10

SEQ ID NO: 258              moltype = AA  length = 11
FEATURE                     Location/Qualifiers
source                      1..11
                            mol_type = protein
                            organism = synthetic construct
SEQUENCE: 258
GPYGLSGRSN A                                                            11

SEQ ID NO: 259              moltype = AA  length = 10
FEATURE                     Location/Qualifiers
source                      1..10
                            mol_type = protein
                            organism = synthetic construct
SEQUENCE: 259
PYGLSGRSNA                                                              10

SEQ ID NO: 260              moltype = AA  length = 12
FEATURE                     Location/Qualifiers
source                      1..12
                            mol_type = protein
                            organism = synthetic construct
SEQUENCE: 260
GPYGLLSGRS NA                                                           12

SEQ ID NO: 261              moltype = AA  length = 11
FEATURE                     Location/Qualifiers
source                      1..11
                            mol_type = protein
                            organism = synthetic construct
SEQUENCE: 261
PYGLLSGRSN A                                                            11

SEQ ID NO: 262              moltype = AA  length = 9
FEATURE                     Location/Qualifiers
source                      1..9
                            mol_type = protein
                            organism = synthetic construct
SEQUENCE: 262
AAPRSPWGL                                                               9

SEQ ID NO: 263              moltype = AA  length = 9
FEATURE                     Location/Qualifiers
source                      1..9
                            mol_type = protein
                            organism = synthetic construct
SEQUENCE: 263
AAPKSPWGL                                                               9

SEQ ID NO: 264              moltype = AA  length = 9
FEATURE                     Location/Qualifiers
source                      1..9
                            mol_type = protein
```

-continued

```
                              organism = synthetic construct
SEQUENCE: 264
APRSPWGLL                                                                  9

SEQ ID NO: 265               moltype = AA  length = 9
FEATURE                      Location/Qualifiers
source                       1..9
                             mol_type = protein
                             organism = synthetic construct
SEQUENCE: 265
APKSPWGLL                                                                  9

SEQ ID NO: 266               moltype = AA  length = 8
FEATURE                      Location/Qualifiers
source                       1..8
                             mol_type = protein
                             organism = synthetic construct
SEQUENCE: 266
APRSPYGL                                                                   8

SEQ ID NO: 267               moltype = AA  length = 8
FEATURE                      Location/Qualifiers
source                       1..8
                             mol_type = protein
                             organism = synthetic construct
SEQUENCE: 267
APKSPWGL                                                                   8

SEQ ID NO: 268               moltype = AA  length = 8
FEATURE                      Location/Qualifiers
source                       1..8
                             mol_type = protein
                             organism = synthetic construct
SEQUENCE: 268
APKSPYGL                                                                   8

SEQ ID NO: 269               moltype = AA  length = 8
FEATURE                      Location/Qualifiers
source                       1..8
                             mol_type = protein
                             organism = synthetic construct
SEQUENCE: 269
APRSPFGL                                                                   8

SEQ ID NO: 270               moltype = AA  length = 8
FEATURE                      Location/Qualifiers
source                       1..8
                             mol_type = protein
                             organism = synthetic construct
SEQUENCE: 270
APKSPFGL                                                                   8

SEQ ID NO: 271               moltype = AA  length = 8
FEATURE                      Location/Qualifiers
source                       1..8
                             mol_type = protein
                             organism = synthetic construct
SEQUENCE: 271
APRSPRGL                                                                   8

SEQ ID NO: 272               moltype =    length =
SEQUENCE: 272
000

SEQ ID NO: 273               moltype =    length =
SEQUENCE: 273
000

SEQ ID NO: 274               moltype =    length =
SEQUENCE: 274
000

SEQ ID NO: 275               moltype =    length =
SEQUENCE: 275
000

SEQ ID NO: 276               moltype =    length =
SEQUENCE: 276
000
```

-continued

```
SEQ ID NO: 277            moltype =   length =
SEQUENCE: 277
000

SEQ ID NO: 278            moltype = AA  length = 8
FEATURE                   Location/Qualifiers
source                    1..8
                          mol_type = protein
                          organism = synthetic construct
SEQUENCE: 278
APKSPRGL                                                          8

SEQ ID NO: 279            moltype = AA  length = 8
FEATURE                   Location/Qualifiers
source                    1..8
                          mol_type = protein
                          organism = synthetic construct
SEQUENCE: 279
APRSPMGL                                                          8

SEQ ID NO: 280            moltype = AA  length = 8
FEATURE                   Location/Qualifiers
source                    1..8
                          mol_type = protein
                          organism = synthetic construct
SEQUENCE: 280
APKSPMGL                                                          8

SEQ ID NO: 281            moltype = AA  length = 8
FEATURE                   Location/Qualifiers
source                    1..8
                          mol_type = protein
                          organism = synthetic construct
SEQUENCE: 281
APRSPKGL                                                          8

SEQ ID NO: 282            moltype = AA  length = 8
FEATURE                   Location/Qualifiers
source                    1..8
                          mol_type = protein
                          organism = synthetic construct
SEQUENCE: 282
APKSPKGL                                                          8

SEQ ID NO: 283            moltype = AA  length = 8
FEATURE                   Location/Qualifiers
source                    1..8
                          mol_type = protein
                          organism = synthetic construct
SEQUENCE: 283
APRSPQGL                                                          8

SEQ ID NO: 284            moltype = AA  length = 8
FEATURE                   Location/Qualifiers
source                    1..8
                          mol_type = protein
                          organism = synthetic construct
SEQUENCE: 284
APKSPQGL                                                          8

SEQ ID NO: 285            moltype = AA  length = 7
FEATURE                   Location/Qualifiers
source                    1..7
                          mol_type = protein
                          organism = synthetic construct
SEQUENCE: 285
PYGLPRS                                                           7

SEQ ID NO: 286            moltype = AA  length = 7
FEATURE                   Location/Qualifiers
source                    1..7
                          mol_type = protein
                          organism = synthetic construct
SEQUENCE: 286
PFGLPRS                                                           7

SEQ ID NO: 287            moltype = AA  length = 7
FEATURE                   Location/Qualifiers
```

-continued

```
source                       1..7
                             mol_type = protein
                             organism = synthetic construct
SEQUENCE: 287
PRGLPRS                                                              7

SEQ ID NO: 288               moltype = AA   length = 7
FEATURE                      Location/Qualifiers
source                       1..7
                             mol_type = protein
                             organism = synthetic construct
SEQUENCE: 288
PMGLPRS                                                              7

SEQ ID NO: 289               moltype = AA   length = 7
FEATURE                      Location/Qualifiers
source                       1..7
                             mol_type = protein
                             organism = synthetic construct
SEQUENCE: 289
PKGLPRS                                                              7

SEQ ID NO: 290               moltype = AA   length = 7
FEATURE                      Location/Qualifiers
source                       1..7
                             mol_type = protein
                             organism = synthetic construct
SEQUENCE: 290
PQGLPRS                                                              7

SEQ ID NO: 291               moltype = AA   length = 7
FEATURE                      Location/Qualifiers
source                       1..7
                             mol_type = protein
                             organism = synthetic construct
SEQUENCE: 291
PWGLPKS                                                              7

SEQ ID NO: 292               moltype = AA   length = 7
FEATURE                      Location/Qualifiers
source                       1..7
                             mol_type = protein
                             organism = synthetic construct
SEQUENCE: 292
PYGLPKS                                                              7

SEQ ID NO: 293               moltype = AA   length = 7
FEATURE                      Location/Qualifiers
source                       1..7
                             mol_type = protein
                             organism = synthetic construct
SEQUENCE: 293
PFGLPKS                                                              7

SEQ ID NO: 294               moltype = AA   length = 7
FEATURE                      Location/Qualifiers
source                       1..7
                             mol_type = protein
                             organism = synthetic construct
SEQUENCE: 294
PRGLPKS                                                              7

SEQ ID NO: 295               moltype = AA   length = 7
FEATURE                      Location/Qualifiers
source                       1..7
                             mol_type = protein
                             organism = synthetic construct
SEQUENCE: 295
PMGLPKS                                                              7

SEQ ID NO: 296               moltype = AA   length = 7
FEATURE                      Location/Qualifiers
source                       1..7
                             mol_type = protein
                             organism = synthetic construct
SEQUENCE: 296
PKGLPKS                                                              7

SEQ ID NO: 297               moltype = AA   length = 7
```

-continued

```
FEATURE              Location/Qualifiers
source               1..7
                     mol_type = protein
                     organism = synthetic construct
SEQUENCE: 297
PQGLPKS                                                            7

SEQ ID NO: 298       moltype = AA  length = 6
FEATURE              Location/Qualifiers
source               1..6
                     mol_type = protein
                     organism = synthetic construct
SEQUENCE: 298
PWGLPR                                                             6

SEQ ID NO: 299       moltype = AA  length = 6
FEATURE              Location/Qualifiers
source               1..6
                     mol_type = protein
                     organism = synthetic construct
SEQUENCE: 299
PYGLPR                                                             6

SEQ ID NO: 300       moltype = AA  length = 6
FEATURE              Location/Qualifiers
source               1..6
                     mol_type = protein
                     organism = synthetic construct
SEQUENCE: 300
PFGLPR                                                             6

SEQ ID NO: 301       moltype = AA  length = 6
FEATURE              Location/Qualifiers
source               1..6
                     mol_type = protein
                     organism = synthetic construct
SEQUENCE: 301
PRGLPR                                                             6

SEQ ID NO: 302       moltype = AA  length = 6
FEATURE              Location/Qualifiers
source               1..6
                     mol_type = protein
                     organism = synthetic construct
SEQUENCE: 302
PMGLPR                                                             6

SEQ ID NO: 303       moltype = AA  length = 6
FEATURE              Location/Qualifiers
source               1..6
                     mol_type = protein
                     organism = synthetic construct
SEQUENCE: 303
PKGLPR                                                             6

SEQ ID NO: 304       moltype = AA  length = 6
FEATURE              Location/Qualifiers
source               1..6
                     mol_type = protein
                     organism = synthetic construct
SEQUENCE: 304
PQGLPR                                                             6

SEQ ID NO: 305       moltype = AA  length = 6
FEATURE              Location/Qualifiers
source               1..6
                     mol_type = protein
                     organism = synthetic construct
SEQUENCE: 305
PWGLPK                                                             6

SEQ ID NO: 306       moltype = AA  length = 6
FEATURE              Location/Qualifiers
source               1..6
                     mol_type = protein
                     organism = synthetic construct
SEQUENCE: 306
PYGLPK                                                             6
```

-continued

```
SEQ ID NO: 307          moltype = AA   length = 6
FEATURE                 Location/Qualifiers
source                  1..6
                        mol_type = protein
                        organism = synthetic construct
SEQUENCE: 307
PFGLPK                                                            6

SEQ ID NO: 308          moltype = AA   length = 6
FEATURE                 Location/Qualifiers
source                  1..6
                        mol_type = protein
                        organism = synthetic construct
SEQUENCE: 308
PRGLPK                                                            6

SEQ ID NO: 309          moltype = AA   length = 6
FEATURE                 Location/Qualifiers
source                  1..6
                        mol_type = protein
                        organism = synthetic construct
SEQUENCE: 309
PMGLPK                                                            6

SEQ ID NO: 310          moltype = AA   length = 6
FEATURE                 Location/Qualifiers
source                  1..6
                        mol_type = protein
                        organism = synthetic construct
SEQUENCE: 310
PKGLPK                                                            6

SEQ ID NO: 311          moltype = AA   length = 6
FEATURE                 Location/Qualifiers
source                  1..6
                        mol_type = protein
                        organism = synthetic construct
SEQUENCE: 311
PQGLPK                                                            6

SEQ ID NO: 312          moltype = AA   length = 8
FEATURE                 Location/Qualifiers
source                  1..8
                        mol_type = protein
                        organism = synthetic construct
SEQUENCE: 312
PKSPWGLL                                                          8

SEQ ID NO: 313          moltype = AA   length = 7
FEATURE                 Location/Qualifiers
source                  1..7
                        mol_type = protein
                        organism = synthetic construct
SEQUENCE: 313
PRSPWGL                                                           7

SEQ ID NO: 314          moltype = AA   length = 7
FEATURE                 Location/Qualifiers
source                  1..7
                        mol_type = protein
                        organism = synthetic construct
SEQUENCE: 314
PKSPWGL                                                           7

SEQ ID NO: 315          moltype = AA   length = 7
FEATURE                 Location/Qualifiers
source                  1..7
                        mol_type = protein
                        organism = synthetic construct
SEQUENCE: 315
PRSPYGL                                                           7

SEQ ID NO: 316          moltype = AA   length = 7
FEATURE                 Location/Qualifiers
source                  1..7
                        mol_type = protein
                        organism = synthetic construct
SEQUENCE: 316
PKSPYGL                                                           7
```

-continued

```
SEQ ID NO: 317          moltype = AA  length = 7
FEATURE                 Location/Qualifiers
source                  1..7
                        mol_type = protein
                        organism = synthetic construct
SEQUENCE: 317
PRSPFGL                                                              7

SEQ ID NO: 318          moltype = AA  length = 7
FEATURE                 Location/Qualifiers
source                  1..7
                        mol_type = protein
                        organism = synthetic construct
SEQUENCE: 318
PKSPFGL                                                              7

SEQ ID NO: 319          moltype = AA  length = 7
FEATURE                 Location/Qualifiers
source                  1..7
                        mol_type = protein
                        organism = synthetic construct
SEQUENCE: 319
PRSPMGL                                                              7

SEQ ID NO: 320          moltype = AA  length = 7
FEATURE                 Location/Qualifiers
source                  1..7
                        mol_type = protein
                        organism = synthetic construct
SEQUENCE: 320
PKSPMGL                                                              7

SEQ ID NO: 321          moltype = AA  length = 7
FEATURE                 Location/Qualifiers
source                  1..7
                        mol_type = protein
                        organism = synthetic construct
SEQUENCE: 321
PRSPRGL                                                              7

SEQ ID NO: 322          moltype = AA  length = 7
FEATURE                 Location/Qualifiers
source                  1..7
                        mol_type = protein
                        organism = synthetic construct
SEQUENCE: 322
PKSPRGL                                                              7

SEQ ID NO: 323          moltype = AA  length = 7
FEATURE                 Location/Qualifiers
source                  1..7
                        mol_type = protein
                        organism = synthetic construct
SEQUENCE: 323
PRSPKGL                                                              7

SEQ ID NO: 324          moltype = AA  length = 7
FEATURE                 Location/Qualifiers
source                  1..7
                        mol_type = protein
                        organism = synthetic construct
SEQUENCE: 324
PKSPKGL                                                              7

SEQ ID NO: 325          moltype = AA  length = 7
FEATURE                 Location/Qualifiers
source                  1..7
                        mol_type = protein
                        organism = synthetic construct
SEQUENCE: 325
PRSPQGL                                                              7

SEQ ID NO: 326          moltype = AA  length = 7
FEATURE                 Location/Qualifiers
source                  1..7
                        mol_type = protein
                        organism = synthetic construct
SEQUENCE: 326
```

-continued

```
PKSPQGL                                                   7

SEQ ID NO: 327        moltype = AA  length = 8
FEATURE               Location/Qualifiers
source                1..8
                      mol_type = protein
                      organism = synthetic construct

SEQUENCE: 327
PRSPYGLL                                                  8

SEQ ID NO: 328        moltype = AA  length = 8
FEATURE               Location/Qualifiers
source                1..8
                      mol_type = protein
                      organism = synthetic construct

SEQUENCE: 328
PRSPFGLL                                                  8

SEQ ID NO: 329        moltype = AA  length = 8
FEATURE               Location/Qualifiers
source                1..8
                      mol_type = protein
                      organism = synthetic construct

SEQUENCE: 329
PRSPRGLL                                                  8

SEQ ID NO: 330        moltype = AA  length = 8
FEATURE               Location/Qualifiers
source                1..8
                      mol_type = protein
                      organism = synthetic construct

SEQUENCE: 330
PRSPMGLL                                                  8

SEQ ID NO: 331        moltype = AA  length = 8
FEATURE               Location/Qualifiers
source                1..8
                      mol_type = protein
                      organism = synthetic construct

SEQUENCE: 331
PRSPKGLL                                                  8

SEQ ID NO: 332        moltype = AA  length = 8
FEATURE               Location/Qualifiers
source                1..8
                      mol_type = protein
                      organism = synthetic construct

SEQUENCE: 332
PRSPQGLL                                                  8

SEQ ID NO: 333        moltype = AA  length = 7
FEATURE               Location/Qualifiers
source                1..7
                      mol_type = protein
                      organism = synthetic construct

SEQUENCE: 333
PYGLSRS                                                   7

SEQ ID NO: 334        moltype = AA  length = 7
FEATURE               Location/Qualifiers
source                1..7
                      mol_type = protein
                      organism = synthetic construct

SEQUENCE: 334
PFGLSRS                                                   7

SEQ ID NO: 335        moltype = AA  length = 7
FEATURE               Location/Qualifiers
source                1..7
                      mol_type = protein
                      organism = synthetic construct

SEQUENCE: 335
PRGLSRS                                                   7

SEQ ID NO: 336        moltype = AA  length = 7
FEATURE               Location/Qualifiers
source                1..7
                      mol_type = protein
                      organism = synthetic construct
```

```
SEQUENCE: 336
PMGLSRS                                                          7

SEQ ID NO: 337           moltype = AA  length = 7
FEATURE                  Location/Qualifiers
source                   1..7
                         mol_type = protein
                         organism = synthetic construct
SEQUENCE: 337
PKGLSRS                                                          7

SEQ ID NO: 338           moltype = AA  length = 7
FEATURE                  Location/Qualifiers
source                   1..7
                         mol_type = protein
                         organism = synthetic construct
SEQUENCE: 338
PQGLSRS                                                          7

SEQ ID NO: 339           moltype = AA  length = 7
FEATURE                  Location/Qualifiers
source                   1..7
                         mol_type = protein
                         organism = synthetic construct
SEQUENCE: 339
PWGLSKS                                                          7

SEQ ID NO: 340           moltype = AA  length = 7
FEATURE                  Location/Qualifiers
source                   1..7
                         mol_type = protein
                         organism = synthetic construct
SEQUENCE: 340
PYGLSKS                                                          7

SEQ ID NO: 341           moltype = AA  length = 7
FEATURE                  Location/Qualifiers
source                   1..7
                         mol_type = protein
                         organism = synthetic construct
SEQUENCE: 341
PFGLSKS                                                          7

SEQ ID NO: 342           moltype = AA  length = 7
FEATURE                  Location/Qualifiers
source                   1..7
                         mol_type = protein
                         organism = synthetic construct
SEQUENCE: 342
PRGLSKS                                                          7

SEQ ID NO: 343           moltype = AA  length = 7
FEATURE                  Location/Qualifiers
source                   1..7
                         mol_type = protein
                         organism = synthetic construct
SEQUENCE: 343
PMGLSKS                                                          7

SEQ ID NO: 344           moltype = AA  length = 7
FEATURE                  Location/Qualifiers
source                   1..7
                         mol_type = protein
                         organism = synthetic construct
SEQUENCE: 344
PKGLSKS                                                          7

SEQ ID NO: 345           moltype = AA  length = 7
FEATURE                  Location/Qualifiers
source                   1..7
                         mol_type = protein
                         organism = synthetic construct
SEQUENCE: 345
PQGLSKS                                                          7

SEQ ID NO: 346           moltype = AA  length = 6
FEATURE                  Location/Qualifiers
source                   1..6
                         mol_type = protein
```

-continued

```
                        organism = synthetic construct
SEQUENCE: 346
PWGLSR                                                              6

SEQ ID NO: 347          moltype = AA   length = 6
FEATURE                 Location/Qualifiers
source                  1..6
                        mol_type = protein
                        organism = synthetic construct
SEQUENCE: 347
PYGLSR                                                              6

SEQ ID NO: 348          moltype = AA   length = 6
FEATURE                 Location/Qualifiers
source                  1..6
                        mol_type = protein
                        organism = synthetic construct
SEQUENCE: 348
PFGLSR                                                              6

SEQ ID NO: 349          moltype = AA   length = 6
FEATURE                 Location/Qualifiers
source                  1..6
                        mol_type = protein
                        organism = synthetic construct
SEQUENCE: 349
PRGLSR                                                              6

SEQ ID NO: 350          moltype = AA   length = 6
FEATURE                 Location/Qualifiers
source                  1..6
                        mol_type = protein
                        organism = synthetic construct
SEQUENCE: 350
PMGLSR                                                              6

SEQ ID NO: 351          moltype = AA   length = 6
FEATURE                 Location/Qualifiers
source                  1..6
                        mol_type = protein
                        organism = synthetic construct
SEQUENCE: 351
PKGLSR                                                              6

SEQ ID NO: 352          moltype = AA   length = 6
FEATURE                 Location/Qualifiers
source                  1..6
                        mol_type = protein
                        organism = synthetic construct
SEQUENCE: 352
PQGLSR                                                              6

SEQ ID NO: 353          moltype = AA   length = 6
FEATURE                 Location/Qualifiers
source                  1..6
                        mol_type = protein
                        organism = synthetic construct
SEQUENCE: 353
PWGLSK                                                              6

SEQ ID NO: 354          moltype = AA   length = 266
FEATURE                 Location/Qualifiers
source                  1..266
                        mol_type = protein
                        organism = synthetic construct
SEQUENCE: 354
QGQSGQCISP RGCPDGPYVM YGSSGGSGGS GGSGISSGLL SGRSDNHGSS GTQILLTQSP   60
VILSVSPGER VSFSCRASQS IGTNIHWYQQ RTNGSPRLLI KYASESISGI PSRFSGSGSG  120
TDFTLSINSV ESEDIADYYC QQNNNWPTTF GAGTKLELKR TVAAPSVFIF PPSDEQLKSG  180
TASVVCLLNN FYPREAKVQW KVDNALQSGN SQESVTEQDS KDSTYSLSST LTLSKADYEK  240
HKVYACEVTH QGLSSPVTKS FNRGEC                                       266

SEQ ID NO: 355          moltype = AA   length = 449
FEATURE                 Location/Qualifiers
source                  1..449
                        mol_type = protein
                        organism = synthetic construct
SEQUENCE: 355
QVQLKQSGPG LVQPSQSLSI TCTVSGFSLT NYGVHWVRQS PGKGLEWLGV IWSGGNTDYN   60
```

```
TPFTSRLSIN KDNSKSQVFF KMNSLQSQDT AIYYCARALT YDYDYEFAYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                      449

SEQ ID NO: 356            moltype = AA  length = 258
FEATURE                   Location/Qualifiers
source                    1..258
                          mol_type = protein
                          organism = synthetic construct
SEQUENCE: 356
QGQSGQCISP RGCPDGPYVM YGGGSSGGSA PRSALAHGLF GGGSQILLTQ SPVILSVSPG   60
ERVSFSCRAS QSIGTNIHWY QQRTNGSPRL LIKYASESIS GIPSRFSGSG SGTDFTLSIN   120
SVESEDIADY YCQQNNNWPT TFGAGTKLEL KRTVAAPSVF IFPPSDEQLK SGTASVVCLL   180
NNFYPREAKV QWKVDNALQS GNSQESVTEQ DSKDSTYSLS STLTLSKADY EKHKVYACEV   240
THQGLSSPVT KSFNRGEC                                                  258

SEQ ID NO: 357            moltype = AA  length = 449
FEATURE                   Location/Qualifiers
source                    1..449
                          mol_type = protein
                          organism = synthetic construct
SEQUENCE: 357
QVQLKQSGPG LVQPSQSLSI TCTVSGFSLT NYGVHWVRQS PGKGLEWLGV IWSGGNTDYN   60
TPFTSRLSIN KDNSKSQVFF KMNSLQSQDT AIYYCARALT YDYDYEFAYWG QGTLVTVSAA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                      449

SEQ ID NO: 358            moltype = AA  length = 271
FEATURE                   Location/Qualifiers
source                    1..271
                          mol_type = protein
                          organism = synthetic construct
SEQUENCE: 358
QGQSGQCISP RGCLDGPYVM YGSSGGSGGS GGSGAVGLLA PPGGLSGRSD NHGSSGTQIL   60
LTQSPVILSV SPGERVSFSC RASQSIGTNI HWYQQRTNGS PRLLIKYASE SISGIPSRFS   120
GSGSGTDFTL SINSVESEDI ADYYCQQNNN WPTTFGAGTK LELKRTVAAP SVFIFPPSDE   180
QLKSGTASVV CLLNNFYPRE AKVQWKVDNA LQSGNSQESV TEQDSKDSTY SLSSTLTLSK   240
ADYEKHKVYA CEVTHQGLSS PVTKSFNRGE C                                   271

SEQ ID NO: 359            moltype = AA  length = 261
FEATURE                   Location/Qualifiers
source                    1..261
                          mol_type = protein
                          organism = synthetic construct
SEQUENCE: 359
QGQSGQCISP RGCPDGPYVM YGSSGGSGGS GGSGISSGLL SSGSSGTQIL LTQSPVILSV   60
SPGERVSFSC RASQSIGTNI HWYQQRTNGS PRLLIKYASE SISGIPSRFS GSGSGTDFTL   120
SINSVESEDI ADYYCQQNNN WPTTFGAGTK LELKRTVAAP SVFIFPPSDE QLKSGTASVV   180
CLLNNFYPRE AKVQWKVDNA LQSGNSQESV TEQDSKDSTY SLSSTLTLSK ADYEKHKVYA   240
CEVTHQGLSS PVTKSFNRGE C                                              261

SEQ ID NO: 360            moltype = AA  length = 261
FEATURE                   Location/Qualifiers
source                    1..261
                          mol_type = protein
                          organism = synthetic construct
SEQUENCE: 360
QGQSGQCISP RGCPDGPYVM YGSSGGSGGS GGSGISSGLL SSGSSGTQIL LTQSPVILSV   60
SPGERVSFSC RASQSIGTNI HWYQQRTNGS PRLLIKYASE SISGIPSRFS GSGSGTDFTL   120
SINSVESEDI ADYYCQQNNN WPTTFGAGTK LELKRTVAAP SVFIFPPSDE QLKSGTASVV   180
CLLNNFYPRE AKVQWKVDNA LQSGNSQESV TEQDSKDSTY SLSSTLTLSK ADYEKHKVYA   240
CEVTHQGLSS PVTKSFNRGE C                                              261

SEQ ID NO: 361            moltype = AA  length = 262
FEATURE                   Location/Qualifiers
source                    1..262
                          mol_type = protein
                          organism = synthetic construct
SEQUENCE: 361
QGQSGQCIS PRGCPDGPYV MYGGGSSGGS APMGLKHLSG RSNIGGGSQI LLTQSPVILS    60
VSPGERVSFS CRASQSIGTN IHWYQQRTNG SPRLLIKYAS ESISGIPSRF SGSGSGTDFT   120
```

```
LSINSVESED  IADYYCQQNN  NWPTTFGAGT  KLELKRTVAA  PSVFIFPPSD  EQLKSGTASV   180
VCLLNNFYPR  EAKVQWKVDN  ALQSGNSQES  VTEQDSKDST  YSLSSTLTLS  KADYEKHKVY   240
ACEVTHQGLS  SPVTKSFNRG  EC                                               262

SEQ ID NO: 362              moltype = AA   length = 259
FEATURE                     Location/Qualifiers
source                      1..259
                            mol_type = protein
                            organism = synthetic construct
SEQUENCE: 362
QGQSGQGCIS  PRGCPDGPYV  MYGGGSSGGS  GPWGLSGRSN  IGGGSQILLT  QSPVILSVSP   60
GERVSFSCRA  SQSIGTNIHW  YQQRTNGSPR  LLIKYASESI  SGIPSRFSGS  GSGTDFTLSI   120
NSVESEDIAD  YYCQQNNNWP  TTFGAGTKLE  LKRTVAAPSV  FIFPPSDEQL  KSGTASVVCL   180
LNNFYPREAK  VQWKVDNALQ  SGNSQESVTE  QDSKDSTYSL  SSTLTLSKAD  YEKHKVYACE   240
VTHQGLSSPV  TKSFNRGEC                                                    259

SEQ ID NO: 363              moltype = AA   length = 259
FEATURE                     Location/Qualifiers
source                      1..259
                            mol_type = protein
                            organism = synthetic construct
SEQUENCE: 363
QGQSGQGCIS  PRGCPDGPYV  MYGGGSSGGS  GPYGLSGRSN  IGGGSQILLT  QSPVILSVSP   60
GERVSFSCRA  SQSIGTNIHW  YQQRTNGSPR  LLIKYASESI  SGIPSRFSGS  GSGTDFTLSI   120
NSVESEDIAD  YYCQQNNNWP  TTFGAGTKLE  LKRTVAAPSV  FIFPPSDEQL  KSGTASVVCL   180
LNNFYPREAK  VQWKVDNALQ  SGNSQESVTE  QDSKDSTYSL  SSTLTLSKAD  YEKHKVYACE   240
VTHQGLSSPV  TKSFNRGEC                                                    259

SEQ ID NO: 364              moltype = AA   length = 261
FEATURE                     Location/Qualifiers
source                      1..261
                            mol_type = protein
                            organism = synthetic construct
SEQUENCE: 364
QGQSGQGCIS  PRGCPDGPYV  MYGGGSSGGS  DHQSRSAPMG  LKHGGGSQIL  LTQSPVILSV   60
SPGERVSFSC  RASQSIGTNI  HWYQQRTNGS  PRLLIKYASE  SISGIPSRFS  GSGSGTDFTL   120
SINSVESEDI  ADYYCQQNNN  WPTTFGAGTK  LELKRTVAAP  SVFIFPPSDE  QLKSGTASVV   180
CLLNNFYPRE  AKVQWKVDNA  LQSGNSQESV  TEQDSKDSTY  SLSSTLTLSK  ADYEKHKVYA   240
CEVTHQGLSS  PVTKSFNRGE  C                                                261

SEQ ID NO: 365              moltype = AA   length = 261
FEATURE                     Location/Qualifiers
source                      1..261
                            mol_type = protein
                            organism = synthetic construct
SEQUENCE: 365
QGQSGQGCIS  PRGCPDGPYV  MYGGGSSGGS  APMGLKHDHQ  SRSGGGSQIL  LTQSPVILSV   60
SPGERVSFSC  RASQSIGTNI  HWYQQRTNGS  PRLLIKYASE  SISGIPSRFS  GSGSGTDFTL   120
SINSVESEDI  ADYYCQQNNN  WPTTFGAGTK  LELKRTVAAP  SVFIFPPSDE  QLKSGTASVV   180
CLLNNFYPRE  AKVQWKVDNA  LQSGNSQESV  TEQDSKDSTY  SLSSTLTLSK  ADYEKHKVYA   240
CEVTHQGLSS  PVTKSFNRGE  C                                                261

SEQ ID NO: 366              moltype = AA   length = 256
FEATURE                     Location/Qualifiers
source                      1..256
                            mol_type = protein
                            organism = synthetic construct
SEQUENCE: 366
QGQSGQGCIS  PRGCPDGPYV  MYGGGSSGGS  APRSPWGLGG  GSQILLTQSP  VILSVSPGER   60
VSFSCRASQS  IGTNIHWYQQ  RTNGSPRLLI  KYASESISGI  PSRFSGSGSG  TDFTLSINSV   120
ESEDIADYYC  QQNNNWPTTF  GAGTKLELKR  TVAAPSVFIF  PPSDEQLKSG  TASVVCLLNN   180
FYPREAKVQW  KVDNALQSGN  SQESVTEQDS  KDSTYSLSST  LTLSKADYEK  HKVYACEVTH   240
QGLSSPVTKS  FNRGEC                                                       256

SEQ ID NO: 367              moltype = AA   length = 449
FEATURE                     Location/Qualifiers
source                      1..449
                            mol_type = protein
                            organism = synthetic construct
SEQUENCE: 367
QVQLKQSGPG  LVQPSQSLSI  TCTVSGFSLT  NYGVHWVRQS  PGKGLEWLGV  IWSGGNTDYN   60
TPFTSRLSIN  KDNSKSQVFF  KMNSLQSQDT  AIYYCARALT  YYDYEFAYWG  QGTLVTVSAA   120
STKGPSVFPL  APSSKSTSGG  TAALGCLVKD  YFPEPVTVSW  NSGALTSGVH  TFPAVLQSSG   180
LYSLSSVVTV  PSSSLGTQTY  ICNVNHKPSN  TKVDKKVEPK  SCDKTHTCPP  CPAPELLGGP   240
SVFLFPPKPK  DTLMISRTPE  VTCVVVDVSH  EDPEVKFNWY  VDGVEVHNAK  TKPREEQYNS   300
TYRVVSVLTV  LHQDWLNGKE  YKCKVSNKAL  PAPIEKTISK  AKGQPREPQV  YTLPPSRDEL   360
TKNQVSLTCL  VKGFYPSDIA  VEWESNGQPE  NNYKTTPPVL  DSDGSFFLYS  KLTVDKSRWQ   420
QGNVFSCSVM  HEALHNHYTQ  KSLSLSPGK                                        449
```

-continued

```
SEQ ID NO: 368                moltype = AA   length = 255
FEATURE                       Location/Qualifiers
source                        1..255
                              mol_type = protein
                              organism = synthetic construct
SEQUENCE: 368
QGQSGQGCIS PRGCPDGPYV MYGGGSSGGS PWGLPRSGGG SQILLTQSPV ILSVSPGERV    60
SFSCRASQSI GTNIHWYQQR TNGSPRLLIK YASESISGIP SRFSGSGSGT DFTLSINSVE   120
SEDIADYYCQ QNNNWPTTFG AGTKLELKRT VAAPSVFIFP PSDEQLKSGT ASVVCLLNNF   180
YPREAKVQWK VDNALQSGNS QESVTEQDSK DSTYSLSSTL TLSKADYEKH KVYACEVTHQ   240
GLSSPVTKSF NRGEC                                                   255

SEQ ID NO: 369                moltype = AA   length = 253
FEATURE                       Location/Qualifiers
source                        1..253
                              mol_type = protein
                              organism = synthetic construct
SEQUENCE: 369
QGQSGQGCIS PRGCPDGPYV MYGGGSSGGK PRGLNGGGSQ ILLTQSPVIL SVSPGERVSF    60
SCRASQSIGT NIHWYQQRTN GSPRLLIKYA SESISGIPSR FSGSGSGTDF TLSINSVESE   120
DIADYYCQQN NNWPTTFGAG TKLELKRTVA APSVFIFPPS DEQLKSGTAS VVCLLNNFYP   180
REAKVQWKVD NALQSGNSQE SVTEQDSKDS TYSLSSTLTL SKADYEKHKV YACEVTHQGL   240
SSPVTKSFNR GEC                                                     253

SEQ ID NO: 370                moltype = AA   length = 255
FEATURE                       Location/Qualifiers
source                        1..255
                              mol_type = protein
                              organism = synthetic construct
SEQUENCE: 370
QGQSGQGCIS PRGCPDGPYV MYGGGSSGGS PWGLRSNGGG SQILLTQSPV ILSVSPGERV    60
SFSCRASQSI GTNIHWYQQR TNGSPRLLIK YASESISGIP SRFSGSGSGT DFTLSINSVE   120
SEDIADYYCQ QNNNWPTTFG AGTKLELKRT VAAPSVFIFP PSDEQLKSGT ASVVCLLNNF   180
YPREAKVQWK VDNALQSGNS QESVTEQDSK DSTYSLSSTL TLSKADYEKH KVYACEVTHQ   240
GLSSPVTKSF NRGEC                                                   255

SEQ ID NO: 371                moltype = AA   length = 255
FEATURE                       Location/Qualifiers
source                        1..255
                              mol_type = protein
                              organism = synthetic construct
SEQUENCE: 371
QGQSGQGCIS PRGCPDGPYV MYGGGSSGGS RSPWGLNGGG SQILLTQSPV ILSVSPGERV    60
SFSCRASQSI GTNIHWYQQR TNGSPRLLIK YASESISGIP SRFSGSGSGT DFTLSINSVE   120
SEDIADYYCQ QNNNWPTTFG AGTKLELKRT VAAPSVFIFP PSDEQLKSGT ASVVCLLNNF   180
YPREAKVQWK VDNALQSGNS QESVTEQDSK DSTYSLSSTL TLSKADYEKH KVYACEVTHQ   240
GLSSPVTKSF NRGEC                                                   255

SEQ ID NO: 372                moltype = AA   length = 254
FEATURE                       Location/Qualifiers
source                        1..254
                              mol_type = protein
                              organism = synthetic construct
SEQUENCE: 372
QGQSGQGCIS PRGCPDGPYV MYGGGSSGGS KPRGLFGGGS QILLTQSPVI LSVSPGERVS    60
FSCRASQSIG TNIHWYQQRT NGSPRLLIKY ASESISGIPS RFSGSGSGTD FTLSINSVES   120
EDIADYYCQQ NNNWPTTFGA GTKLELKRTV AAPSVFIFPP SDEQLKSGTA SVVCLLNNFY   180
PREAKVQWKV DNALQSGNSQ ESVTEQDSKD STYSLSSTLT LSKADYEKHK VYACEVTHQG   240
LSSPVTKSFN RGEC                                                    254

SEQ ID NO: 373                moltype = AA   length = 256
FEATURE                       Location/Qualifiers
source                        1..256
                              mol_type = protein
                              organism = synthetic construct
SEQUENCE: 373
QGQSGQGCIS PRGCPDGPYV MYGGGSSGGS PWGLSGRSGG GSQILLTQSP VILSVSPGER    60
VSFSCRASQS IGTNIHWYQQ RTNGSPRLLI KYASESISGI PSRFSGSGSG TDFTLSINSV   120
ESEDIADYYC QQNNNWPTTF GAGTKLELKR TVAAPSVFIF PPSDEQLKSG TASVVCLLNN   180
FYPREAKVQW KVDNALQSGN SQESVTEQDS KDSTYSLSST LTLSKADYEK HKVYACEVTH   240
QGLSSPVTKS FNRGEC                                                  256

SEQ ID NO: 374                moltype = AA   length = 255
FEATURE                       Location/Qualifiers
source                        1..255
                              mol_type = protein
                              organism = synthetic construct
SEQUENCE: 374
QGQSGQGCIS PRGCPDGPYV MYGGGSSGGS PWGLSRSGGG SQILLTQSPV ILSVSPGERV    60
```

```
SFSCRASQSI GTNIHWYQQR TNGSPRLLIK YASESISGIP SRFSGSGSGT DFTLSINSVE   120
SEDIADYYCQ QNNNWPTTFG AGTKLELKRT VAAPSVFIFP PSDEQLKSGT ASVVCLLNNF   180
YPREAKVQWK VDNALQSGNS QESVTEQDSK DSTYSLSSTL TLSKADYEKH KVYACEVTHQ   240
GLSSPVTKSF NRGEC                                                    255

SEQ ID NO: 375            moltype = AA   length = 255
FEATURE                   Location/Qualifiers
source                    1..255
                          mol_type = protein
                          organism = synthetic construct
SEQUENCE: 375
QGQSGQGCIS PRGCPDGPYV MYGGGSSGGS PFGLSRSGGG SQILLTQSPV ILSVSPGERV   60
SFSCRASQSI GTNIHWYQQR TNGSPRLLIK YASESISGIP SRFSGSGSGT DFTLSINSVE   120
SEDIADYYCQ QNNNWPTTFG AGTKLELKRT VAAPSVFIFP PSDEQLKSGT ASVVCLLNNF   180
YPREAKVQWK VDNALQSGNS QESVTEQDSK DSTYSLSSTL TLSKADYEKH KVYACEVTHQ   240
GLSSPVTKSF NRGEC                                                    255

SEQ ID NO: 376            moltype = AA   length = 256
FEATURE                   Location/Qualifiers
source                    1..256
                          mol_type = protein
                          organism = synthetic construct
SEQUENCE: 376
QGQSGQGCIS PRGCPDGPYV MYGGGSSGGS PRSPWGLLGG GSQILLTQSP VILSVSPGER   60
VSFSCRASQS IGTNIHWYQQ RTNGSPRLLI KYASESISGI PSRFSGSGSG TDFTLSINSV   120
ESEDIADYYC QQNNNWPTTF GAGTKLELKR TVAAPSVFIFP PPSDEQLKSG TASVVCLLNN   180
FYPREAKVQW KVDNALQSGN SQESVTEQDS KDSTYSLSST LTLSKADYEK HKVYACEVTH   240
QGLSSPVTKS FNRGEC                                                   256

SEQ ID NO: 377            moltype = AA   length = 256
FEATURE                   Location/Qualifiers
source                    1..256
                          mol_type = protein
                          organism = synthetic construct
SEQUENCE: 377
QGQSGQGCIS PRGCPDGPYV MYGGGSSGGS GRSPWGLLGG GSQILLTQSP VILSVSPGER   60
VSFSCRASQS IGTNIHWYQQ RTNGSPRLLI KYASESISGI PSRFSGSGSG TDFTLSINSV   120
ESEDIADYYC QQNNNWPTTF GAGTKLELKR TVAAPSVFIF PPSDEQLKSG TASVVCLLNN   180
FYPREAKVQW KVDNALQSGN SQESVTEQDS KDSTYSLSST LTLSKADYEK HKVYACEVTH   240
QGLSSPVTKS FNRGEC                                                   256

SEQ ID NO: 378            moltype = AA   length = 254
FEATURE                   Location/Qualifiers
source                    1..254
                          mol_type = protein
                          organism = synthetic construct
SEQUENCE: 378
QGQSGQGCIS PRGCPDGPYV MYGGGSSGGS APRSLLGGGS QILLTQSPVI LSVSPGERVS   60
FSCRASQSIG TNIHWYQQRT NGSPRLLIKY ASESISGIPS RFSGSGSGTD FTLSINSVES   120
EDIADYYCQQ NNNWPTTFGA GTKLELKRTV AAPSVFIFPP SDEQLKSGTA SVVCLLNNFY   180
PREAKVQWKV DNALQSGNSQ ESVTEQDSKD STYSLSSTLT LSKADYEKHK VYACEVTHQG   240
LSSPVTKSFN RGEC                                                     254

SEQ ID NO: 379            moltype = AA   length = 254
FEATURE                   Location/Qualifiers
source                    1..254
                          mol_type = protein
                          organism = synthetic construct
SEQUENCE: 379
QGQSGQGCIS PRGCPDGPYV MYGGGSSGGS APRGLLGGGS QILLTQSPVI LSVSPGERVS   60
FSCRASQSIG TNIHWYQQRT NGSPRLLIKY ASESISGIPS RFSGSGSGTD FTLSINSVES   120
EDIADYYCQQ NNNWPTTFGA GTKLELKRTV AAPSVFIFPP SDEQLKSGTA SVVCLLNNFY   180
PREAKVQWKV DNALQSGNSQ ESVTEQDSKD STYSLSSTLT LSKADYEKHK VYACEVTHQG   240
LSSPVTKSFN RGEC                                                     254

SEQ ID NO: 380            moltype = AA   length = 253
FEATURE                   Location/Qualifiers
source                    1..253
                          mol_type = protein
                          organism = synthetic construct
SEQUENCE: 380
QGQSGQGCIS PRGCPDGPYV MYGGGSSGGS APRSYGGGSQ ILLTQSPVIL SVSPGERVSF   60
SCRASQSIGT NIHWYQQRTN GSPRLLIKYA SESISGIPSR FSGSGSGTDF TLSINSVESE   120
DIADYYCQQN NNWPTTFGAG TKLELKRTVA APSVFIFPPS DEQLKSGTAS VVCLLNNFYP   180
REAKVQWKVD NALQSGNSQE SVTEQDSKDS TYSLSSTLTL SKADYEKHKV YACEVTHQGL   240
SSPVTKSFNR GEC                                                      253

SEQ ID NO: 381            moltype = AA   length = 255
FEATURE                   Location/Qualifiers
```

-continued

```
source                   1..255
                         mol_type = protein
                         organism = synthetic construct
SEQUENCE: 381
QGQSGQGCIS PRGCPDGPYV MYGGGSSGGS VAPRSMRGGG SQILLTQSPV ILSVSPGERV   60
SFSCRASQSI GTNIHWYQQR TNGSPRLLIK YASESISGIP SRFSGSGSGT DFTLSINSVE   120
SEDIADYYCQ QNNNWPTTFG AGTKLELKRT VAAPSVFIFP PSDEQLKSGT ASVVCLLNNF   180
YPREAKVQWK VDNALQSGNS QESVTEQDSK DSTYSLSSTL TLSKADYEKH KVYACEVTHQ   240
GLSSPVTKSF NRGEC                                                    255

SEQ ID NO: 382            moltype = AA  length = 4
FEATURE                   Location/Qualifiers
source                    1..4
                          mol_type = protein
                          organism = synthetic construct
SEQUENCE: 382
APRG                                                                4

SEQ ID NO: 383            moltype = AA  length = 5
FEATURE                   Location/Qualifiers
source                    1..5
                          mol_type = protein
                          organism = synthetic construct
SEQUENCE: 383
APRSM                                                               5

SEQ ID NO: 384            moltype = AA  length = 5
FEATURE                   Location/Qualifiers
source                    1..5
                          mol_type = protein
                          organism = synthetic construct
SEQUENCE: 384
APRGY                                                               5

SEQ ID NO: 385            moltype = AA  length = 5
FEATURE                   Location/Qualifiers
source                    1..5
                          mol_type = protein
                          organism = synthetic construct
SEQUENCE: 385
APRGM                                                               5

SEQ ID NO: 386            moltype = AA  length = 256
FEATURE                   Location/Qualifiers
source                    1..256
                          mol_type = protein
                          organism = synthetic construct
SEQUENCE: 386
QGQSGQGCIS PRGCPDGPYV MYGGGSSGGS PWGLSGKSGG GSQILLTQSP VILSVSPGER   60
VSFSCRASQS IGTNIHWYQQ RTNGSPRLLI KYASESISGI PSRFSGSGSG TDFTLSINSV   120
ESEDIADYYC QQNNNWPTTF GAGTKLELKR TVAAPSVFIF PPSDEQLKSG TASVVCLLNN   180
FYPREAKVQW KVDNALQSGN SQESVTEQDS KDSTYSLSST LTLSKADYEK HKVYACEVTH   240
QGLSSPVTKS FNRGEC                                                   256

SEQ ID NO: 387            moltype = AA  length = 256
FEATURE                   Location/Qualifiers
source                    1..256
                          mol_type = protein
                          organism = synthetic construct
SEQUENCE: 387
QGQSGQGCIS PRGCPDGPYV MYGGGSSGGS PYGLSGRSGG GSQILLTQSP VILSVSPGER   60
VSFSCRASQS IGTNIHWYQQ RTNGSPRLLI KYASESISGI PSRFSGSGSG TDFTLSINSV   120
ESEDIADYYC QQNNNWPTTF GAGTKLELKR TVAAPSVFIF PPSDEQLKSG TASVVCLLNN   180
FYPREAKVQW KVDNALQSGN SQESVTEQDS KDSTYSLSST LTLSKADYEK HKVYACEVTH   240
QGLSSPVTKS FNRGEC                                                   256

SEQ ID NO: 388            moltype = AA  length = 256
FEATURE                   Location/Qualifiers
source                    1..256
                          mol_type = protein
                          organism = synthetic construct
SEQUENCE: 388
QGQSGQGCIS PRGCPDGPYV MYGGGSSGGS PFGLSGRSGG GSQILLTQSP VILSVSPGER   60
VSFSCRASQS IGTNIHWYQQ RTNGSPRLLI KYASESISGI PSRFSGSGSG TDFTLSINSV   120
ESEDIADYYC QQNNNWPTTF GAGTKLELKR TVAAPSVFIF PPSDEQLKSG TASVVCLLNN   180
FYPREAKVQW KVDNALQSGN SQESVTEQDS KDSTYSLSST LTLSKADYEK HKVYACEVTH   240
QGLSSPVTKS FNRGEC                                                   256

SEQ ID NO: 389            moltype = AA  length = 256
```

```
FEATURE              Location/Qualifiers
source               1..256
                     mol_type = protein
                     organism = synthetic construct
SEQUENCE: 389
QGQSGQGCIS PRGCPDGPYV MYGGGSSGGS PRGLSGRSGG GSQILLTQSP VILSVSPGER   60
VSFSCRASQS IGTNIHWYQQ RTNGSPRLLI KYASESISGI PSRFSGSGSG TDFTLSINSV  120
ESEDIADYYC QQNNNWPTTF GAGTKLELKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                  256

SEQ ID NO: 390        moltype = AA  length = 256
FEATURE              Location/Qualifiers
source               1..256
                     mol_type = protein
                     organism = synthetic construct
SEQUENCE: 390
QGQSGQGCIS PRGCPDGPYV MYGGGSSGGS PAGLSGRSGG GSQILLTQSP VILSVSPGER   60
VSFSCRASQS IGTNIHWYQQ RTNGSPRLLI KYASESISGI PSRFSGSGSG TDFTLSINSV  120
ESEDIADYYC QQNNNWPTTF GAGTKLELKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                  256

SEQ ID NO: 391        moltype = AA  length = 257
FEATURE              Location/Qualifiers
source               1..257
                     mol_type = protein
                     organism = synthetic construct
SEQUENCE: 391
QGQSGQGCIS PRGCPDGPYV MYGGGSSGGS LSGRSPWGLG GGSQILLTQS PVILSVSPGE   60
RVSFSCRASQ SIGTNIHWYQ QRTNGSPRLL IKYASESISG IPSRFSGSGS GTDFTLSINS  120
VESEDIADYY CQQNNNWPTT FGAGTKLELK RTVAAPSVFI FPPSDEQLKS GTASVVCLLN  180
NFYPREAKVQ WKVDNALQSG NSQESVTEQD SKDSTYSLSS TLTLSKADYE KHKVYACEVT  240
HQGLSSPVTK SFNRGEC                                                 257

SEQ ID NO: 392        moltype = AA  length = 257
FEATURE              Location/Qualifiers
source               1..257
                     mol_type = protein
                     organism = synthetic construct
SEQUENCE: 392
QGQSGQGCIS PRGCPDGPYV MYGGGSSGGS LSGKSPWGLG GGSQILLTQS PVILSVSPGE   60
RVSFSCRASQ SIGTNIHWYQ QRTNGSPRLL IKYASESISG IPSRFSGSGS GTDFTLSINS  120
VESEDIADYY CQQNNNWPTT FGAGTKLELK RTVAAPSVFI FPPSDEQLKS GTASVVCLLN  180
NFYPREAKVQ WKVDNALQSG NSQESVTEQD SKDSTYSLSS TLTLSKADYE KHKVYACEVT  240
HQGLSSPVTK SFNRGEC                                                 257

SEQ ID NO: 393        moltype = AA  length = 258
FEATURE              Location/Qualifiers
source               1..258
                     mol_type = protein
                     organism = synthetic construct
SEQUENCE: 393
QGQSGQGCIS PRGCPDGPYV MYGGGSSGGS LSGRSPWGLS GGGSQILLTQ SPVILSVSPG   60
ERVSFSCRAS QSIGTNIHWY QQRTNGSPRL LIKYASESIS GIPSRFSGSG SGTDFTLSIN  120
SVESEDIADY YCQQNNNWPT TFGAGTKLEL KRTVAAPSVF IFPPSDEQLK SGTASVVCLL  180
NNFYPREAKV QWKVDNALQS GNSQESVTEQ DSKDSTYSLS STLTLSKADY EKHKVYACEV  240
THQGLSSPVT KSFNRGEC                                                258

SEQ ID NO: 394        moltype =    length =
SEQUENCE: 394
000

SEQ ID NO: 395        moltype =    length =
SEQUENCE: 395
000

SEQ ID NO: 396        moltype =    length =
SEQUENCE: 396
000

SEQ ID NO: 397        moltype =    length =
SEQUENCE: 397
000

SEQ ID NO: 398        moltype =    length =
SEQUENCE: 398
000
```

-continued

```
SEQ ID NO: 399          moltype =    length =
SEQUENCE: 399
000

SEQ ID NO: 400          moltype =    length =
SEQUENCE: 400
000

SEQ ID NO: 401          moltype =    length =
SEQUENCE: 401
000

SEQ ID NO: 402          moltype =    length =
SEQUENCE: 402
000

SEQ ID NO: 403          moltype =    length =
SEQUENCE: 403
000

SEQ ID NO: 404          moltype =    length =
SEQUENCE: 404
000

SEQ ID NO: 405          moltype =    length =
SEQUENCE: 405
000

SEQ ID NO: 406          moltype =    length =
SEQUENCE: 406
000

SEQ ID NO: 407          moltype =    length =
SEQUENCE: 407
000

SEQ ID NO: 408          moltype =    length =
SEQUENCE: 408
000

SEQ ID NO: 409          moltype =    length =
SEQUENCE: 409
000

SEQ ID NO: 410          moltype =    length =
SEQUENCE: 410
000

SEQ ID NO: 411          moltype =    length =
SEQUENCE: 411
000

SEQ ID NO: 412          moltype =    length =
SEQUENCE: 412
000

SEQ ID NO: 413          moltype =    length =
SEQUENCE: 413
000

SEQ ID NO: 414          moltype =    length =
SEQUENCE: 414
000

SEQ ID NO: 415          moltype =    length =
SEQUENCE: 415
000

SEQ ID NO: 416          moltype =    length =
SEQUENCE: 416
000

SEQ ID NO: 417          moltype =    length =
SEQUENCE: 417
000

SEQ ID NO: 418          moltype =    length =
SEQUENCE: 418
000
```

```
SEQ ID NO: 419          moltype =    length =
SEQUENCE: 419
000

SEQ ID NO: 420          moltype =    length =
SEQUENCE: 420
000

SEQ ID NO: 421          moltype =    length =
SEQUENCE: 421
000

SEQ ID NO: 422          moltype =    length =
SEQUENCE: 422
000

SEQ ID NO: 423          moltype =    length =
SEQUENCE: 423
000

SEQ ID NO: 424          moltype =    length =
SEQUENCE: 424
000

SEQ ID NO: 425          moltype =    length =
SEQUENCE: 425
000

SEQ ID NO: 426          moltype =    length =
SEQUENCE: 426
000

SEQ ID NO: 427          moltype =    length =
SEQUENCE: 427
000

SEQ ID NO: 428          moltype =    length =
SEQUENCE: 428
000

SEQ ID NO: 429          moltype =    length =
SEQUENCE: 429
000

SEQ ID NO: 430          moltype =    length =
SEQUENCE: 430
000

SEQ ID NO: 431          moltype =    length =
SEQUENCE: 431
000

SEQ ID NO: 432          moltype =    length =
SEQUENCE: 432
000

SEQ ID NO: 433          moltype =    length =
SEQUENCE: 433
000

SEQ ID NO: 434          moltype =    length =
SEQUENCE: 434
000

SEQ ID NO: 435          moltype =    length =
SEQUENCE: 435
000

SEQ ID NO: 436          moltype =    length =
SEQUENCE: 436
000

SEQ ID NO: 437          moltype =    length =
SEQUENCE: 437
000

SEQ ID NO: 438          moltype =    length =
SEQUENCE: 438
```

-continued

```
000

SEQ ID NO: 439          moltype =   length =
SEQUENCE: 439
000

SEQ ID NO: 440          moltype =   length =
SEQUENCE: 440
000

SEQ ID NO: 441          moltype =   length =
SEQUENCE: 441
000

SEQ ID NO: 442          moltype =   length =
SEQUENCE: 442
000

SEQ ID NO: 443          moltype =   length =
SEQUENCE: 443
000

SEQ ID NO: 444          moltype =   length =
SEQUENCE: 444
000

SEQ ID NO: 445          moltype =   length =
SEQUENCE: 445
000

SEQ ID NO: 446          moltype =   length =
SEQUENCE: 446
000

SEQ ID NO: 447          moltype =   length =
SEQUENCE: 447
000

SEQ ID NO: 448          moltype =   length =
SEQUENCE: 448
000

SEQ ID NO: 449          moltype =   length =
SEQUENCE: 449
000

SEQ ID NO: 450          moltype =   length =
SEQUENCE: 450
000

SEQ ID NO: 451          moltype =   length =
SEQUENCE: 451
000

SEQ ID NO: 452          moltype =   length =
SEQUENCE: 452
000

SEQ ID NO: 453          moltype =   length =
SEQUENCE: 453
000

SEQ ID NO: 454          moltype =   length =
SEQUENCE: 454
000

SEQ ID NO: 455          moltype =   length =
SEQUENCE: 455
000

SEQ ID NO: 456          moltype =   length =
SEQUENCE: 456
000

SEQ ID NO: 457          moltype =   length =
SEQUENCE: 457
000

SEQ ID NO: 458          moltype =   length =
```

-continued

```
SEQUENCE: 458
000

SEQ ID NO: 459          moltype =   length =
SEQUENCE: 459
000

SEQ ID NO: 460          moltype =   length =
SEQUENCE: 460
000

SEQ ID NO: 461          moltype =   length =
SEQUENCE: 461
000

SEQ ID NO: 462          moltype =   length =
SEQUENCE: 462
000

SEQ ID NO: 463          moltype =   length =
SEQUENCE: 463
000

SEQ ID NO: 464          moltype =   length =
SEQUENCE: 464
000

SEQ ID NO: 465          moltype =   length =
SEQUENCE: 465
000

SEQ ID NO: 466          moltype =   length =
SEQUENCE: 466
000

SEQ ID NO: 467          moltype =   length =
SEQUENCE: 467
000

SEQ ID NO: 468          moltype =   length =
SEQUENCE: 468
000

SEQ ID NO: 469          moltype =   length =
SEQUENCE: 469
000

SEQ ID NO: 470          moltype =   length =
SEQUENCE: 470
000

SEQ ID NO: 471          moltype =   length =
SEQUENCE: 471
000

SEQ ID NO: 472          moltype =   length =
SEQUENCE: 472
000

SEQ ID NO: 473          moltype =   length =
SEQUENCE: 473
000

SEQ ID NO: 474          moltype =   length =
SEQUENCE: 474
000

SEQ ID NO: 475          moltype =   length =
SEQUENCE: 475
000

SEQ ID NO: 476          moltype =   length =
SEQUENCE: 476
000

SEQ ID NO: 477          moltype =   length =
SEQUENCE: 477
000
```

-continued

```
SEQ ID NO: 478          moltype =   length =
SEQUENCE: 478
000

SEQ ID NO: 479          moltype =   length =
SEQUENCE: 479
000

SEQ ID NO: 480          moltype =   length =
SEQUENCE: 480
000

SEQ ID NO: 481          moltype =   length =
SEQUENCE: 481
000

SEQ ID NO: 482          moltype =   length =
SEQUENCE: 482
000

SEQ ID NO: 483          moltype =   length =
SEQUENCE: 483
000

SEQ ID NO: 484          moltype =   length =
SEQUENCE: 484
000

SEQ ID NO: 485          moltype =   length =
SEQUENCE: 485
000

SEQ ID NO: 486          moltype =   length =
SEQUENCE: 486
000

SEQ ID NO: 487          moltype =   length =
SEQUENCE: 487
000

SEQ ID NO: 488          moltype =   length =
SEQUENCE: 488
000

SEQ ID NO: 489          moltype =   length =
SEQUENCE: 489
000

SEQ ID NO: 490          moltype =   length =
SEQUENCE: 490
000

SEQ ID NO: 491          moltype =   length =
SEQUENCE: 491
000

SEQ ID NO: 492          moltype =   length =
SEQUENCE: 492
000

SEQ ID NO: 493          moltype =   length =
SEQUENCE: 493
000

SEQ ID NO: 494          moltype =   length =
SEQUENCE: 494
000

SEQ ID NO: 495          moltype = AA  length = 4
FEATURE                 Location/Qualifiers
source                  1..4
                        mol_type = protein
                        organism = synthetic construct
SEQUENCE: 495
GGSG                                                                    4

SEQ ID NO: 496          moltype = AA  length = 5
FEATURE                 Location/Qualifiers
source                  1..5
```

-continued

```
                            mol_type = protein
                            organism = synthetic construct
SEQUENCE: 496
GGSGG                                                             5

SEQ ID NO: 497            moltype = AA   length = 5
FEATURE                   Location/Qualifiers
source                    1..5
                          mol_type = protein
                          organism = synthetic construct
SEQUENCE: 497
GSGSG                                                             5

SEQ ID NO: 498            moltype = AA   length = 5
FEATURE                   Location/Qualifiers
source                    1..5
                          mol_type = protein
                          organism = synthetic construct
SEQUENCE: 498
GSGGG                                                             5

SEQ ID NO: 499            moltype = AA   length = 5
FEATURE                   Location/Qualifiers
source                    1..5
                          mol_type = protein
                          organism = synthetic construct
SEQUENCE: 499
GGGSG                                                             5

SEQ ID NO: 500            moltype = AA   length = 5
FEATURE                   Location/Qualifiers
source                    1..5
                          mol_type = protein
                          organism = synthetic construct
SEQUENCE: 500
GSSSG                                                             5

SEQ ID NO: 501            moltype = AA   length = 11
FEATURE                   Location/Qualifiers
source                    1..11
                          mol_type = protein
                          organism = synthetic construct
SEQUENCE: 501
GSSGGSGGSG G                                                      11

SEQ ID NO: 502            moltype = AA   length = 4
FEATURE                   Location/Qualifiers
source                    1..4
                          mol_type = protein
                          organism = synthetic construct
SEQUENCE: 502
GGGS                                                              4

SEQ ID NO: 503            moltype = AA   length = 8
FEATURE                   Location/Qualifiers
source                    1..8
                          mol_type = protein
                          organism = synthetic construct
SEQUENCE: 503
GGGSGGGS                                                          8

SEQ ID NO: 504            moltype = AA   length = 12
FEATURE                   Location/Qualifiers
source                    1..12
                          mol_type = protein
                          organism = synthetic construct
SEQUENCE: 504
GGGSGGGSGG GS                                                     12

SEQ ID NO: 505            moltype = AA   length = 15
FEATURE                   Location/Qualifiers
source                    1..15
                          mol_type = protein
                          organism = synthetic construct
SEQUENCE: 505
GGGGSGGGGS GGGGS                                                  15

SEQ ID NO: 506            moltype = AA   length = 25
FEATURE                   Location/Qualifiers
```

-continued

```
source                   1..25
                         mol_type = protein
                         organism = synthetic construct
SEQUENCE: 506
GGGGSGGGGS GGGGSGGGGS GGGGS                                          25

SEQ ID NO: 507           moltype = AA  length = 10
FEATURE                  Location/Qualifiers
source                   1..10
                         mol_type = protein
                         organism = synthetic construct
SEQUENCE: 507
GGGGSGGGGS                                                           10

SEQ ID NO: 508           moltype = AA  length = 5
FEATURE                  Location/Qualifiers
source                   1..5
                         mol_type = protein
                         organism = synthetic construct
SEQUENCE: 508
GGGGS                                                                5

SEQ ID NO: 509           moltype = AA  length = 7
FEATURE                  Location/Qualifiers
source                   1..7
                         mol_type = protein
                         organism = synthetic construct
SEQUENCE: 509
GGGGSGS                                                              7

SEQ ID NO: 510           moltype = AA  length = 17
FEATURE                  Location/Qualifiers
source                   1..17
                         mol_type = protein
                         organism = synthetic construct
SEQUENCE: 510
GGGGSGGGGS GGGGSGS                                                   17

SEQ ID NO: 511           moltype = AA  length = 12
FEATURE                  Location/Qualifiers
source                   1..12
                         mol_type = protein
                         organism = synthetic construct
SEQUENCE: 511
GGSLDPKGGG GS                                                        12

SEQ ID NO: 512           moltype = AA  length = 20
FEATURE                  Location/Qualifiers
source                   1..20
                         mol_type = protein
                         organism = synthetic construct
SEQUENCE: 512
PKSCDKTHTC PPCPAPELLG                                                20

SEQ ID NO: 513           moltype = AA  length = 17
FEATURE                  Location/Qualifiers
source                   1..17
                         mol_type = protein
                         organism = synthetic construct
SEQUENCE: 513
SKYGPPCPPC PAPEFLG                                                   17

SEQ ID NO: 514           moltype = AA  length = 12
FEATURE                  Location/Qualifiers
source                   1..12
                         mol_type = protein
                         organism = synthetic construct
SEQUENCE: 514
GKSSGSGSES KS                                                        12

SEQ ID NO: 515           moltype = AA  length = 14
FEATURE                  Location/Qualifiers
source                   1..14
                         mol_type = protein
                         organism = synthetic construct
SEQUENCE: 515
GSTSGSGKSS EGKG                                                      14

SEQ ID NO: 516           moltype = AA  length = 18
```

-continued

```
FEATURE                  Location/Qualifiers
source                   1..18
                         mol_type = protein
                         organism = synthetic construct
SEQUENCE: 516
GSTSGSGKSS EGSGSTKG                                                        18

SEQ ID NO: 517           moltype = AA  length = 18
FEATURE                  Location/Qualifiers
source                   1..18
                         mol_type = protein
                         organism = synthetic construct
SEQUENCE: 517
GSTSGSGKPG SGEGSTKG                                                        18

SEQ ID NO: 518           moltype = AA  length = 16
FEATURE                  Location/Qualifiers
source                   1..16
                         mol_type = protein
                         organism = synthetic construct
SEQUENCE: 518
GSTSGSGKPG SSEGST                                                          16

SEQ ID NO: 519           moltype = AA  length = 8
FEATURE                  Location/Qualifiers
source                   1..8
                         mol_type = protein
                         organism = synthetic construct
SEQUENCE: 519
GGGSSGGS                                                                    8

SEQ ID NO: 520           moltype = AA  length = 11
FEATURE                  Location/Qualifiers
source                   1..11
                         mol_type = protein
                         organism = synthetic construct
SEQUENCE: 520
GGGGSGGGGS S                                                               11

SEQ ID NO: 521           moltype = AA  length = 15
FEATURE                  Location/Qualifiers
source                   1..15
                         mol_type = protein
                         organism = synthetic construct
SEQUENCE: 521
GGGSSGGSGG SSGGS                                                           15

SEQ ID NO: 522           moltype = AA  length = 16
FEATURE                  Location/Qualifiers
source                   1..16
                         mol_type = protein
                         organism = synthetic construct
SEQUENCE: 522
GSTSGSGKPG SSEGST                                                          16

SEQ ID NO: 523           moltype = AA  length = 229
FEATURE                  Location/Qualifiers
source                   1..229
                         mol_type = protein
                         organism = synthetic construct
VARIANT                  229
                         note = May be absent
SEQUENCE: 523
ESKYGPPCPP CPAPEFEGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV CTLPPSQEEM TKNQVSLSCA VKGFYPSDIA VEWESNGQPE NNYKTTPPVL  180
DSDGSFFLVS RLTVDKSRWQ EGNVFSCSVM HEALHNHYTQ KSLSLSLGK             229

SEQ ID NO: 524           moltype = AA  length = 230
FEATURE                  Location/Qualifiers
source                   1..230
                         mol_type = protein
                         organism = synthetic construct
VARIANT                  230
                         note = May be absent
SEQUENCE: 524
GSSKYGPPCP PCPAPEFEGG PSVFLFPPKP KDTLMISRTP EVTCVVVDVS QEDPEVQFNW  60
YVDGVEVHNA KTKPREEQFN STYRVVSVLT VLHQDWLNGK EYKCKVSNKG LPSSIEKTIS  120
KAKGQPREPQ VYTLPPCQEE MTKNQVSLWC LVKGFYPSDI AVEWESNGQP ENNYKTTPPV  180
```

-continued

```
LDSDGSFFLY SRLTVDKSRW QEGNVFSCSV MHEALHNHYT QKSLSLSLGK              230

SEQ ID NO: 525          moltype = AA   length = 330
FEATURE                 Location/Qualifiers
source                  1..330
                        mol_type = protein
                        organism = synthetic construct
VARIANT                 330
                        note = May be absent
SEQUENCE: 525
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 526          moltype = AA   length = 326
FEATURE                 Location/Qualifiers
source                  1..326
                        mol_type = protein
                        organism = synthetic construct
VARIANT                 326
                        note = May be absent
SEQUENCE: 526
ASTKGPSVFP LAPCSRSTSE STAALGCLVK DYFPEPVTVS WNSGALTSGV HTFPAVLQSS   60
GLYSLSSVVT VPSSNFGTQT YTCNVDHKPS NTKVDKTVER KCCVECPPCP APPVAGPSVF   120
LFPPKPKDTL MISRTPEVTC VVVDVSHEDP EVQFNWYVDG VEVHNAKTKP REEQFNSTFR   180
VVSVLTVVHQ DWLNGKEYKC KVSNKGLPAP IEKTISKTKG QPREPQVYTL PPSREEMTKN   240
QVSLTCLVKG FYPSDISVEW ESNGQPENNY KTTPPMLDSD GSFFLYSKLT VDKSRWQQGN   300
VFSCSVMHEA LHNHYTQKSL SLSPGK                                        326

SEQ ID NO: 527          moltype = AA   length = 377
FEATURE                 Location/Qualifiers
source                  1..377
                        mol_type = protein
                        organism = synthetic construct
VARIANT                 377
                        note = May be absent
SEQUENCE: 527
ASTKGPSVFP LAPCSRSTSG GTAALGCLVK DYFPEPVTVS WNSGALTSGV HTFPAVLQSS   60
GLYSLSSVVT VPSSSLGTQT YTCNVNHKPS NTKVDKRVEL KTPLGDTTHT CPRCPEPKSC   120
DTPPPCPRCP EPKSCDTPPP CPRCPEPKSC DTPPPCPRCP APELLGGPSV FLFPPKPKDT   180
LMISRTPEVT CVVVDVSHED PEVQFKWYVD GVEVHNAKTK PREEQYNSTF RVVSVLTVLH   240
QDWLNGKEYK CKVSNKALPA PIEKTISKTK GQPREPQVYT LPPSREEMTK NQVSLTCLVK   300
GFYPSDIAVE WESSGQPENN YNTTPPMLDS DGSFFLYSKL TVDKSRWQQG NIFSCSVMHE   360
ALHNRFTQKS LSLSPGK                                                  377

SEQ ID NO: 528          moltype = AA   length = 327
FEATURE                 Location/Qualifiers
source                  1..327
                        mol_type = protein
                        organism = synthetic construct
VARIANT                 327
                        note = May be absent
SEQUENCE: 528
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPSCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                       327

SEQ ID NO: 529          moltype = AA   length = 8
FEATURE                 Location/Qualifiers
source                  1..8
                        mol_type = protein
                        organism = synthetic construct
SEQUENCE: 529
PRFKIIGG                                                            8

SEQ ID NO: 530          moltype = AA   length = 8
FEATURE                 Location/Qualifiers
source                  1..8
                        mol_type = protein
                        organism = synthetic construct
SEQUENCE: 530
PRFRIIGG                                                            8
```

-continued

```
SEQ ID NO: 531          moltype = AA   length = 9
FEATURE                 Location/Qualifiers
source                  1..9
                        mol_type = protein
                        organism = synthetic construct
SEQUENCE: 531
SSRHRRALD                                                          9

SEQ ID NO: 532          moltype = AA   length = 14
FEATURE                 Location/Qualifiers
source                  1..14
                        mol_type = protein
                        organism = synthetic construct
SEQUENCE: 532
RKSSIIIRMR DVVL                                                    14

SEQ ID NO: 533          moltype = AA   length = 15
FEATURE                 Location/Qualifiers
source                  1..15
                        mol_type = protein
                        organism = synthetic construct
SEQUENCE: 533
SSSFDKGKYK KGDDA                                                   15

SEQ ID NO: 534          moltype = AA   length = 15
FEATURE                 Location/Qualifiers
source                  1..15
                        mol_type = protein
                        organism = synthetic construct
SEQUENCE: 534
SSSFDKGKYK RGDDA                                                   15

SEQ ID NO: 535          moltype = AA   length = 4
FEATURE                 Location/Qualifiers
source                  1..4
                        mol_type = protein
                        organism = synthetic construct
SEQUENCE: 535
IEGR                                                               4

SEQ ID NO: 536          moltype = AA   length = 4
FEATURE                 Location/Qualifiers
source                  1..4
                        mol_type = protein
                        organism = synthetic construct
SEQUENCE: 536
IDGR                                                               4

SEQ ID NO: 537          moltype = AA   length = 7
FEATURE                 Location/Qualifiers
source                  1..7
                        mol_type = protein
                        organism = synthetic construct
SEQUENCE: 537
GGSIDGR                                                            7

SEQ ID NO: 538          moltype = AA   length = 6
FEATURE                 Location/Qualifiers
source                  1..6
                        mol_type = protein
                        organism = synthetic construct
SEQUENCE: 538
PLGLWA                                                             6

SEQ ID NO: 539          moltype = AA   length = 8
FEATURE                 Location/Qualifiers
source                  1..8
                        mol_type = protein
                        organism = synthetic construct
SEQUENCE: 539
GPQGIAGQ                                                           8

SEQ ID NO: 540          moltype = AA   length = 8
FEATURE                 Location/Qualifiers
source                  1..8
                        mol_type = protein
                        organism = synthetic construct
SEQUENCE: 540
GPQGLLGA                                                           8
```

-continued

```
SEQ ID NO: 541              moltype = AA  length = 5
FEATURE                     Location/Qualifiers
source                      1..5
                            mol_type = protein
                            organism = synthetic construct
SEQUENCE: 541
GIAGQ                                                                   5

SEQ ID NO: 542              moltype = AA  length = 8
FEATURE                     Location/Qualifiers
source                      1..8
                            mol_type = protein
                            organism = synthetic construct
SEQUENCE: 542
GPLGIAGI                                                                8

SEQ ID NO: 543              moltype = AA  length = 8
FEATURE                     Location/Qualifiers
source                      1..8
                            mol_type = protein
                            organism = synthetic construct
SEQUENCE: 543
GPEGLRVG                                                                8

SEQ ID NO: 544              moltype = AA  length = 8
FEATURE                     Location/Qualifiers
source                      1..8
                            mol_type = protein
                            organism = synthetic construct
SEQUENCE: 544
YGAGLGVV                                                                8

SEQ ID NO: 545              moltype = AA  length = 8
FEATURE                     Location/Qualifiers
source                      1..8
                            mol_type = protein
                            organism = synthetic construct
SEQUENCE: 545
AGLGVVER                                                                8

SEQ ID NO: 546              moltype = AA  length = 8
FEATURE                     Location/Qualifiers
source                      1..8
                            mol_type = protein
                            organism = synthetic construct
SEQUENCE: 546
AGLGISST                                                                8

SEQ ID NO: 547              moltype = AA  length = 8
FEATURE                     Location/Qualifiers
source                      1..8
                            mol_type = protein
                            organism = synthetic construct
SEQUENCE: 547
EPQALAMS                                                                8

SEQ ID NO: 548              moltype = AA  length = 8
FEATURE                     Location/Qualifiers
source                      1..8
                            mol_type = protein
                            organism = synthetic construct
SEQUENCE: 548
QALAMSAI                                                                8

SEQ ID NO: 549              moltype = AA  length = 8
FEATURE                     Location/Qualifiers
source                      1..8
                            mol_type = protein
                            organism = synthetic construct
SEQUENCE: 549
AAYHLVSQ                                                                8

SEQ ID NO: 550              moltype = AA  length = 8
FEATURE                     Location/Qualifiers
source                      1..8
                            mol_type = protein
                            organism = synthetic construct
SEQUENCE: 550
```

-continued

```
MDAFLESS                                                             8

SEQ ID NO: 551           moltype = AA   length = 8
FEATURE                  Location/Qualifiers
source                   1..8
                         mol_type = protein
                         organism = synthetic construct
SEQUENCE: 551
ESLPVVAV                                                             8

SEQ ID NO: 552           moltype = AA   length = 8
FEATURE                  Location/Qualifiers
source                   1..8
                         mol_type = protein
                         organism = synthetic construct
SEQUENCE: 552
SAPAVESE                                                             8

SEQ ID NO: 553           moltype = AA   length = 8
FEATURE                  Location/Qualifiers
source                   1..8
                         mol_type = protein
                         organism = synthetic construct
SEQUENCE: 553
DVAQFVLT                                                             8

SEQ ID NO: 554           moltype = AA   length = 8
FEATURE                  Location/Qualifiers
source                   1..8
                         mol_type = protein
                         organism = synthetic construct
SEQUENCE: 554
VAQFVLTE                                                             8

SEQ ID NO: 555           moltype = AA   length = 8
FEATURE                  Location/Qualifiers
source                   1..8
                         mol_type = protein
                         organism = synthetic construct
SEQUENCE: 555
AQFVLTEG                                                             8

SEQ ID NO: 556           moltype = AA   length = 8
FEATURE                  Location/Qualifiers
source                   1..8
                         mol_type = protein
                         organism = synthetic construct
SEQUENCE: 556
PVQPIGPQ                                                             8

SEQ ID NO: 557           moltype = AA   length = 449
FEATURE                  Location/Qualifiers
source                   1..449
                         mol_type = protein
                         organism = synthetic construct
SEQUENCE: 557
QVQLKQSGPG LVQPSQSLSI TCTVSGFSLT NYGVHWVRQS PGKGLEWLGV IWSGGNTDYN   60
TPFTSRLSIN KDNSKSQVFF KMNSLQSQDT AIYYCARALT YYDYEFAYWG QGTLVTVSAA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 558           moltype = AA   length = 214
FEATURE                  Location/Qualifiers
source                   1..214
                         mol_type = protein
                         organism = synthetic construct
SEQUENCE: 558
QILLTQSPVI LSVSPGERVS FSCRASQSIG TNIHWYQQRT NGSPRLLIKY ASESISGIPS   60
RFSGSGSGTD FTLSINSVES EDIADYYCQQ NNNWPTTFGA GTKLELKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 559           moltype =   length =
SEQUENCE: 559
000
```

-continued

```
SEQ ID NO: 560          moltype = AA   length = 6
FEATURE                 Location/Qualifiers
source                  1..6
                        mol_type = protein
                        organism = synthetic construct
SEQUENCE: 560
PYGLSK                                                          6

SEQ ID NO: 561          moltype = AA   length = 6
FEATURE                 Location/Qualifiers
source                  1..6
                        mol_type = protein
                        organism = synthetic construct
SEQUENCE: 561
PFGLSK                                                          6

SEQ ID NO: 562          moltype = AA   length = 6
FEATURE                 Location/Qualifiers
source                  1..6
                        mol_type = protein
                        organism = synthetic construct
SEQUENCE: 562
PRGLSK                                                          6

SEQ ID NO: 563          moltype = AA   length = 6
FEATURE                 Location/Qualifiers
source                  1..6
                        mol_type = protein
                        organism = synthetic construct
SEQUENCE: 563
PMGLSK                                                          6

SEQ ID NO: 564          moltype = AA   length = 6
FEATURE                 Location/Qualifiers
source                  1..6
                        mol_type = protein
                        organism = synthetic construct
SEQUENCE: 564
PKGLSK                                                          6

SEQ ID NO: 565          moltype = AA   length = 6
FEATURE                 Location/Qualifiers
source                  1..6
                        mol_type = protein
                        organism = synthetic construct
SEQUENCE: 565
PQGLSK                                                          6

SEQ ID NO: 566          moltype = AA   length = 13
FEATURE                 Location/Qualifiers
source                  1..13
                        mol_type = protein
                        organism = synthetic construct
SEQUENCE: 566
APMGLKHDHQ SKS                                                  13

SEQ ID NO: 567          moltype = AA   length = 12
FEATURE                 Location/Qualifiers
source                  1..12
                        mol_type = protein
                        organism = synthetic construct
SEQUENCE: 567
PMGLKHDHQS RS                                                   12

SEQ ID NO: 568          moltype = AA   length = 12
FEATURE                 Location/Qualifiers
source                  1..12
                        mol_type = protein
                        organism = synthetic construct
SEQUENCE: 568
PMGLKHDHQS KS                                                   12

SEQ ID NO: 569          moltype = AA   length = 12
FEATURE                 Location/Qualifiers
source                  1..12
                        mol_type = protein
                        organism = synthetic construct
SEQUENCE: 569
```

-continued

```
APMGLKHDHQ SR                                                          12

SEQ ID NO: 570          moltype = AA  length = 12
FEATURE                 Location/Qualifiers
source                  1..12
                        mol_type = protein
                        organism = synthetic construct
SEQUENCE: 570
APMGLKHDHQ SK                                                          12

SEQ ID NO: 571          moltype = AA  length = 11
FEATURE                 Location/Qualifiers
source                  1..11
                        mol_type = protein
                        organism = synthetic construct
SEQUENCE: 571
PMGLKHDHQS R                                                           11

SEQ ID NO: 572          moltype = AA  length = 11
FEATURE                 Location/Qualifiers
source                  1..11
                        mol_type = protein
                        organism = synthetic construct
SEQUENCE: 572
PMGLKHDHQS K                                                           11

SEQ ID NO: 573          moltype = AA  length = 11
FEATURE                 Location/Qualifiers
source                  1..11
                        mol_type = protein
                        organism = synthetic construct
SEQUENCE: 573
PMGLKDHQSR S                                                           11

SEQ ID NO: 574          moltype = AA  length = 11
FEATURE                 Location/Qualifiers
source                  1..11
                        mol_type = protein
                        organism = synthetic construct
SEQUENCE: 574
PMGLKDHQSK S                                                           11

SEQ ID NO: 575          moltype = AA  length = 11
FEATURE                 Location/Qualifiers
source                  1..11
                        mol_type = protein
                        organism = synthetic construct
SEQUENCE: 575
PMGLKHHQSR S                                                           11

SEQ ID NO: 576          moltype = AA  length = 11
FEATURE                 Location/Qualifiers
source                  1..11
                        mol_type = protein
                        organism = synthetic construct
SEQUENCE: 576
PMGLKHHQSK S                                                           11

SEQ ID NO: 577          moltype = AA  length = 10
FEATURE                 Location/Qualifiers
source                  1..10
                        mol_type = protein
                        organism = synthetic construct
SEQUENCE: 577
PMGLKHQSRS                                                             10

SEQ ID NO: 578          moltype = AA  length = 10
FEATURE                 Location/Qualifiers
source                  1..10
                        mol_type = protein
                        organism = synthetic construct
SEQUENCE: 578
PMGLKHQSKS                                                             10

SEQ ID NO: 579          moltype = AA  length = 10
FEATURE                 Location/Qualifiers
source                  1..10
                        mol_type = protein
                        organism = synthetic construct
```

-continued

```
SEQUENCE: 579
PMGLKDHQSR                                                              10

SEQ ID NO: 580           moltype = AA  length = 10
FEATURE                  Location/Qualifiers
source                   1..10
                         mol_type = protein
                         organism = synthetic construct
SEQUENCE: 580
PMGLKDHQSK                                                              10

SEQ ID NO: 581           moltype = AA  length = 10
FEATURE                  Location/Qualifiers
source                   1..10
                         mol_type = protein
                         organism = synthetic construct
SEQUENCE: 581
PMGLKHHQSR                                                              10

SEQ ID NO: 582           moltype = AA  length = 10
FEATURE                  Location/Qualifiers
source                   1..10
                         mol_type = protein
                         organism = synthetic construct
SEQUENCE: 582
PMGLKHHQSK                                                              10

SEQ ID NO: 583           moltype = AA  length = 9
FEATURE                  Location/Qualifiers
source                   1..9
                         mol_type = protein
                         organism = synthetic construct
SEQUENCE: 583
PMGLKHQSR                                                               9

SEQ ID NO: 584           moltype = AA  length = 9
FEATURE                  Location/Qualifiers
source                   1..9
                         mol_type = protein
                         organism = synthetic construct
SEQUENCE: 584
PMGLKHQSK                                                               9

SEQ ID NO: 585           moltype = AA  length = 9
FEATURE                  Location/Qualifiers
source                   1..9
                         mol_type = protein
                         organism = synthetic construct
SEQUENCE: 585
PYGLKHQSR                                                               9

SEQ ID NO: 586           moltype = AA  length = 9
FEATURE                  Location/Qualifiers
source                   1..9
                         mol_type = protein
                         organism = synthetic construct
SEQUENCE: 586
PFGLKHQSR                                                               9

SEQ ID NO: 587           moltype = AA  length = 9
FEATURE                  Location/Qualifiers
source                   1..9
                         mol_type = protein
                         organism = synthetic construct
SEQUENCE: 587
PRGLKHQSR                                                               9

SEQ ID NO: 588           moltype = AA  length = 9
FEATURE                  Location/Qualifiers
source                   1..9
                         mol_type = protein
                         organism = synthetic construct
SEQUENCE: 588
PWGLKHQSR                                                               9

SEQ ID NO: 589           moltype = AA  length = 9
FEATURE                  Location/Qualifiers
source                   1..9
                         mol_type = protein
```

-continued

```
                         organism = synthetic construct
SEQUENCE: 589
PKGLKHQSR                                                               9

SEQ ID NO: 590          moltype = AA   length = 9
FEATURE                 Location/Qualifiers
source                  1..9
                        mol_type = protein
                        organism = synthetic construct
SEQUENCE: 590
PQGLKHQSR                                                               9

SEQ ID NO: 591          moltype = AA   length = 9
FEATURE                 Location/Qualifiers
source                  1..9
                        mol_type = protein
                        organism = synthetic construct
SEQUENCE: 591
PYGLKHQSK                                                               9

SEQ ID NO: 592          moltype = AA   length = 9
FEATURE                 Location/Qualifiers
source                  1..9
                        mol_type = protein
                        organism = synthetic construct
SEQUENCE: 592
PFGLKHQSK                                                               9

SEQ ID NO: 593          moltype = AA   length = 9
FEATURE                 Location/Qualifiers
source                  1..9
                        mol_type = protein
                        organism = synthetic construct
SEQUENCE: 593
PRGLKHQSK                                                               9

SEQ ID NO: 594          moltype = AA   length = 9
FEATURE                 Location/Qualifiers
source                  1..9
                        mol_type = protein
                        organism = synthetic construct
SEQUENCE: 594
PWGLKHQSK                                                               9

SEQ ID NO: 595          moltype = AA   length = 9
FEATURE                 Location/Qualifiers
source                  1..9
                        mol_type = protein
                        organism = synthetic construct
SEQUENCE: 595
PKGLKHQSK                                                               9

SEQ ID NO: 596          moltype = AA   length = 9
FEATURE                 Location/Qualifiers
source                  1..9
                        mol_type = protein
                        organism = synthetic construct
SEQUENCE: 596
PQGLKHQSK                                                               9

SEQ ID NO: 597          moltype = AA   length = 12
FEATURE                 Location/Qualifiers
source                  1..12
                        mol_type = protein
                        organism = synthetic construct
SEQUENCE: 597
HQSRSAPMGL KH                                                           12

SEQ ID NO: 598          moltype = AA   length = 12
FEATURE                 Location/Qualifiers
source                  1..12
                        mol_type = protein
                        organism = synthetic construct
SEQUENCE: 598
DHQSRSPMGL KH                                                           12

SEQ ID NO: 599          moltype = AA   length = 11
FEATURE                 Location/Qualifiers
source                  1..11
```

```
                    mol_type = protein
                    organism = synthetic construct
SEQUENCE: 599
HQSRSPMGLK H                                                      11

SEQ ID NO: 600     moltype = AA   length = 13
FEATURE            Location/Qualifiers
source             1..13
                   mol_type = protein
                   organism = synthetic construct
SEQUENCE: 600
DHQSKSAPMG LKH                                                    13

SEQ ID NO: 601     moltype = AA   length = 12
FEATURE            Location/Qualifiers
source             1..12
                   mol_type = protein
                   organism = synthetic construct
SEQUENCE: 601
HQSKSAPMGL KH                                                     12

SEQ ID NO: 602     moltype = AA   length = 12
FEATURE            Location/Qualifiers
source             1..12
                   mol_type = protein
                   organism = synthetic construct
SEQUENCE: 602
DHQSKSPMGL KH                                                     12

SEQ ID NO: 603     moltype = AA   length = 11
FEATURE            Location/Qualifiers
source             1..11
                   mol_type = protein
                   organism = synthetic construct
SEQUENCE: 603
HQSKSPMGLK H                                                      11

SEQ ID NO: 604     moltype = AA   length = 12
FEATURE            Location/Qualifiers
source             1..12
                   mol_type = protein
                   organism = synthetic construct
SEQUENCE: 604
DHQSRSAPMG LK                                                     12

SEQ ID NO: 605     moltype = AA   length = 11
FEATURE            Location/Qualifiers
source             1..11
                   mol_type = protein
                   organism = synthetic construct
SEQUENCE: 605
HQSRSAPMGL K                                                      11

SEQ ID NO: 606     moltype = AA   length = 11
FEATURE            Location/Qualifiers
source             1..11
                   mol_type = protein
                   organism = synthetic construct
SEQUENCE: 606
DHQSRSPMGL K                                                      11

SEQ ID NO: 607     moltype = AA   length = 10
FEATURE            Location/Qualifiers
source             1..10
                   mol_type = protein
                   organism = synthetic construct
SEQUENCE: 607
HQSRSPMGLK                                                        10

SEQ ID NO: 608     moltype = AA   length = 12
FEATURE            Location/Qualifiers
source             1..12
                   mol_type = protein
                   organism = synthetic construct
SEQUENCE: 608
DHQSKSAPMG LK                                                     12

SEQ ID NO: 609     moltype = AA   length = 11
FEATURE            Location/Qualifiers
```

-continued

```
source                   1..11
                         mol_type = protein
                         organism = synthetic construct
SEQUENCE: 609
HQSKSAPMGL K                                                      11

SEQ ID NO: 610           moltype = AA   length = 11
FEATURE                  Location/Qualifiers
source                   1..11
                         mol_type = protein
                         organism = synthetic construct
SEQUENCE: 610
DHQSKSPMGL K                                                      11

SEQ ID NO: 611           moltype = AA   length = 10
FEATURE                  Location/Qualifiers
source                   1..10
                         mol_type = protein
                         organism = synthetic construct
SEQUENCE: 611
HQSKSPMGLK                                                        10

SEQ ID NO: 612           moltype = AA   length = 11
FEATURE                  Location/Qualifiers
source                   1..11
                         mol_type = protein
                         organism = synthetic construct
SEQUENCE: 612
DHQSRSAPMG L                                                      11

SEQ ID NO: 613           moltype = AA   length = 10
FEATURE                  Location/Qualifiers
source                   1..10
                         mol_type = protein
                         organism = synthetic construct
SEQUENCE: 613
HQSRSAPMGL                                                        10

SEQ ID NO: 614           moltype = AA   length = 10
FEATURE                  Location/Qualifiers
source                   1..10
                         mol_type = protein
                         organism = synthetic construct
SEQUENCE: 614
DHQSRSPMGL                                                        10

SEQ ID NO: 615           moltype = AA   length = 9
FEATURE                  Location/Qualifiers
source                   1..9
                         mol_type = protein
                         organism = synthetic construct
SEQUENCE: 615
HQSRSPMGL                                                         9

SEQ ID NO: 616           moltype = AA   length = 11
FEATURE                  Location/Qualifiers
source                   1..11
                         mol_type = protein
                         organism = synthetic construct
SEQUENCE: 616
DHQSKSAPMG L                                                      11

SEQ ID NO: 617           moltype = AA   length = 10
FEATURE                  Location/Qualifiers
source                   1..10
                         mol_type = protein
                         organism = synthetic construct
SEQUENCE: 617
HQSKSAPMGL                                                        10

SEQ ID NO: 618           moltype = AA   length = 10
FEATURE                  Location/Qualifiers
source                   1..10
                         mol_type = protein
                         organism = synthetic construct
SEQUENCE: 618
DHQSKSPMGL                                                        10

SEQ ID NO: 619           moltype = AA   length = 9
```

-continued

```
FEATURE                  Location/Qualifiers
source                   1..9
                         mol_type = protein
                         organism = synthetic construct
SEQUENCE: 619
HQSKSPMGL                                                              9

SEQ ID NO: 620           moltype = AA  length = 9
FEATURE                  Location/Qualifiers
source                   1..9
                         mol_type = protein
                         organism = synthetic construct
SEQUENCE: 620
HQSRSPRGL                                                              9

SEQ ID NO: 621           moltype = AA  length = 9
FEATURE                  Location/Qualifiers
source                   1..9
                         mol_type = protein
                         organism = synthetic construct
SEQUENCE: 621
HQSRSPKGL                                                              9

SEQ ID NO: 622           moltype = AA  length = 9
FEATURE                  Location/Qualifiers
source                   1..9
                         mol_type = protein
                         organism = synthetic construct
SEQUENCE: 622
HQSRSPQGL                                                              9

SEQ ID NO: 623           moltype = AA  length = 9
FEATURE                  Location/Qualifiers
source                   1..9
                         mol_type = protein
                         organism = synthetic construct
SEQUENCE: 623
HQSKSPRGL                                                              9

SEQ ID NO: 624           moltype = AA  length = 9
FEATURE                  Location/Qualifiers
source                   1..9
                         mol_type = protein
                         organism = synthetic construct
SEQUENCE: 624
HQSKSPKGL                                                              9

SEQ ID NO: 625           moltype = AA  length = 9
FEATURE                  Location/Qualifiers
source                   1..9
                         mol_type = protein
                         organism = synthetic construct
SEQUENCE: 625
HQSKSPQGL                                                              9

SEQ ID NO: 626           moltype = AA  length = 8
FEATURE                  Location/Qualifiers
source                   1..8
                         mol_type = protein
                         organism = synthetic construct
SEQUENCE: 626
HQSRPMGL                                                               8

SEQ ID NO: 627           moltype = AA  length = 8
FEATURE                  Location/Qualifiers
source                   1..8
                         mol_type = protein
                         organism = synthetic construct
SEQUENCE: 627
HQSRPRGL                                                               8

SEQ ID NO: 628           moltype = AA  length = 8
FEATURE                  Location/Qualifiers
source                   1..8
                         mol_type = protein
                         organism = synthetic construct
SEQUENCE: 628
HQSRPKGL                                                               8
```

-continued

```
SEQ ID NO: 629          moltype = AA   length = 8
FEATURE                 Location/Qualifiers
source                  1..8
                        mol_type = protein
                        organism = synthetic construct
SEQUENCE: 629
HQSRPQGL                                                            8

SEQ ID NO: 630          moltype = AA   length = 8
FEATURE                 Location/Qualifiers
source                  1..8
                        mol_type = protein
                        organism = synthetic construct
SEQUENCE: 630
HQSKPMGL                                                            8

SEQ ID NO: 631          moltype = AA   length = 8
FEATURE                 Location/Qualifiers
source                  1..8
                        mol_type = protein
                        organism = synthetic construct
SEQUENCE: 631
HQSKPRGL                                                            8

SEQ ID NO: 632          moltype = AA   length = 8
FEATURE                 Location/Qualifiers
source                  1..8
                        mol_type = protein
                        organism = synthetic construct
SEQUENCE: 632
HQSKPKGL                                                            8

SEQ ID NO: 633          moltype = AA   length = 8
FEATURE                 Location/Qualifiers
source                  1..8
                        mol_type = protein
                        organism = synthetic construct
SEQUENCE: 633
HQSKPQGL                                                            8

SEQ ID NO: 634          moltype = AA   length = 9
FEATURE                 Location/Qualifiers
source                  1..9
                        mol_type = protein
                        organism = synthetic construct
SEQUENCE: 634
PMGLHQSRS                                                           9

SEQ ID NO: 635          moltype = AA   length = 9
FEATURE                 Location/Qualifiers
source                  1..9
                        mol_type = protein
                        organism = synthetic construct
SEQUENCE: 635
PYGLHQSRS                                                           9

SEQ ID NO: 636          moltype = AA   length = 9
FEATURE                 Location/Qualifiers
source                  1..9
                        mol_type = protein
                        organism = synthetic construct
SEQUENCE: 636
PFGLHQSRS                                                           9

SEQ ID NO: 637          moltype = AA   length = 9
FEATURE                 Location/Qualifiers
source                  1..9
                        mol_type = protein
                        organism = synthetic construct
SEQUENCE: 637
PRGLHQSRS                                                           9

SEQ ID NO: 638          moltype = AA   length = 9
FEATURE                 Location/Qualifiers
source                  1..9
                        mol_type = protein
                        organism = synthetic construct
SEQUENCE: 638
PKGLHQSRS                                                           9
```

-continued

```
SEQ ID NO: 639            moltype = AA   length = 9
FEATURE                   Location/Qualifiers
source                    1..9
                          mol_type = protein
                          organism = synthetic construct SEQUENCE: 639
PQGLHQSRS                                                          9

SEQ ID NO: 640            moltype = AA   length = 9
FEATURE                   Location/Qualifiers
source                    1..9
                          mol_type = protein
                          organism = synthetic construct SEQUENCE: 640
PMGLHQSKS                                                          9

SEQ ID NO: 641            moltype = AA   length = 9
FEATURE                   Location/Qualifiers
source                    1..9
                          mol_type = protein
                          organism = synthetic construct SEQUENCE: 641
PYGLHQSKS                                                          9

SEQ ID NO: 642            moltype = AA   length = 9
FEATURE                   Location/Qualifiers
source                    1..9
                          mol_type = protein
                          organism = synthetic construct SEQUENCE: 642
PFGLHQSKS                                                          9

SEQ ID NO: 643            moltype = AA   length = 9
FEATURE                   Location/Qualifiers
source                    1..9
                          mol_type = protein
                          organism = synthetic construct SEQUENCE: 643
PRGLHQSKS                                                          9

SEQ ID NO: 644            moltype = AA   length = 9
FEATURE                   Location/Qualifiers
source                    1..9
                          mol_type = protein
                          organism = synthetic construct SEQUENCE: 644
PKGLHQSKS                                                          9

SEQ ID NO: 645            moltype = AA   length = 9
FEATURE                   Location/Qualifiers
source                    1..9
                          mol_type = protein
                          organism = synthetic construct SEQUENCE: 645
PQGLHQSKS                                                          9

SEQ ID NO: 646            moltype = AA   length = 8
FEATURE                   Location/Qualifiers
source                    1..8
                          mol_type = protein
                          organism = synthetic construct SEQUENCE: 646
PMGLHQSR                                                           8

SEQ ID NO: 647            moltype = AA   length = 8
FEATURE                   Location/Qualifiers
source                    1..8
                          mol_type = protein
                          organism = synthetic construct SEQUENCE: 647
PYGLHQSR                                                           8

SEQ ID NO: 648            moltype = AA   length = 8
FEATURE                   Location/Qualifiers
source                    1..8
                          mol_type = protein
                          organism = synthetic construct

SEQUENCE: 648
```

```
PFGLHQSR                                                          8

SEQ ID NO: 649              moltype = AA   length = 8
FEATURE                     Location/Qualifiers
source                      1..8
                            mol_type = protein
                            organism = synthetic construct
SEQUENCE: 649
PRGLHQSR                                                          8

SEQ ID NO: 650              moltype = AA   length = 8
FEATURE                     Location/Qualifiers
source                      1..8
                            mol_type = protein
                            organism = synthetic construct
SEQUENCE: 650
PKGLHQSR                                                          8

SEQ ID NO: 651              moltype = AA   length = 8
FEATURE                     Location/Qualifiers
source                      1..8
                            mol_type = protein
                            organism = synthetic construct
SEQUENCE: 651
PQGLHQSR                                                          8

SEQ ID NO: 652              moltype = AA   length = 8
FEATURE                     Location/Qualifiers
source                      1..8
                            mol_type = protein
                            organism = synthetic construct
SEQUENCE: 652
PMGLHQSK                                                          8

SEQ ID NO: 653              moltype = AA   length = 8
FEATURE                     Location/Qualifiers
source                      1..8
                            mol_type = protein
                            organism = synthetic construct
SEQUENCE: 653
PYGLHQSK                                                          8

SEQ ID NO: 654              moltype = AA   length = 8
FEATURE                     Location/Qualifiers
source                      1..8
                            mol_type = protein
                            organism = synthetic construct
SEQUENCE: 654
PFGLHQSK                                                          8

SEQ ID NO: 655              moltype = AA   length = 8
FEATURE                     Location/Qualifiers
source                      1..8
                            mol_type = protein
                            organism = synthetic construct
SEQUENCE: 655
PRGLHQSK                                                          8

SEQ ID NO: 656              moltype = AA   length = 8
FEATURE                     Location/Qualifiers
source                      1..8
                            mol_type = protein
                            organism = synthetic construct
SEQUENCE: 656
PKGLHQSK                                                          8

SEQ ID NO: 657              moltype = AA   length = 8
FEATURE                     Location/Qualifiers
source                      1..8
                            mol_type = protein
                            organism = synthetic construct
SEQUENCE: 657
PQGLHQSK                                                          8

SEQ ID NO: 658              moltype = AA   length = 6
FEATURE                     Location/Qualifiers
source                      1..6
                            mol_type = protein
                            organism = synthetic construct
```

```
SEQUENCE: 658
RPRGLN                                                                          6

SEQ ID NO: 659          moltype = AA  length = 6
FEATURE                 Location/Qualifiers
source                  1..6
                        mol_type = protein
                        organism = synthetic construct
SEQUENCE: 659
RPKGLN                                                                          6

SEQ ID NO: 660          moltype = AA  length = 6
FEATURE                 Location/Qualifiers
source                  1..6
                        mol_type = protein
                        organism = synthetic construct
SEQUENCE: 660
KPKGLN                                                                          6

SEQ ID NO: 661          moltype = AA  length = 6
FEATURE                 Location/Qualifiers
source                  1..6
                        mol_type = protein
                        organism = synthetic construct
SEQUENCE: 661
RPRGLF                                                                          6

SEQ ID NO: 662          moltype = AA  length = 6
FEATURE                 Location/Qualifiers
source                  1..6
                        mol_type = protein
                        organism = synthetic construct
SEQUENCE: 662
RPKGLF                                                                          6

SEQ ID NO: 663          moltype = AA  length = 6
FEATURE                 Location/Qualifiers
source                  1..6
                        mol_type = protein
                        organism = synthetic construct
SEQUENCE: 663
KPKGLF                                                                          6

SEQ ID NO: 664          moltype = AA  length = 5
FEATURE                 Location/Qualifiers
source                  1..5
                        mol_type = protein
                        organism = synthetic construct
SEQUENCE: 664
KPRGL                                                                           5

SEQ ID NO: 665          moltype = AA  length = 5
FEATURE                 Location/Qualifiers
source                  1..5
                        mol_type = protein
                        organism = synthetic construct
SEQUENCE: 665
RPRGL                                                                           5

SEQ ID NO: 666          moltype = AA  length = 5
FEATURE                 Location/Qualifiers
source                  1..5
                        mol_type = protein
                        organism = synthetic construct
SEQUENCE: 666
RPKGL                                                                           5

SEQ ID NO: 667          moltype = AA  length = 5
FEATURE                 Location/Qualifiers
source                  1..5
                        mol_type = protein
                        organism = synthetic construct
SEQUENCE: 667
KPKGL                                                                           5

SEQ ID NO: 668          moltype = AA  length = 6
FEATURE                 Location/Qualifiers
source                  1..6
                        mol_type = protein
```

```
                           organism = synthetic construct
SEQUENCE: 668
APKSLL                                                                    6

SEQ ID NO: 669            moltype = AA  length = 5
FEATURE                   Location/Qualifiers
source                    1..5
                          mol_type = protein
                          organism = synthetic construct
SEQUENCE: 669
APRSL                                                                     5

SEQ ID NO: 670            moltype = AA  length = 5
FEATURE                   Location/Qualifiers
source                    1..5
                          mol_type = protein
                          organism = synthetic construct
SEQUENCE: 670
APKSL                                                                     5

SEQ ID NO: 671            moltype = AA  length = 6
FEATURE                   Location/Qualifiers
source                    1..6
                          mol_type = protein
                          organism = synthetic construct
SEQUENCE: 671
APKGLL                                                                    6

SEQ ID NO: 672            moltype = AA  length = 5
FEATURE                   Location/Qualifiers
source                    1..5
                          mol_type = protein
                          organism = synthetic construct
SEQUENCE: 672
APRGL                                                                     5

SEQ ID NO: 673            moltype = AA  length = 5
FEATURE                   Location/Qualifiers
source                    1..5
                          mol_type = protein
                          organism = synthetic construct
SEQUENCE: 673
APKGL                                                                     5

SEQ ID NO: 674            moltype = AA  length = 6
FEATURE                   Location/Qualifiers
source                    1..6
                          mol_type = protein
                          organism = synthetic construct
SEQUENCE: 674
AAPRSY                                                                    6

SEQ ID NO: 675            moltype = AA  length = 6
FEATURE                   Location/Qualifiers
source                    1..6
                          mol_type = protein
                          organism = synthetic construct
SEQUENCE: 675
AAPKSY                                                                    6

SEQ ID NO: 676            moltype = AA  length = 5
FEATURE                   Location/Qualifiers
source                    1..5
                          mol_type = protein
                          organism = synthetic construct
SEQUENCE: 676
APKSY                                                                     5

SEQ ID NO: 677            moltype = AA  length = 7
FEATURE                   Location/Qualifiers
source                    1..7
                          mol_type = protein
                          organism = synthetic construct
SEQUENCE: 677
AAPRSMR                                                                   7

SEQ ID NO: 678            moltype = AA  length = 7
FEATURE                   Location/Qualifiers
source                    1..7
```

```
                              mol_type = protein
                              organism = synthetic construct
SEQUENCE: 678
VAPRSMK                                                          7

SEQ ID NO: 679               moltype = AA   length = 7
FEATURE                      Location/Qualifiers
source                       1..7
                             mol_type = protein
                             organism = synthetic construct
SEQUENCE: 679
VAPKSMR                                                          7

SEQ ID NO: 680               moltype = AA   length = 7
FEATURE                      Location/Qualifiers
source                       1..7
                             mol_type = protein
                             organism = synthetic construct
SEQUENCE: 680
VAPKSMK                                                          7

SEQ ID NO: 681               moltype = AA   length = 7
FEATURE                      Location/Qualifiers
source                       1..7
                             mol_type = protein
                             organism = synthetic construct
SEQUENCE: 681
AAPKSMR                                                          7

SEQ ID NO: 682               moltype = AA   length = 7
FEATURE                      Location/Qualifiers
source                       1..7
                             mol_type = protein
                             organism = synthetic construct
SEQUENCE: 682
AAPRSMK                                                          7

SEQ ID NO: 683               moltype = AA   length = 7
FEATURE                      Location/Qualifiers
source                       1..7
                             mol_type = protein
                             organism = synthetic construct
SEQUENCE: 683
AAPKSMK                                                          7

SEQ ID NO: 684               moltype = AA   length = 6
FEATURE                      Location/Qualifiers
source                       1..6
                             mol_type = protein
                             organism = synthetic construct
SEQUENCE: 684
PWGLSG                                                           6

SEQ ID NO: 685               moltype = AA   length = 7
FEATURE                      Location/Qualifiers
source                       1..7
                             mol_type = protein
                             organism = synthetic construct
SEQUENCE: 685
WGLSGRS                                                          7

SEQ ID NO: 686               moltype = AA   length = 8
FEATURE                      Location/Qualifiers
source                       1..8
                             mol_type = protein
                             organism = synthetic construct
SEQUENCE: 686
AWGLSGRS                                                         8

SEQ ID NO: 687               moltype = AA   length = 8
FEATURE                      Location/Qualifiers
source                       1..8
                             mol_type = protein
                             organism = synthetic construct
SEQUENCE: 687
PAGLSGRS                                                         8

SEQ ID NO: 688               moltype = AA   length = 8
FEATURE                      Location/Qualifiers
```

-continued

```
source                 1..8
                       mol_type = protein
                       organism = synthetic construct
SEQUENCE: 688
PWALSGRS                                                           8

SEQ ID NO: 689         moltype = AA  length = 8
FEATURE                Location/Qualifiers
source                 1..8
                       mol_type = protein
                       organism = synthetic construct
SEQUENCE: 689
PWGASGRS                                                           8

SEQ ID NO: 690         moltype = AA  length = 8
FEATURE                Location/Qualifiers
source                 1..8
                       mol_type = protein
                       organism = synthetic construct
SEQUENCE: 690
PWGLAGRS                                                           8

SEQ ID NO: 691         moltype = AA  length = 8
FEATURE                Location/Qualifiers
source                 1..8
                       mol_type = protein
                       organism = synthetic construct
SEQUENCE: 691
PWGLSARS                                                           8

SEQ ID NO: 692         moltype = AA  length = 8
FEATURE                Location/Qualifiers
source                 1..8
                       mol_type = protein
                       organism = synthetic construct
SEQUENCE: 692
PWGLSGAS                                                           8

SEQ ID NO: 693         moltype = AA  length = 8
FEATURE                Location/Qualifiers
source                 1..8
                       mol_type = protein
                       organism = synthetic construct
SEQUENCE: 693
PWGLSGRA                                                           8

SEQ ID NO: 694         moltype = AA  length = 9
FEATURE                Location/Qualifiers
source                 1..9
                       mol_type = protein
                       organism = synthetic construct
SEQUENCE: 694
LSGRSPAGL                                                          9

SEQ ID NO: 695         moltype = AA  length = 10
FEATURE                Location/Qualifiers
source                 1..10
                       mol_type = protein
                       organism = synthetic construct
SEQUENCE: 695
LSGRSPWGLS                                                         10

SEQ ID NO: 696         moltype = AA  length = 5
FEATURE                Location/Qualifiers
source                 1..5
                       mol_type = protein
                       organism = synthetic construct
SEQUENCE: 696
GSGGS                                                              5

SEQ ID NO: 697         moltype = AA  length = 12
FEATURE                Location/Qualifiers
source                 1..12
                       mol_type = protein
                       organism = synthetic construct
SITE                   1
                       note = 7-methoxycoumarin-4-acetyl Serine
VARIANT                8
                       note = R or K
```

-continued

```
SITE                    11
                        note = 2,4-dinitrophenyl Lysine
SITE                    12
                        note = D-amino acid
SEQUENCE: 697
SPWGLSGXSG KR                                                              12

SEQ ID NO: 698          moltype = AA  length = 14
FEATURE                 Location/Qualifiers
source                  1..14
                        mol_type = protein
                        organism = synthetic construct
SITE                    1
                        note = 7-methoxycoumarin-4-acetyl Glycine
VARIANT                 3
                        note = May be absent
VARIANT                 4
                        note = May be absent
VARIANT                 9
                        note = May be absent
VARIANT                 10
                        note = May be absent
SITE                    13
                        note = 2,4-dinitrophenyl Lysine
SITE                    14
                        note = D-amino acid
SEQUENCE: 698
GSRSPWGLRS GSKR                                                            14

SEQ ID NO: 699          moltype = AA  length = 12
FEATURE                 Location/Qualifiers
source                  1..12
                        mol_type = protein
                        organism = synthetic construct
SITE                    1
                        note = 7-methoxycoumarin-4-acetyl Serine
SITE                    11
                        note = 2,4-dinitrophenyl Lysine
SITE                    12
                        note = D-amino acid
SEQUENCE: 699
SPWGLSGRSG KR                                                              12

SEQ ID NO: 700          moltype = AA  length = 12
FEATURE                 Location/Qualifiers
source                  1..12
                        mol_type = protein
                        organism = synthetic construct
SITE                    1
                        note = 7-methoxycoumarin-4-acetyl Serine
SITE                    11
                        note = 2,4-dinitrophenyl Lysine
SITE                    12
                        note = D-amino acid
SEQUENCE: 700
SPWGLSGRGS KR                                                              12

SEQ ID NO: 701          moltype = AA  length = 12
FEATURE                 Location/Qualifiers
source                  1..12
                        mol_type = protein
                        organism = synthetic construct
SITE                    1
                        note = 7-methoxycoumarin-4-acetyl Serine
SITE                    11
                        note = 2,4-dinitrophenyl Lysine
SITE                    12
                        note = D-amino acid
SEQUENCE: 701
SPWGLSGGGS KR                                                              12

SEQ ID NO: 702          moltype = AA  length = 12
FEATURE                 Location/Qualifiers
source                  1..12
                        mol_type = protein
                        organism = synthetic construct
SITE                    1
                        note = 7-methoxycoumarin-4-acetyl Glycine
SITE                    11
```

-continued

```
                       note = 2,4-dinitrophenyl Lysine
SITE                   12
                       note = D-amino acid
SEQUENCE: 702
GSWGLSGRSG KR                                                           12

SEQ ID NO: 703         moltype = AA  length = 13
FEATURE                Location/Qualifiers
source                 1..13
                       mol_type = protein
                       organism = synthetic construct
SITE                   1
                       note = 7-methoxycoumarin-4-acetyl Serine
VARIANT                5
                       note = R or K
VARIANT                8
                       note = W or A
SITE                   12
                       note = 2,4-dinitrophenyl Lysine
SITE                   13
                       note = D-amino acid
SEQUENCE: 703
SLSGXSPXGL GKR                                                          13

SEQ ID NO: 704         moltype = AA  length = 13
FEATURE                Location/Qualifiers
source                 1..13
                       mol_type = protein
                       organism = synthetic construct
SITE                   1
                       note = 7-methoxycoumarin-4-acetyl Histidine
SITE                   12
                       note = 2,4-dinitrophenyl Lysine
SITE                   13
                       note = D-amino acid
SEQUENCE: 704
HQPAGLSGRS GKR                                                          13

SEQ ID NO: 705         moltype = AA  length = 11
FEATURE                Location/Qualifiers
source                 1..11
                       mol_type = protein
                       organism = synthetic construct
SITE                   1
                       note = 7-methoxycoumarin-4-acetyl Leucine
SITE                   10
                       note = 2,4-dinitrophenyl Lysine
SITE                   11
                       note = D-amino acid
SEQUENCE: 705
LSGRSPWGLK R                                                            11
```